United States Patent
Lubys et al.

(10) Patent No.: US 11,739,316 B2
(45) Date of Patent: Aug. 29, 2023

(54) OLIGONUCLEOTIDE-TETHERED NUCLEOTIDES

(71) Applicants: THERMO FISHER SCIENTIFIC BALTICS UAB, Vilnius (LT); LIFE TECHNOLOGIES CORPORATION, Carlsbad, CA (US)

(72) Inventors: Arvydas Lubys, Vilnius (LT); Inga Cikotiene, Vilnius (LT); Zana Kapustina, Vilnius (LT); Arturas Berezniakovas, Vilnius (LT); Justina Medziune, Vilnius (LT); Simona Zeimyte, Vilnius (LT); Mark Andersen, Carlsbad, CA (US); Michael Allen, San Marcos, CA (US); Sihong Chen, Vista, CA (US)

(73) Assignees: Thermo Fisher Scientific Baltics UAB, Vilnius (LT); Life Technologies Corporation, Carlsbad, CA (US)

( * ) Notice: Subject to any disclaimer, the term of this patent is extended or adjusted under 35 U.S.C. 154(b) by 352 days.

(21) Appl. No.: 16/908,567

(22) Filed: Jun. 22, 2020

(65) Prior Publication Data

US 2020/0399633 A1 Dec. 24, 2020

Related U.S. Application Data

(60) Provisional application No. 63/032,297, filed on May 29, 2020, provisional application No. 62/864,589, filed on Jun. 21, 2019.

(51) Int. Cl.
| | | |
|---|---|---|
| *C12N 15/10* | (2006.01) | |
| *C12N 15/115* | (2010.01) | |
| *C12Q 1/6806* | (2018.01) | |

(52) U.S. Cl.
CPC ........ *C12N 15/1065* (2013.01); *C12N 15/115* (2013.01); *C12Q 1/6806* (2013.01); *C12N 2310/3517* (2013.01)

(58) Field of Classification Search
CPC ................................................. C12N 15/1065
See application file for complete search history.

(56) References Cited

U.S. PATENT DOCUMENTS

| | | |
|---|---|---|
| 9,096,856 B2 | 8/2015 | Wang et al. |
| 9,347,093 B2 | 5/2016 | Klimasauskas et al. |
| 9,932,623 B2 | 4/2018 | Kim |
| 2015/0368710 A1 | 12/2015 | Fuller et al. |
| 2016/0251700 A1 | 9/2016 | Ost et al. |
| 2017/0088888 A1 | 3/2017 | El-Sagheer et al. |
| 2018/0127816 A1 | 5/2018 | Teo et al. |

FOREIGN PATENT DOCUMENTS

| | | |
|---|---|---|
| WO | WO-2015026845 A2 | 2/2015 |
| WO | WO-2015026853 A2 | 2/2015 |
| WO | WO-2017223517 A1 | 12/2017 |
| WO | WO-2018129120 A1 | 7/2018 |

OTHER PUBLICATIONS

Anderson J.P., et al., "Incorporation of Reporter-labeled Nucleotides by DNA Polymerases", BioTechniques, Feb. 2005, vol. 38(2), pp. 257-264.
Baccaro A et al., "Barcoded Nucleotides", Angewandte Chemie International Edition, vol. 51, No. 1, Jan. 2, 2012 (Jan. 2, 2012), pp. 254-257, XP055294152, DE ISSN: 1433-7851, DOI: 10.1002/anie.201105717.
Baccaro A et al., "Supporting Information "Barcoded Nucleotides**" Chemical Synthesis of ODN barcode modified nucleotides", Angewandte Chemie International Edition, Jan. 2, 2012 (Jan. 2, 2012), pp. 1-25, XP055744759, Retrieved from the Internet: URL: https://onlinelibrary.wiley.com/action/downloadSupplement?doi=10.1002/anie.201105717&file=anie_201105717_sm_miscellaneous_information.pdf. [retrieved on Oct. 28, 2020].
Hocek M: "Synthesis of Base-Modified 2'-Deoxyribonucleoside Triphosphates and Their Use in Enzymatic Synthesis of Modified DNA for Applications in Bioanalysis and Chemical Biology", Journal of Organic Chemistry, vol. 79, No. 21, Oct. 16, 2014 (Oct. 16, 2014), pp. 9914-9921, XP055544211, ISSN: 0022-3263, DOI: 10.1021/jo5020799.
Olsen T.K., et al., "Introduction to Single-Cell RNA Sequencing", Current Protocols in Molecular Biology, Apr. 2018, vol. 122(1), e57, 14 pages.
Panattoni A et al., "Flexible Alkyne-Linked Thymidine Phosphoramidites and Triphosphates for Chemical or Polymerase Synthesis and Fast Postsynthetic DNA Functionalization through Copper-Catalyzed Alkyne-Azide 1,3-Dipolar Cycloaddition", Organic Letters, vol. 20, No. 13, Jun. 13, 2018 (Jun. 13, 2018), pp. 3962-3965, XP055744633, ISSN: 1523-7060, DOI: 10.1021/acs.orglett.8b01533.
PCT/US2020/039009, International Search Report and Written Opinion, dated Nov. 13, 2020, 17 pages.
Rao H et al., "Posttranscriptional chemical functionalization of azide-modified oligoribonucleotides by bioorthogonal click and Staudinger reactions", Chemical Communications, vol. 48, No. 4, Jan. 1, 2012 (Jan. 1, 2012), pp. 498-500, XP055744548, ISSN: 1359-7345, DOI: 10.1039/C1CC15659D.
Stasevskij Z., et al., "Tethered Oligonucleotide-Primed Sequencing, TOP-Seq: A High-Resolution Economical Approach for DNA Epigenome Profiling", Molecular Cell, Feb. 2, 2017, vol. 65(3), pp. 554-564.e6.

(Continued)

*Primary Examiner* — Teresa E Strzelecka

(57) ABSTRACT

The present disclosure describes oligonucleotide-tethered nucleotides, methods of making them, and methods of using them. The oligonucleotide-tethered nucleotides comprise, in some embodiments, a nucleotide linked to an oligonucleotide of from about 3 to about 100 nucleotides in length. These oligonucleotide-tethered nucleotides can be used to label a plurality of different types of nucleic acids in a plurality of different situations with a known oligonucleotide, which can serve as a barcode in some embodiments. The resulting oligonucleotide-labeled nucleic acids oligonucleotides can be used in a variety of nucleic acid sequencing methods.

11 Claims, 57 Drawing Sheets

Specification includes a Sequence Listing.

(56) References Cited

OTHER PUBLICATIONS

Sulgaite J., et al., Synthesis of Functionalized dNTPs for Enzymatic Applications, Balticum Organicum Syntheticum 2018, Jul. 1-4, 2018.

Thoresen L.H., et al., "Rigid, Conjugated, Fluoresceinated Thymidine Triphosphates: Syntheses and Polymerase Mediated Incorporation into DNA Analogues," Chemistry—A European Journal, Oct. 6, 2003, vol. 9(19), pp. 4603-4610.

Verga D et al., "DNA polymerase-catalyzed incorporation of nucleotides modified with a G-quadruplex-derived DNAzyme", Chemical Communications, vol. 51, No. 34, Mar. 25, 2015 (Mar. 25, 2015), pp. 7379-7381, XP055292261, ISSN: 1359-7345, DOI: 10.1039/C5CC01387A.

Verga D et al., "Sequence selective naked-eye detection of DNA harnessing extension of oligonucleotide-modified nucleotides", Bioorganic and Medicinal Chemistry Letters, vol. 26, No. 3, Dec. 24, 2015 (Dec. 24, 2015), pp. 841-844, XP029391935, ISSN: 0960-894X, DOI: 10.1016/J.BMCL.2015.12.082.

Verga D et al., "Supporting Information Sequence selective naked-eye detection of DNA harnessing extension of oligonucleotide-modified nucleotides", Bioorganic and Medicinal Chemistry Letters, vol. 26, Feb. 1, 2016 (Feb. 1, 2016), pp. S1-S14, XP055744555, Retrieved from the Internet: URL: https://www.researchgate.net/publication/288056287. [retrieved on Oct. 27, 2020].

Welter M et al., "Combining the Sensitivity of LAMP and Simplicity of Primer Extension via a DNA-Modified Nucleotide", Chemistry, vol. 2, No. 2, May 14, 2020 (May 14, 2020), pp. 490-498, XP055744550, DOI: 10.3390/chemistry2020029.

Winz M.L., et al., "Nucleotidyl Transferase Assisted DNA Labeling with Different Click Chemistries", Nucleic Acids Research, Sep. 30, 2015, vol. 43(17), e110.

SEQ ID NO: 29  Cy5— CCGGGGATCCCCATGTG
SEQ ID NO: 30  gagccaugggcccuagguacacugccugulagcccuuugcgguucccucuaaua
caugggcuccuucuuacagcgaccugccauagcgcuuuuacauuuucgaaaggg

Figure 12A

SEQ ID No: 24  Cy5-TGCAGACATGGGTAGGCATCCTTGGCGTA                              29nt
SEQ ID No: 27  ACGTCTGTACCCATCCGTAGGAACCGCATGACATCGACTCAACTCGCTG            49nt

Figure 31

SEQ ID No: 24  Cy5-TGCAGACATGGGTAGGCATCCTTGGCGTA       29nt
SEQ ID No: 28  ACGTCTGTACCCATCCGTAGGAACCGCATG         30nt

Figure 32

SEQ ID No: 31  5-aaaaaaaaaaaatacgccaaggatgcctacccatgtctgca->
                                                      ||||||||||||||||||||||||||||||
SEQ ID No: 32                          <-atgcggttcctacggatgggtacagacgt-5

Simplified Barcoding Workflow Using Oligo-Tethered ddNTPs:

OLIGONUCLEOTIDE-TETHERED NUCLEOTIDES

CROSS-REFERENCE TO RELATED APPLICATIONS

This application claims the benefit of priority to U.S. Provisional Application with Ser. No. 62/864,589 filed on Jun. 21, 2019 and titled "Tethered Oligos and Uses Thereof," and U.S. Provisional Application with Ser. No. 63/032,297, filed May 29, 2020, and titled "Tethered Oligos and Uses Thereof."

SEQUENCE LISTING

The instant application contains a Sequence Listing which has been submitted electronically in ASCII format and is hereby incorporated by reference in its entirety. Said ASCII copy, created on Dec. 14, 2022, is named LT01475_SL_EAamd_14Dec2022.txt and is 13,738 bytes in size.

FIELD

The present disclosure relates to oligonucleotide-tethered nucleotides and methods of nucleic acid tagging using the same. The present disclosure further relates to next-generation sequencing and particularly, but not exclusively, compositions, methods, and kits for preparing a next-generation sequencing library.

BACKGROUND

The ability to manipulate and modify DNA molecules forms the basis of the modern molecular biology. The rise of next generation sequencing (NGS), especially when applied at the single-cell level, has opened new needs for the DNA modification and synthesis toolkit. Maximal nucleic acid modification efficiency, minimal bias, ease of automation and miniaturization are examples of significant needs that current methods do not adequately address.

Nucleic acid library preparation is an important step in the next generation sequencing workflow. It includes the ligation of platform-specific adapters, which varies by more than a factor of 10 between different vendors, with some ligation efficiencies so low that they could impair the original library complexity and diminish the sequencing results. Although sequencing of minute amounts or even individual DNA molecules is possible, this currently requires pre-amplification techniques. Multiple displacement reaction (MDA), performed by processive DNA polymerases under isothermal conditions offers high genome coverage, but results in sequence-dependent bias, causing over-amplification in certain genomic regions and under amplification in other regions. Pre-amplification of cDNA, often performed in the case of single-cell or ultra-low input RNA sequencing library preparation, may cause dropouts of certain sequences or distort the original composition of the transcriptome in other ways. This indicates a need for new approaches to overcome the challenges in genomic and single-cell DNA and RNA sequencing.

Typical NGS library preparation workflow includes random fragmentation of the DNA or cDNA sample followed by 5' and 3' adapter ligation. Usually fragmentation and adapter addition are performed as separate steps. Adapter-ligated fragments are then optionally amplified with PCR and purified. Library amplification steps require unbiased replication of highly complex populations of molecules. Extremely high-fidelity amplification limits PCR errors that may result in false genetic variant calls. Alternatively, "tagmentation" combines the fragmentation and ligation reactions into a single step that simplifies the library preparation process. Alternatively, adapters can be added with transposons.

The present disclosure is provided to address one or more of the problems described above and to provide further improved methods for preparing nucleic acid libraries for next-generation sequencing platforms.

SUMMARY

The present disclosure provides improved nucleic acid labeling techniques and methods for preparing libraries for next generation sequencing.

Accordingly, some embodiments provide a method for tagging a nucleic acid with an oligonucleotide including the steps of: a. providing the nucleic acid to be tagged, b. contacting the nucleic acid with a polymerase and at least one oligonucleotide-tethered nucleotide of Formula (A):

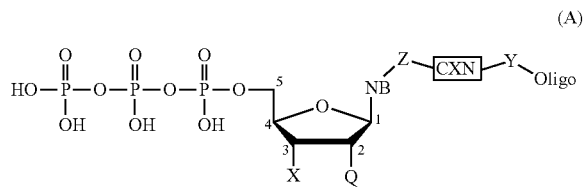

or a salt thereof, wherein:
NB is a nucleobase;
Oligo is an oligonucleotide of 3 to 100 nucleotides;
each of X and Q are independently chosen from, H, OH, $N_3$, halo, alkyl, alkoxy, alkyl, alkenyl, alkynyl, acyl, cyano, amino, ester, and amido;
each of Z and Y are independently chosen from a bond, amino, amido, alkyl, alkenyl, alkynyl, thioether, sulfonyl, sulfonamido, ether, ketone, carbonyl, anhydride, ester, imido, urea, urethane, and combinations thereof; and
CXN is chosen from alkylene, alkenylene, alkynylene, ketone, carbonate, ester, ether, anhydride, amido, amino, aminoalkylene, imino, imido, diazo, carbamate ester, phosphodiester, sulfide, disulfide, sulfonyl, sulfonamido, and a heterocyclic group containing from one to four N, O, S atom(s) or a combination thereof where heterocyclic group is optionally substituted at carbon, nitrogen or sulfur atom(s), thereby producing the first tagged nucleic acid.

In some embodiments, the contacting can include contacting the nucleic acid with at least one oligonucleotide-tethered nucleotide, at least one nucleotide not tethered to an oligonucleotide, and a polymerase.

In some embodiments, the method further includes the step of annealing a primer to the nucleic acid.

In some embodiments, the oligonucleotide-tethered nucleotide is a dideoxynucleotide, optionally wherein the dideoxynucleotide is chosen from dideoxyadenosine triphosphate, dideoxyguanosine triphosphate, dideoxythymidine triphosphate, dideoxyuridine triphosphate, dideoxycytidine triphosphate, and any combination thereof.

In some embodiments, the method includes the further steps of: annealing a primer which is at least partially complementary to the tethered oligonucleotide after producing a first tagged nucleic acid strand; contacting the first tagged nucleic acid strand and annealed primer with a nucleic acid polymerase and at least one nucleotide not tethered to an oligonucleotide; and allowing a polymerase to extend from a 3' hydroxyl of the primer annealed to the tethered oligonucleotide to form a second nucleic acid strand.

In some embodiments, the method includes the further steps of annealing a splint oligonucleotide which is at least partially complementary to the tethered oligonucleotide after producing a first tagged nucleic acid strand; contacting the first tagged nucleic acid strand and annealed splint oligonucleotide with a nucleic acid polymerase and at least one nucleotide not tethered to an oligonucleotide; and allowing a polymerase to extend across the splint oligonucleotide from the 3' hydroxyl of the tethered oligonucleotide.

Also provided are methods for generating a library of nucleic acids from a sample comprising one or more nucleic acids. Accordingly, some embodiments provide a method for generating a library of nucleic acids from a sample comprising one or more nucleic acids, optionally wherein the sample comprises a plurality of cells. The method can include the steps of: annealing a first primer which is at least partially complementary to the one or more nucleic acids, contacting the one or more nucleic acids with a nucleic acid polymerase, at least one nucleotide not tethered to an oligonucleotide, and at least one oligonucleotide-tethered dideoxynucleotide to form a plurality of nucleic acid strands comprising the oligonucleotide-tethered dideoxynucleotide at their 3' end; annealing a second primer which is at least partially complementary to the tethered oligonucleotide, and allowing the polymerase to extend from a 3' hydroxyl of the second primer annealed to the tethered oligonucleotide, thereby producing a library of nucleic acids.

Some embodiments provide a method for generating a library of nucleic acids from a sample comprising one or more nucleic acids, optionally wherein the sample comprises a plurality of cells or cell nuclei, including the steps of: annealing a first pruner which is at least partially complementary to the one or more nucleic acids, contacting the one or more nucleic acids with a first nucleic acid polymerase, at least one nucleotide not tethered to an oligonucleotide, and at least one oligonucleotide-tethered dideoxynucleotide to form a plurality of first extension products comprising the oligonucleotide-tethered dideoxynucleotide at the 3' end; annealing a splint oligonucleotide which is at least partially complementary to the tethered oligonucleotide of the first extension products, and contacting the first extension products with a nucleic acid polymerase and one or more nucleotides to allow the polymerase to extend across the annealed splint from the 3' hydroxyl of the tethered oligonucleotide to produce a second extension product, thereby producing a library of nucleic acids.

In some embodiments, the library of nucleic acids is a library of double-stranded nucleic acids.

In some embodiments, the library of nucleic acids is a library of first extension products, comprising a universal handle at the 5' end, and wherein the first extension products comprise or are further manipulated to add an a universal handle at the 3' end, wherein the universal handles enable annealing of amplification primers.

In some embodiments, the one or more nucleic acids in the sample comprises an oligonucleotide of an oligonucleotide-tethered binding agent (OTBA). In some embodiments, the tethered oligonucleotide of the OTBA comprises a cell marker binding agent index, and wherein binding agent of the OTBA comprises an aptamer or an antibody or a functional fragment thereof.

In some embodiments wherein the sample is contacted with a splint oligonucleotide, and wherein the sample comprises more than one cell or cell nuclei, a subpopulation of the cells or cell nuclei may comprise one or more cell markers.

The sample can be split into two or more first portions before step of annealing the first primer to the one or more nucleic acids, wherein each first portion comprises a subpopulation of cells or cell nuclei of the original sample. The first primer includes a first universal handle sequence and a first barcode, said first barcode being common among the first primers in each first portion, but different from the first barcodes present in first primers in other first portions; and wherein the oligonucleotide of the oligonucleotide-tethered dideoxynucleotide comprises a second universal handle sequence. The method can also include performing the following further steps before the splint oligonucleotides are annealed: combining the first portions after formation of the first nucleic extension products and splitting the combined first portions into two or more second portions, wherein the second portions comprise the splint oligonucleotide; wherein the splint oligonucleotide comprises: an oligonucleotide sequence that anneals to the second universal handle on the tethered oligonucleotide; a template sequence for a second barcode, wherein the second barcodes of each second portion are common, but are different from the second barcodes of other second portions, and a template sequence for a third universal handle. A library of nucleic acids comprising second extension products are thus generated that include, at the 3' end of the first extension products, the second barcode and third universal handle.

In some embodiments, the method can include the further steps of: combining the second portions; splitting the combined second portions into two or more third portions; contacting each third portion with amplification primers, wherein the amplification primers are capable of hybridising to and extending from the first universal handle and the third universal handle to amplify the second extension products. The amplification primers optionally comprise third and/or fourth barcodes respectively, and first and/or second adapter sequences, respectively. The combination of the first, second, and third barcode sequences (or complements thereof) of the amplification products are unique to the amplification products originating from a single cell or nucleus.

In some embodiments of the methods for tagging a nucleic acid and/or the methods of generating a nucleic acid library from a sample comprising one or more nucleic acids, the primer, the tethered oligonucleotide, or both comprises a random sequence, a target-specific sequence or both.

In some embodiments of the methods for tagging a nucleic acid and/or the methods of generating a nucleic acid library from a sample comprising one or more nucleic acids, one or more of the primer, the tethered oligonucleotide, or the splint oligonucleotide comprises a universal handle, a universal sequence, a unique molecular identifier, an adapter sequence, a promoter sequence, a barcode sequence, an index sequence, or any combination thereof.

In some embodiments of the methods for tagging a nucleic acid and/or the methods of generating a nucleic acid library from a sample comprising one or more nucleic acids, the polymerase is a DNA-dependent DNA polymerase, an RNA-dependent DNA polymerase, a template-independent DNA polymerase, a DNA-dependent RNA polymerase, an RNA-dependent RNA polymerase, or template-independent RNA polymerase.

In some embodiments of the methods for tagging an nucleic acid and/or the methods of generating a nucleic acid library from a sample comprising one or more nucleic acids, the nucleic acid is DNA or RNA.

Also provided herein is an oligonucleotide-tethered nucleotide of Formula (A):

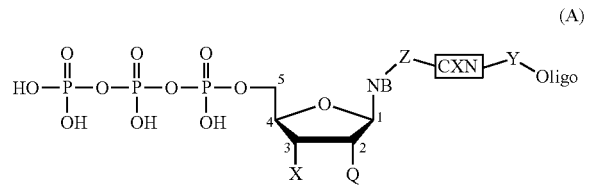

(A)

or a salt thereof
wherein NB is a nucleobase;
Oligo is an oligonucleotide of 3 to 100 nucleotides;
each of N and Q are independently chosen from, H, OH, N$_3$, halo, alkyl, alkoxy, alkyl, alkenyl, alkynyl, acyl, cyano, amino, ester, and amido;
each of Z and Y are independently chosen from a bond, amino, amido, alkyl, alkenyl, alkynyl, thioether, sulfonyl, sulfonamido, ether, ketone, carbonyl, anhydride, ester, amido, urea, urethane, and combinations thereof; and
CXN is chosen from alkylene, alkenylene, alkynylene, ketone, carbonate, ester, ether, anhydride, amido, amino, aminoalkylene, amino, imido, diazo, carbamate ester, phosphodiester, sulfide, disulfide, sulfonyl, sulfonamido, and a heterocyclic group containing from one to four N, O, S atom(s) or a combination thereof where heterocyclic group is optionally substituted at carbon, nitrogen or sulfur atom(s).

IN some embodiments, CXN is Click and wherein Click is a product of a click reaction between one of the following pairs of functional groups:
  i) alkynyl and azido;
  ii) thiol and alkynyl;
  iii) thiol and alkenyl;
  iv) azido and cyclooctanyl; and
  v) cyclooctanyl and nitrone.

Also provided herein are uses of an oligonucleotide-tethered nucleotide as described herein, in the preparation of a nucleic acid library or for use in tagging a nucleic acid.

In some embodiments, the oligonucleotide-tethered nucleotides used herein generally have a structure according to formula (A), or a salt thereof:

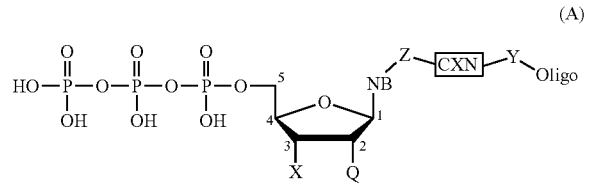

(A)

wherein NB is a nucleobase; Oligo is an oligonucleotide of 3 to 100 nucleotides; each of N and Q are independently chosen from, H, OH, N$_3$, halo, alkyl, alkoxy, alkyl, alkenyl, alkenyl, acyl, cyano, amino, ester, and amido; each of Z and Y are independently chosen from a bond, amino, amido, alkylene, alkenylene, alkynylene, thioether, sulfonyl, sulfonamido, ether, ketone, carbonyl, anhydride, ester, imido, urea, urethane, and combinations thereof; and CXN is chosen from alkylene, alkenylene, alkynylene, ketone, carbonate, ester, ether, anhydride, amido, amino, aminoalkyl, imino, amido, diazo, carbamate ester, phosphodiester, sulfide, disulfide, sulfonyl, sulfonamido, and a heterocyclic group containing from one to four N, O, S atom(s) or a combination thereof where heterocyclic group is optionally substituted at carbon, nitrogen or sulfur atom(s).

In some embodiments, the salt of the compound of Formula (A) is a quaternary ammonium salt.

In some embodiments, X is chosen from H, OH, F, N$_3$, and amino. In other embodiments, X is chosen from H, N$_3$, and OH. In some embodiments, X is OH. In other embodiments, X is H.

In some embodiments, Q is H, OH, F, Cl, Br, I, an N$_3$. In other embodiments, Q is H.

In some embodiments Oligo is chosen from

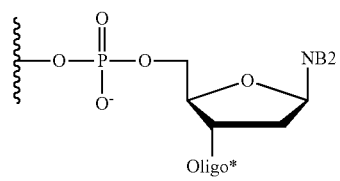

(C1)

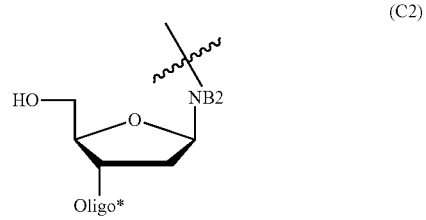

(C2)

where Oligo* is the remaining 2 to 99 nucleotides from the Oligo group and NB2 is a nucleobase.

In some embodiments, CXN is chosen from 5-membered heterocycles and 6-membered heterocycles each having from 1 to 3 heteroatoms. In some embodiments, CXN is chosen from pyrrolo, thiophenyl, furanyl, pyrrolidinyl, thiolanyl, tetrahydrofuranyl, isoxazolyl, oxazolo, pyrazolo, imidazolyl, isothiazolo, thiazolyl, triazolo, oxadiazolo, thiadiazolo, pyranyl, thiopyranyl, pyridinyl, tetrahydropyranyl, tetrahydrothiopyranyl, piperidinyl, pyridazinyl, pyrimidinyl, pyrazinyl, hexahydropyridazinyl, hexahydropyrimidinyl, piperazinyl, dioxanyl, morpholino, thiazinyl, oxazino, dithianyl, triazinyl, dithiazino, thiadiazino, triazinanyl, and oxathiazino.

In other embodiments, CXN is Click, wherein Click is a product of a click reaction. In some embodiments, Click is a product of a click reaction between one of the following pairs of functional groups: i) alkynyl and azido; ii) thiol and alkynyl; thiol and alkenyl; iv) azido and cyclooctanyl; and v) cyclooctanyl and nitron In some embodiments, CXN is

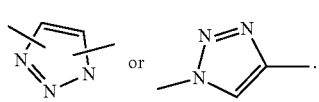

or

In some embodiments, Z and Y are each linkers, or linking moieties, which refers to certain functional groups that may be varied to provide the overall tether between the ddNTP or dNTP and the oligonucleotide with the desired properties.

In some embodiments each of Z and Y are independently chosen from a bond, amino, amido, alkylene, alkenylene, alkynylene, thioether, sulfonyl, sulfonamido, ether, ketone, carbonyl, anhydride, ester, imido, urea, urethane, and combinations thereof. In some embodiments, each Z and Y are independently chosen from amino, amido, alkylene, alkenylene, alkynylene, ether, ketone, carbonyl, anhydride, ester, imide, or any combination thereof. In other embodiments, Y is alkylene or alkynylene.

In other embodiments, Z is a combination of one or more of alkynylene, alkylene, ether and amido. In still other embodiments, the combination of —NB—Z— is

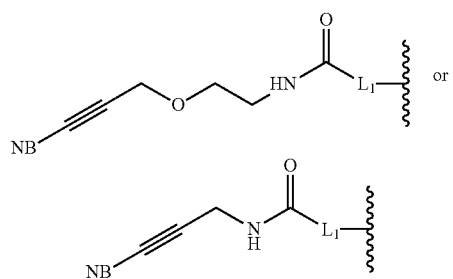

where $L_1$ is chosen from alkylene, alkenylene, alkynylene, and polyalkylene glycol.

In some embodiments the compound of Formula (A): is selected from the compounds of Formula (B1)-(B4)

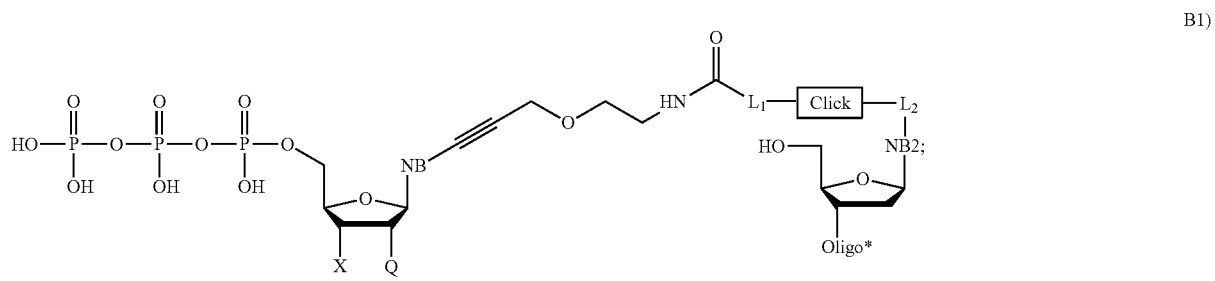

(B1)

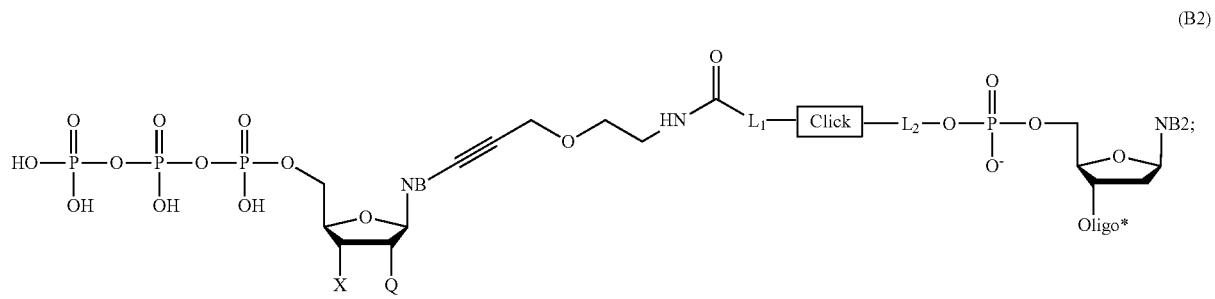

(B2)

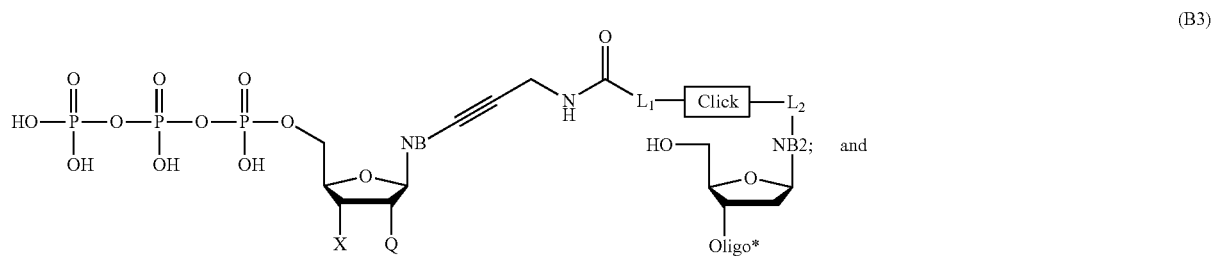

(B3)

and

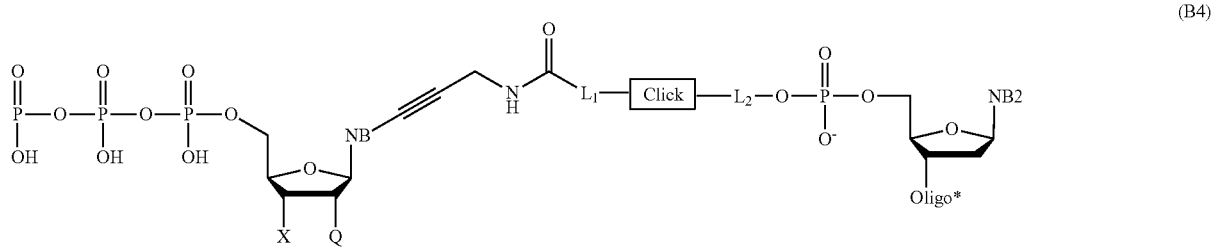

(B4)

and salts thereof wherein oligo* is the remaining 2 to 99 nucleotides from the Oligo group and NB2 is a nucleobase; L₁ is chosen from alkylene, alkenylene, alkynylene, and polyalkylene glycol; L₂ is alkylene or alkynylene.

In other embodiments, L₁ is C1-C12 alkylene, C2-C12 alkenylene, C2-C12 alkenylene, and polyalkylene glycol having from 2 to 8 glycol units. In other embodiments, L₁ is chosen from polyethylene glycol with 2 glycol units (PEG2), polyethylene glycol with 4 glycol units (PEG34), or polyethylene glycol with 6 glycol units (PEG6), methylene, ethylene, n-propylene, isopropylene, 1-butylene, cis-2-butylene, trans-2-butylene, isobutylene, 1-pentylene, cis-2-pentylene, trans-2-pentylene, isopentylene, and hexylene. In yet other embodiments, L₁ is chosen from —CH₂—, —(CH₂)₃—, —(CH₂)₅—, PEG2, and PEG4.

In some embodiments the linking group Y comprises the subgroup of L₂ which is chosen from alkylene or alkynylene. In other embodiments L₂ is C1-C12 alkylene or C1-C12 alkynylene. In other embodiments the combination of L₂-Oligo is chosen from —(CH₂)₄-Oligo or —(CH₂)₄CC-Oligo.

In some embodiments, Oligo is tethered to the nucleotide either through its 5'-phosphate to the nucleobase of the dNTP or ddNTP. In some embodiments Oligo is tethered through a nucleobase (NB2).

In some embodiments, NB and NB2 are independently a nucleobase. In some embodiments the nucleobase is chosen from adenine, 7-deaza-adenine, cytosine, guanine, 7-deazaguanine, thymine, uracil and inosine.

In some embodiments, NB is a pyrimidine and the pyrimidine is tethered to the oligonucleotide at the 5 position of the nucleobase. In other embodiments, NB is a purine, and wherein the purine is tethered to the oligonucleotide at the 7 position of the nucleobase.

In some embodiments, an oligonucleotide-tethered nucleotide of formula (I) or a salt thereof is provided:

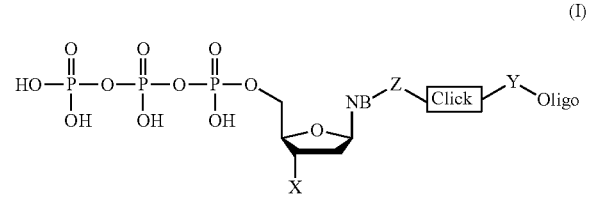

(I)

wherein N is H, N₃, or OH;
NB represents a nucleobase chosen from adenine, 7-deaza-adenine, cytosine, guanine, 7-deazaguanine, thymine, uracil and inosine;
Z and Y are linkers, wherein Z and Y each independently comprise at least one linking moiety chosen from amino, amido, alkyl, alkenyl, alkynyl, thioether, sulfonyl, sulfonamido, ether, ketone, carbonyl, anhydride, ester, imide, urea, urethane, or any combination thereof;
Click is the product of a click reaction; and
Oligo is an oligonucleotide of 3 to 100 nucleotides in length.

In some embodiments, "Click" is a product of a click reaction between one of the following pairs of functional groups:

i) alkynyl and azido;

ii) azido and alkynyl, iii) thiol and alkynyl;

iv) alkynyl and thiol;

v) thiol and alkenyl;

vi) alkenyl and thiol;

vii) azido and cyclooctanyl;

viii) cyclooctanyl and azido;

xi) nitrone and cyclooctanyl; and xii) cyclooctanyl and nitrone;

In some embodiments, an oligonucleotide-tethered nucleotide of formula (II) or a salt thereof is provided:

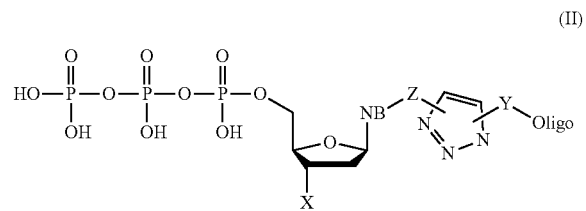

(II)

wherein N is H, OH, N₃;

NB represents a nucleobase chosen from adenine, 7-deaza-adenine, cytosine, guanine, 7-deazaguanine, thymine, uracil and inosine;

Z and Y are linkers, wherein Z and Y each independently comprise at least one linking moiety chosen from amino, amido, alkyl, alkenyl, alkynyl, thioether, sulfonyl, sulfonamido, ether, ketone, carbonyl, anhydride, ester, imide, urea, urethane, or any combination thereof; and Oligo is an oligonucleotide of 3 to 100 nucleotides in length.

In some embodiments of the oligonucleotide-tethered nucleotide of formula (I) or (II), X is OH. In other embodiments, X is H.

In some embodiments, the alkylene is a C₁-C₆ alkylene. In some embodiments, the alkenylene is a C₂-C₆ alkenylene.

In some embodiments, the alkynylene is a C₂-C₆ alkynylene.

In some embodiments, the polyalkylene glycol has 2 to 8 glycol units.

In some embodiments, the oligonucleotide is tethered to the nucleotide at its 5' end.

In some embodiments, one of Z and Y is covalently bound to the 1 position of the triazole ring, and the other of Z and Y is covalently bound to the 4 position of the triazole ring. In some embodiments, Z is covalently bound to the 1 position of the triazole ring, and Y is covalently bound to the 1 position of the triazole ring. In other embodiments, Z is covalently bound to the 4 position of the triazole ring and Y is covalently bound to the 1 position of the triazole ring.

In some embodiments, an oligonucleotide-tethered nucleotide of formula (III) or a salt thereof is provided:

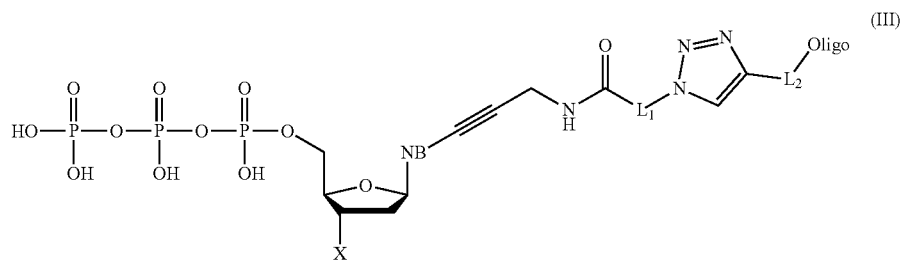

wherein
L1 is a linker comprising an alkylene, a polyalkylene glycol, or a combination thereof, and
L2 is a linker comprising an alkynylene.

In some embodiments, $L_1$ comprises a polyalkenylene glycol having 2, 4, or 6 alkenylene glycol groups. In some embodiments, the polyalkenylene glycol is polyethylene glycol.

In some embodiments, $L_1$ comprises an alkylene having 1 to 12 carbon atoms. In some embodiments, the alkylene is methylene, ethylene, n-propylene, isopropylene, 1-butylene, cis-2-butylene, trans-2-butylene, isobutylene, 1-pentylene, cis-2-pentylene, trans-2-pentylene, isopentylene, or hexylene.

In some embodiments, $L_2$ is hexynyl.

In some embodiments, the nucleobase is a pyrimidine, and wherein the pyrimidine is tethered to the oligonucleotide at the 5 position of the nucleobase. In other embodiments, the nucleobase is a purine, and the purine is tethered to the oligonucleotide at the 7 position of the nucleobase.

In some embodiments of the oligonucleotide-tethered nucleotide of formulas (I), II) or (III), the salt is a quaternary ammonium salt.

In some embodiments, the oligonucleotide comprises a barcode sequence, an adapter sequence, a unique molecular identifier, or any combination thereof.

In some embodiments, a method for tagging a nucleic acid with an oligonucleotide is provided, the method comprising:
providing the nucleic acid to be tagged,
contacting the nucleic acid with at least one oligonucleotide-tethered
nucleotide and a polymerase, thereby producing the tagged nucleic acid.

In some embodiments of a nucleotide tagging reaction as described herein, the method further comprises contacting the nucleic acid with at least one oligonucleotide-tethered nucleotide, at least one nucleotide not tethered to an oligonucleotide, and a polymerase.

In some embodiments of a nucleotide tagging reaction as described herein, the method further comprises annealing a primer to the nucleic acid.

In some embodiments of a nucleotide tagging reaction as described herein, the method further comprises annealing a splint oligonucleotide to the tagged nucleic acid.

In some embodiments of a nucleotide tagging reaction as described herein the nucleic acid is tagged at the 5' end, the 3' end, or both.

In some embodiments of a nucleotide tagging reaction as described herein, the nucleic acid is tagged at multiple positions.

In some embodiments of a nucleotide tagging reaction as described herein, the nucleic acid is tagged with the oligonucleotide-tethered nucleotide during a nick translation or a gap-filling reaction.

In some embodiments of a nucleotide tagging reaction as described herein, the method further comprises adding an adapter sequence to the 3' end of the nucleic acid, e.g. by ligation or a polymerization reaction.

In some embodiments of a nucleotide tagging reaction as described herein the method further comprises adding one or more sequences (e.g., a barcode sequence, a universal sequence, a unique molecular identifier sequence, an index sequence, a promoter sequence, sequence, an adapter sequence or the like), to the 3' end of oligonucleotide of the oligonucleotide-tethered nucleotide, e.g., by ligation or a polymerization reaction.

In some embodiments of a nucleotide tagging reaction as described herein, the method further comprises subjecting the tagged nucleic acid to PCR In some embodiments of a nucleotide tagging reaction as described herein, the method further comprises contacting the tagged nucleic acid with a splint oligonucleotide that is partially complementary to a universal handle sequence on the tethered oligonucleotide of the tagged nucleic acid, and allowing the polymerase to extend through the 3' OH of the tethered oligonucleotide across the splint oligonucleotide.

In some embodiments of a nucleotide tagging reaction as described herein, the nucleic acid is DNA, while in other embodiments, the nucleic acid is RNA.

In some embodiments of a nucleotide tagging reaction as described herein, the polymerase is a Type-A DNA polymerase, a Type B DNA polymerase, a Type X DNA polymerase, or a reverse transcriptase. In other embodiments, the polymerase is Taq DNA polymerase, Vent® DNA polymerase, Deep Vent™ DNA polymerase, Pfx DNA polymerase, Pwo polymerase, SuperScript™ IV, SuperScript™ II, SuperScript™ III, Maxima™, RevertAid™ reverse transcriptases, Thermo Sequenase™, Sequenase™ V2.0, Cycle-Seg™, Phusion exo-, Terminal deoxynucleotidyl Transferase (TdT), Maxima H, Therminator™ polymerase, Q5 DNA polymerase, AccuTaq DNA polymerase, T7 DNA polymerase, T3 DNA polymerase, T4 DNA polymerase, T7 RNA polymerase, T3 RNA polymerase, SP6 RNA polymerase, DNA polymerase 1, Klenow fragment, Tth DNA polymerase, Phusion® DNA polymerase, SuperFi DNA polymerase, Platinum Taq DNA polymerase, Herculase II Fusion DNA polymerase, PfuUltra Fusion II HS DNA polymerase, Bst DNA polymerase large fragment, Stoeffel fragment, 9° N™ DNA polymerase, Pfu DNA polymerase, Tfl DNA polymerase, Phi29 polymerase, Tli DNA polymerase, eukaryotic DNA polymerase beta, telomerase, KOD HiFi DNA polymerase, KOD DNA polymerase, Q-beta replicase, AMV reverse transcriptase, M-MLV reverse transcriptase, Phi6 reverse transcriptase, HIV-1 reverse transcriptase, polyA polymerase (PAP, polyU polymerase (PUP), and variants and derivatives thereof.

In some embodiments of a nucleotide tagging reaction as described herein, the polymerase is TdT.

In some embodiments of a nucleotide tagging reaction as described herein, the nucleotide the oligonucleotide-tethered nucleotide is a deoxynucleotide, optionally wherein the deoxynucleotide is chosen from deoxyadenosine triphosphate, deoxyguanosine triphosphate, deoxythymidine triphosphate, deoxyuridine triphosphate, deoxycytidine triphosphate and any combinations thereof.

In some embodiments of a nucleotide tagging reaction as described herein, the nucleotide the oligonucleotide-tethered nucleotide is a dideoxynucleotide, optionally wherein the dideoxynucleotide is chosen from dideoxyadenosine triphosphate, dideoxyguanosine triphosphate, dideoxythymidine triphosphate, dideoxyuridine triphosphate, dideoxycytidine triphosphate, and any combination thereof.

In some embodiments, of a nucleotide tagging reaction as described herein, the concentration of oligonucleotide-tethered nucleotide in the method ranges from 1 fmol to 10 µmol.

In some embodiments of a nucleotide tagging reaction as described herein, the molar ratio of oligonucleotide-tethered nucleotide to a corresponding native nucleotide (i.e., at least one nucleotide not tethered to an oligonucleotide or a nucleotide lacking a tethered oligonucleotide, but including both naturally occurring and other modified nucleotides that do not have a tethered oligo) ranges from 1:1 to 1:1000.

In some embodiments of a nucleotide tagging reaction as described herein, the method further comprises performing at least one clean up step.

In some embodiments, a method for tagging a nucleic acid with an oligonucleotide is provided, the method comprising providing the nucleic acid to be tagged, contacting the nucleic acid with a first terminal deoxynucleotidyl transferase and at least one oligonucleotide-tethered nucleotide, thereby producing a first tagged nucleic acid strand. In some embodiments, the method further comprises annealing a primer which is at least partially complementary to the tethered oligonucleotide after producing a first tagged nucleic acid strand, contacting the first tagged nucleic acid strand and annealed primer with a nucleic acid polymerase and at least one nucleotide not tethered to an oligonucleotide; and allowing a polymerase to extend from a 3' hydroxyl on the primer annealed to the tethered oligonucleotide to form a second nucleic acid strand. In some embodiments, the method optionally further comprises contacting the tagged nucleic acid strands with an exonuclease after forming the second nucleic acid strand, wherein the first nucleic acid strand is degraded by the exonuclease. In some examples, when the first nucleic acid strand has a 5'-phosphate, Lambda exonuclease may be used for degrading the first nucleic acid strand.

In some embodiments, a first method for generating a library of nucleic acids from a sample comprising one or more nucleic acids is provided, the method comprising:
  a. annealing a first primer which is at least partially complementary to the one or more nucleic acids;
  b. contacting the one or more nucleic acids with a nucleic acid polymerase, at least one nucleotide not tethered to an oligonucleotide, and at least one oligonucleotide-tethered dideoxynucleotide to form one or more first nucleic acid strands comprising a first oligonucleotide-tethered dideoxynucleotide at their 3'end;
  c. annealing a second primer that is at least partially complementary to the tethered oligonucleotide; and
  d. allowing the polymerase to extend from a 3' hydroxyl of the send primer annealed to the tethered oligonucleotide, thereby producing a library of nucleic acids.

In some embodiments, a second method for generating a library of nucleic acids from a sample comprising one or more nucleic acids, optionally wherein the sample comprises a plurality of cells or nuclei is provided, the method comprising:
  a. annealing a first primer which is at least partially complementary to the one or more nucleic acids;
  b. contacting the one or more nucleic acids with a first nucleic acid polymerase, at least one nucleotide not tethered to an oligonucleotide, and at least one oligonucleotide-tethered dideoxynucleotide to a plurality of first extension products comprising the oligonucleotide-tethered dideoxynucleotide at their 3' ends;
  c. annealing a splint oligonucleotide that is at least partially complementary to the tethered oligonucleotide of the first extension products; and
  d. contacting the first extension products with a second nucleic acid polymerase and allowing the polymerase to extend across the annealed splint oligonucleotide from the 3' hydroxyl of the tethered oligonucleotide, thereby producing a library of nucleic acids to produce second extension products, thereby producing the library of nucleic acids.

In some aspects of the first or second methods for generating a library of nucleic acids, the one or more polynucleotides comprise a plurality of polynucleotide fragments generated before annealing of the first primer.

In some aspects of the first method for generating a library of nucleic acids, the contacting the second annealed primer with the nucleic acid polymerase is done in the presence of at least one nucleotide not tethered to an oligonucleotide and a second oligonucleotide-tethered dideoxynucleotide, and the second nucleic acid strand comprises the oligonucleotide-tethered dideoxynucleotide at its 3' end. In some embodiments of a method for generating a library of nucleic acids, the tethered oligonucleotide in the first oligonucleotide-tethered dideoxynucleotide and the tethered oligonucleotide in the second oligonucleotide-tethered dideoxynucleotide are different.

In some aspects of the second method for generating a library of nucleic acids, the one or more nucleic acids in the sample is an oligonucleotide of an oligonucleotide-tethered binding agent (OTBA). In some embodiments, the oligonucleotide of the OTBA comprises a cell marker binding agent index, wherein the binding agent of the OTBA comprises and aptamer or an antibody or functional fragment thereof. In some embodiments, an antibody is a functional antibody fragment. For example, an antibody fragment can be a portion of an antibody such as F(ab')2, Fab', Fab, Fv, sFv and the like. An antibody fragment can bind with the same antigen that is recognized by the full-length antibody. An antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for cancer cells, antibodies for viruses, antibodies that bind to cell surface receptors (for example, CD8, CD34, and CD45), and therapeutic antibodies. As used herein, the an "index" or "cell marker binding agent index" refers to an oligonucleotide sequence that identifies and is specific for the cell marker binding agent (i.e., is a universal sequence that is unique for each cell marker binding agent).

In some aspects of the second method for generating a library of nucleic acids, the sample comprising one or more nucleic acids comprises more than one cell or nuclei, and wherein the cells or cell nuclei (or subpopulations thereof) can comprise one or more cell markers. In some aspects, the cell marker is expressed by a portion of the cells in the sample. In some aspects, the cell marker is a cell surface marker.

In some aspects of the second method for generating a library of nucleic acids, the sample is split into two or more first portions that each comprise a subpopulation of the cells or cell nuclei of the original sample before the first primer that is at least partially complementary to the one or more nucleic acids of the sample is annealed. The first primer can include a first universal handle and a first barcode, and the tethered oligonucleotide can include a second universal handle. The first barcode sequence is common among the first primers in each portion, but is different from the first barcode sequences of other first primers in other first portions, wherein said first portions are contacted under conditions that enable extension of the annealed first primers to form first nucleic acid extension products. The method can include the further step of combining the first portions after formation of the first nucleic extension products, and splitting the combined first portions into two or more second portions. Each second portion can be contacted with a splint oligonucleotide, a polymerase, and one or more nucleotides (e.g., dNTPs). The splint oligonucleotides can include (i) an oligonucleotide sequence that anneals to the second universal handle of the tethered oligonucleotide, (ii) a template sequence for a second barcode, wherein the second barcodes of the splint oligonucleotides in each second portion are common, but are different from the second barcodes of splint oligonucleotides of other second portions, and (iii) a template sequence for a third universal handle. The polymerase extends the 3' OH of the tethered oligonucleotide across the splint oligonucleotides, thereby generating second nucleic acid extension products that comprise 5' to 3': a first universal handle, a first barcode, a copy of the sample nucleic acid sequence, a second universal handle, a second barcode, and a third universal handle. The method can further include the step of combining the second portions, and splitting the combined second portions into two or more third portions.

The third portions can be contacted with amplification primers that hybridize to the first and third universal sequences of the 5' and 3' end of the second extension products, a polymerase and nucleotides (e.g., dNTPs), in order to generate a library of nucleic acids comprising the amplification products. The amplification primers can include, e.g., sequencing adapters, or any other desired sequence. The combination of the first, second, and third barcode sequences (or complements thereof) of the amplification products are unique to the amplification products originating from sample nucleic acids of a single cell.

In some aspects of the first and second methods of generating a library of nucleic acids as described herein, the oligonucleotide-tethered nucleotide is an oligonucleotide tethered nucleotide having any one of formulas (A), (I), (II) or (III).

In some aspects of the first and second method of generating a library of nucleic acids as described herein, the primers, the tethered oligonucleotides, or both comprises a random sequence, a target-specific sequence or both.

In some aspects of the first and second methods of generating a library of nucleic acids as described herein, the primers, the tethered oligonucleotide, or the splint oligonucleotide comprises a universal handle, a universal sequence, a unique molecular identifier, an adapter sequence, a promoter sequence, a barcode sequence, an index sequence, or any combination thereof.

In some aspects of the first and second method of generating a library of nucleic acids as described herein, the oligonucleotide-tethered nucleotide or the splint oligonucleotide or both further comprise an affinity tag.

In some aspects of the first and second methods of generating a library of nucleic acids as described herein, the polymerase is a Type-A DNA polymerase, Type B DNA polymerase, Type X DNA polymerase, or a reverse transcriptase. Examples of Type B polymerases include those of the *Pyrococcus* and *Thermococcus* genera, such as the Deep Vent polymerase and Family B polymerases of *P. furiosus, P. calidifontis, P. aerophilum, T. kodakarensis, T. gorgonarius*, and *Thermococcus* sp. 9°N-7.

In some embodiments of the method of generating a library of nucleic acids as described herein, the polymerase is chosen from Taq DNA polymerase, Vent® DNA polymerase, Deep Vent™ DNA polymerase, Pfx DNA polymerase, Pwo polymerase, SuperScript™ IV, SuperScript™ II, SuperScript™ III, Maxima™, RevertAid™ reverse transcriptases, Thermo Sequenase™, Sequenase™ V2.0, Cycle-Seg™, Phusion exo-, Terminal deoxynucleotidyl Transferase (TdT), Maxima H, Therminator™ polymerase, Q5 DNA polymerase, AccuTaq DNA polymerase, T7 DNA polymerase, T3 DNA polymerase, T4 DNA polymerase, T7 RNA polymerase, T3 RNA polymerase, SP6 RNA polymerase, DNA polymerase 1, Klenow fragment, Tth DNA polymerase, Phusion® DNA polymerase, SuperFi DNA polymerase, Platinum Taq DNA polymerase, Herculase II Fusion DNA polymerase, PfuUltra Fusion II HS DNA polymerase, Bst DNA polymerase large fragment, Stoeffel fragment, 9° N™ DNA polymerase, Pfu DNA polymerase, Tfl DNA polymerase, Phi29 polymerase, Tli DNA polymerase, eukaryotic DNA polymerase beta, telomerase, KOD HiFi DNA polymerase, KOD DNA polymerase, Q-beta replicase, AMV reverse transcriptase, M-MLV reverse transcriptase, Phi6 reverse transcriptase, HIV-1 reverse transcriptase, polyA polymerase (PAP), polyU polymerase (PUP), and variants and derivatives thereof.

In some aspects of the first and second methods of generating a library of nucleic acids as described herein, the nucleotide is chosen from deoxyadenosine triphosphate, dideoxyadenosine triphosphate, deoxyguanosine triphosphate, dideoxyguanosine triphosphate, deoxythymidine triphosphate, dideoxythymidine triphosphate, deoxycytidine triphosphate, dideoxycytidine triphosphate, and any combination thereof.

In some aspects of the first and second methods of generating a library of nucleic acids as described herein, the method further comprises amplifying the library.

In some aspects of the first and second methods of generating a library of nucleic acids as described herein, and in some embodiments of the methods of tagging nucleic acids as described herein, the concentration of oligonucleotide-tethered nucleotide in step (a) ranges from 1 fmol to 10 μmol.

In some embodiments of the method of generating a library of nucleic acids as described herein, the molar ratio of oligonucleotide-tethered nucleotide to a corresponding native nucleotide ranges from 1:1 to 1:1000.

In some embodiments of the method of generating a library of nucleic acids as described herein, the method further comprises performing at least one clean up step.

In some embodiments of the method of generating a library of nucleic acids as described herein, the nucleic acid is DNA, e.g., genomic DNA or the like.

In some embodiments of the method of generating a library of nucleic acids as described herein, the nucleic acid is RNA. In some embodiments, the method further comprises reverse transcribing the RNA to produce a corresponding cDNA.

In some embodiments of the method of generating a library of nucleic acids as described herein, the method further comprises fixing and permeabilizing the cells prior to annealing a first primer and/or splitting the sample.

In some embodiments of the method of generating a library of nucleic acids as described herein, the method further comprises lysing the cells after generating one or more extension products.

In some embodiments of the method of generating a library of nucleic acids as described herein, after generating first nucleic acid extension products, the first portions or combined first portions are contacted with a blocking oligonucleotide, wherein the blocking oligonucleotide prevents hybridisation of first extension primers to cellular nucleic acids.

In some embodiments of the method of generating a library of nucleic acids as described herein, the method further comprises the step of removing the splint oligonucleotides after generating the second nucleic acid extension products and prior to contacting the third portion with a second extension primer.

In some embodiments of the method of generating a library of nucleic acids as described herein, the splint oligonucleotides comprise a binding moiety, the method comprising the step of contacting the second portions or combined second portions with a compound comprising a capture moiety that facilitates binding and removal of splint oligonucleotides comprising cognate binding moieties.

In some embodiments of the method of generating a library of nucleic acids as described herein, the binding moiety and the cognate capture moiety are a binding pair chosen from the binding pairs of streptavidin and biotin, maltose and maltose binding protein, glutathione and glutathione S-transferase, chitin and chitin binding ding protein, or an aptamer and its antigen.

In some embodiments of the method of generating a library of nucleic acids as described herein, the capture moiety is immobilized on a solid support. In some embodiments of the method of generating a library of nucleic acids as described herein, the solid support comprises a bead. In some embodiments of the method of generating a library of nucleic acids as described herein, the bead is a magnetic or paramagnetic bead. In some embodiments of the method of generating a library of nucleic acids as described herein, the first extension primer comprises a sequence capable of hybridizing to an mRNA of interest under the extension conditions. In some embodiments of the method of generating a library of nucleic acids as described herein, the first extension primer comprises a poly(T) at the 3' end. In some embodiments of the method of generating a library of nucleic acids as described herein, the first extension primer comprises a random hexamer sequence at the 3' end. In some embodiments of the method of generating a library of nucleic acids as described herein, the first portion is contacted with a mixture of extension primers, wherein at least one first extension primer comprises a poly(T) sequence at the 3' end and at least one first extension primer comprises a random hexamer sequence. In some embodiments of the method of generating a library of nucleic acids as described herein, the optional first and second adapters comprise adapters for sequencing on various NGS platforms, such as the Illumina platforms, ION Torrent Platforms, and the like.

In some embodiments, a method for preparing an oligonucleotide-tethered nucleotide of formulas (A), (I), (II), or (III) is provided, the method comprising:
a. providing a nucleotide covalently bound to a first functional group capable of undergoing a click reaction with a second functional group;
providing an oligonucleotide covalently bound to the second functional group capable of undergoing a click reaction to form the triazole ring;
contacting the nucleotide with the oligonucleotide to form the click reaction product,
wherein, the first and second functional groups are, respectively, chosen from:
  i) alkynyl and azido;
  ii) azido and alkynyl,
  iii) thiol and alkynyl;
  iv) alkynyl and thiol;
  v) thiol and alkenyl;
  vi) alkenyl and thiol;
  vii) azido and cyclooctanyl;
  viii) cyclooctanyl and azido;
  xi) nitrone and cyclooctanyl; and
  xii) cyclooctanyl and nitrone;

In some embodiments, the first and second functional groups are, respectively, chosen from i) alkynyl and azido; and ii) azido and alkynyl. In some embodiments, the nucleotide is a deoxynucleotide or dideoxynucleotide.

In some embodiments, step (c) comprises contacting the nucleotide with the oligonucleotide in the presence of a copper catalyst and copper (I) ligand to form a 1,2,3-triazole. In some embodiments, the copper catalyst comprises copper (I), or copper (II), wherein when the catalyst is copper (II), a reducing agent is present. In some embodiments, the copper catalyst is $Cu(NO_3)_2 Cu(OAc)$, $CuSO_4$ or any combination thereof.

In some embodiments, the reducing agent comprises ascorbate, Tris(2-Carboxyethyl) Phosphine (TCEP), 2.4.6-trichlorophenol (TCP), NADH, NADPH, thiosulfate, metallic copper, quinone, hydroquinone, Vitamin K, glutathione, cysteine, 2-mercaptoethanol, dithiothreitol, Fe(II), Co(II), an applied electric potential, Al, Be, Co, Cr, Fe, Mg, Mn, Ni, Zn, Au, Ag, Hg, Cd, Zr, Ru, Fe, Co, Pt, Pd, Ni, Rh, W, or any combination thereof. In some embodiments, the reducing agent comprises sodium ascorbate. In some embodiments, the ligand comprises tris(benzyltriazolylmethyl)amine or tris(3-hydroxypropyltriazolylmethyl)amine.

In some embodiments, a kit for producing a sequencing library is provided, the kit comprising
a. an oligonucleotide-tethered nucleotide, and
at least one of
  (i) A, C, G, U and/or T nucleotides or combinations thereof,
  (ii) a polymerase,
  (iii) a primer and/or an adapter sequence,
  (iv) a buffer, or
  (v) a salt.

In some embodiments, the kit comprises the A, C, G, U, and/or T nucleotides.

In some embodiments, the kit can include a polymerase. In some embodiments, the polymerase is a wild type polymerase, a modified polymerase, mutant polymerase, an engineered polymerase, or a combination thereof.

In some embodiments, the polymerase is Taq DNA polymerase, Vent® DNA polymerase, Deep Vent™ DNA polymerase, Pfx DNA polymerase, Pwo polymerase, SuperScript™ IV, SuperScript™ II, SuperScript™ III, Maxima™, RevertAid™ reverse transcriptases, Thermo Sequenase™, Sequenase™ V2.0, CycleSeq™, Phusion exo-, Terminal deoxynucleotidyl Transferase (TdT), Maxima H, Therminator™ polymerase, Q5 DNA polymerase, AccuTaq DNA polymerase, T7 DNA polymerase, T3 DNA polymerase, T4 DNA polymerase, T7 RNA polymerase, T3 RNA polymerase, SP6 RNA polymerase, DNA polymerase 1, Klenow fragment, Tth DNA polymerase, Phusion® DNA polymerase, SuperFi DNA polymerase, Platinum Taq DNA polymerase, Herculase II Fusion DNA polymerase, PfuUltra Fusion II HS DNA polymerase, Bst DNA polymerase large fragment, Stoeffel fragment, 9° N™ DNA polymerase, Pfu DNA polymerase, Tfl DNA polymerase, Phi29 polymerase, Tli DNA polymerase, eukaryotic DNA polymerase beta, telomerase, KOD HiFi DNA polymerase, KOD DNA polymerase, Q-beta replicase, AMV reverse transcriptase, M-MLV reverse transcriptase, Phi6 reverse transcriptase, and HIV-1 reverse transcriptase, polyA polymerase (PAP), polyU polymerase (PUP), and variants and derivatives thereof.

In some embodiments, the kit comprises one or more primer, adapter, barcode, or unique molecular identifier sequences.

In some embodiments, the kit comprises at least one buffer.

In some embodiments, the kit comprises at least one salt.

Some embodiments provided herein include a kit for combinatorial barcoding. The kit can include:
a. an oligonucleotide-tethered nucleotide, and
at least one of
(i) A, C, G, U and/or T nucleotides or combinations thereof,
(ii) a polymerase,
(iii) a primer and/or an adapter sequence,
(iv) a buffer, or
(v) a salt In some embodiments, the combinatorial barcoding kit is provided with one or more of the following polymerases: Taq DNA polymerase, Vent® DNA polymerase, Deep Vent™ DNA polymerase, Pfx DNA polymerase, Pwo polymerase, SuperScript™ IV, SuperScript™ II, SuperScript™ III, Maxima™, RevertAid™ reverse transcriptases, Thermo Sequenase™, Sequenase™ V2.0, CycleSeq™, Phusion exo-, Terminal deoxynucleotidyl Transferase (TdT), Maxima H, Therminator™ polymerase, Q5 DNA polymerase, AccuTaq DNA polymerase, T7 DNA polymerase, T3 DNA polymerase, T4 DNA polymerase, T7 RNA polymerase, T3 RNA polymerase, SP6 RNA polymerase, DNA polymerase 1, Klenow fragment, Tth DNA polymerase, Phusion® DNA polymerase, SuperFi DNA polymerase, Platinum Taq DNA polymerase, Herculase II Fusion DNA polymerase, PfuUltra Fusion II HS DNA polymerase, Bst DNA polymerase large fragment, Stoeffel fragment, 9° N™ DNA polymerase, Pfu DNA polymerase, Tfl DNA polymerase, Phi29 polymerase, Tli DNA polymerase, eukaryotic DNA polymerase beta, telomerase, KOD HiFi DNA polymerase, KOD DNA polymerase, Q-beta replicase, AMV reverse transcriptase, M-MLV reverse transcriptase, Phi6 reverse transcriptase, and HIV-1 reverse transcriptase, polyA polymerase (PAP), polyU polymerase (PUP), and variants and derivatives thereof. For example, in preferred embodiments, the combinatorial barcoding kit can include a reverse. By way of example, the combinatorial barcoding kit can include a SuperScript™ reverse transcriptase and a Pfusion-exo-polymerase.

In some embodiments, the kit further includes a container that provides a plurality of compartments, wherein each compartment includes a primer that includes a compartment-specific barcode. For example, in some embodiments, the Reference will now be made in detail to certain embodiments of the disclosure, examples of which are illustrated m the accompanying drawings. While the present disclosure will be described in conjunction with the illustrated embodiments, it will be understood that they are not intended to limit the disclosure to those embodiments. On the contrary, this disclosure is intended to cover all alternatives, modifications, and equivalents, which may be included within the disclosure as defined by the appended claims.

BRIEF DESCRIPTION OF THE DRAWINGS

FIGS. 12A-12B show results from an oligonucleotide-tethered incorporation experiment. Specifically, FIG. 12A depicts a nucleic acid substrate for multiple oligonucleotide-tethered nucleotide incorporation experiment. Arrows show possible oligonucleotide-tethered dCTP incorporation sites (SEQ ID NO: 30 is 112 nt long and continues over two lines in FIG. 12A). FIG. 12B is an image of a gel demonstrating the incorporation of oligonucleotide-tethered nucleotide on a DNA/RNA substrate. K– lane shows Cy5-labeled strand before the reaction, K+ lane shows reaction product using the 4 native dNTPs, lanes 2 to 5 show polymerization reaction product of incorporation of various amounts of a oligonucleotide-tethered nucleotide (C2-B2 denotes an OTDN resulting from a click reaction between Azido-C2-dCTP and SEQ ID NO: 23) in the absence of native dNTPs. The products in lane 8 indicate the occurrence of multiple oligonucleotide-tethered cytosine incorporation events.

FIG. 17B is an image of a gel demonstrating the results (FIG. 17B). The primer extension product from the scheme in FIG. 12 is used as a starting template (SEQ ID NOS 30 and 31). Full circle denotes Cy5 dye, empty circle denotes Cy3 dye.

FIG. 18A shows the alignment of reads obtained upon sequencing of amplicon library generated by the extension of two M13mp18-specific primers and random termination by the incorporation of oligonucleotide-tethered ddNTPs. The alignment (FIG. 18B) indicates coverage of two M13mp18 genomic loci with 5' ends of both inserts located at fixed positions corresponding to the priming sites, while 3' ends occur at random regions corresponding to the oligonucleotide-tethered ddNTP incorporation sites.

FIG. 20A shows a 16S rRNA gene map and the strategy of semi-targeted fragment library preparation employing oligonucleotide-tethered ddNTP termination, i.e. starting from a single outward-facing primer. FIGS. 20B and 20C are corresponding Agilent 2100 Bioanalyzer electropherograms. V1-V9 denote regions of variable sequence within 16S rRNA gene.

FIG. 22 discloses "TTTTTTTTTTTT" as SEQ ID NO: 41 and "AAAAAAAAAAAA" as SEQ ID NO: 47.

FIG. 24 discloses "TTTTTTTTTTTT" as SEQ ID NO: 41 and "AAAAAAAAAAAA" as SEQ ID NO: 47.

(FIG. 26A) shows Agilent 2100 Bioanalyzer electropherograms of resulting libraries, and (FIG. 26B) shows the base composition of sequencing reads starting from the oligonucleotide-tethered nucleotide incorporation site. The "A" at the first position corresponds to a ddUTP incorporation site.

FIG. 27A shows Agilent 2100 Bioanalyzer electropherogram of the prepared library, FIG. 27B shows the distribution of detected transcript biotypes, FIGS. 27C and 27D show the estimation of the mean gene count and the unique molecular identifier (UMI) count per cell barcode, respectively.

FIG. 28 discloses "TTTTTTTTTTTTT" as SEQ ID NO: 41 and "AAAAAAAAAAAAA" as SEQ ID NO: 47.

FIG. 31 depicts a duplex showing the alignment of SEQ ID NOS: 24 (Cy5 labeled) and 27.

FIG. 32 depicts a duplex showing alignment of SEQ ID NOS: 24 (Cy5 labeled and biotinylated) and 28.

FIG. 33 depicts a duplex showing alignment of SEQ ID NOS: 31 and 32.

FIG. 35A discloses "AAAAAAAAAAAA" as SEQ ID NO: 42 and "TTTTTTTTTTTT" as SEQ ID NO: 48.

FIGS. 36A and 36B show the principle of template-independent DNA end labeling with oligonucleotide-tethered dideoxynucleotides by terminal deoxynucleotidyl transferase (TdT); (A) Labeling scheme and results of labeling without the removal of template DNA oligonucleotide prior to the second labeling step; and (B) labeling scheme and results of labeling upon removal of template strand by exonuclease treatment.

FIG. 40 discloses SEQ ID NOS 43, 44, 43, 44, 43, 44, 44 and 44, respectively, in order of appearance.

FIG. 44 discloses "PolyT30" as SEQ ID NO: 40.

DESCRIPTION OF THE SEQUENCES

Figure 1:
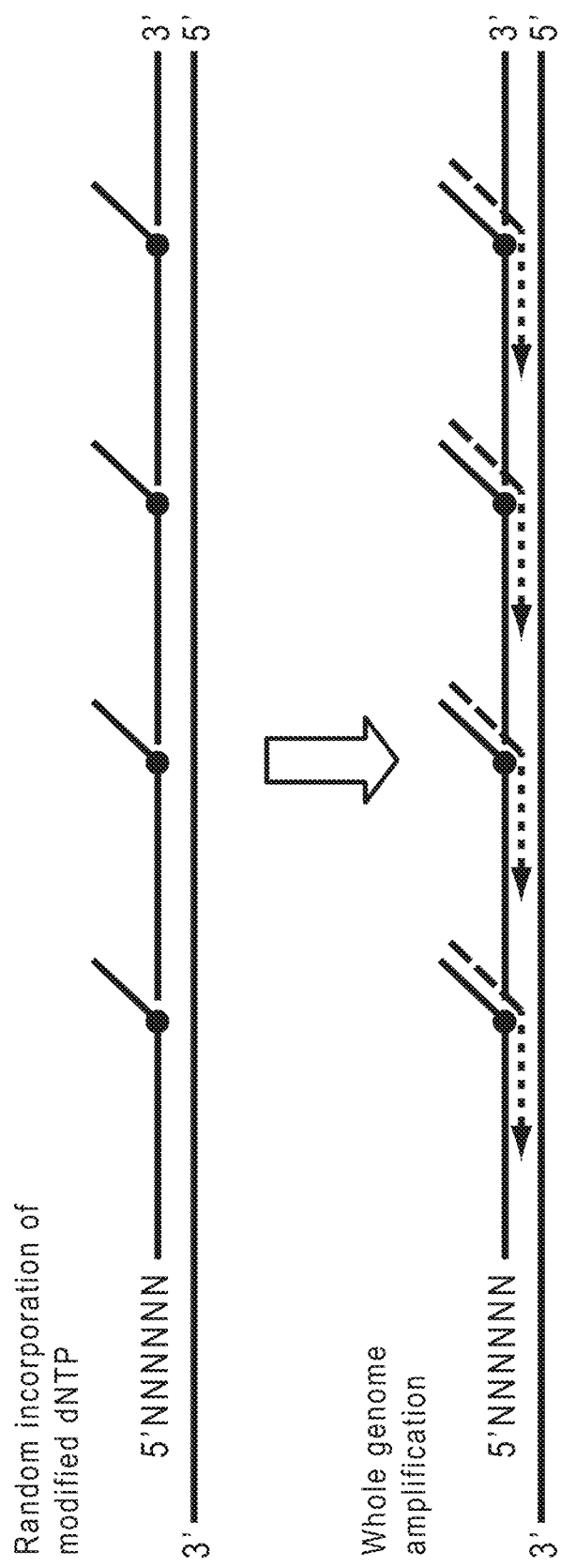
FIG. 1 shows a schematic of an application of an oligonucleotide-tethered deoxynucleotide triphosphate (dNTP) in NGS library preparation. In this embodiment, an oligonucleotide-tethered dNTP is incorporated in multiple locations in a nucleic acid (top panel). The bottom panel shows extension of a primer annealed to the tethered oligonucleotide and subsequent read-through of a polymerase through the unnatural linker.

The following table provides a listing of certain sequences referenced herein.

Description of the Sequences

| Description | Sequences | SEQ ID NO |
|---|---|---|
| Oligonucleotide-tethered ddUTP with 3' terminal biotin | ddUTP-AldU-AGATCGGAAGAGCACACGTCTG-3'-biotin | 1 |
| Oligonucleotide-tethered ddUTP with 3' terminal phosphate | ddUTP-AldU-AGATCGGAAGAGCACACGTCTG-3'-phosphate | 2 |
| Oligonucleotide-tethered ddCTP with 3' terminal biotin | ddCTP-AldU-AGATCGGAAGAGCACACGTCTG-3'-biotin | 3 |
| Oligonucleotide-tethered ddUTP with 3' terminal biotin | ddUTP-hexynyl-AGATCGGAAGAGCACACGTCTG-3'-biotin | 4 |
| T7 promoter sequence | TAATACGACTCACTATAG | 5 |
| Oligonucleotide-tethered ddUTP with random sequence and with 3' terminal biotin | ddUTP-AldU-NNNNNNNNAGATCGGAAGAGCGTCGTGTA-3'-biotin | 6 |
| Oligonucleotide-tethered nucleotide bearing platform-specific adapter sequence | ddUTP-AldU-AGATCGGAAGAGCACACGTCTGAACTCCAGTCACATGCCTAAATCTCGTATGCCGTCTTCTGCTTG-3'-biotin | 7 |
| Primer | TACACGACGCTCTTCCGATCTAACGGTACGCCAGAATCTTG | 8 |
| Primer | TACACGACGCTCTTCCGATCTAGAGCCACCACCGGAAC | 9 |
| Primer | TACACGACGCTCTTCCGATCTNNNNNNNNNN | 10 |
| Primer | CTCTTTCCCTACACGACGCTCTTCCGATCTAAGTCGTAACAAGGTAACCG | 11 |
| Primer | CTCTTTCCCTACACGACGCTCTTCCGATCTCTGAGCCAKRATCAAACTCT, wherein K is G or T, R is A or G. | 12 |
| Primer | CTCTTTCCCTACACGACGCTCTTCCGATCTCTGAACCAAGATCAAATTCT | 13 |
| Primer | CTCTTTCCCTACACGACGCTCTTCCGATCTCTAAGCCAGGATCAAACTCT | 14 |
| Primer | CTCTTTCCCTACACGACGCTCTTCCGATCTCTGAGCCAGAATCGAACCCT | 15 |
| Reverse Transcription Primer | AAGCAGTGGTATCAACGCAGAGTACTTTTTTTTTTTTTTTTTTTTTTTTTTT | 16 |
| Indexing primer | AATGATACGGCGACCACCGAGATCTACACGCCTGTCCGCGGAAGCAGTGGTATCAACGCAGAGTAC | 17 |

-continued

Description of the Sequences

| Description | Sequences | SEQ ID NO |
|---|---|---|
| Indexing primer | CAAGCAGAAGACGGCATACGAGATGTGACT GGAGTTCAGACGTGTGCTCTTCCGATCT | 18 |
| Primer | CAAGCAGAAGACGGCATACGA | 19 |
| Template switch oligonucleotide, wherein r preceding the G indicates a ribonucleotide base | CCAGGACCAGCGATTCNNNNNNNNNrGrGrG | 20 |
| Primer | CAGTGGTATCAACGCAGAGTACCCAGGACCA GCGATTC | 21 |
| Oligonucleotide-tethered dCTP | dCTP-AldU-TTTATATATTTATTGGAGACTGACTACCAGAT GTAACACCTATAGTGAGTCGTATTAG | 22 |
| Oligonucleotide | T(AldU)ATATATTTATTGGAGACTGACTACCA GATGTAACA | 23 |
| Primer | TGCAGACATGGGTAGGCATCCTTGGCGTA | 24 |
| Oligonucleotide | GTACGCCAAGGATGCCTACCCATGTCTGCA | 25 |
| Complementary strand | CTAATACGACTCACTATAGGTGTTACATCTG GTAGTCAGTCTCCAATAAATATATAAA | 26 |
| Oligonucleotide | GTCGCTCAAC TCAGCTACAG TACGCCAAGG ATGCCTACCC ATGTCTGCA | 27 |
| Oligonucleotide | GTACGCCAAG GATGCCTACC CATGTCTGCA | 28 |
| Primer | Cy5-CCGGGGATCCCATGTG | 29 |
| Oligonucleotide | GGGAAAGCUU UUACAUUUUC GCGAUACCGU CCAGCGACAU UCUUCCUCGG UACAUAAUCU CCUUUGGCGU UUCCCGAUGU CCGUCACGCA CAUGGGAUCC CCGGGUACCG AG | 30 |
| Primer | AAAAAAAAAATACGCCAAGGATGCCTACC CATGTCTGCA | 31 |
| Oligonucleotide | TGCAGACATG GGTAGGCATC CTTGGCGTA | 32 |
| Oligonucleotide | (AldU)TTATATATTTATTGGAGACTGACTACCA GATGTAACA | 33 |
| Reverse transcription primer | AATGATACGGCGACCACCGAGATCTACACTC TTTCCCTACACGACGCTCTTCCGATCTTTTTT TTTTTTTTTTTTTTTTTTTTTTT | 34 |
| Oligonucleotide-tethered ddCTP | ddCTP-AldU-AGATCGGAAGAGCACACGTCTGAACTCC AGTCACATGCCTAAATCTCGTATGCCGTC TTCTGCTTG-3'-BIOTIN | 35 |
| Template oligonucleotide | Phosphate-5'-GCGGCGACCAAATCGTTGTAAAGATCGGAA GAGCGTCGTGTA | 36 |
| Labeled primer | Cy5-5'-CAGACGTGTGCTCTTCCGATCT | 37 |
| Unlabeled primer | CAGACGTGTGCTCTTCCGATCT | 38 |
| Primer | AAGTCGTAACAAGGTAACCG | 39 |

DETAILED DESCRIPTION

The present disclosure provides oligonucleotide-tethered nucleotides, methods of making them, and methods of using them. The oligonucleotide-tethered nucleotides comprise a nucleotide linked to an oligonucleotide of from about 3 to about 100 nucleotides in length. These oligonucleotide-tethered nucleotides can be used to label or tag a plurality of different types of nucleic acids in a plurality of different applications with a known oligonucleotide, which can carry unique sequences and serve as a barcode (for example, cell or nucleus barcode, compartment barcode, index UMI, or the like), an extension primer, or an annealing site, or sequences coding specific promoters (e.g. a T7 promoter sequence) used m downstream applications.

In one embodiment, a polymerase incorporates the oligonucleotide-tethered nucleotide into a nucleic acid strand to provide a new priming site for nucleic acid synthesis initiation. A primer at least partially complementary to the tethered oligonucleotide is provided and allowed to anneal to the tethered oligonucleotide. The polymerase can extend the annealed primer through an unnatural linker on the oligonucleotide-tethered nucleotide thereby generating a new nucleic acid strand.

In other embodiments, the polymerase incorporates the oligonucleotide-tethered nucleotide into a nucleic acid strand to provide a universal handle sequence for annealing a splint oligonucleotide. The splint oligonucleotide includes a (i) sequence capable of annealing to the universal handle sequence of the tethered nucleotide and a (ii) template for a desired sequence. The polymerase can extend the 3' OH of tethered oligonucleotide across the annealed splint oligonucleotide via template-directed polymerization, thereby incorporating any desired sequence (barcodes, unique molecular identifiers, universal sequences, random sequences, unique molecular identifiers, promoters, and the like) and generating a new nucleic acid strand.

The resulting new nucleic acid strand may be further manipulated (e.g., using subsequent amplification, extension, ligation, or other treatments). By way of example, the resulting new nucleic acid strand can be amplified and/or subjected to an adapter addition reaction to provide a next generation sequencing library. The sequencing library is useful in numerous sequencing methods, and across a variety of platforms.

In some embodiments, the oligonucleotide may be tethered to dNTP via the dNTP nucleobase. When an oligonucleotide is tethered to a dNTP, multiple incorporations of the nucleotide into a nucleic acid are possible (see, e.g., FIGS. 1 and 12). Alternatively, the oligonucleotide is tethered to ddNTP (OTDDN) via the ddNTP nucleobase. In embodiments wherein the oligonucleotide is tethered to a ddNTP, incorporation of the oligonucleotide-tethered nucleotide terminates the nucleic acid synthesis (see FIG. 3).

In some embodiments, the oligonucleotide-tethered nucleotides can be prepared using "Click" chemistry. For example, the oligonucleotide is tethered to the nucleobase of a dNTP or ddNTP as a result of a click reaction, such as a (3+2) cycloaddition reaction between azide and alkyne groups, thus forming a 1,2,3-triazole ring that chemically joins the oligonucleotide and the dNTP or ddNTP In some embodiments, the tethered oligonucleotide can be used as a priming site for nucleic acid synthesis by nucleic acid polymerases. A primer complementary to the tethered oligonucleotide may have tailed sequences, which are used for adding adapters and/or barcodes for sequencing (e.g., P5 and P7 sequences used to hybridize to Illumina flow cells).

In the embodiments described herein, the oligonucleotide-tethered nucleotide can be modified with an affinity tag to facilitate target product enrichment.

I. Oligonucleotide-Tethered Nucleotides

Figure 2:
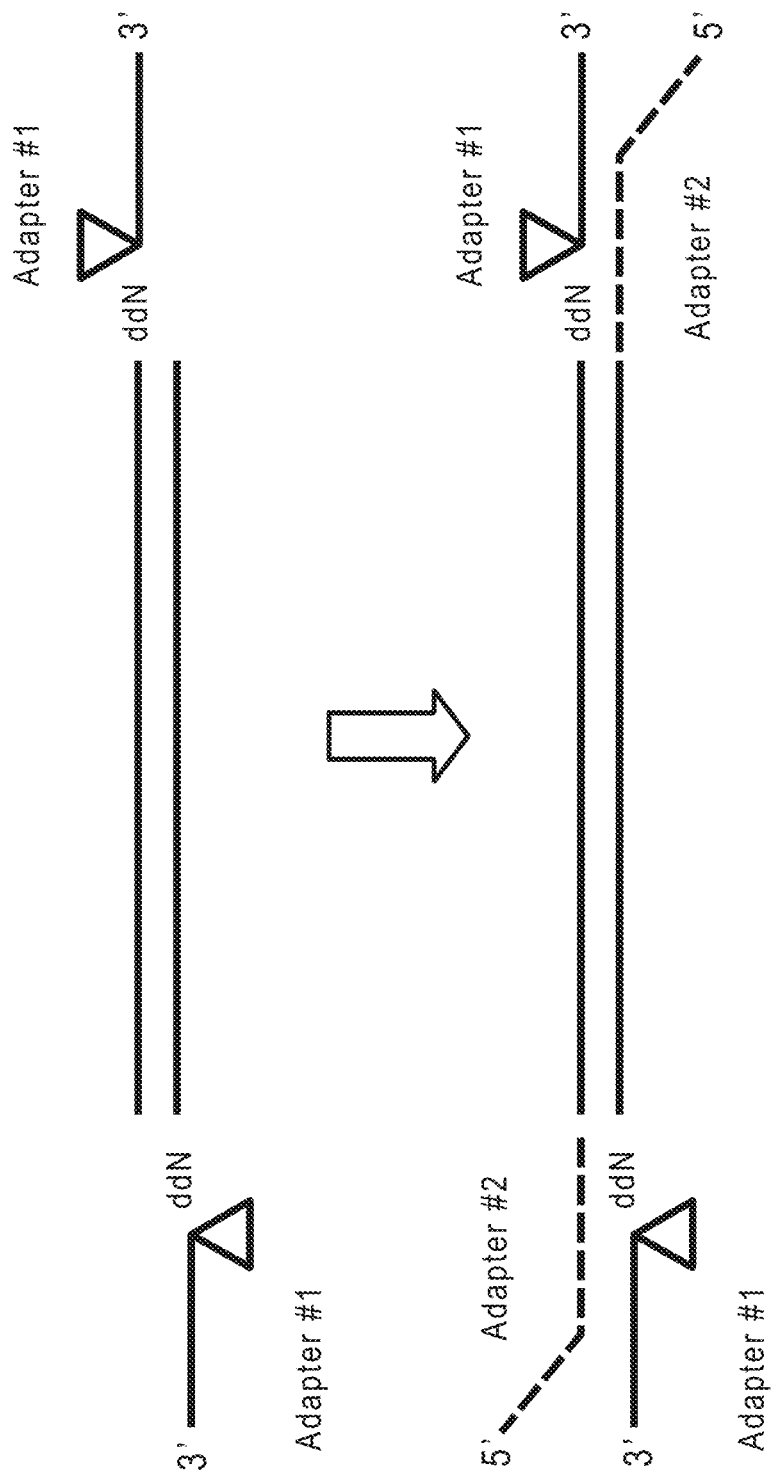
FIG. 2 provides a schematic of an application of an oligonucleotide-tethered dideoxynucleotide triphosphate (ddNTP) in NGS library preparation. In this embodiment, terminal deoxynucleotidyl transferase (TdT) adds a single oligonucleotide-tethered ddNTP comprising a first adapter sequence to the 3' terminus of a nucleic acid in a template-independent manner (top panel). Further, a second adapter is annealed and ligated to provide a library of polynucleotides having adapters with complementary and mismatched regions at both ends (bottom panel).

The present approach is based on incorporation of oligonucleotide-modified nucleotides into a nucleic acid. Various nucleic acid polymerases have the ability to incorporate modified nucleotides bearing bulky groups attached to their nucleobases and it was expected that such modified nucleotides might be incorporated into the growing nucleic acid strand by nucleic acid polymerases during the nucleic acid copying process, initiated for instance from randomized hexamers, or will be added to the very 3' end of single- or double-stranded nucleic acid by template-independent polymerases, such as terminal transferases (for example, see FIGS. 1 and 2). When modified nucleotides have a 3'-hydroxyl group on their sugar moiety, at least one and optionally multiple incorporations of the oligonucleotide-bearing nucleotide into the copied nucleic acid are expected. Having multiple priming sites on such newly synthesized nucleic acid would, for example, facilitate unbiased isothermal amplification using both random hexamers and oligonucleotides which are complementary to the tethered oligonucleotides attached to incorporated nucleotides (FIG. 1) as extension primers Oligonucleotide-bearing nucleotides incorporated at 3' termini into the structure of double-stranded DNA with terminal transferase (TdT) may be used to add the fully or partially complementary oligonucleotide to the opposite DNA strand (complementary and mismatched adapter regions, see FIG. 2). By using appropriately designed oligonucleotides it is possible to generate DNA ends which are compatible with sequencing on various platforms, including but not limited to the Illumina platform.

While not being bound by theory, it is believed that efficient incorporation of modified nucleotides, during nucleic acid synthesis is highly dependent on the size of attached label. For example, the length of the linking group (or groups) (i.e. the —Y—CXN—Z— group of Formula (A)), between nucleotide heterocyclic base and label, may have significant impact on incorporation. The linker should be long enough to reduce label steric hindrance and changes of nucleotide steric stricture. At the same time, it should be short enough to avoid back-folding onto the nucleic acid strand. Moreover, the terminal functional groups of the linker must be tolerated by nucleic acid polymerase enzymes. A properly designed linker will allow incorporation of nucleotides bearing large labels.

Figure 3:
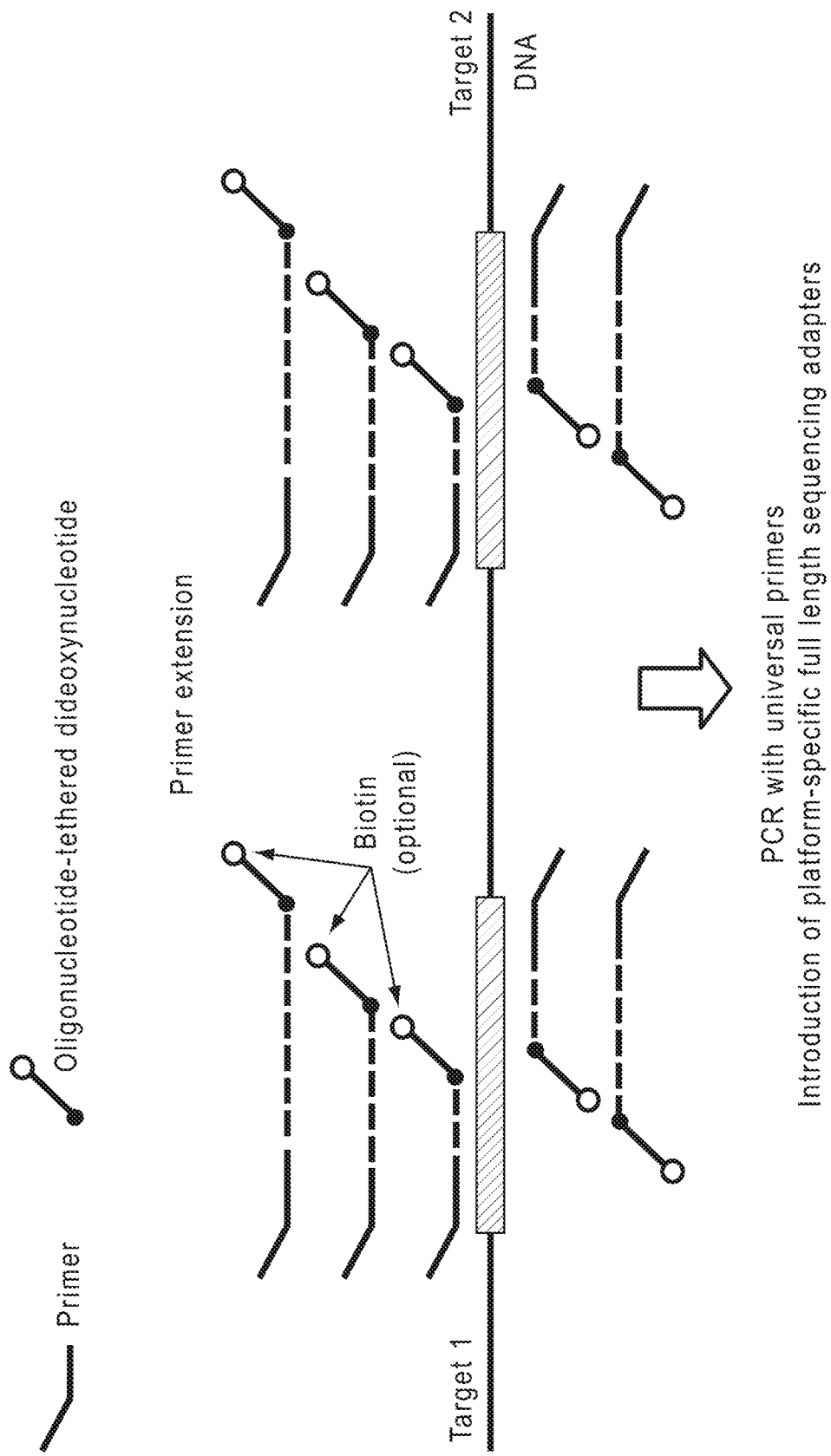
FIG. 3 depicts the basic principle of primer extension and random DNA synthesis termination by the incorporation of oligonucleotide-tethered dideoxynucleotides, which introduce pre-designed sequence tags on both ends of the resulting DNA fragments. The library of tagged DNA fragments may then be amplified using PCR primers, which in turn introduce platform-specific adapter sequences. Optionally, the tethered oligonucleotide may comprise an affinity tag (e.g. biotin, scheme on the left), which may be used for nucleic acid target enrichment. The length of tagged DNA fragments may be controlled through the adjustment of the oligonucleotide-tethered ddNTP concentration and/or ratio relative to the corresponding native deoxynucleotide.

When the oligonucleotide-tethered nucleotide has 3'-H instead of the 3'-hydroxyl group (for example, a dideoxy-modified nucleotide), incorporation of such a oligonucleotide-tethered nucleotide would terminate the nucleic acid synthesis (FIG. 3). When an oligonucleotide-tethered dideoxynucleotide (OTDDN) is used in synthesis reactions, a set of randomly terminated fragments is generated.

By adjusting the concentration of the OTDDN in the synthesis reaction, e.g., relative to the corresponding native nucleotides, the synthesis (and length of the synthesized strand) can be manipulated. In some embodiments, the synthesis reaction includes, e.g., a single type of OTDDN (e.g., an OTddATP, OTddTTP, OTddCTP, OTddCTP, OTddUTP). In some examples, the synthesis reaction includes, e.g., a combination of two or more OTDDNs (e.g., OTddTTP and OTddCTP; or other combinations). In some embodiments, wherein there is a single type of OTDDN present in the reaction (accompanied by other, native nucleotides), the reaction does not contain e.g., the corresponding native nucleotide. In some embodiments, wherein there is a single type of OTDDN present in the reaction, the reaction contains relatively more OTDDN present, compared to the corresponding native nucleotide, about equal amounts of the OTDDN and corresponding native nucleotide, or relatively less OTDDN present, compared to the corresponding native nucleotide.

The resulting nucleic acids from an extension reaction (e.g., from an extension primer hybridized to the tethered oligonucleotide, or from extension of the tethered oligonucleotide across a splint oligonucleotide) or from an amplification reaction utilizing an OTDDN can be further manipulated (e.g., using subsequent amplification, extension, ligation, or other treatments). By way of example, the extension products that incorporate an OTDDN can then be subjected to downstream manipulations as described above (e.g., further extension reactions, amplification reactions, and the like). In some examples, the extension products with incorporated OTDDN can be used in downstream extension or amplification (e.g. PCR) reactions for platform-specific full-length sequencing adaptor introduction. In some embodiments, this method can also be used to overcome the need for nucleic acid fragmentation.

The oligonucleotide-tethered nucleotides described herein may optionally comprise affinity labels (for example, be biotin-modified) to facilitate enrichment. Alternatively, the oligonucleotide-tethered nucleotides may comprise other labels.

The method of the present disclosure advantageously allows tethering of an oligonucleotide to any nucleotide and its later incorporation into a nucleic acid sequence while performing strand synthesis with nucleic acid polymerase. Thus, methods provided herein advantageously allow the attachment of an oligonucleotide to any final (i.e., terminal, such as for example 3' terminal) nucleotide of any nucleic acid sequence composition.

In some embodiments, the oligonucleotide-tethered nucleotides used herein generally have a structure according to formula (A), or a salt thereof:

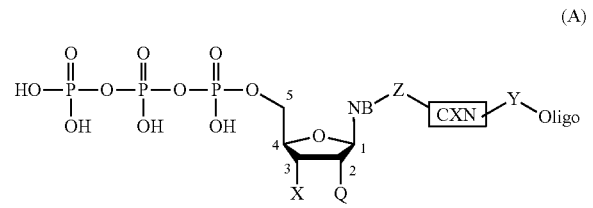

(A)

wherein NB is a nucleobase; Oligo is an oligonucleotide of 3 to 100 nucleotides; each of X and Q are independently chosen from, H, OH, N3, halo, alkyl, alkoxy, alkyl, alkenyl, alkynyl, acyl, cyano, amino, ester, and amido; each of Z and Y are independently chosen from a bond, amino, amido, alkylene, alkenylene, alkynylene, thioether, sulfonyl, sulfonamido, ether, ketone, carbonyl, anhydride, ester, imido, urea, urethane, and combinations thereof; and CXN is chosen from alkylene, alkenylene, alkynylene, ketone, carbonate, ester, ether, anhydride, amido, amino, aminoalkyl, amino, amido, diazo, carbamate ester, phosphodiester, sulfide, disulfide, sulfonyl, sulfonamido, and a heterocyclic group containing from one to four N, O, S atom(s) or a combination thereof where heterocyclic group is optionally substituted at carbon, nitrogen or sulfur atom(s).

In some embodiments, the salt of the compound of Formula (A) is a quaternary ammonium salt.

In some embodiments, X is chosen from H, OH, F, $N_3$, and amino. In other embodiments, X is chosen from H, $N_3$, and OH. In some embodiments, X is OH. In other embodiments, X is H.

In some embodiments, Q is H, OH, F, Cl, Br, I, an $N_3$. In other embodiments, Q is H.

In some embodiments, X and Q are H.

The oligonucleotide, "Oligo", may be tethered to the nucleotide either through a 5'-phosphate to the nucleobase of the dNTP or ddNTP as shown in C1 below, or through a nucleobase (NB2) as shown in C2 below.

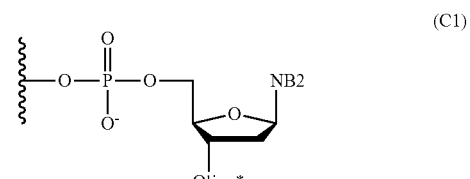

(C1)

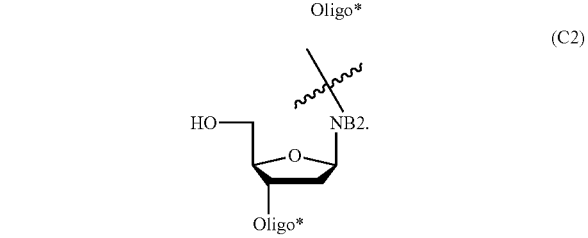

(C2)

Structures C1 and C2 provide a more detailed view of how Oligo of Formula (A) is tethered the dNTP or ddNTP, Oligo* therefore represents all but one unit of the original Oligo sequence present in compounds of Formula (A).

"CXN" is a group formed by a reaction between functional groups on intermediates that results in coupling of the intermediates to form the oligonucleotide-tethered nucleotides disclosed herein.

In other embodiments the reaction can form a heterocyclic group containing from one to four N, O, S atom(s) or a combination thereof where heterocyclic group is optionally substituted at carbon, nitrogen or sulfur atom(s). In some embodiments the reaction can form a heterocyclic group chosen from i) 5-membered heterocycles having one hetero atom (e.g. pyrroles, thiophenes, furans, pyrrolidine, thiolane, tetrahydrofuran); ii) 5-membered heterocycles bearing two heteroatoms at 1,2 or 1,3 positions (e.g. isoxazoles, oxazoles, pyrazoles, imidazoles, isothiazoles, thiazoles); 5-membered heterocycles bearing three heteroatoms (e.g. triazoles, oxadiazoles, thiadiazoles); iv) 6-membered heterocycles bearing one heteroatom (e.g. pyrans, thiopyrans, pyridines, tetrahydropyrans, tetrahydrothiopyrans, piperidines); v) 6-membered heterocycles bearing two heteroatoms (e.g. pyridazines, pyrimidines, pyrazines, hexahydropyridazines, hexahydropyrimiduies, piperazines, dioxanes, morpholines, thiazines, oxazines, dithianes); and vi) 6-membered heterocycles bearing three heteroatoms (e.g. triazines, dithiazines, thiadiazines, triazinanes, oxathiazines).

In some embodiments, CXN is chosen from 5-membered heterocycles and 6-membered heterocycles each having from 1 to 3 heteroatoms. In some embodiments, CXN is chosen from pyrrolo, thiophenyl, furanyl, pyrrolidinyl, thiolanyl, tetrahydrofuranyl, isoxazolyl, oxazolo, pyrazolo, imidazolyl, isothiazolo, thiazolyl, triazolo, oxadiazolo, thiadiazolo, pyranyl, thiopyranyl, pyridinyl, tetrahydropyranyl, tetrahydrothiopyranyl, piperidinyl, pyridazinyl, pyrimidinyl, pyrazinyl, hexahydropyridazinyl, hexahydropyrimidinyl, piperazinyl, dioxanyl, morpholino, thiazinyl, oxazino, dithianyl, triazinyl, dithiazino, thiadiazino, triazinanyl, and oxathiazino.

In some embodiments, CXN is

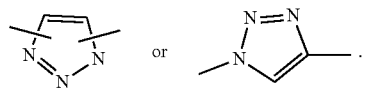

In some embodiments, Z and Y are each linkers, or linking moieties, which refers to certain functional groups that may be varied to provide the overall tether between the ddNTP or dNTP and the oligonucleotide with the desired properties. In some embodiments each of Z and Y are independently chosen from a bond, amino, amido, alkylene, alkenylene, alkynylene, thioether, sulfonyl, sulfonamido, ether, ketone, carbonyl, anhydride, ester, imido, urea, urethane, and combinations thereof. In some embodiments, each Z and Y are independently chosen from amino, amido, alkylene, alkenylene, alkynylene, ether, ketone, carbonyl, anhydride, ester, imide, or any combination thereof. In other embodiments, Y is alkylene or alkynylene. In other embodiments, Z is a combination of one or more of alkynylene, alkylene, ether and amido. In other embodiments, Z is —(CH=CH)C(O)(CH$_2$CH$_2$)NHC(O)(CH$_2$)$_5$— or —HN—. In still other embodiments, the combination of —NB—Z— is

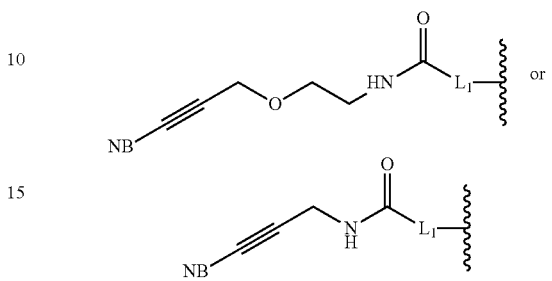

or NB—HN-L$_1$-, —NB—(CH=CH)C(O)(CH$_2$CH$_2$)NHC(O)-L$_1$, where L$_1$ is chosen from alkylene, alkenylene, alkynylene, and polyalkylene glycol.

In some embodiments the compound of Formula (A) is selected from the compounds of Formula (B1)-(B4)

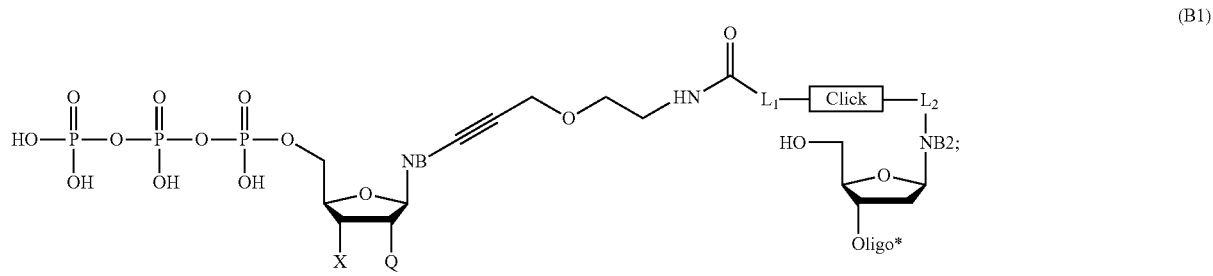

(B1)

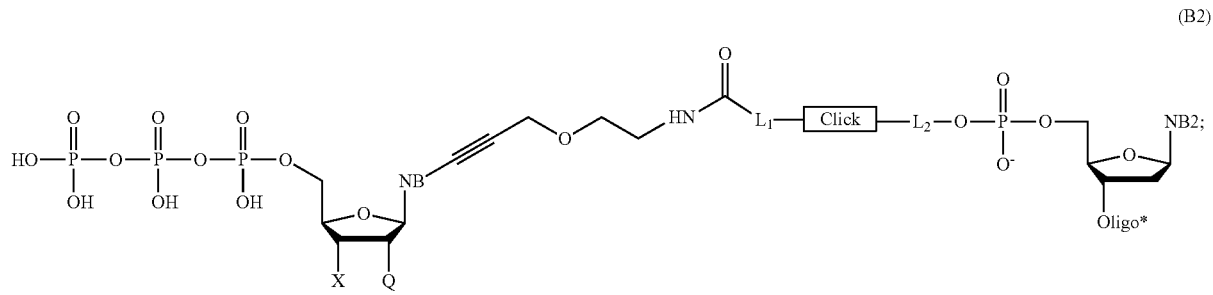

(B2)

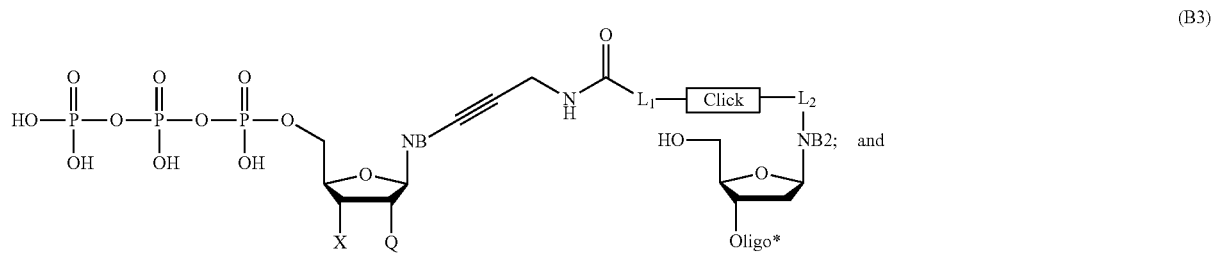

(B3)

(B4)

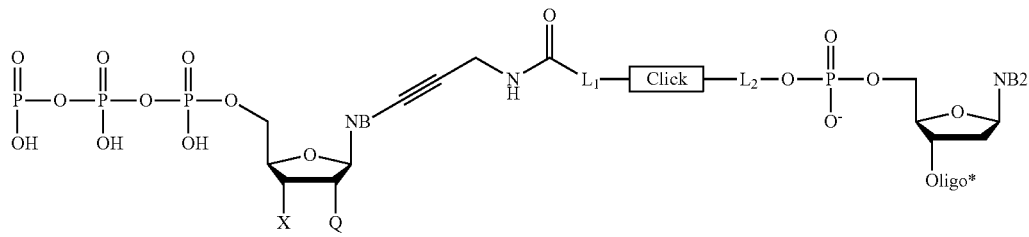

and salts thereof wherein oligo* is the remaining 2 to 99 nucleotides from the Oligo group and NB2 is a nucleobase; L$_1$ is chosen from alkylene, alkenylene, alkynylene, and polyalkylene glycol; L$_2$ is alkylene or alkynylene.

In some embodiments CXN includes one or more of the groups recited herein made using click chemistry.

In some embodiments the linking group Z comprises the subgroup of L$_1$ which is chosen from alkylene, alkenylene, alkynylene, and polyalkylene glycol. In other embodiments, L$_1$ is C1-C12 alkylene, C2-C12 alkenylene, C2-C12 alkynylene, and polyalkylene glycol having from 2 to 8 glycol units. In other embodiments, L$_1$ is chosen from polyethylene glycol with 2 glycol units (PEG2), polyethylene glycol with 4 glycol units (PEG4), or polyethylene glycol with 6 glycol units (PEG6), methylene, ethylene, n-propylene, isopropylene, 1-butylene, cis-2-butylene, trans-2-butylene, isobutylene, 1-pentylene, cis-2-pentylene, trans-2-pentylene, isopentylene, and hexylene. In yet other embodiments, L$_1$ is chosen from —CH$_2$—, —(CH$_2$)$_3$—, —(CH$_2$)$_5$—, PEG2, and PEG4.

In some embodiments the linking group Y comprises the subgroup of L$_2$ which is chosen from alkylene or alkynylene. In other embodiments L$_2$ is C1-C12 alkylene or C1-C12 alkynylene. In other embodiments the combination of L$_2$-Oligo is chosen from —(CH$_2$)$_4$-Oligo or —(CH$_2$)$_4$CC-Oligo. The oligonucleotide, "Oligo", maybe tethered to the nucleotide either through a 5'-phosphate to the nucleobase of the dNTP or ddNTP, or through a nucleobase (NB2).

NB and NB2 are independently a nucleobase. In some embodiments the nucleobase is chosen from adenine, 7-deazaadenine, cytosine, guanine, 7-deazaguanine, thymine, uracil and inosine. NB2 is a single nucleotide of the Oligo group so that the combination of NB-Oligo* is Oligo.

In some embodiments, NB is a pyrimidine and the pyrimidine is tethered to the oligonucleotide at the 5 position of the nucleobase. In other embodiments, NB is a purine, and wherein the purine is tethered to the oligonucleotide at the 7 position of the nucleobase.

The oligonucleotide-tethered nucleotides used herein generally have a structure according to formula (I), or a salt thereof:

(I)

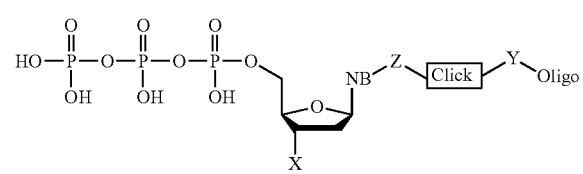

wherein X is H, OH or N$_3$, NB represents a nucleobase, Z and Y are linkers, Oligo represents an oligonucleotide of 3 to 100 nucleotides in length, and Click represents the reaction product of a Click reaction, which covalently binds the Z and Y linkers. In some embodiments, the nucleobase is chosen from adenine, 7-deazaadenine, cytosine, guanine, 7-deazaguanine, thymine, uracil and inosine. In some embodiments, Z and Y each independently comprise at least one linking moiety chosen from bond, amino, amido, alkyl, alkenyl, alkynyl, thioether, sulfonyl, sulfonamido, ether, ketone, carbonyl, anhydride, ester, imide, urea, urethane, or any combination thereof, or any combination thereof.

Alternatively, the oligonucleotide-tethered nucleotide can be acyclic (I').

(I')

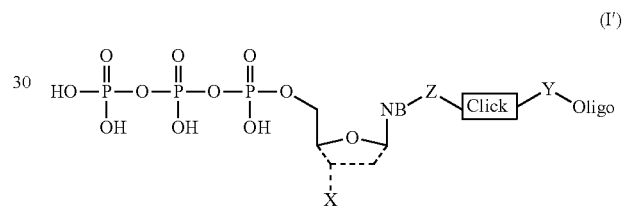

The Click reaction product includes the products of reactions such as, but not limited to, copper catalyzed azide-alkyne cycloaddition (CuAAC); strain-promoted azide-alkyne cycloaddition (SPAAC) also known as copper-free click chemistry; strain-promoted alkyne-nitrone cycloaddition (SPANC); alkyne hydrothiolation; and alkene hydrothiolation.

In some embodiments, the Click reaction is a (3+2) cycloaddition reaction of an azide and an alkyne, resulting an 1,2,3-triazole. The reaction product provides triazole product, thereby providing an oligonucleotide-tethered nucleotide of formula (II), or a salt thereof:

(II)

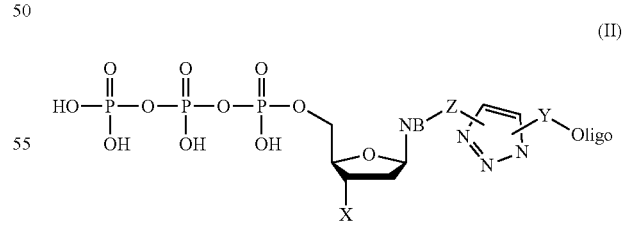

wherein, X, NB, Z, Y and Oligo are as defined above. In formula (II), one of Z and Y is covalently bound to the 1 position of the triazole, while the other of Z and Y is covalently bound to the 4 or 5 position of the triazole. In one embodiment, X is OH, and in another embodiment, X is H, and in yet another embodiment X is N$_3$.

In some embodiments, the linkers Z and/or Y include a carbon-based chain, for example an alkyl chain having 1 to 12 carbon atoms that may be linear or branched. In some embodiments, the alkylene is a straight or branched $C_1$-$C_6$ alkylene. Linkers Z and/or Y may also include a straight or branch alkenylene having 2 to 12 carbons. Alternatively, the alkenylene is a straight or branched $C_2$-$C_6$ alkenylene. In some embodiments, linkers Z and Y include a straight or branched alkynylene chain of 2 to 12 carbons. In some embodiments, the alkynylene is a straight or branched C2 to C6 alkynylene.

In some embodiments, Z and/or Y includes a polyalkylene glycol having from 2 to 20 alkylene glycol units, while in other embodiments, the polyalkylene glycol has 2 to 8 alkylene glycol units. In some embodiments, the polyalkylene glycol has 2, 4, or 6 to 8 glycol units. Suitable alkylene glycol units include ethylene glycol, 1,2-propanediol, 1,2-butylene glycol, and the like.

The oligonucleotide-tethered nucleotide may more particularly have the structure of formula (III), or a salt thereof:

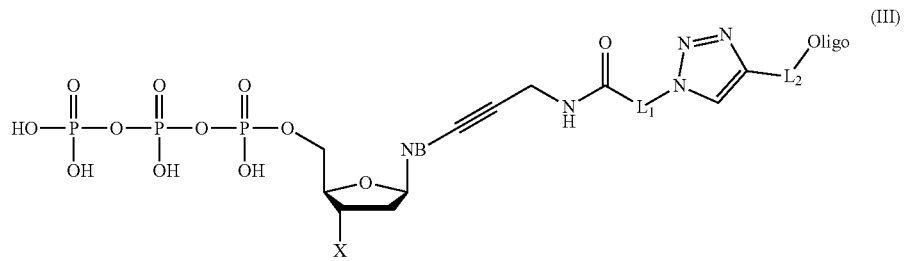

(III)

wherein $L^1$ and $L^2$ are each linkers independently comprising an alkylene, an alkynylene, a polyalkylene glycol, or any combination thereof.

In some embodiments, the oligonucleotide-tethered nucleotide may have the structure of formula (III), or a salt thereof, wherein $L^1$ is a linker comprising an alkylene, a polyalkylene glycol, or a combination thereof, and $L^2$ is a linker comprising an alkynylene having from 2 to 12 carbons. More particularly, $L^2$ is hexynyl. The polyalkylene glycol may be a polyethylene glycol having from 2 to 6 ethylene glycol units. In another embodiment, $L^1$ comprises an alkylene having 1 to 12 carbon atoms. More particularly, the alkylene is methylene, ethylene, n-propylene, isopropylene, 1-butylene, cis-2-butylene, trans-2-butylene, isobutylene, 1-pentylene, cis-2-pentylene, trans-2-pentylene, isopentylene, or hexylene.

Alternatively, when strain-promoted azide-alkyne cycloaddition (SPARC) also known as copper-free click chemistry, is used to generate oligonucleotide-tethered nucleotides, the resulting oligonucleotide-tethered nucleotides described herein generally have a structure according to formula (IV), or a salt thereof:

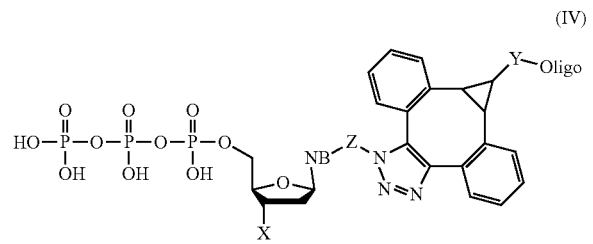

(IV)

wherein X is H or OH or $N_3$, NB represents a nucleobase, Z and Y are linkers, Oligo represents an oligonucleotide of 3 to 100 nucleotides in length. In some embodiments, the nucleobase is chosen from adenine, 7-deazaadenine, cytosine, guanine, 7-deazaguanine, thymine, uracil and inosine. In some embodiments, Z and Y each independently comprise at least one linking moiety chosen from—amino, amido, alkyl, alkenyl, alkynyl, thioether, sulfonyl, sulfonamido, ether, ketone, carbonyl, anhydride, ester, imide, urea, urethane, or any combination thereof, or any combination thereof.

Alternatively, in some embodiments azide modification can be introduced at the 3' position of the nucleotide and therefore oligonucleotide can be covalently tethered to the 3' position of the nucleotide (V and VI).

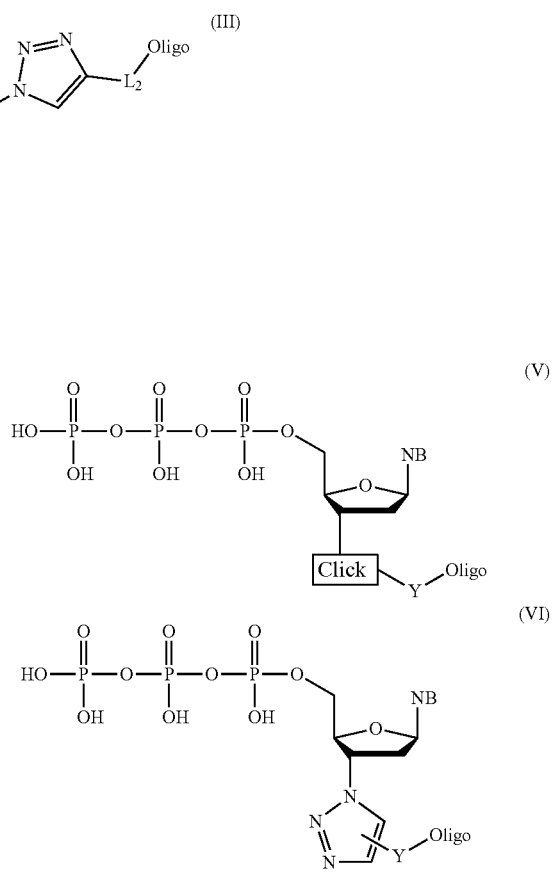

NB represents a nucleobase, Y is a linker, Oligo represents an oligonucleotide of 3 to 100 nucleotides in length. In some embodiments, the nucleobase is chosen from adenine, 7-deazaadenine, cytosine, guanine, 7-deazaguanine, thymine, uracil and inosine. In some embodiments, Z and Y each independently comprise at least one linking moiety chosen from —C(O)NH—, —C(O)C—, —NH—, —S—, —O—, alkyl, alkenyl, and alkynyl, or any combination thereof.

The oligonucleotide-tethered nucleotide of the present disclosure comprises, in some embodiments, a pyrimidine nucleobase. In these embodiments, the pyrimidine nucleobase is bound to the oligonucleotide at the 5 position of the pyrimidine (see, for example, compound E1). Alternatively, when the oligonucleotide-tethered nucleotide comprises a purine base, the purine nucleobase is bound to the oligonucleotide at the 7 position of the nucleobase. In other embodiments, an oligonucleotide-tethered nucleotide is obtained using oligonucleotide with C6(hexynyl)-alkyne motif on a phosphate group at the 5' end (see, for example, compound E2)

In some embodiments, the oligonucleotide of an oligonucleotide-tethered nucleotide comprises deoxyribonucleotides. In some embodiments, the oligonucleotide of an oligonucleotide-tethered nucleotide comprises ribonucleotides. In some embodiments, the oligonucleotide of an oligonucleotide-tethered nucleotide comprises deoxyribonucleotides and ribonucleotides.

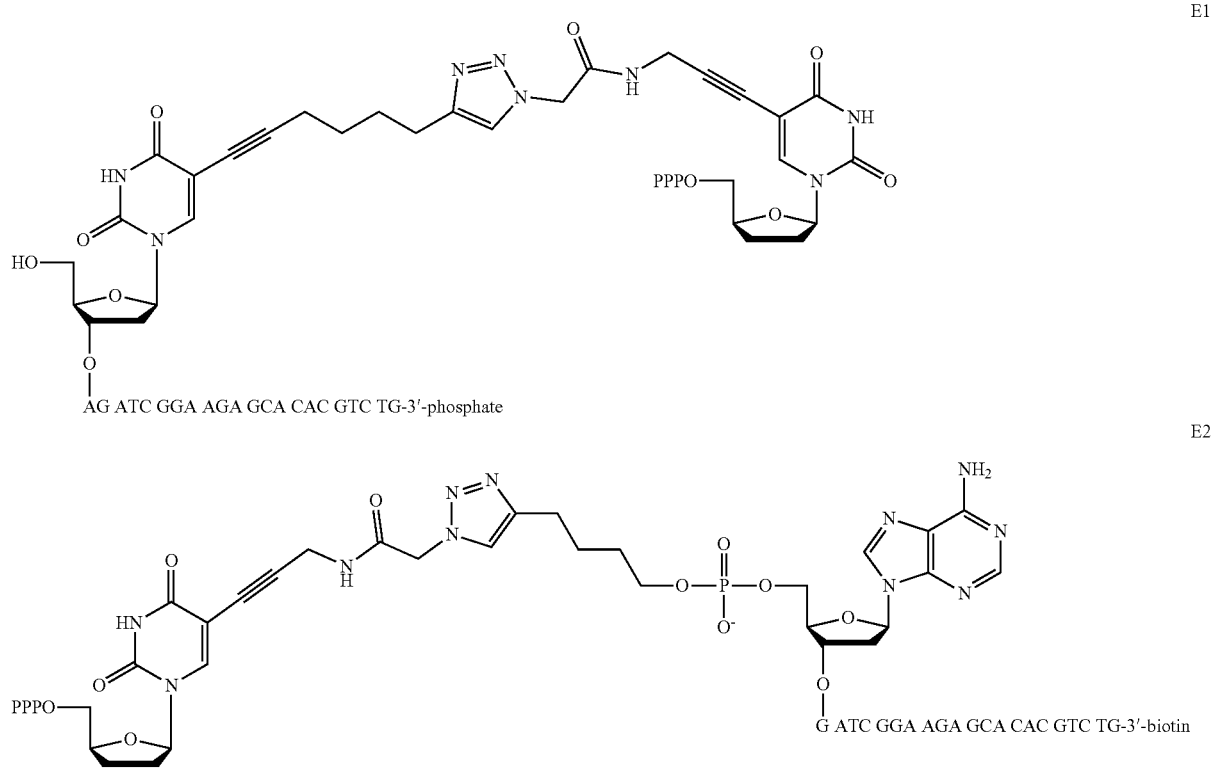

Salts of the oligonucleotide-tethered nucleotides of the present disclosure include quaternary ammonium salts, sodium salts, potassium salts and the like.

In some embodiments, the oligonucleotide of the oligonucleotide tethered nucleotide, is tethered to the nucleotide at its 5' end. In some embodiments, alkyne modification is added to the oligonucleotide nucleobase via a spacer of 8 carbon atoms and is referred as "Ald" modification, or alternatively the alkyne group is attached to the phosphate of the 5' terminus of the oligonucleotide via hexynyl linker. As used throughout the current description, when an oligonucleotide-tethered nucleotide is indicated to have "Ald" (for example, ddUTP-AldU-[Oligonucleotide sequence]), it is understood that the oligonucleotide has been tethered (covalently linked) to the nucleotide during the reaction of alkyne group attached via a spacer of 8 carbon atoms to the oligonucleotide's nucleobase. Alternatively, when an oligonucleotide-tethered nucleotide is indicated to have "HEXYNYL" (for example, ddUTP-HFXYNYL-[Oligonucleotide sequence]), it is understood that the oligonucleotide has been tethered (covalently linked) to the nucleotide during the reaction of alkyne group attached via hexynyl linker to the phosphate of the 5' terminus of the oligonucleotide. In some examples, the oligonucleotide has a modification, for example, at its 3' end. In some examples, the modification is biotin, phosphate, amine or phosphorothioate modifications.

The length of oligonucleotide that is tethered depends on a method where oligonucleotide-tethered nucleotide is used. In some examples, oligonucleotide is from 3 to 100 nucleotides, from 10 to 100 nucleotides, from 10 to 50 nucleotides, or from 20 to 40 nucleotides. In some examples, oligonucleotide may be more that 100 nucleotides in length, for example, up to 1000 nt.

The oligonucleotides of the oligonucleotide-tethered nucleotides described herein is not limited to any specific sequence. Rather, the oligonucleotide of the oligonucleotide-tethered nucleotides described herein may comprise a barcode sequence, an adapter sequence, a unique molecular identifier, an index sequence, an annealing site for polymerases, a handle sequence, a universal handle, a universal sequence, or the like, a random sequence, a target-specific sequence or any combination thereof.

In some examples, oligonucleotide-tethered nucleotides are selected from compounds of Formula B1 and B3, where X is OH, Q is H, $L_1$ is C1 alkylene, C3 alkylene, C5 alkylene, polyethylene glycol with 2 glycol units (PEG2), or polyethylene glycol with 4 glycol units (PEG4), and $L_2$ is C1-C12 alkylene or C1-C12 alkynylene. In some examples, the combination of $L_2$-Oligo is $(CH_2)_4C{\equiv}C$-Oligo.

In some examples, oligonucleotide-tethered nucleotides are selected from compounds of Formula B2 and B4, where X is OH, Q is H, $L_1$ is C1 alkylene, C3 alkylene, C5 alkylene, polyethylene glycol with 2 glycol units (PEG-2), or polyethylene glycol with 4 glycol units (PEG4), and $L_2$ is C1-C12 alkylene or C1-C12 alkynylene. In some examples, the combination of $L_2$-Oligo is —$(CH_2)_4$-Oligo.

In some examples, oligonucleotide-tethered nucleotides are selected from compounds of Formula B1 and B3, where X is H, Q is H, $L_1$ is C1 alkylene, C3 alkylene, C5 alkylene, polyethylene glycol with 2 glycol units (PEG2), or polyethylene glycol with 4 glycol units (PEG4), and $L_2$ is C1-C12 alkylene or C1-C12 alkynylene. In some examples, the combination of $L_2$-Oligo is $(CH_2)_4C{\equiv}C$-Oligo.

In some examples, oligonucleotide-tethered nucleotides are selected from compounds of Formula B2 and B4, where X is H, Q is H, $L_1$ is C1 alkylene, C3 alkylene, C5 alkylene, polyethylene glycol with 2 glycol units (PEG2), or polyethylene glycol with 4 glycol units PEG), and $L_2$ is C1-C12 alkylene or C1-C12 alkynylene. In some examples, the combination of $L_2$-Oligo is —$(CH_2)_4$-Oligo.

Further exemplary oligonucleotide-tethered nucleotides are selected from compounds of Formula B1 and B3, where X is H, Q is H, L1 is C1 alkylene, the combination of $L_2$-Oligo is $(CH_2)_4C{\equiv}C$-Oligo, and NB and NB2 are independently selected from thymine, adenine, guanine, cytosine, or uracil.

Further exemplary oligonucleotide-tethered nucleotides are selected from compounds of Formula B2 and B4, where X is H, Q is H, $L_1$ is C1 alkylene, the combination of $L_2$-Oligo is —$(CH_2)_4$-Oligo, NB and NB2 are independently selected from thymine, adenine, guanine, cytosine, or uracil.

The following list provides some further representative oligonucleotide-tethered nucleotides.

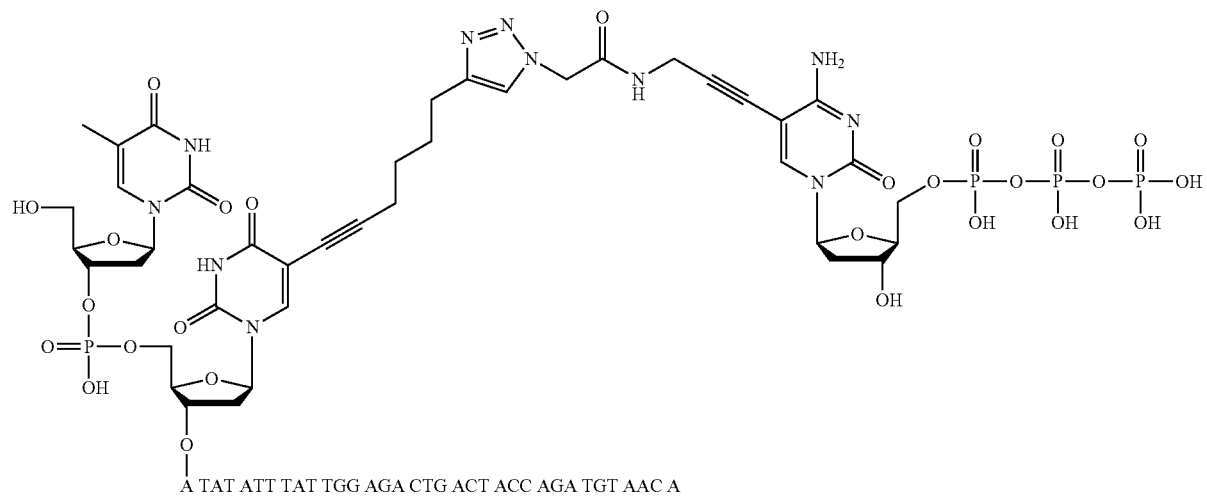

E3

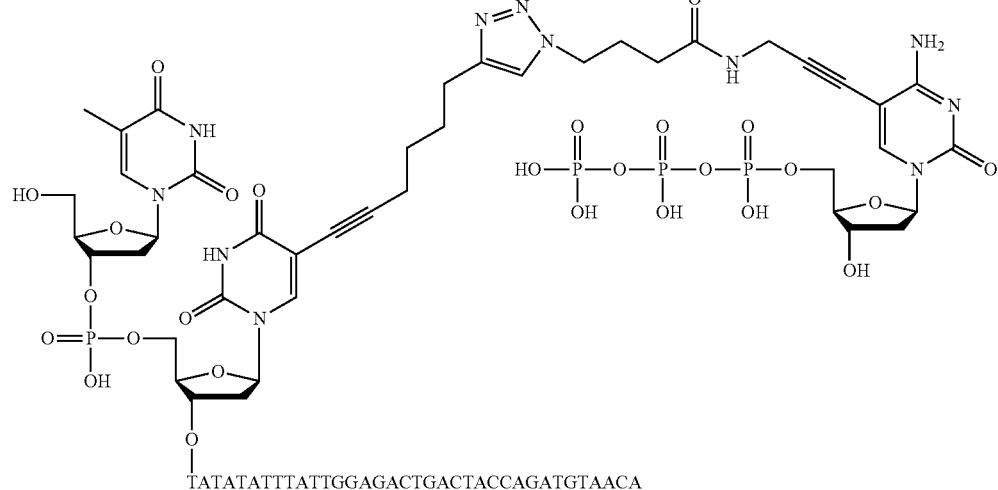

E4

-continued
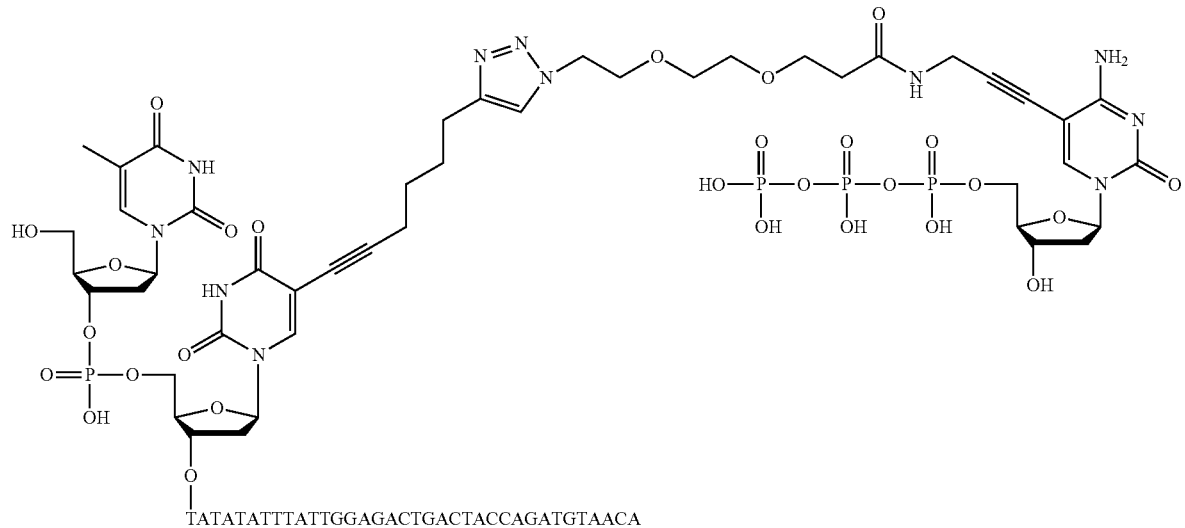
E5
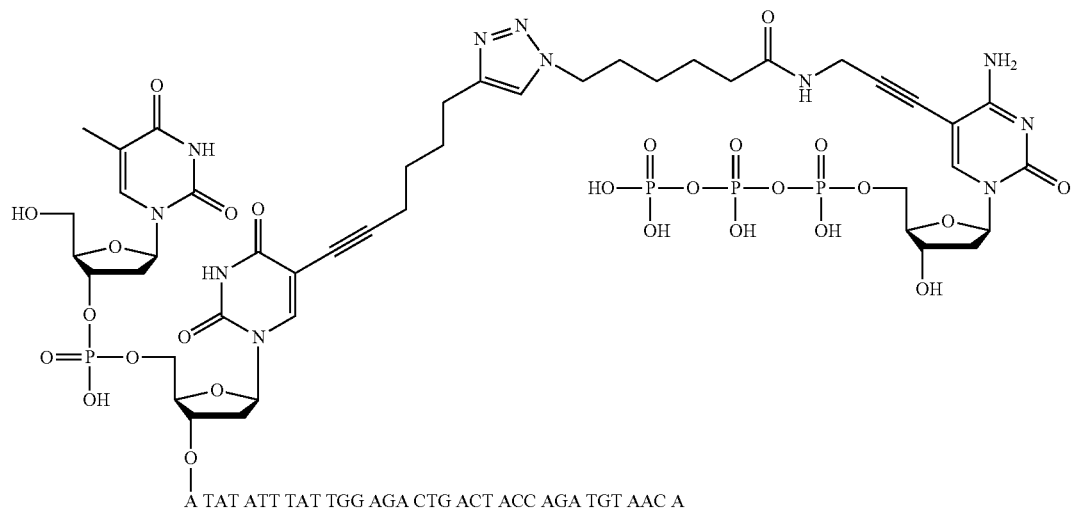
E6
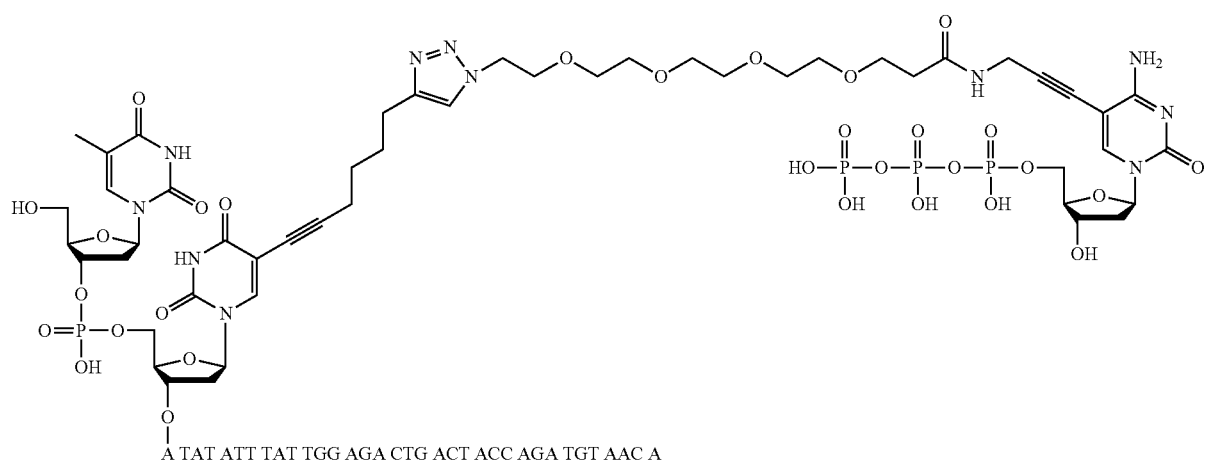
E7

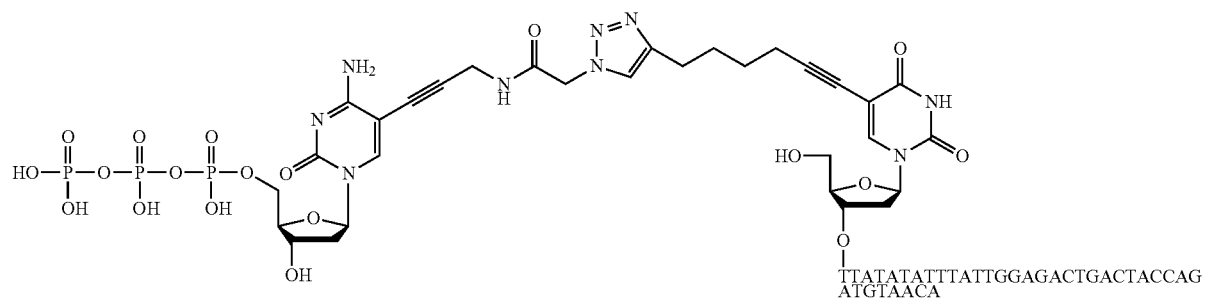
E8
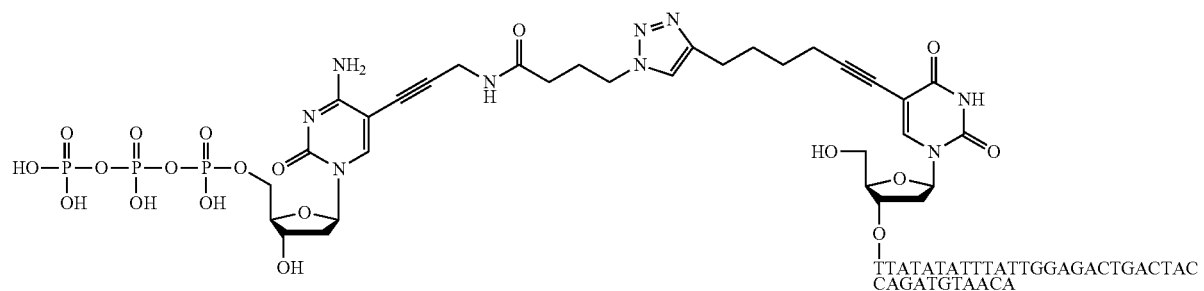
E9
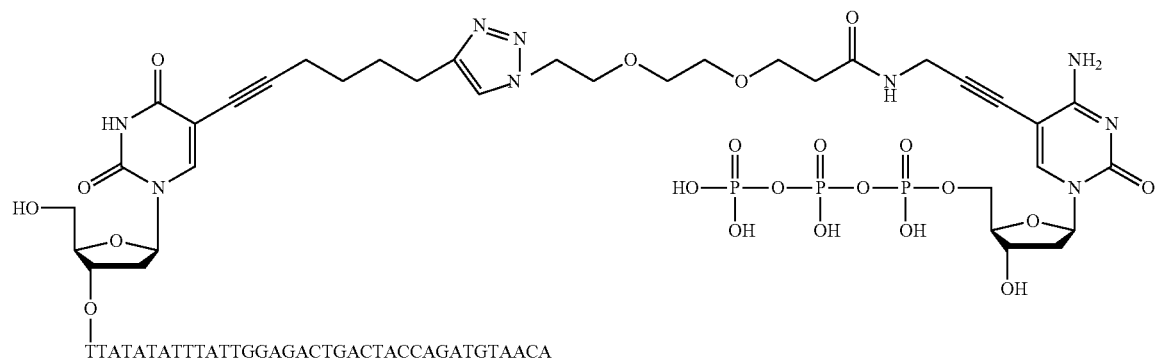
E10
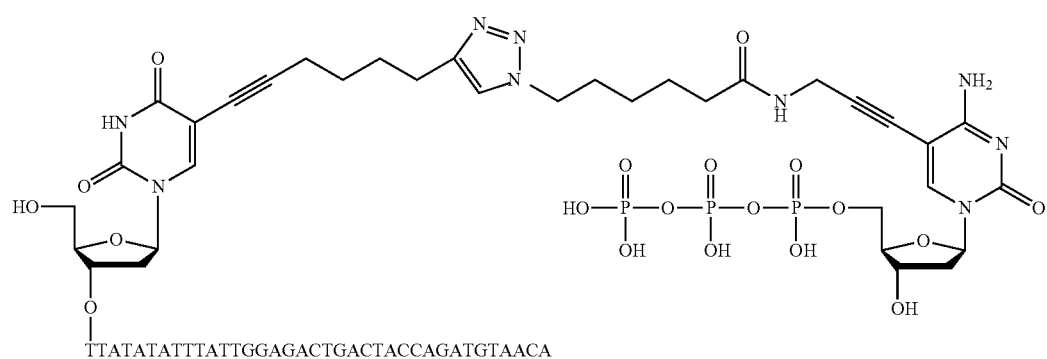
E11

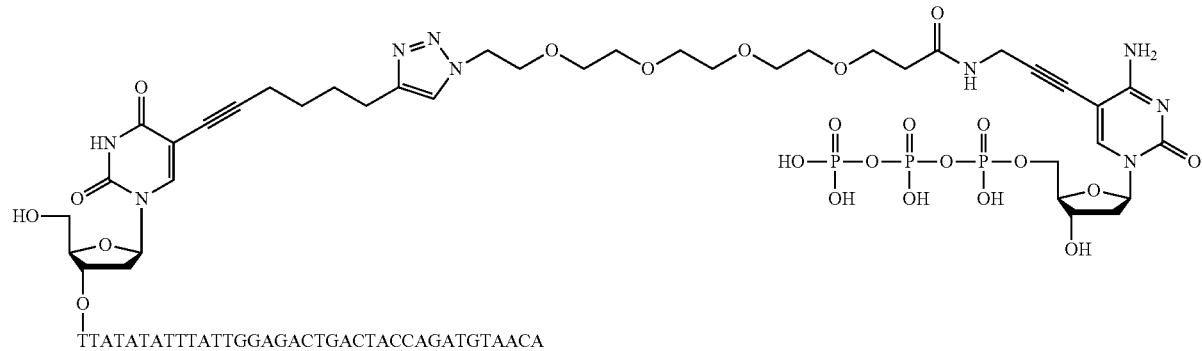
E12
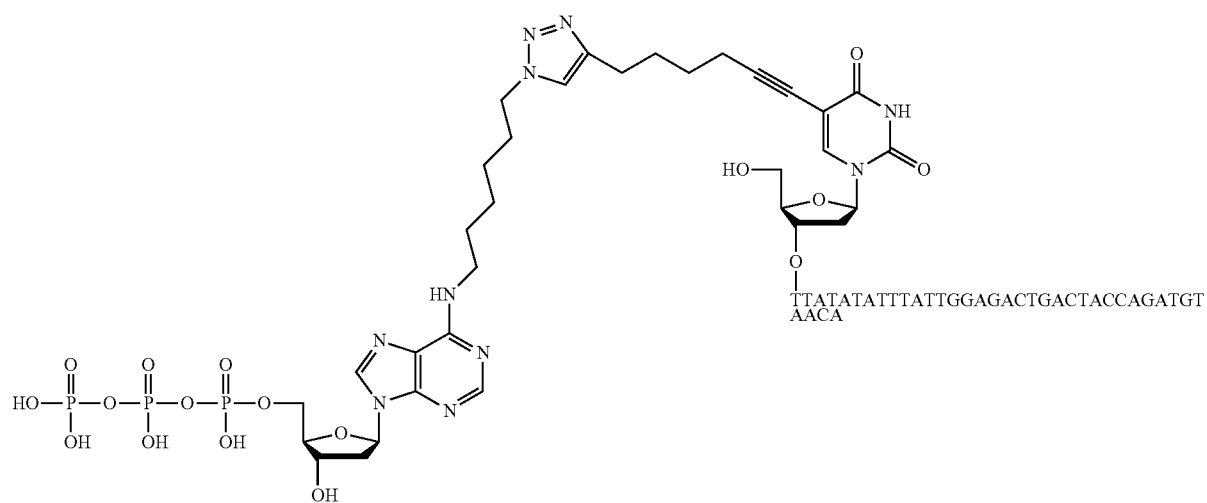
E13
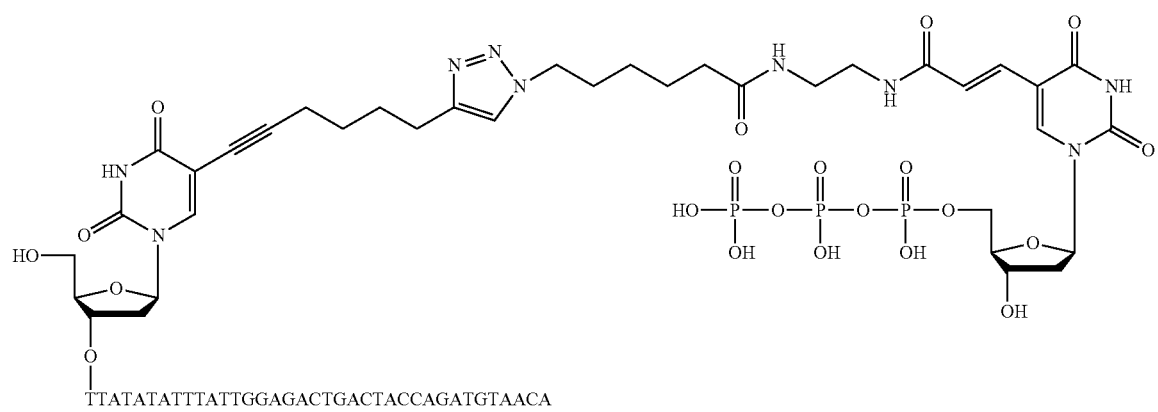
E14

-continued

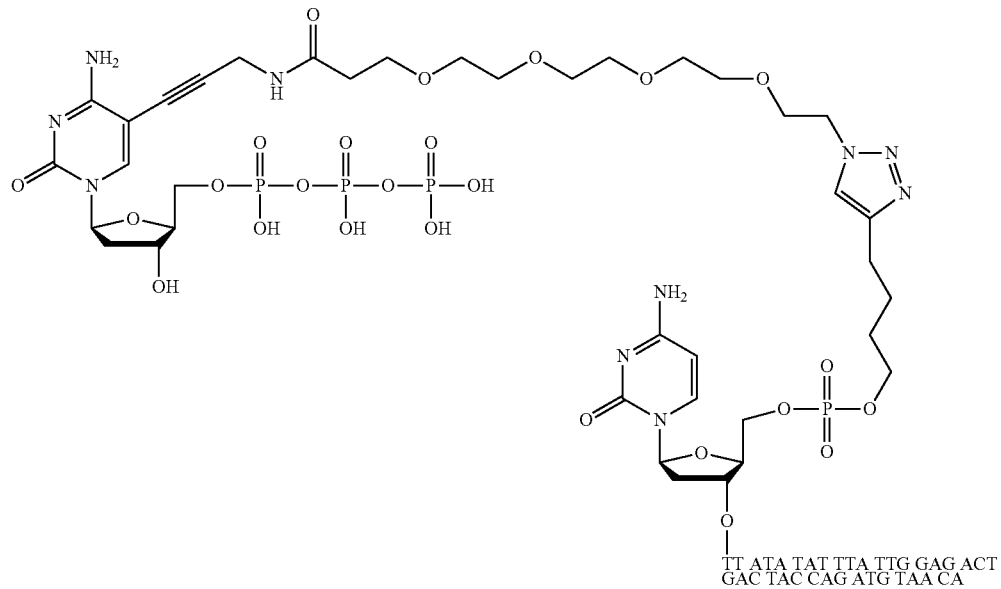

E15

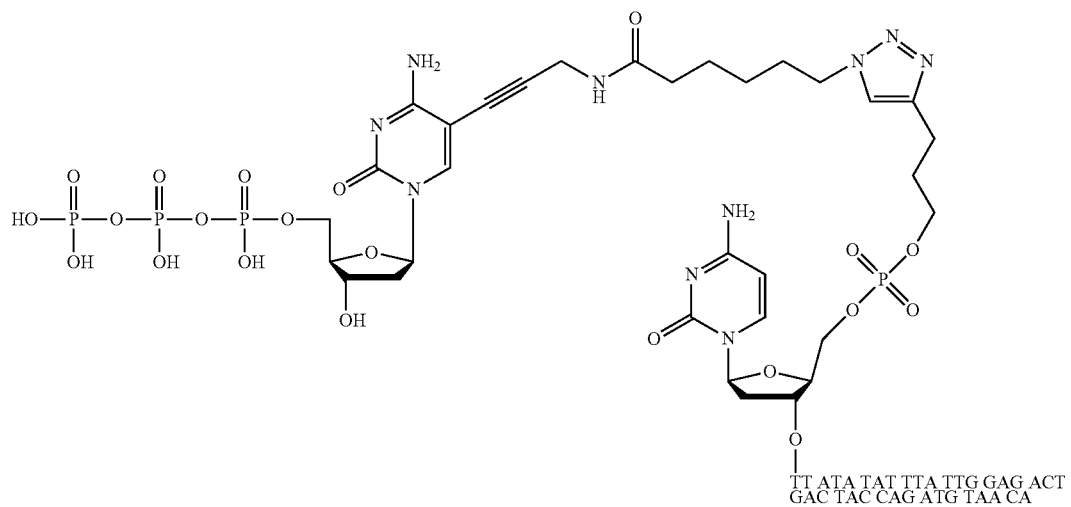

E16

II. Methods of Making Oligonucleotide-Tethered Nucleotides

Various strategies may be used to prepare the oligonucleotide-tethered nucleotides and the claimed compositions and methods of using them are not limited by any description of the methods of making these useful compounds.

A. Click Chemistry in Nucleic Acid Modification

The term "click chemistry" is well understood in the art and generally refers to fast reactions that easily purified and regiospecific. Click chemistry is a class of reactions allowing the joining of substrates of choice with specific molecules. Click chemistry is not a single specific reaction, but describes a way of generating products that follow examples in nature, which also generates substances by joining small modular units. In many applications, click reactions join a biomolecule and a reporter molecule. Click chemistry is not limited to biological conditions: the concept of a "click" reaction has been used in pharmacological and various biomimetic applications. However, they have been made notably useful in the detection, localization and qualification of biomolecules. The classic click reaction is the copper-catalyzed reaction of an azide with an alkyne to form a 5-membered heteroatom ring a Cu(I)-catalyzed azide-alkyne cycloaddition (CuAAC). Additional reactions, including strain-promoted azide-alkyne cycloaddition (SPARC) or copper free reactions; strain-promoted alkyne-nitron cycloaddition (SPANC); alkyne hydrothiolation; and alkene hydrothiolation are known in the art and are useful for creating the CXN group of this disclosure.

As used herein, and unless otherwise indicated, the terms "contacting," "adding," "reacting," "treating," or the like means contacting one reactant, reagent, solvent, catalyst, reactive group or the like with another reactant, reagent, solvent, catalyst, reactive group or the like. Reactants, reagents, solvents, catalysts, reactive groups or the like can be added individually, simultaneously or separately and can be added in any order that achieves a desired result. They can be added in the presence or absence of a heating or cooling apparatus and can optionally be added under an inert atmosphere.

In the case of the present application, click-reaction is performed on nucleotides to produce oligonucleotide-tethered nucleotides which eliminates the need to remove unreacted click reaction precursors and other residues which may interfere with further applications. The methods presented herein also have advantages of simplifying the workflow as DNA synthesis termination (which also has the similar effect as fragmentation, result of synthesis termination reaction is a set of different shorter DNA fragments) and tagging are being performed in a single step.

In some embodiments, a method for preparing an oligonucleotide-tethered nucleotide according to the present disclosure comprises providing a nucleotide covalently bound to a first functional group capable of undergoing a click reaction with a second functional group; providing an oligonucleotide covalently bound to the second functional group capable of undergoing a click reaction, wherein the first and second functional groups are respectively chosen from the following pairs: alkynyl and azido; azido and alkynyl, thiol and alkynyl; alkynyl and thiol; thiol and alkenyl; alkenyl and thiol; azido and cyclooctanyl; cyclooctanyl and azido; nitrone and cyclooctanyl; cyclooctanyl and nitrone; contacting the nucleotide with the oligonucleotide in the presence of a copper catalyst and copper (I) ligand to form a click reaction product.

In a particular embodiment, the method comprises a click reaction of an azide and an alkyne to form a 1,2,3-triazole. Azides and terminal or internal alkynes can undergo a 1,3-dipolar cycloaddition (Huisgen cycloaddition) reaction to give a 1,2,3-triazole. However, this reaction requires long reaction times and elevated temperatures. Alternatively, azides and terminal alkynes can undergo Copper(I)-catalyzed Azide-Alkyne Cycloaddition (CuAAC) at room temperature. Such copper(I)-catalyzed azide-alkyne cycloadditions, also known as "click chemistry," is a variant of the Huisgen 1,3-dipolar cycloaddition, wherein organic azides and terminal alkynes react to give 1,4-regioisomers of 1,2,3-triazoles. Examples of "click" chemistry reactions are described by Sharpless et al. (U.S. Patent Application Publication No. 20050222427, published Oct. 6, 2005, PCT/US03/17311; Lewis W. G. et al., Angewandte Chemie-Int'l Ed. 41 (6): 1053; method reviewed in Kolb, H. C., et al., Angew. Chem. Inst. Ed. 2001, 40:2004-2021), which developed reagents that react with each other in high yield and with few side reactions in a heteroatom linkage (as opposed to carbon-carbon bonds) in order to create libraries of chemical compounds.

The copper used as a catalyst for the "click chemistry" reaction used in the methods described herein to conjugate a label (reporter group, solid support or carrier molecule) to a nucleic acid is in the Cu (I) reduction state. The sources of copper(I) used in such copper(I)-catalyzed azide-alkyne cycloadditions can be any cuprous salt including, but not limited to, cuprous halides such as cuprous bromide or cuprous iodide. However, this regioselective cycloaddition can also be conducted in the presence of a metal catalyst and a reducing agent.

In certain embodiments, copper can be provided in the Cu(II) reduction state (for example, as a salt, such as but not limited to $Cu(NO_3)_2$, $Cu(OAc)_2$, or $CuSO_4$), in the presence of a reducing agent wherein Cu(I) is formed in situ by the reduction of Cu(II). Such reducing agents include, but are not limited to, ascorbate, Tris(2-Carboxyethyl) Phosphine (TCEP), 2.4.6-trichlorophenol (TCP), NADH, NADPH, thiosulfate, metallic copper, quinone, hydroquinone, Vitamin K, glutathione, cysteine, 2-mercaptoethanol, dithiothreitol, Fe(II), Co(II), or an applied electric potential. In other embodiments, the reducing agents include metals chosen from Al, Be, Co, Cr, Fe, Mg, Mn, Ni, Zn, Au, Ag, Hg, Cd, Zr, Ru, Fe, Co, Pt, Pd, Ni, Rh, and W. In particular embodiments, the reducing agent is ascorbate.

In some embodiments, the (3+2) cycloaddition of azides and alkynes is conducted in the presence of a ligand. While not being bound by theory, the ligand is believed to stabilize the Cu(I) ion, thereby preventing its oxidation to the Cu(II) ion. For example, ligands may be chosen from: 3-[4-({bis[(1-tert-butyl-1H-1,2,3-triazol-4-yl)methyl]amino}methyl)-1H-1,2,3-triazol-1-yl]propanol (BLIP); 3-[4-({bis[(1-tert-butyl-1H-1,2,3-triazol-4-yl)methyl]amino}methyl)-1H-1,2,3-triazol-1-yl]propyl hydrogen sulfate (BTTPS); 2-[4-({bis[(1-tert-butyl-1H-1,2,3-triazol-4-yl)methyl]amino}methyl)-1H-1,2,3-triazol-1-yl]ethyl hydrogen sulfate (BTTES); bathophenanthroline disulphonate disodium salt (BTTAA); Nε-((1R,2R)-2-azidocyclopentyloxy)carbonyl)-L-lysine (BPS); pentamethyldiethylenetriamine (PMDETA); tris(2-benzimidazolylmethyl)amine ((BimH)3) tris-(benzyltriazolylmethyl)amine (TBTA); or tris(3-hydroxypropyltriazolylmethyl)amine (THPTA). In a particular embodiments, the ligand is THPTA.

The copper(I)-catalyzed azide-alkyne cycloadditions for labeling nucleic acids can be performed in water and a variety of solvents, including mixtures of water and a variety of (partially) miscible organic solvents including alcohols, dimethyl sulfoxide (DMSO), dimethyl formamide (DMF), tert-butanol (tBuOH) and acetone.

In some embodiments the click reaction that forms CXN is a reaction between i) alkynyl and azido groups.

Figure 7:
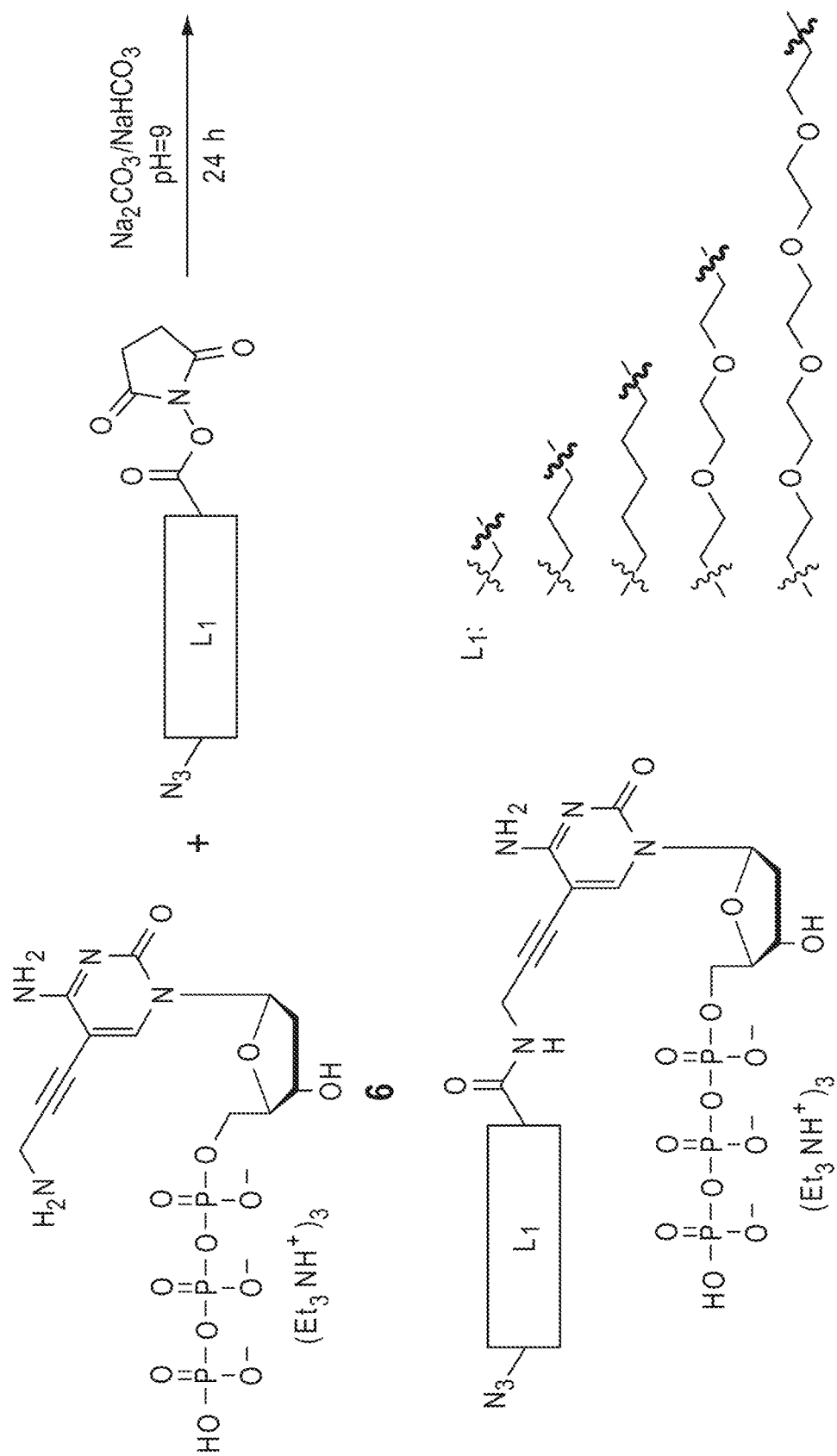
FIG. 7 depicts an exemplary synthesis scheme for preparing an azido-modified dCTP and the structure of several exemplary linkers.
Figure 8:
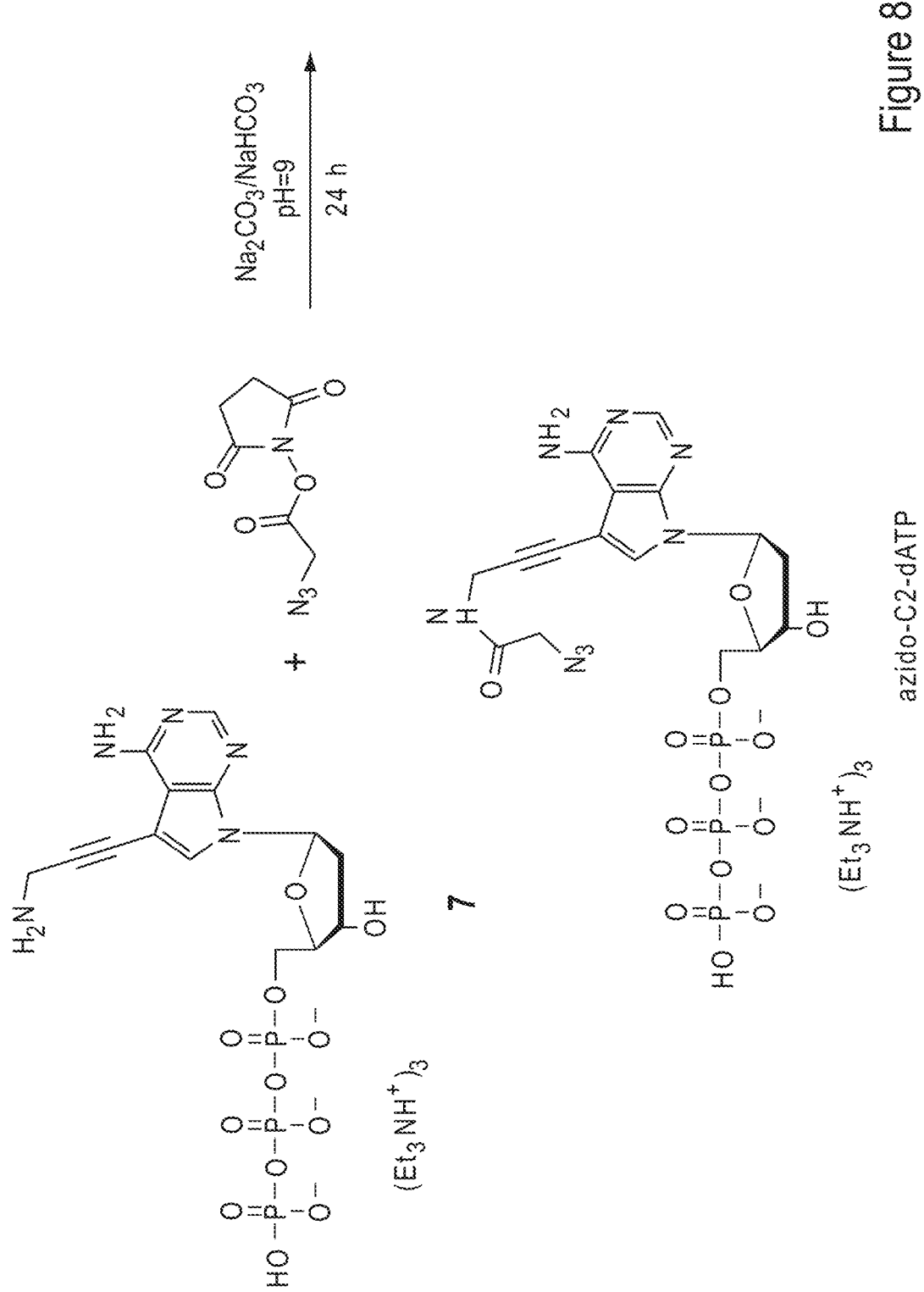
FIG. 8 depicts an exemplary synthesis scheme for preparing azido-modified dATP.

The azide intermediates may be prepared using the methods shown in FIG. 7 and FIG. 8. Various dNTP and ddNTP starting materials are commercially available. In some embodiments, azide intermediates of D1 and D2 below are provided, where NB, $L_1$, X and Q are as described herein.

D1

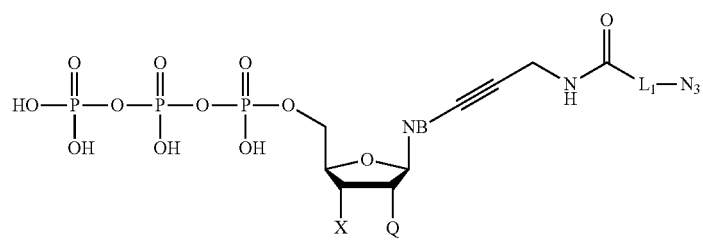

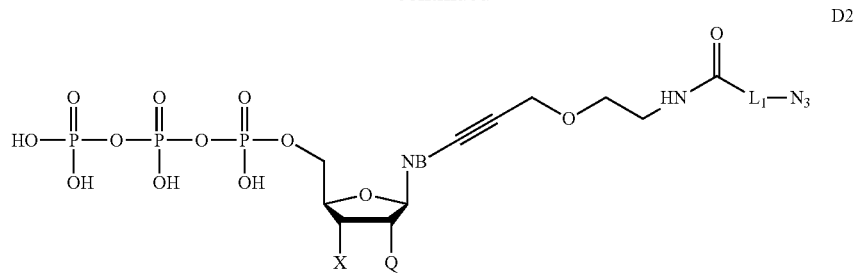

Azide intermediates of D2 may be prepared, for example, using the principle scheme of the methods shown in FIGS. 7 and 8, using the starting materials of appropriate structure.

Example intermediate alkyne compounds, C3 and C4 are commercially available

Figure 9:
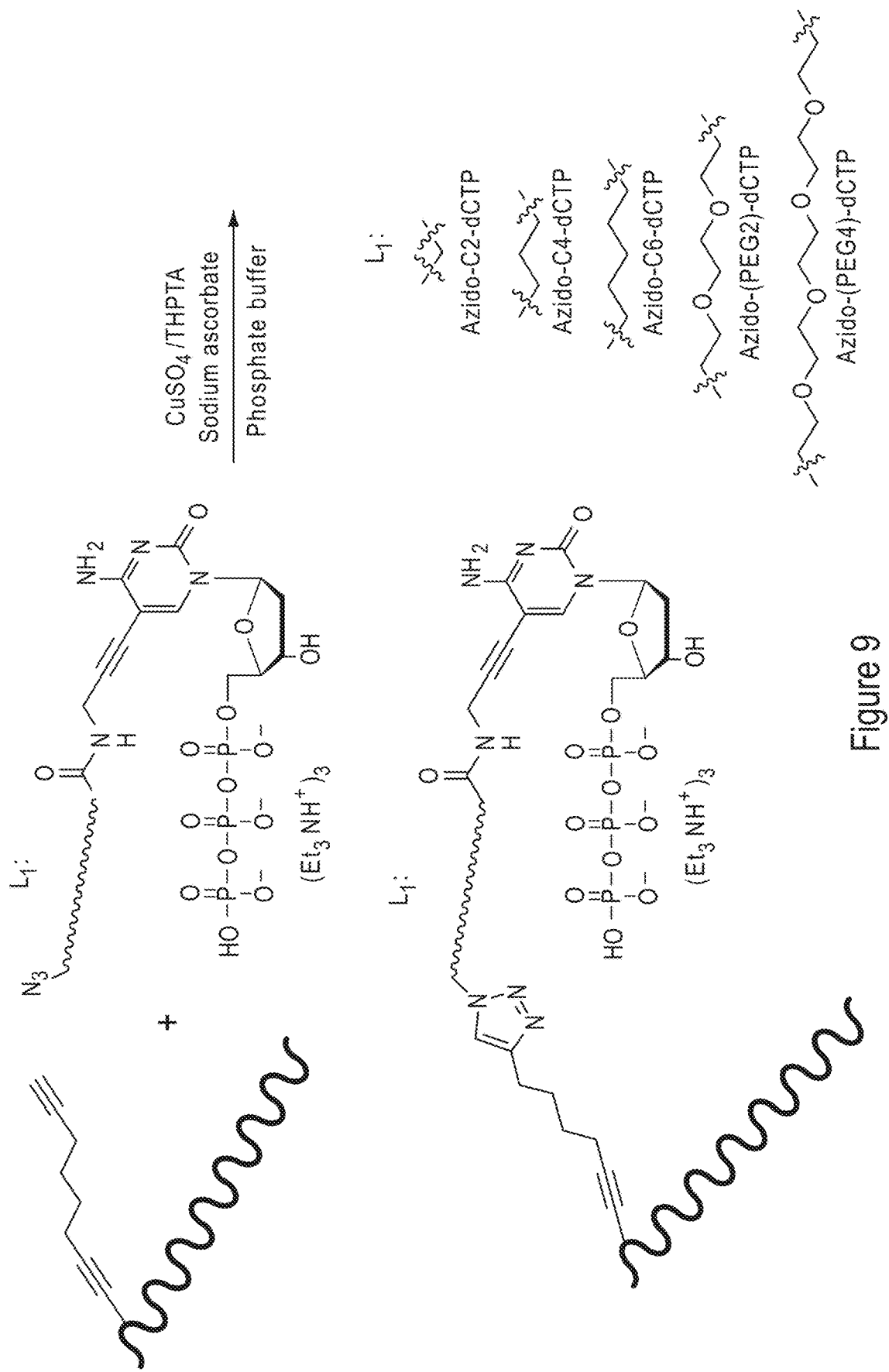
FIG. 9 depicts an exemplary Click reaction scheme for preparing an oligonucleotide-tethered dCTP, along with the structure of several exemplary linkers.
Figure 10:
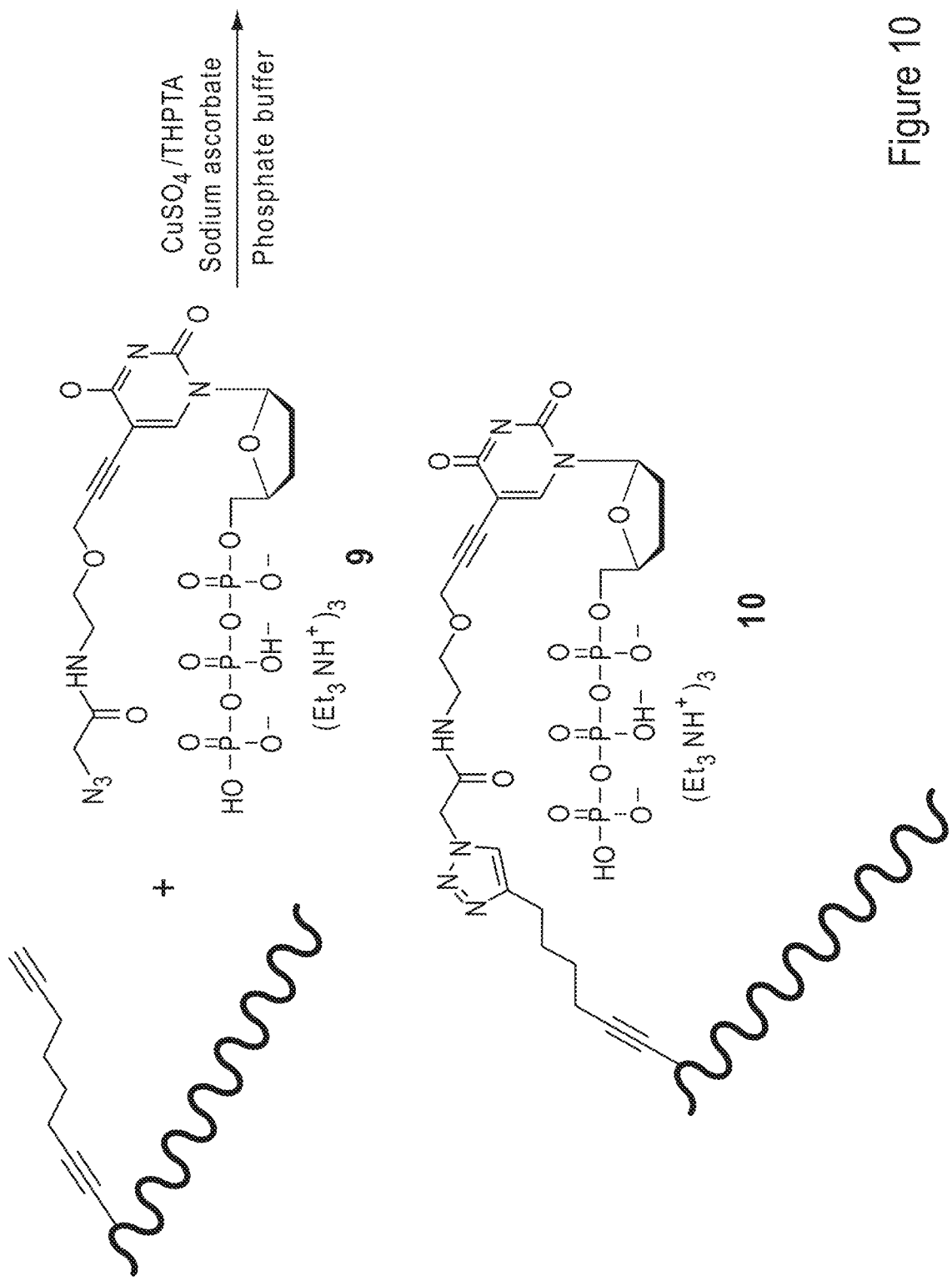
FIG. 10 depicts an exemplary Click reaction scheme for preparing an oligonucleotide-tethered ddUTP.

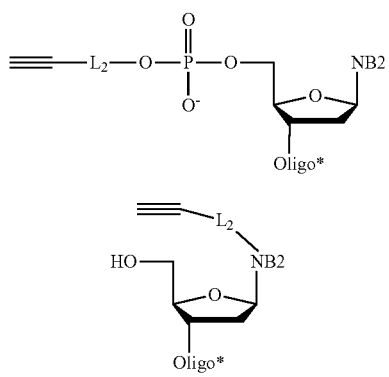

wherein NB2, $L_2$, and Oligo* are as described herein. Oligonucleotide-tethered nucleotides may be prepared from the above described azide intermediates and intermediate alkyne compounds, using the methods shown, for example, in FIG. 9 and FIG. 10. Various dNTP and ddNTP starting materials are commercially available. FIGS. 9 and 10 show exemplary preparation methods when intermediate alkyne compound C4 and azide intermediate of D1 are used. Alternatively, combination of intermediate alkyne compound C3 and azide intermediate of DE or C3 and D2, or C4 and D2 may be used in a reaction as exemplified, to prepare oligonucleotide-tethered nucleotides.

In some embodiments, provided herein are methods for preparing an oligonucleotide-tethered nucleotide as disclosed herein wherein the method includes:
a. providing a nucleotide covalently bound to a first functional group capable of undergoing a click reaction with a second functional group;
providing an oligonucleotide covalently bound to the second functional group capable of undergoing a click reaction to form the triazole ring;
contacting the nucleotide with the oligonucleotide to form the click reaction product,
wherein, the first and second functional groups are, respectively, chosen from:
i) alkynyl and azido;
ii) azido and alkynyl,
iii) thiol and alkynyl;
iv) alkynyl and thiol;
v) thiol and alkenyl;
vi) alkenyl and thiol;
vii) azido and cyclooctanyl;
viii) cyclooctanyl and azido;
xi) nitrone and cyclooctanyl; and
xii) cyclooctanyl and nitrone.

In some embodiments, the first and second functional groups are, respectively, chosen from i) alkynyl and azido; and ii) azido and alkynyl.

In some embodiments, step (c) comprises contacting the nucleotide with the oligonucleotide in the presence of a copper catalyst and copper (I) ligand to form a 1,2,3-triazole.

In some embodiments, the nucleotide is a deoxynucleotide or dideoxynucleotide. In some embodiments, the nucleotide is a ribonucleotide or a 3'-deoxy ribonucleotide.

In some embodiments, the copper catalyst comprises copper (I), or copper (II), wherein when the catalyst is copper (II), a reducing agent is present. In other embodiments, the copper catalyst is $Cu(NO_3)_2 Cu(OAc)$, $CuSO_4$ or any combination thereof.

In some embodiments, the reducing agent comprises ascorbate, Tris(2-Carboxyethyl) Phosphine (TCEP), 2.4.6-trichlorophenol (TCP), NADH, NADPH, thiosulfate, metallic copper, quinone, hydroquinone, Vitamin K, glutathione, cysteine, 2-mercaptoethanol, dithiothreitol, Fe(II), Co(II), an applied electric potential, Al, Be, Co, Cr, Fe, Mg, Mn, Ni, Zn, Au, Ag, Hg, Cd, Zr, Ru, Fe, Co, Pt, Pd, Ni, Rh, W, or any combination thereof. In other embodiments, the reducing agent comprises sodium ascorbate.

In some embodiments, the ligand of the copper (I) ligand comprises tris(benzyltriazolylmethyl)amine.

III. Methods of Using Oligonucleotide-Tethered Nucleotides

The oligonucleotide-tethered nucleotides may be used as reagents in nucleic acid synthesis reactions such that the nucleotide with oligonucleotide tether may be incorporated into a nucleic acid formed from the synthesis reaction (e.g., extension reaction, amplification reaction, TdT reaction or the like). Advantageously, this allows for the incorporation of various types of functional sequences (e.g., sequencing adapters, promoter sequences, barcodes, unique molecular identifiers, handle sequences, and the like) either directly, i.e., when the oligonucleotide of the oligonucleotide-tethered nucleotide provides the functional sequence, or indirectly, e.g., by providing sequences that enable the addition of various functional sequences, as described further herein.

As such, aspects provided herein disclose the use of oligonucleotide-tethered nucleotides to directly tag nucleic acids, e.g., sample nucleic acids or sample polynucleotides, with specific oligonucleotide sequences.

For example, provided are methods for generating a library of nucleic acids from a polynucleotide sample. Such a method may include the steps of:
 a. annealing a first extension primer to one or more sample polynucleotides or sample nucleic acids;
 b. contacting the one or more sample polynucleotides or sample nucleic acids with a nucleic acid polymerase, at least one nucleotide, and an oligonucleotide-tethered nucleotide described herein to form a first extension product comprising the oligonucleotide-tethered nucleotide;
 c. annealing a second primer which is at least partially complementary to the tethered oligonucleotide to form a second annealed complex;
 d. contacting the second annealed complex with the nucleic acid polymerase to produce a nucleic acid molecule from the tethered oligonucleotide,
 thereby producing a library of polynucleotides comprising the tethered oligonucleotide sequence at at least one of its ends.

In some embodiments, a first extension primer comprises universal sequence, thereby a library of polynucleotides comprising universal sequence and tethered oligonucleotide sequence at its ends is produced. (See, FIG. 3). In some embodiments, a first extension primer comprises a universal sequence, and a second primer comprises a universal sequence, thereby a library of polynucleotides comprising universal sequences and tethered oligonucleotide sequence at its ends is produced. In some embodiments, a first and second primers comprise different universal sequences.

In some aspects, the polynucleotides are fragmented prior to the step of annealing the first extension primer to the sample polynucleotides.

In the methods described above, nucleic acids may be tagged with specific oligonucleotide sequences at predetermined or at random positions by using a combination of oligonucleotide-tethered nucleotides and its corresponding unmodified native nucleotides. The frequency of random incorporation of oligonucleotide-tethered nucleotides may be controlled through modulation of molar ratio of oligonucleotide-tethered nucleotides and corresponding native nucleotides.

In some aspects where the first extension primer includes a universal sequence and a random sequence, the method could be useful for whole genome or whole transcriptome sequencing. In other embodiments, where the first primer comprises specific primers, the method could be useful for targeted DNA/RNA sequencing.

In other examples, the oligonucleotide-tethered nucleotides may be used to facilitate addition of information, such as barcodes, unique molecular identifiers, handles and/or sequencing adapters, e.g., in a template dependent manner. Accordingly, in some embodiments provided is a method of adding nucleic acid sequences in a template-dependent manner to a sample polynucleotide. The method can include the steps of: (a) annealing a first primer to one or more sample polynucleotides or sample nucleic acids; (b) contacting the one or more sample polynucleotides or sample nucleic acids with a nucleic acid polymerase, at least one nucleotide, and an oligonucleotide-tethered dideoxynucleotide (OTDDN) described herein to form a first extension product comprising a copy of at least part of the one or more sample polynucleotides or sample nucleic acids with the OTDDN incorporated at the 3' end. Desired information can be added to the 3' end of the first extension product \, by contacting the extension product with a splint oligonucleotide comprising (i) a sequence that hybridizes to the oligonucleotide portion of the OTDDN, and (ii) a template for a desired, additional sequence, in the presence of a polymerase and nucleotides (which may or may not be present from the first extension reaction), thereby producing a second extension product. By this means, desired additional sequences such as barcodes, indexes, unique molecular identifiers, adapters (e.g. a sequencing adapter), a handle sequences, promoter sequences, or any combination thereof, or any other desired sequence, is added to the 3' end of the tethered oligonucleotide of the first extension products.

In some examples, the splint oligonucleotide can include a blocking group that prevents extension from the 3' end of the splint. For example, the splint can include a 3' amino, a 3' phosphate, a dideoxy, or other modification that prevents extension. In some examples the splint oligonucleotides can include a functional moiety to enable purification of the splint oligonucleotides (e.g., a binding moiety that specifically binds to a cognate capture moiety, such as biotin/streptavidin or the like).

The sample polynucleotides may be RNA molecules, DNA molecules, or the like. In some embodiments, the sample polynucleotides are mRNA molecules. In some embodiments, the sample polynucleotides are DNA molecules. In some embodiments, the sample polynucleotides are oligonucleotides that are tethered to (e.g., covalently or non-covalently linked) to a molecule of interest (e.g., a cell binding agent such as an antibody or fragment thereof, an aptamer, or the like).

The first primer that anneals to the sample nucleic acids or sample polynucleotides can include a hybridization sequence that enables annealing to the sample polynucleotides under extension conditions. For example, in some embodiments, the hybridization sequence can be a poly(T) tail that enables binding of the first extension primer to mRNA. In some embodiments, the hybridization sequence can be a random sequence (e.g., a random hexamer, or the like) that enables non-selective binding of the first extension primer to sample polynucleotides. In some embodiments, the hybridization sequence can be a target-specific sequence, e.g., that enables hybridization to a specific target nucleic acid sequence. In some embodiments, the sample nucleic acids or sample polynucleotides are contacted with first primers that include more than one type of hybridization sequence (e.g., a mixture of first extension primers having a poly(T) hybridization sequences and first extension primers that have random hybridization sequences such a random hexamers).

Figure 38:
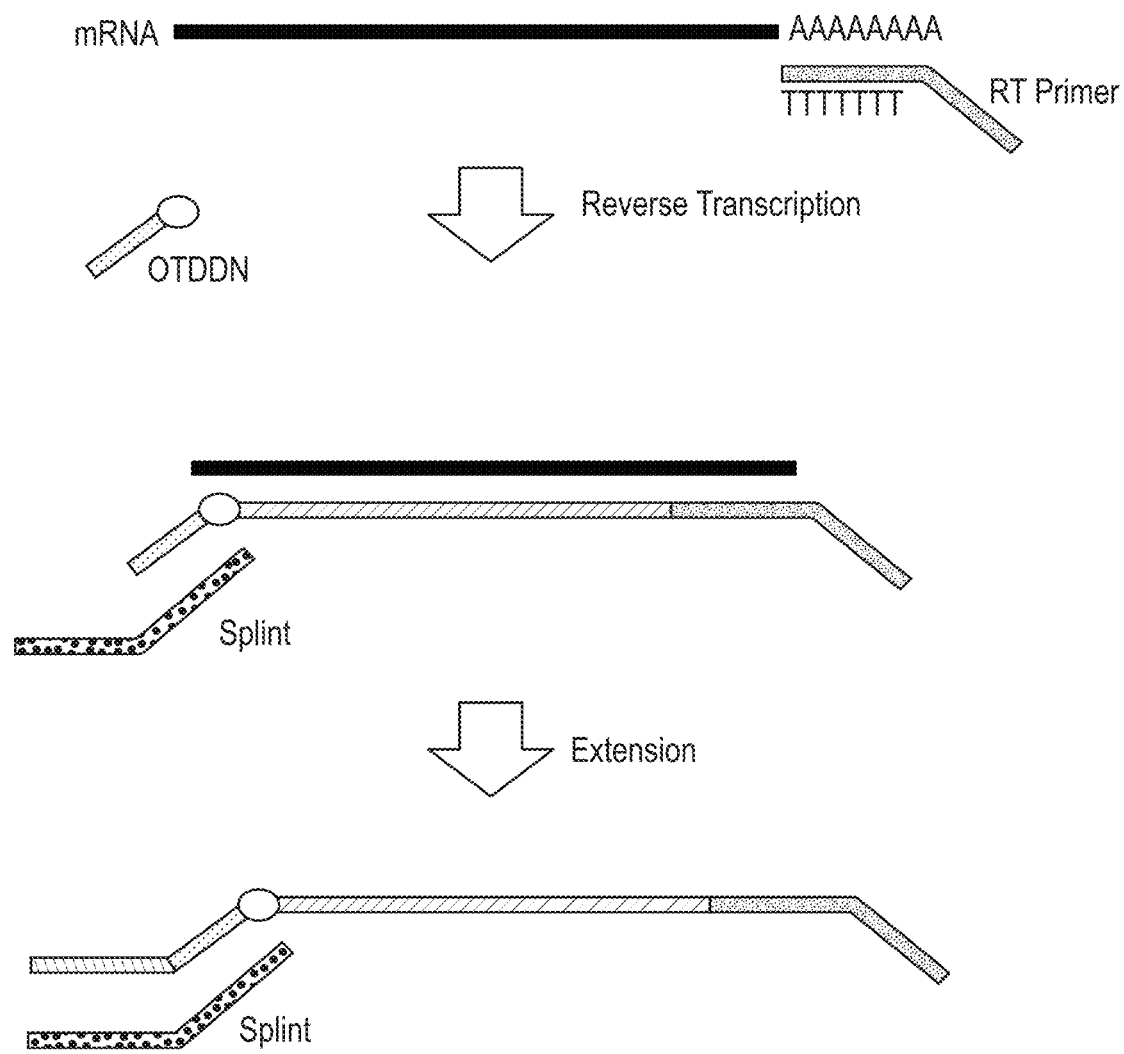
FIG. 38 shows the principle of 3' end-labeling nucleic acids via template-directed extension of an oligonucleotide-tethered dideoxynucleotide (OTDDN).
Figure 44:
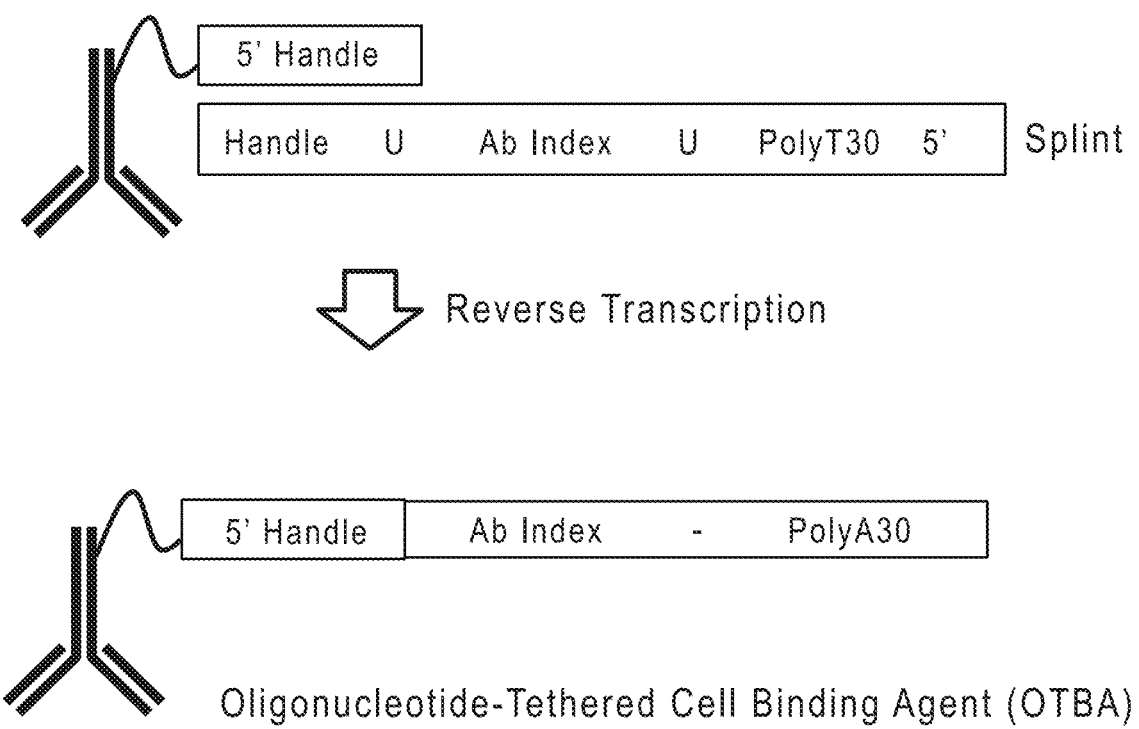
FIG. 44 shows an exemplary scheme for making an oligonucleotide-tethered cell marker binding agent (OTBA), comprising an antibody attached to an oligonucleotide. The oligonucleotide includes, in a 5' to 3' direction, a 5' handle (5' Handle), a cell binding agent index (AbIndex), and a Poly(A) sequence with a 3' OH, (PolyA30, SEQ ID NO: 46). Also shown is a splint used as a template to facilitate template-directed extension of the 5' handle sequence tethered to the antibody.

FIG. 38 depicts a scheme showing an exemplary workflow illustrating how the oligo-tethered nucleotides described herein can be used to facilitate the addition of genetic information on the 3' end of a terminated primer extension product. Although FIG. 38 exemplifies a workflow in which the sample polynucleotide is an mRNA, as described above, the workflow can be used in the context wherein the sample nucleotide is a DNA (e.g., gDNA), an oligonucleotide tethered to a molecule of interest (e.g., a cell marker binding agent as shown in FIG. 44), or the like.

In some embodiments, the present methods optionally include performing at least one clean up step.

The oligonucleotide-tethered nucleotides used in the methods above and described herein may range from 1 fmol to 10 µmol. In certain situations, the ratio of oligonucleotide-tethered nucleotide to a corresponding native nucleotide ranges from 1:1 to 1:1000. For example, the ratio of oligonucleotide-tethered nucleotide to a corresponding native nucleotide is 1:10, 1:50, or 1:100. In some embodiments, the sample is contacted with a two or more of oligonucleotide-tethered thymine, adenine, guanine, cytosine, or uracil nucleotides.

In the methods hereinabove, a single polymerase may be used. Alternatively, two different polymerases may be used, a first polymerase for incorporation of the oligonucleotide-tethered nucleotide and a second polymerase for primer extension/read-through. The polymerase reaction during which a polymerase incorporates oligonucleotide-tethered nucleotide, reads-through the unnatural linker of incorporated oligonucleotide-tethered nucleotide and/or extends a primer/oligonucleotide may be performed under conditions suitable for the polymerase activity. For example, primer/template system, polymerase reaction buffer, incubation temperature and incubation time may be as typically recommended for a corresponding polymerase.

In another embodiment TdT incorporates a single oligonucleotide-tethered dideoxynucleotide to the 3' termini of single stranded or double stranded DNA/RNA in a template independent manner By such means, adapters, e.g., for NGS and the like can be added on to sample nucleic acids. In some embodiments, the oligonucleotide sequence of the OTDDN may include a first adapter sequence. Second adapters that are partially complementary to the first adapter sequences can be annealed and ligated to the template nucleic acids. (See, e.g., FIG. 2). The resulting library has adapters at both ends, the adapters having complementary and mismatched regions. The library may be further amplified.

In some embodiments, the oligonucleotide tethered to the nucleotide (or an oligonucleotide added to a sample polynucleotide indirectly as described herein) in the methods described herein comprise a T7 promoter sequence. As such provided herein are means of introducing in vitro transcription initiation site to sample nucleic acids or polynucleotides.

The methods described hereinabove may also be used for single cell or nuclei sequencing applications. The use of oligonucleotide-tethered dideoxynucleotides can improve single cell or nuclei sequencing methods that are not performed in traditional compartments such as wells or tubes, e.g., by eliminating the need for pre-amplification of nucleic acids derived from single cells or nuclei. For example, oligonucleotide-tethered dideoxynucleotides can be used to improve methods used to spatially resolve transcriptomic, genomic, and proteinomic data in tissue samples.

In some embodiments the methods disclosed herein may be useful for analysis of large genomes. Specific primers targeting gene ends and facing outwards can be designed to employ oligonucleotide-tethered nucleotide technology for the analysis of genomic context. The principle is applicable for any experimental system which aims to investigate unknown sequence regions nearby known specific loci.

As another example, the oligonucleotide-tethered nucleotides may be used in a method for tagging a nucleic acid with an oligonucleotide comprising:

e. annealing a primer to the nucleic acid,
contacting the nucleic acid with an oligonucleotide-tethered nucleotide as described herein, and a polymerase, thereby producing the tagged nucleic acid.

In some embodiments, the contacting comprises contacting the nucleic acid with at least one oligonucleotide-tethered nucleotide, at least one nucleotide not tethered to an oligonucleotide, and a polymerase.

In some embodiments, incorporation of a single type of oligonucleotide-tethered nucleotide is performed. In other embodiments incorporation of a plurality of different oligonucleotide-tethered nucleotides is desirable.

In some applications, the method comprises adding (e.g. ligating) adapter sequences to the 5' end and/or 3' end of the nucleic acid. The method can also further comprise subjecting the tagged nucleic acid to amplification, e.g. by PCR, such as indexing PCR.

Figure 4:
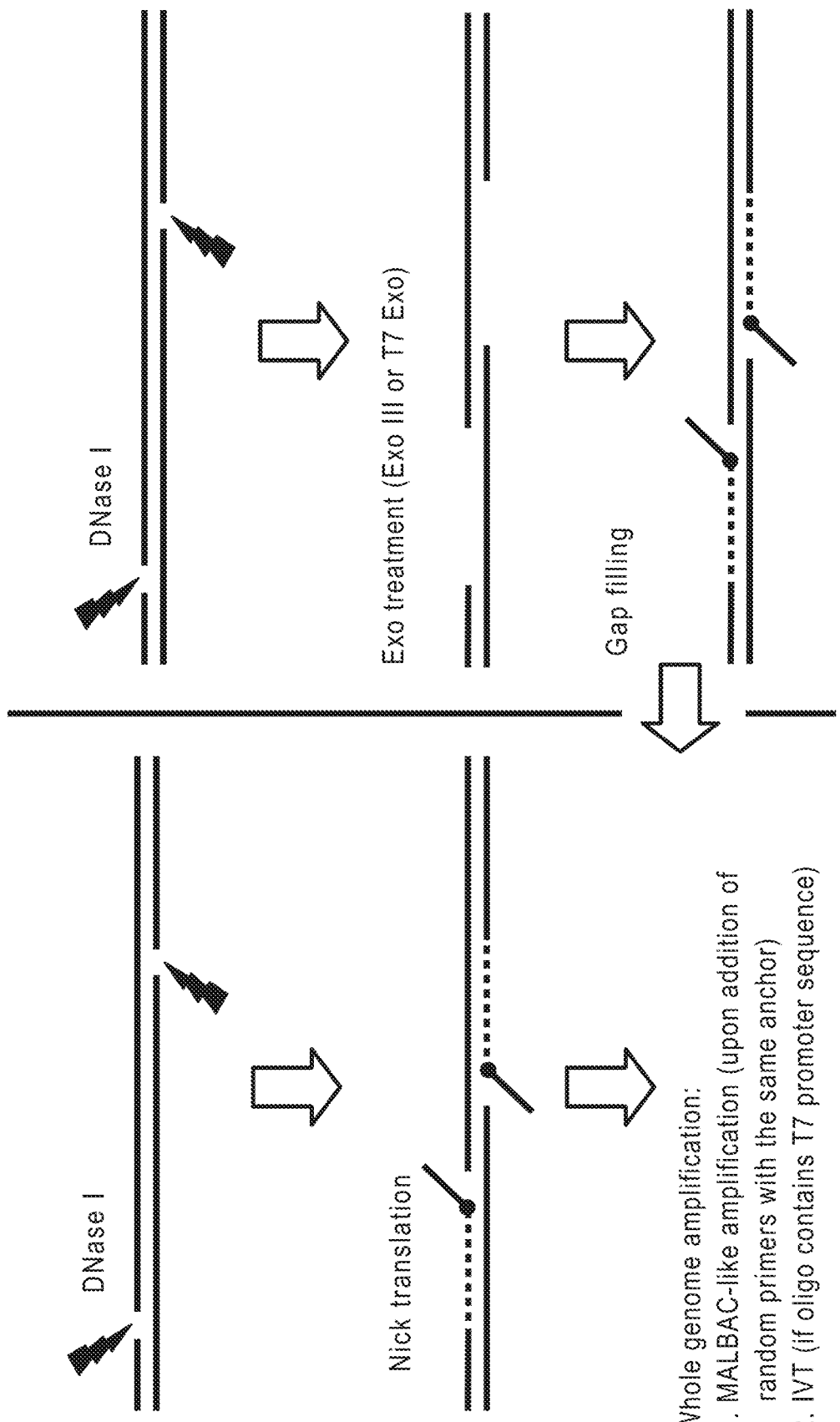
FIG. 4 shows a principle of DNA labeling by the incorporation of an oligonucleotide-tethered ddNTP during nick translation or gap filling reactions.

The oligonucleotide-tethered nucleotide can be employed in synthesis reactions of different types of nucleic acids, including RNA, DNA, or both. In some examples, the nucleic acid is tagged with the oligonucleotide-tethered nucleotide during a gap-filing reaction or a nick translation. For example, double-stranded DNA is randomly labeled by pre-designed specific sequence tag by the incorporation of an oligonucleotide-tethered dideoxynucleotide during the nick translation or gap filling reaction (FIG. 4). The frequency of oligonucleotide incorporation may be controlled through the adjustment of DNA nicking rate (for example, by changing the DNase I treatment time). The resulting polynucleotide library will have pre-designed tags at 3' termini. As the average fragment length is controlled through nicking rate, tagging may be performed by complete substitution of a single native nucleotide with oligonucleotide-tethered nucleotide in nick translation or gap filling reaction mixtures.

Figure 5:
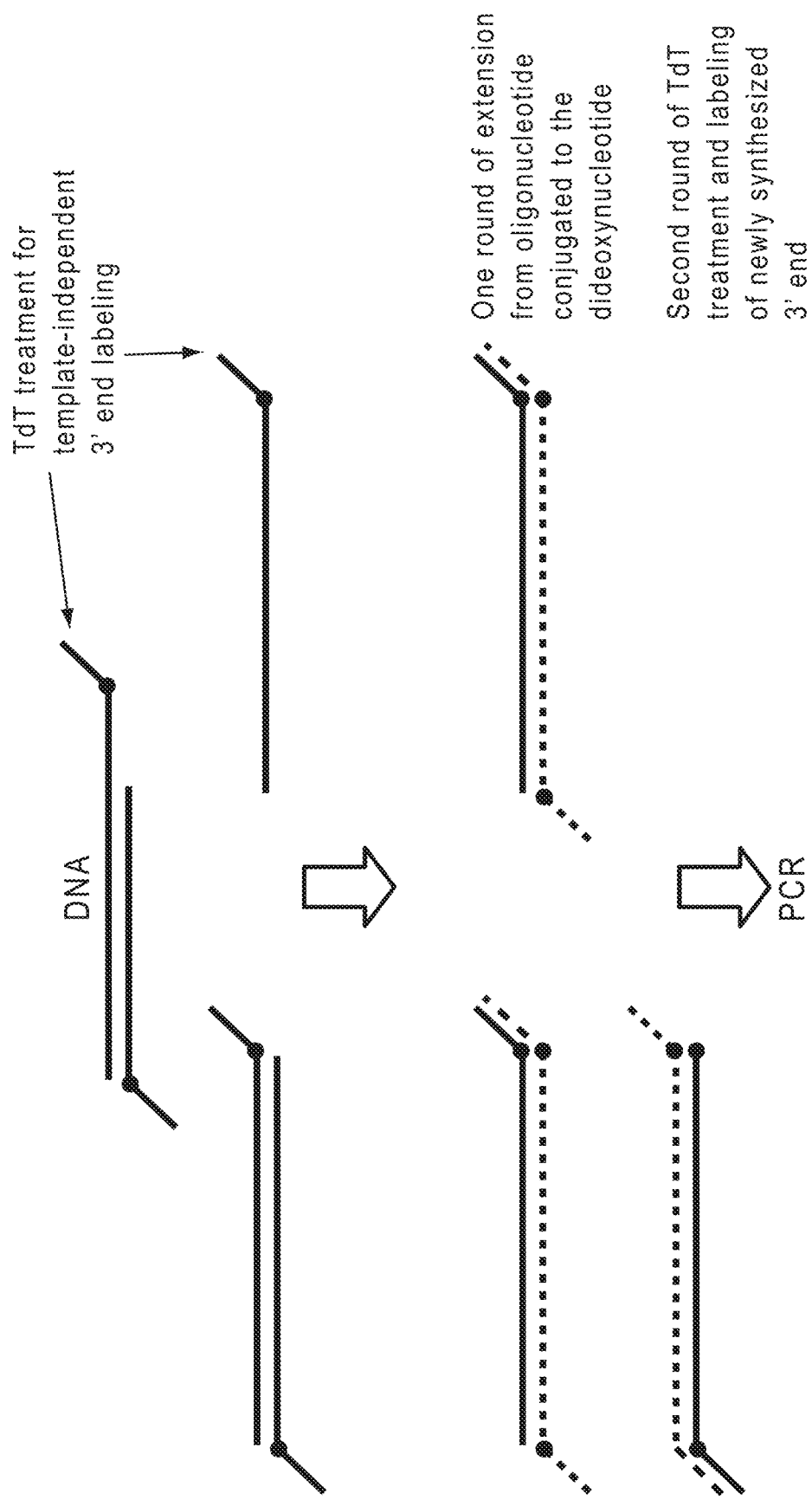
FIG. 5 shows the basic principle of DNA end labeling by template-independent incorporation of oligonucleotide-tethered ddNTPs by (TdT).

DNA end labeling template-independent DNA 3' end labeling with any pre-designed sequence is achieved through the incorporation of an oligonucleotide-tethered dideoxynucleotides by terminal deoxynucleotidyl transferase (TdT). For this purpose, the oligonucleotide tethered to the dideoxynucleotide may have a blocked 3' end (for example, bearing 3' phosphate or 3' amino modification, or dideoxynucleotide), so that it is not extended. After a first round of labeling, a complementary strand is synthesized upon primer extension from the oligonucleotide conjugated to the dideoxynucleotide by any polymerase capable of reading through the conjugation linker. The second round of DNA end labeling is then performed as newly synthesized strands will have accessible 3' ends (FIG. 5).

Figure 6:
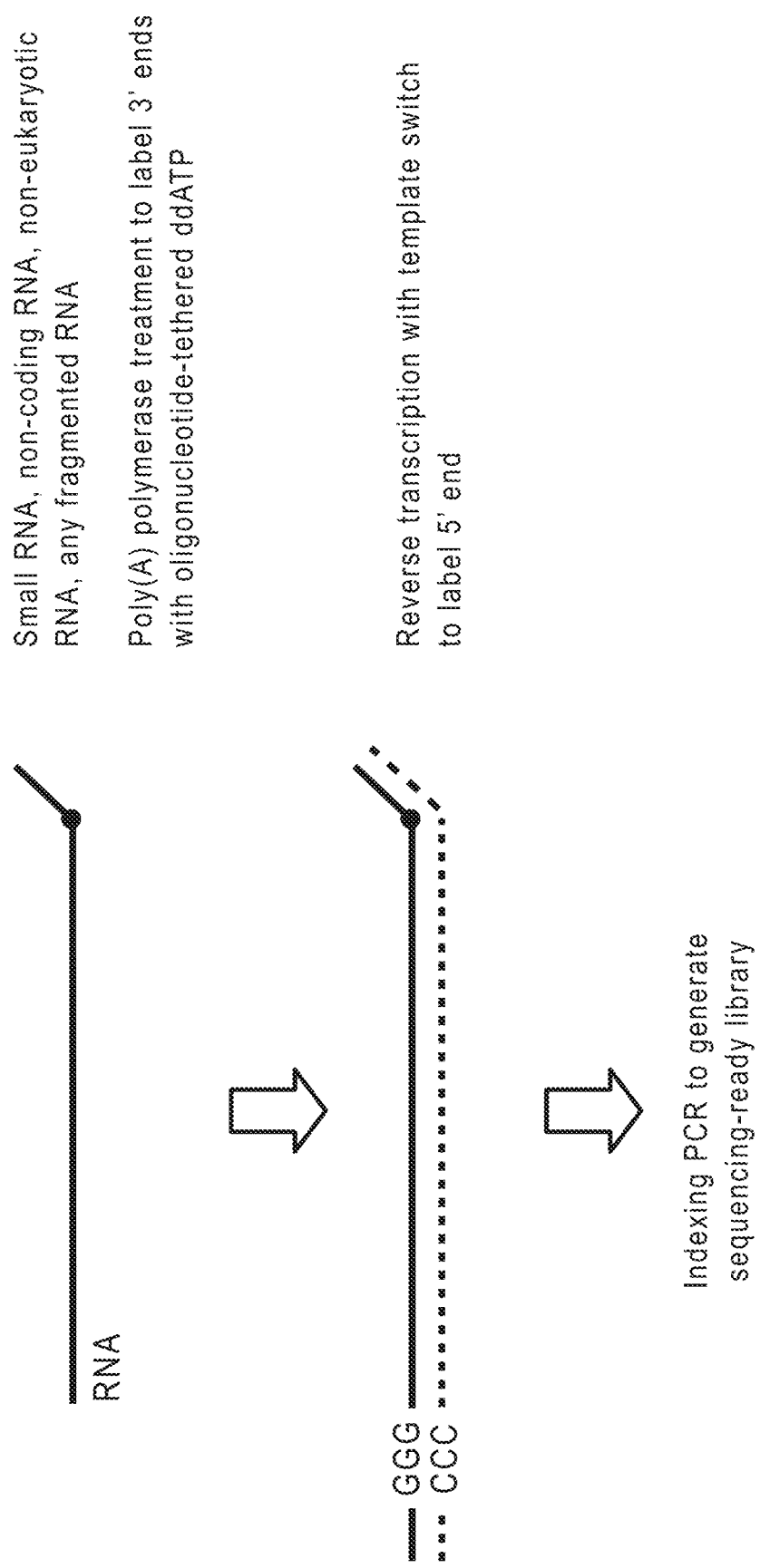
FIG. 6 shows the basic principle of RNA end labeling by the template-independent incorporation of oligonucleotide-tethered ddNTPs by poly(A) or poly(U) polymerases.

RNA end labeling. Template-independent RNA 3' end labeling with any pre-designed sequence may be achieved through the incorporation of oligonucleotide-tethered dideoxynucleotides by poly(A) or poly(U) polymerases (Tailing and 3'-end labeling of RNA with yeast poly(A) polymerase and various nucleotides. G. Martin and W. Keller. RNA (1998), 4:226-230, Cambridge University Press). The incorporated oligonucleotide may then serve as universal priming site for reverse transcription with the possibility to label 5' ends via template switch activity of the reverse transcriptase. The resulting tagged cDNAs is converted to a sequencing-ready library through PCR, which in turn introduces platform-specific full-length adapters (FIG. 6).

PCR-free DNA and RNA sequencing-ready library preparation. As long as polymerases integrated into sequencing platforms are able to read through the unnatural linker, PCR-free sequencing-ready library preparation is possible both from DNA and RNA samples. One-step primer extension, using a primer with a 5' anchor corresponding to the full-length adapter, and termination by incorporation of oligonucleotide-tethered dideoxynucleotides bearing the second full-length platform-specific adapter sequence, enables generation of sequencing-ready single-stranded libraries, which may be subjected to sequencing without any other enzymatic manipulations. This provides advantage that less library preparation steps are needed. When RNA samples are used, such strategy provides further advantage in that only synthesis of first strand cDNA is needed to achieve a sequencing-ready single stranded DNA comprising adapters at 5' and 3' ends.

Template-Directed Addition of Sequences to Tethered Nucleotides. Once a tethered nucleotide is incorporated into a nucleic acid, the tethered oligonucleotide can be used to facilitate the addition of information, such as barcodes, indexes, unique molecular tags, handles, promoters, and/or sequencing adapters in a template dependent manner. The tethered oligonucleotide can include a 3' handle that provides an annealing site for a splint oligonucleotide. Annealing of the splint oligonucleotide to the tethered oligonucleotide forms a second annealed complex. When contacted with a polymerase and nucleotides under extension conditions, the 3' end of the tethered oligonucleotide is extended in a template dependent manner to incorporate the desired information provided by the 5' end of the splint oligonucleotide. By this way, the methods disclosed herein can be used to incorporate adapter sequences and advantageously improve traditional workflows for preparing NGS libraries by greatly simplifying workflow.

A. Polymerases Capable of Incorporating Modified Nucleotide

In order to incorporate the oligonucleotide-tethered nucleotide into a nucleic acid synthesis product, a polymerase may be used.

DNA polymerases, RNA polymerases, reverse transcriptases and telomerases have been shown to accept modified nucleoside triphosphates as enzyme substrates. For example, modified nucleoside triphosphates are accepted by DNA polymerases commonly used for primer extension and amplification protocols, e.g. thermostable DNA polymerases such as Taq polymerase, Vent polymerase, Pfx polymerase, Pwo polymerase, or Therminator polymerase. Alternatively, modified nucleoside triphosphates are accepted by, for example, mesophilic polymerases such as MMLV reverse transcriptase, T7 DNA polymerase, Terminal deoxynucleotide Transferase.

Polymerases capable of incorporating modified nucleotides, in particular oligonucleotide-tethered nucleotides as described herein, may be chosen from DNA and RNA polymerases. In some embodiments, DNA polymerase is a DNA-dependent DNA polymerase, an RNA-dependent DNA polymerase, or a template-independent DNA polymerase. In some embodiments, RNA polymerase is a DNA-dependent RNA polymerase, or an RNA-dependent RNA polymerase, or a template-independent RNA polymerase. These polymerases include wild-type, mutant isoforms, chimeric forms, and genetically engineered variants such as exo-polymerases and other mutants, e.g., that tolerate modified nucleotides and are capable to incorporate them more efficiently into a strand of nucleic acid.

In some embodiments, the polymerase is chosen from an A family DNA polymerase; a B family DNA polymerase; a X family polymerase and RT family polymerase; and variants and derivatives thereof.

In some embodiments, polymerase is a template-independent RNA polymerase, such as polyA polymerase (PAP) or polyU polymerase (PUP). In some embodiments, nucleic acid polymerase is a template-dependent RNA polymerase. In some examples, an RNA polymerase is a DNA-dependent RNA polymerase such as T7 RNA polymerase, T3 RNA polymerase, SP6 RNA polymerase and other RNA polymerases from T7-type bacteriophages. In other examples, an RNA polymerase is an RNA-dependent RNA polymerase such as Q-beta replicase. These polymerases include wild-type, mutant isoforms, chimeric forms, and genetically engineered variants and mutants, e.g., that tolerate modified nucleotides and are capable to incorporate them more efficiently into a strand of nucleic acid.

In some embodiments, the A family DNA polymerase is a thermophilic or a mesophilic polymerase. In some embodiments, the B family DNA polymerase is a thermophilic (e.g. archaeal) or a mesophilic polymerase.

In some embodiments, the DNA polymerase is an A family DNA polymerase chosen from a Pol I-type DNA polymerase such as *E. coli* DNA polymerase, the Klenow fragment of *E. coli* DNA polymerase, polymerase from *T. aquaticus* (Taq DNA polymerase), *T. thermophilus* (Tth DNA polymerase), *Bacillus stearothermophilus* (Bst DNA polymerase), from bacteriophages such as T3 (T3 DNA polymerase) or T7 (T7 DNA polymerase); and variants and derivatives thereof. Variants and derivatives of A family DNA polymerases may be, for example, Thermo Sequenase™ (a mutant Taq DNA polymerase capable of more efficiently incorporating modified nucleotides such as dideoxynucleotides), CycleSeg™ (a combination of Taq DNA polymerase mutants capable of more efficiently incorporating modified nucleotides such as dideoxynucleotides), Stoeffel fragment (Truncated version of Taq DNA polymerase), Sequenase™ V2.0 (T7 DNA Polymerase mutant capable of more efficiently incorporating modified nucleotides such as dideoxynucleotides).

In other embodiments, the DNA polymerase is a B family DNA polymerase chosen from Tli polymerase, Pfu polymerase, Pwo polymerase, KOD polymerase, Sac polymerase, Sso polymerase, Poc polymerase, Pab polymerase, Mth polymerase, phage Phi29 polymerase, and phage B103 polymerase, a Type B polymerase from *Pyrococcus* and *Thermococcus* genera, such as the *Pyrococcus* strain GB-D (Deep Vent polymerase), *P. furiosus* (Pfu DNA polymerase), *P. calidifontis* (Pca DNA polymerase), *P. aerophilum, T. kodakarensis* (KOD DNA polymerases), *T. gorgonarius* (Tgo DNA polymerase), and *Thermococcus* sp. 9° N-7 (9° N DNA polymerase); and variants and derivatives thereof. In some embodiments, B type DNA polymerase is a modified *Pyrococcus furiosus* DNA polymerase. In some embodiments the DNA polymerase is a chimeric Pyrococcus-like DNA polymerase fused with dsDNA binding domain, for example, Phusion DNA polymerase, SuperFi DNA polymerase, Q5 DNA polymerase, Herculase II Fusion DNA polymerase, PfuUltra Fusion II HS DNA polymerase. In some embodiments, DNA polymerase is Phusion exo- or other Pyrococcus-like DNA polymerase as described in U.S. patent application Ser. No. 15/405,574 filed Jan. 13, 2017, which is hereby incorporated by reference. Exonuclease minus modification comprises modifications (D141A and E143A) or other respective modifications in exonuclease domain to inhibit exonuclease activity. Other variants and derivatives of B family DNA polymerases may be, for example, Therminator polymerase (9° N™ DNA Polymerase variant with an enhanced ability to incorporate modified nucleotides such as dideoxynucleotides).

In other embodiments, the DNA polymerase is an X-type polymerase chosen from Terminal deoxynucleotidyl transferase (TdT), poly(A) polymerase, and poly(U) polymerase; and variants and derivatives thereof.

In other embodiments, the polymerase is an RT polymerase chosen from HIV reverse transcriptase, M-MLV reverse transcriptase and AMA/reverse transcriptase; and variants and derivatives thereof.

In some instances, the polymerase is chosen from Taq DNA polymerase, Vent® DNA polymerase, Deep Vent™ DNA polymerase, Pfx DNA polymerase, Pwo polymerase, SuperScript™ IV (mutant MMLV RT), SuperScript™ II (mutant MMLV RT), SuperScript™ III (mutant MMLV RT), Maxima™ (mutant MMLV RT), RevertAid™ (mutant MMLV RT) reverse transcriptases, Thermo Sequenase™, Sequenase™ V2.0, CycleSeg™, Phusion exo-, Terminal deoxynucleotidyl Transferase (WI), Maxima H (mutant MMLV RT), Therminator™ polymerase, Q5 DNA polymerase, AccuTaq DNA polymerase, T7 DNA polymerase, T3 DNA polymerase, T4 DNA polymerase, T7 RNA polymerase, T3 RNA polymerase, SP6 RNA polymerase, DNA polymerase 1, Klenow fragment, Tth DNA polymerase, Phusion® DNA polymerase, SuperFi DNA polymerase, Platinum Taq DNA polymerase, Herculase II Fusion DNA polymerase, PfuUltra Fusion II HS DNA polymerase, Bst DNA polymerase large fragment, Stoeffel fragment, 9° N™ DNA polymerase, Pfu DNA polymerase, Tfl DNA polymerase, Phi29 polymerase, Tli DNA polymerase, eukaryotic DNA polymerase beta, telomerase, KOD HiFi DNA polymerase, KOD DNA polymerase, Q-beta replicase, AMV reverse transcriptase, M-MLV reverse transcriptase, Phi6 reverse transcriptase, and HIV-1 reverse transcriptase, polyA polymerase (PAP), polyU polymerase (PUP), and variants and derivatives thereof.

In some examples, the polymerase is chosen from Taq DNA polymerase, SuperScript™ IV (mutant MMLV RT), Thermo Sequenase™, Sequenase™ V2.0, CycleSeg™, Phusion exo-, Maxima H (mutant MMLV RT), Therminator™ polymerase, T7 DNA polymerase, T7 RNA polymerase, T3 RNA polymerase, Phusion (exo-) DNA polymerase, polyA polymerase (PAP), polyU polymerase (PUP), and variants and derivatives thereof.

In some embodiments, polymerase is a wild type polymerase, a modified polymerase (for example, a polymerase with a chemical modification), mutant polymerase, chimeric polymerase, exonuclease minus polymerase, an engineered polymerase, or a combination thereof. Genetically engineered variants such as exo-polymerases and other mutants that tolerate modified nucleotides and incorporate them into a strand of nucleic acid may be used.

In some embodiments, the polymerase is capable of reading through the conjugation linker. Polymerases capable of reading through the unnatural linker provided upon incorporation of oligonucleotide-tethered nucleotide may be the same or different compared to the polymerases capable of incorporating oligonucleotide-tethered nucleotide. In some embodiments, DNA polymerases commonly used for primer extension and/or amplification protocols are used. In some embodiments, polymerases capable of reading through the unnatural linker are chosen from DNA-dependent DNA polymerases, RNA-dependent DNA polymerases, DNA-dependent RNA polymerases and RNA-dependent RNA polymerases.

B. Nucleic Acid Sequencing

In some embodiments, the present disclosure relates to preparing libraries of nucleic acids to be used in nucleic acid sequencing. In some embodiments, the template nucleic acid sequence is DNA or RNA. In some embodiments, the template nucleic acid sequence is from double-stranded DNA and can be genomic DNA. Alternatively, the template nucleic acid sequence may be single-stranded DNA. In other embodiments the template nucleic sequence is total RNA, mRNA, or miRNA. In some embodiments, the template nucleic acids are nucleotide sequences provided by oligonucleotide-tethered binding agents (OTBA). In some embodiments, sequencing is massively parallel nucleic acid sequencing.

In some embodiments, library preparation for sequencing is performed by the following steps using an oligonucleotide-tethered nucleotide. First, a complementary primer is annealed to the template nucleic acid strand, contacted with oligonucleotide-tethered nucleotide and polymerase to be incorporated into a synthesized complementary nucleic acid strand. In some embodiments, where a deoxy version of the oligonucleotide-tethered nucleotide is used, the nucleic acid strand can be further extended by incorporating conventional nucleotides and oligonucleotide-tethered nucleotides. In some embodiments, where a dideoxy version of the oligonucleotide-tethered nucleotide is used, further extension of the strand by the polymerase is blocked by the terminating group on the incorporated oligonucleotide-tethered nucleotide. In some embodiments, the strand is then subjected to a primer extension-based reaction, e.g. PCR, including but not limited to, asymmetric PCR, indexing PCR, or a reverse transcription reaction and used in various sequencing methods. In some sequencing libraries are prepared by incorporating a tethered oligonucleotide that includes a universal handle sequence, and annealing a splint oligonucleotide to the universal handle sequence, wherein the splint oligonucleotide comprises sequencing adapters.

Methods of amplifying nucleic acid fragments are well known to a person skilled in this art. The amplification may, in some embodiments, be achieved by means of a polymerase chain reaction (PCR) or any isothermal DNA amplification method including but not limited to MDA, RCA, NASBA, LAMP, HDA, ICAN, NEAR and, EXPAR. The nucleic acid fragments may be quantified using a quantitative polymerase chain reaction, microarray, fluorometric or spectrophotometric analysis.

The technology described herein is not limited to any particular sequencing platform but is generally applicable and platform independent. In some embodiments, the technology is applicable to emulsion PCR-based methods, bead-based, and non-bead based methods.

Suitable methods of sequencing the produced nucleic acid molecules are well known to a person skilled in this art. For example, a nucleic acid fragment may be sequenced using any appropriate technique known in the art, such as Maxam-Gilbert, Sanger, pyrosequencing, sequencing-by-synthesis, sequencing-by-ligation, single-molecule real-time sequencing, mass spectrometry, massively parallel signature sequencing, polony sequencing, Illumina (Solexa) sequencing, semiconductor sequencing, DNA nanoball sequencing, Heliscope and single molecule sequencing.

C. Combinatorial Barcoding for Single Cell or Single Nuclei Analysis

Oligonucleotide-tethered dideoxynucleotides (OTDDN's) can be used to vastly simplify and improve combinatorial barcoding methods. In the context of single cell and single nuclei analysis, the quality of single cell/nuclei analysis protocols, e.g., that are based upon combinatorial barcoding of biomolecules of interest (e.g., cell surface molecules, proteins, nucleic acids including DNA, RNA, miRNA, and the like) are improved.

Combinatorial Barcoding Workflows

Figure 39:
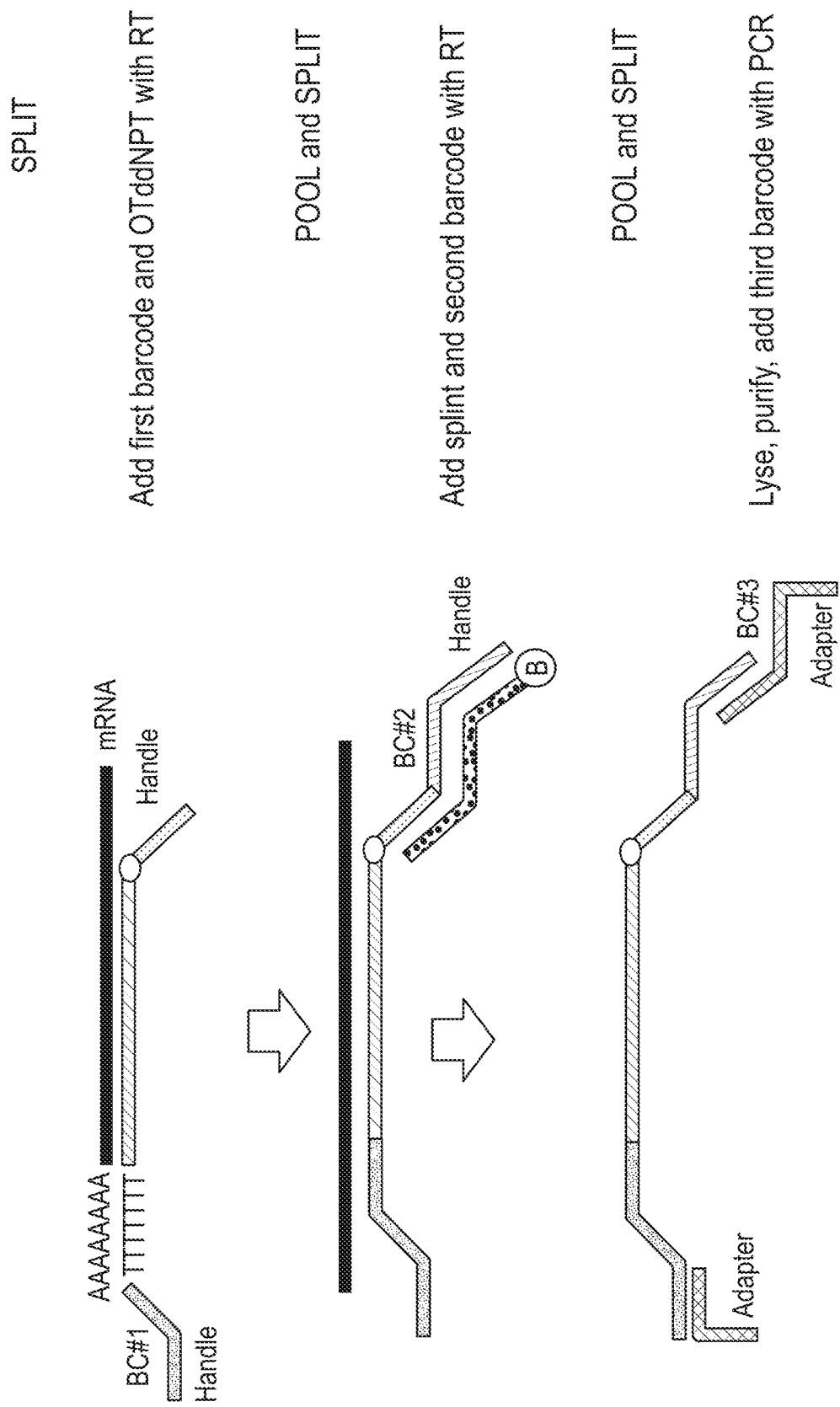
FIG. 39 is a schematic of an exemplary workflow showing the use of oligonucleotide-tethered dideoxynucleotides in a combinatorial barcoding workflow for single cell, whole transcriptome analysis. BC=barcode; B=biotin; SA=streptavidin.

Methods for improving whole transcriptome analysis at the cellular level are provided herein, as depicted in FIG. 39. While FIG. 39 depicts whole transcriptome analysis, the combinatorial barcoding workflows described herein can readily be adapted and multiplexed in order to analyze one or more specific nucleic acid and/or protein targets, e.g., by using a first extension primer with a target-specific sequence (such as a target mRNA or DNA sequence of interest, or a nucleotide that is tethered to a biomolecule of interest, such as OTBA as described elsewhere herein). Similarly, the combinatorial barcoding workflows described herein can be adapted for whole genome analysis (WGA), by randomly tagging gDNA with an OTDDN as described elsewhere herein, and following the combinatorial barcoding workflow provided herein. In the methods described herein, the biomolecules of individual sample cells are fixed, and the sample cells are subsequently permeabilized. When the combinatorial workflows provided herein are used to analyze proteins by using a oligonucleotide-tethered cell binding agent as described further below, the sample cells are treated with the OTBAs to allow binding prior to fixation.

Fixation and permeabilization methods useful in the methods disclosed herein are well known in the art. By way of example, fixation agents that can be used in the methods disclosed herein include, but are not limited to, formaldehyde, formalin, methanol, paraformaldehyde, methanol:acetic acid, and the like. For example, in some aspects, cells can be fixed by contacting the cells with, e.g., 1%, 2%, 3%, 4%, 5%, 6%, 7%, 8%, 9%, 10%, (v/v) or more, or any range in between of formaldehyde or paraformaldehyde, e.g., in phosphate buffered saline.

Agents for permeabilizing cells useful in the embodiments disclosed herein include, but are not limited to, triton 100, saponin, Tween 20, and organic solvents such as methanol, acetone, and the like. For example, in some aspects, cells can be treated with, e.g., 0.01 to 10% (v/v) tritonX 100, 1%, 2%, 3%, 4%, 5%, 6%, 7%, 8%, 9%, 10%, or more formaldehyde.

A fixed and permeabilized sample cell population to be analyzed is split into a plurality of first portions. By way of example, each of the first portions can be added to a different microwell or tube, such that each individual cell is randomly distributed to a first portion. Each of the first portions are subjected to a first extension reaction to generate a first extension product. For example, reverse transcriptase (RT) can be used for the first extension reaction to generate a first extension product that is cDNA. Each of the first portions is contacted with (i) a polymerase (e.g., reverse transcriptase to analyze RNA sample nucleic acids/polynucleotides), (iii) a first primer (e.g., a reverse transcriptase (RY) extension primer) that includes a first barcode (i.e., a first extension barcode or a 1$^{st}$ well-specific barcode) unique to each of the different first portions, (iv) nucleotides, and (v) at least one oligonucleotide-tethered ddNTP that includes a universal handle. The contacting step can be done under extension conditions (e.g., typical conditions for the polymerase used in the extension step).

For whole transcriptome analysis, the first extension primer can include a sequence to enable unbiased amplification of mRNAs. As such, first extension primers can include a poly(T) to enable unbiased priming of mRNAs. Alternatively, the first extension primers can include a sequence to facilitate random priming of cellular RNAs (e.g., a random hexamer). In some embodiments, the poly (T) or random primer is comprised at the 3' end of the first extension primer. In yet other methods, a combination of primers with poly(T) and primers that include a sequence to facilitate random priming are used in the extension reaction.

The improved combinatorial barcoding workflows described herein can be used in the context of analyzing target biomolecules, such as target mRNAs, target DNAs, target proteins, and the like. In workflows for targeted nucleic acid and protein analysis, the first extension primer can include a target-specific sequence. In the context of a target mRNA or DNA, for example, the first extension primer can include a sequence that specifically hybridizes to the target sequence(s) of interest. In the context of analysis of target proteins (or cell markers), an oligonucleotide-tethered binding agent that (i) specifically binds to the protein, biomolecule, or cell marker of interest and (ii) includes an associated oligonucleotide sequence that identifies the binding agent is allowed to bind to the sample cells prior to fixation. As such, the OTBA functions in the same manner as a target-specific sequence used to analyze a target nucleic acid. In this way, OTBA can bind a protein and be used translate data on protein expression into a format that can analyzed using equipment and methodology used for sequencing of nucleic acids. As methods using fluorophore-labeled antibodies can have issues with spectral overlap of fluorophores, converting a protein signal into a format that can be analyzed using equipment and methodology for sequencing of nucleic acids can allow for greater resolution of multiple protein signals. Also, methods with OTBAs can be performed without a need for use of a fluorophore and equipment for analysis of fluorophores (such as would be used for FACS sorting).

The skilled artisan will readily appreciate that the combinatorial workflows described herein below can readily be multiplexed. For example, by multiplexing the combinatorial barcoding workflow described herein, the transcriptome and one or more target biomolecules (e.g., target proteins, or the like) can be processed and analyzed simultaneously. For example, as described hereinbelow, cell populations can be contacted with one or more OTBA's (e.g., 1, 2, 3, 4, 5, 6, 7, 8, 9, 10 or more OTBA's) that include an oligonucleotide comprising a binding agent index and a 3' poly(A) tail. (See, FIG. 44). The fixed and permeabilized cells can be split into the first compartments and processed the same way as cells are processed for whole transcriptome analysis, i.e., using a first extension primer comprising a 3' poly(T) sequence.

In methods wherein the first compartments are microwells or tubes, the microwells or tubes can be provided that each include a first extension primer, and oligonucleotide-tethered ddNTPs. Optionally, microwells or tubes can further include a polymerase, nucleotides, or both. For example, in some embodiments, the microwells or tubes can include pre-loaded (e.g., dried down or in solution) first extension primers, etc.

The first extension results in the random incorporation of oligonucleotide-tethered ddNTPs into the first extension products (e.g., cDNA when the sample nucleic acids to be analyzed are RNA), thereby generating random termination points of each first nucleic acid extension product. The "stop" point of each extension product can advantageously be used as an identifier to determine the progeny of each first extension product. Each first nucleic acid extension product includes a first barcode (at its 5' end) that is common to all of the nucleic acid extension products within each individual first portion and unique relative to the first barcodes in other compartments/first extension products generated in other compartments, and a second universal handle at the 3' end that provides a 3' OH that can be extended in a subsequent reaction.

The plurality of first portions are combined, or pooled, e.g., into a single tube or well, and subsequently split into a plurality of second portions, e.g. within individual microwells, tubes or the like. The individual cells are thus again randomly distributed among individual second portions.

The second portions are contacted with splint oligonucleotides, a polymerase, and nucleotides. The splint oligonucleotides include a sequence at the 3' end that anneals to the second universal handle on the first nucleic acid extension product. The splint oligonucleotides may also contain a modification at the 3' end (e.g., a 3' amino, a 3' phosphate, a 3' dideoxynucleotide, or the like), to prevent extension of the splint. A template sequence for a third universal handle sequence is present at the 5' end of the splint oligonucleotide. Between the sequence that hybridizes to the second universal handle and the third universal handle, the splint oligonucleotides include a template sequence for a second barcode that is unique to each second portion. As such, the first extension products within the second portions are further extended to generate second extension products that comprise, from the 5' to 3' direction, a first universal handle sequence, cDNA, dideoxynucleotide, second universal handle, second barcode and a third universal handle.

In some examples, a third barcode and fourth universal handle can be added to the nucleic acid samples of the sample. Specifically, second portions can be combined/pooled, and split into a plurality of third portions, e.g., within individual microwells, tubes or the like. The individual cells are thus randomly distributed among individual third portions. Extension reactions using a second set of splint oligonucleotides to add barcodes unique to each portion following pooling and splitting can be performed multiple times, each iteration resulting in the addition of another barcodes unique to each portion (but common to all cells distributed to a particular portion) to the nucleic acids.

In some embodiments, the method includes a step of removing, blocking or digesting splint oligonucleotides, e.g., after generating the second nucleic acid extension products and prior to contacting a third portion with a second extension primer. In some embodiments, the splint oligonucleotides comprise a binding moiety, the method comprising the step of contacting the second portions or combined second portions with a compound comprising a capture moiety that facilitates binding and removal of splint oligonucleotides comprising cognate binding moieties. In some embodiments, the binding moiety and the cognate capture moiety are a binding pair chosen from the binding pairs of streptavidin and biotin, maltose and maltose binding protein, glutathione and glutathione S-transferase, chitin and chitin binding protein, or an aptamer and its antigen. In some embodiments, the capture moiety is immobilized on a solid support. In some embodiments, the solid support comprises a bead. In some embodiments, the bead is a magnetic or paramagnetic bead.

After a desired number of barcodes have been added to the nucleic acid extension products within each cell, the final portions can be contacted under lysis conditions, in order to lyse the cells and release the nucleic acid extension products. For example, a method may comprise combining the second portions, splitting the combined second portions, splitting into third portions, and generating a third nucleotide extension product, wherein the combination of the first, second, and third barcode sequences (or complements thereof) within each third nucleotide extension product is unique to each nucleic acid extension product originating from a single cell. By "unique," it means that the combination of the first, second, and third barcode sequences may be almost entirely unique, this term but does not exclude a chance repeat of one or more barcode.

In some embodiments, the OTDDNs can be incorporated into single cell or single nuclei workflows such as whole transcriptome analysis, whole genome analysis, directed mRNA analysis, short RNA (e.g., miRNAs), and the like, and combinations of these. By way of example only, provided herein is a workflow to analyze the transcriptomes of single cells or nuclei within a population of cells (See, FIG. 39).

In some embodiments, the combinatorial barcoding methods provided herein further include steps to fix and permeabilize cells or nuclei within a cell population, such that nucleic acids, proteins, and other biomolecules within the cell or nuclei remain intact and fixed within their cell of origin. At the same time, the permeabilization step functions to enable reagents (e.g., polymerases, nucleotides, primers, and the like) to enter the cells or nuclei wherein they can function in, e.g. reverse transcription, amplification reactions and the like. Many methods of fixing and permeabilizing cells and nuclei are known in the art. By way of example, methods for fixing and permeabilizing cells useful in the embodiments disclosed herein include, but are not limited to, those described in Rosenberg, et al. (2018) *Science* (360) 176-182, Supplementary Materials, U.S. Patent Application Publication No. U.S. 2016/0138086, and International Patent Application Publication No. WO 2014/060843.

In some embodiments, the combinatorial barcoding methods provided herein may further comprise lysing the cells after generating one or more extension products. Additionally, the combinatorial barcoding methods provided herein can also include one or more amplification reactions following the addition of the last barcode. In some embodiments, the amplification primers can anneal to universal handles present at the 3' and 5' ends of the extension products. The amplification primers can optionally include adapter sequences (e.g., sequencing adapters to enable the nucleic acid library to be processed and analyzed on a desired NGS platform as described elsewhere herein).

The combinatorial barcoding methods may also include one or more sample preparation steps including but not limited to purification of nucleic acids away from cellular debris following a lysis step, or the like.

D. Spatial Resolution of Biomolecules of Interest

The improved nucleic acid tagging and nucleic acid library preparation methods described herein can also be used to spatially resolve biomolecules of interest in tissue samples.

In some methods, a tissue sample can be contacted with an array of addressable primer that includes, in a 5' to 3' direction an addressable barcode domain (e.g., a first barcode that encodes positional information on the array) and a hybridization domain. (i e, a domain that enables hybridization of the addressable primer to polynucleotides of the tissue sample). The addressable barcode can include information relating to the x-coordinate and the y-coordinate on the array. Arrays of addressable barcode domains useful in the embodiments described herein are known in the art.

As used herein, the term "array" refers to a population of features or sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). Non-limiting examples of arrays of addressable barcodes that can be used in the embodiments described herein include the arrays described in International Patent Application No's. WO 2016/168825, WO 2012/140224, WO 2014/060483, WO 2016/162309, and the like. In some embodiments, the addressable primers are covalently linked to a solid surface.

The polynucleotides of the tissue sample can be RNA (e.g., mRNA), oligonucleotides of OTBA's bound to the tissue sample, or the like. Accordingly, the hybridization domain can facilitate unbiased hybridization to sequences of interest (e.g., a poly(T), or random sequence), or that enables hybridization to a specific target sequence (e.g., a specific mRNA sequence), or that enables hybridization to oligonucleotides of OTBA's.

The tissue sample can be contacted with the array of addressable primers to generate a first annealed complex in the presence of an oligonucleotide-tethered dideoxy nucleotide, non-tethered nucleotides, and a polymerase. Extension of the first annealed complex results in incorporation of the oligonucleotide tethered nucleotide (e.g., an oligonucleotide-tethered dideoxynucleotide) into a first extension product. The first extension products comprising the incorporated OTDDN can be manipulated as described elsewhere herein, e.g., to produce a nucleic acid library suitable for NGS sequencing.

The addressable primers may be covalently linked to the different features on the array. The addressable primers can further include a cleavage domain that provides a means of releasing at least a portion of the addressable primers from the feature on the array, wherein the released portion would comprise the positional barcode and the hybridization sequence. For example, the addressable primers can include a sequence that facilitates cleavage by a restriction enzyme, e.g., upon extension of the addressable primer in the presence of the tissue nucleic acids.

The tissue section may be visualized or imaged, e.g., stained and photographed, before or after the first extension products are Formed. Accordingly, in some aspects, the addressable barcode is correlated with a position within the tissue sample. In some embodiments, the methods described herein can be performed on a plurality of consecutive tissue sections to generate a three-dimensional profile of the biomolecules (e.g., RNA, DNA, protein) analyzed. As such, in some embodiments, the barcode(s) in the addressable printers further include a z-coordinate.

IV. Kits

Also provided are kits comprising the oligonucleotide-tethered nucleotides and/or oligo-tethered cell marker binding agents described herein. In some embodiments, the kit is for producing a nucleic acid sequencing library comprising: an oligonucleotide-tethered nucleotide and/or a oligo-tethered cell marker bus binding agent (OTBA) according as described above; and at least one of (i) A, C, G, U and/or T nucleotides, (ii) a polymerase, a primer and a buffer.

The polymerase that may be included in the kit may be chosen from Taq DNA polymerase, Vent® DNA polymerase, Deep Vent™ DNA polymerase, Pfx DNA polymerase, Pwo polymerase, SuperScript™ IV, SuperScript™ II, SuperScript III, SuperScript IV, Maxima™, RevertAid™ reverse transcriptases, Thermo Sequenase™, Sequenase™ V2.0, CycleSeg™, Phusion exo-, terminal deoxynucleotidyl transferase (TdT), Maxima H, Therminator™ polymerase, T7 DNA polymerase, T3 DNA polymerase, T4 DNA polymerase, T7 RNA polymerase, T3 RNA polymerase, SP6 RNA polymerase, DNA polymerase, Klenow fragment, *Thermophilus aquaticus* DNA polymerase, Tth DNA polymerase, Phusion™ DNA polymerase, SuperFi™ DNA polymerase, Bst DNA polymerase large fragment, Stoeffel fragment, 9° N™ DNA polymerase, Pfu DNA polymerase, Tfl DNA polymerase, Phi29 polymerase, Tli DNA polymerase, eukaryotic DNA polymerase beta, telomerase, KOD HiFi DNA polymerase, KOD DNA polymerase, Q-beta replicase, AMV reverse transcriptase, M-MLV reverse transcriptase, Phi6 reverse transcriptase, and HIV-1 reverse transcriptase and also various derivatives or mutants thereof.

Some embodiments relate to kits for combinatorial barcoding. The kits can include an oligonucleotide-tethered dideoxynucleotide as described herein and one or more of: a polymerase, one or more nucleotides, a plurality of first extension primers comprising a plurality of first barcodes, a plurality of second extension primers comprising a plurality of second barcodes, a plurality of amplification primers, comprising a plurality of third barcodes, and at least one splint oligonucleotide, or combinations thereof.

V. Definitions

While describing the present teachings in detail, it is to be understood that the disclosure is not limited to specific compositions or process steps, as such may vary. It should be noted that, as used in this specification and the appended claims, the singular form "a", "an" and "the" include plural references unless the context clearly dictates otherwise. Thus, for example, reference to "a dye" includes a plurality of dyes and reference to "a cell" includes a plurality of cells and the like.

Measured and measurable values are understood to be approximate, taking into account significant digits and the error associated with the measurement. All ranges are to be interpreted as encompassing the endpoints in the absence of express exclusions such as "not including the endpoints"; thus, for example, "within 10-15" includes the values 10 and 15. The use of "comprise", "comprises", "comprising", "contain", "contains", "containing", "include", "includes", and "including" are not untended to be limiting. It is to be understood that both the foregoing general description and detailed description are exemplary and explanatory only and are not restrictive of the teachings. Unless specifically noted in the specification, embodiments in the specification that recite "comprising" various components are also contemplated as "consisting of" or "consisting essentially of" the recited components.

The section headings used herein are for organizational purposes only and are not to be construed as limiting the desired subject matter iii any way. In the event that any literature incorporated by reference contradicts any term defined in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall prevail.

To facilitate an understanding of the present technology, a number of terms and phrases are defined below. Additional definitions are set forth throughout the detailed description.

The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the disclosure may be readily combined, without departing from the scope or spirit of the disclosure.

As used in this specification, the singular forms "a", "an", and "the" include plural reference unless the context clearly dictates otherwise. Thus, for example, a reference to "a part" includes a plurality of such parts, and so forth. The term "comprises" and grammatical equivalents thereof are used in this specification to mean that, in addition to the features specifically identified, other features are optionally present. Where reference is made in this specification to a method comprising two or more defined steps, the defined steps can be carried out in any order or simultaneously (except where the context excludes that possibility), and the method can optionally include one or more other steps which are carried out before any of the defined steps, between two of the defined steps, or after all the defined steps (except where the context excludes that possibility). Where reference is made hereinto "first" and "second" features, this is generally done for identification purposes; unless the context requires otherwise, the first and second features can be the same or different, and reference to a first feature does not mean that a second feature is necessarily present (though it may be present). Where reference is made herein to "a" or "an" feature, this includes the possibility that there are two or more such features.

The term "nucleotide" according to the present disclosure particularly relates to ribonucleotides, 2'-deoxyribonucleotides or 2',3'-dideoxyribonucleotides. Nucleotide analogues may be chosen from sugar- or backbone modified nucleotides, particularly of nucleotide analogs which can be enzymatically incorporated into nucleic acids. In some embodiments of the sugar-modified nucleotides, the 2'-OH or H-group of the ribose sugar is replaced by a group chosen from OR, R, halo, SH, SR, $NH_2$, NHR, $NR_2$ or CN, wherein R is C1-C6 alkyl, alkenyl or alkynyl and halo is F, Cl, Br or I. The ribose itself can be replaced by other carbocyclic or heterocyclic 5- or 6-membered groups such as a cyclopentane or a cyclohexene group. In one embodiment of a backbone modified nucleotide, the phospho(tri)ester group may be replaced by a modified group, e.g. by a phosphorothioate group or a H-phosphonate group. In further embodiments, nucleotide analogues include building blocks for the synthesis of nucleic acid analogs, such as morpholino nucleic acids, peptide nucleic acids or locked nucleic acids.

The term "nucleobase" refers to either native or non-native purine or pyrimidine bases. Nucleobases include adenine, cytosine, guanine, thymine, uracil, hypoxanthine, xanthine, 7-deaza-adenine and 7-deazaguanine, inosine.

As used herein, the phrase "dNTP" means deoxynucleotidetriphosphate, where the nucleotide comprises a native or non-native nucleobase.

As used herein, the phrase "ddNTP" means 2',3'-dideoxynucleotidetriphosphate, where the nucleotide comprises a native or non-native nucleobase.

As used herein, the term "oligonucleotide" is defined as a molecule comprising two or more deoxyribonucleotides and/or ribonucleotides. Its exact size will depend on many factors, which in turn depend on the ultimate function or use of the oligonucleotide. The oligonucleotide may be derived synthetically or by cloning.

As used herein, the term "polynucleotide" refers to a polymer molecule composed of nucleotide monomers covalently bonded in a chain. DNA (deoxyribonucleic acid) and RNA (ribonucleic acid) are examples of polynucleotides. The polynucleotide as used herein refers to double stranded or single stranded nucleic acids, such as DNA, RNA, linear or circular dsDNA/ssDNA, fragmented dsDNA/RNA, linear or circular RNA and other known forms or nucleic acids.

As used herein, the term "oligonucleotide-tethered nucleotide" refers to a molecule including two or more deoxyribonucleotides and/or ribonucleotides that is covalently attached to a nucleotide nucleobase. For example, two or more deoxyribonucleotides and/or ribonucleotides are covalently attached through triazole ring to a nucleotide nucleobase. Such covalent attachment may be a result of "click chemistry" process. In some examples oligonucleotide-tethered nucleotides can be referred to as OTDN (oligonucleotide-tethered deoxynucleotide) or OTDDN (oligonucleotide-tethered dideoxynucleotide).

As used herein, the term "double-stranded," when used in reference to a polynucleotide, means that some or all of the nucleotides between complementary strands of a polynucleotide are hydrogen bonded together to form a partial or complete double helix. A partially double stranded polynucleotide can have at least 10%, 25%, 50%, 60%, 70%, 80%, 90% or 95% of its nucleotides hydrogen bonded to a complementary nucleotide.

A single-stranded polynucleotide refers to a polynucleotide that has few to none hydrogen bonds with another polynucleotide such that a double helix is not formed or is unstable under a given set of hybridization conditions.

A "polymerase" is generally an enzyme that catalyzes the reaction between 3'-OH and 5'-triphosphate in nucleotides, oligomers, and their analogs to form nucleic acid polymers. Polymerases include, but are not limited to, DNA-dependent DNA polymerases, DNA-dependent RNA polymerases, RNA-dependent DNA polymerases, RNA-dependent RNA polymerases, template-independent DNA polymerase, template-independent RNA polymerases, T7 DNA polymerase, T3 DNA polymerase, T4 DNA polymerase, T7 RNA polymerase, T3 RNA polymerase, SP6 RNA polymerase, DNA polymerase 1, Klenow fragment, *Thermophilus aquaticus* DNA polymerase, Tth DNA polymerase, Phusion DNA Polymerase, SuperFi DNA Polymerase, Vent DNA polymerase, Deep Vent DNA polymerase, Bst DNA Polymerase Large Fragment, Stoeffel Fragment, 9° N DNA Polymerase, Pfu DNA Polymerase, Tfl DNA Polymerase, Phi29 Polymerase, Tli DNA polymerase, eukaryotic DNA polymerase beta, telomerase, KOD HiFi, KOD1 DNA polymerase, Q-beta replicase, terminal transferase (TdT), AMV reverse transcriptase, M-MLV reverse transcriptase, Phi6 reverse transcriptase, HIV-1 reverse transcriptase, Thermo Sequenase (Thermo Fisher Scientific). These polymerases include wild-type, mutant isoforms, chimeric forms, and genetically engineered variants such as exo-polymerases and other mutants, e.g., that tolerate modified nucleotides and incorporate them into a strand of nucleic acid.

As used herein, the term "barcode" refers to a known nucleic acid sequence that allows some feature of a nucleic acid with which the barcode is associated to be identified. In some embodiments, the feature of the nucleic acid to be identified is the sample or source from which the nucleic acid is derived. By way of example only, some embodiments described herein describe the addition of multiple barcodes (e.g., 2, 3, 4, 5, 6, or more) to the nucleic acids of interest in a single cell present in a population of cells. The unique combination of barcodes added to the nucleic acids of each individual cells can advantageously enable the identification of the cell from which the tagged nucleic acid of interest was derived. In some embodiments, barcodes are at least 3, 4, 5, 6, 7, 8, 9, 10, 11, 12, 13, 14, 15, or more nucleotides in length. In some embodiments, barcodes are shorter than 10, 9, 8, 7, 6, 5, or 4 nucleotides in length. In some embodiments, barcodes associated with some nucleic acids are of a different length than barcodes associated with other nucleic acids. In general, barcodes are of sufficient length and comprise sequences that are sufficiently different to allow the identification of samples based on barcodes with which they are associated. In some embodiments, a barcode and the sample source with which it is associated can be identified accurately after the mutation, insertion, or deletion of one or more nucleotides in the barcode sequence, such as the mutation, insertion, or deletion. In some embodiments, each barcode in a plurality of barcodes differs from every other barcode in the plurality at two or more nucleotide positions, such as at 2, 3, 4, 5, 6, 7, 8, 9, 10, or more positions. In some embodiments, one or more adaptors comprise(s) at least one of a plurality of barcode sequences. In some embodiments, methods of the technology further comprise identifying the sample or source from which a target nucleic acid is derived based on a barcode sequence to which the target nucleic acid is joined. In some embodiments, methods of the technology further comprise identifying the target nucleic acid based on a barcode sequence to which the target nucleic acid is joined. Some embodiments of the method further comprise identifying a source or sample of the target nucleotide sequence by determining a barcode nucleotide sequence. Some embodiments of the method further comprise molecular counting applications (e.g., digital barcode enumeration and/or binning) to determine expression levels or copy number status of desired targets. In general, a barcode may comprise a nucleic acid sequence that when joined to a target nucleic acid serves as an identifier of the sample from which the target polynucleotide was derived.

As used herein, the term "primer" or "extension primer" refers to an oligonucleotide, whether occurring naturally or produced synthetically, that is capable of acting as a point of initiation of nucleic acid synthesis when placed under appropriate conditions, e.g., in the presence of nucleotide triphosphates and a polymerase enzyme (for example, a thermostable polymerase enzyme) in an appropriate buffer ("buffer" includes appropriate pH, ionic strength, cofactors, etc.) and at a suitable temperature. The primer may be, in some embodiments, single-stranded for maximum efficiency in amplification but may alternatively be double-stranded. If double-stranded, the primer is first treated to separate its strands before being used to prepare extension products. In some embodiments, the primer is an oligodeoxyribonucleotide. The primer must be sufficiently long to prime the synthesis of extension products. The exact lengths of the primers will depend on many factors, including temperature, source of primer, the polymerase enzyme (for example, whether it is thermostable), and use of the method. As used herein, the term "adapter" refers generally to any linear oligonucleotide that can be added, for example, ligated, to a nucleic acid molecule, thereby generating nucleic acid products that can be sequenced on a sequencing platform. In some embodiments, adapters include two reverse complementary oligonucleotides forming a double-stranded structure.

In some embodiments, an oligonucleotide such as a primer, adapter, etc. comprises a "universal" sequence. A universal sequence is a known sequence, e.g., for use as a primer or probe binding site using a primer or probe of a known sequence (e.g., complementary to the universal sequence). While a template-specific sequence of a primer, a barcode sequence of a primer, and/or a barcode sequence of an adaptor might differ in embodiments of the technology, e.g., from fragment to fragment, from sample to sample, from source to source, or from region of interest to region of interest, embodiments of the technology provide that a universal sequence is the same from fragment to fragment, from sample to sample, from source to source, or from region of interest to region of interest so that all fragments comprising the universal sequence can be handled and/or treated in a same or similar manlier, e.g., amplified, identified, sequenced, isolated, etc., using similar methods or techniques (e.g., using the same primer or probe).

As used herein, the term "handle" (interchangeably used with the terms "amplification handle" or "PCR handle") refers to a functional component an oligonucleotide sequence which itself is an oligonucleotide or polynucleotide sequence that provides an annealing site for amplification of the construct oligonucleotide sequence. Handles used in the present embodiments can be formed of polymers of DNA, RNA, PNA, modified bases or combinations of these bases, or polyamides, etc. In some embodiments, the universal handles used in the embodiments disclosed herein are about 10 of such monomeric components, e.g., nucleotide bases, in length. In other embodiments, the universal handle is at least about 5 to 100 monomeric components, e.g., nucleotides, in length. Thus in various embodiments, the universal handles described herein are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 80, 91, 92, 93, 94, 95, 96, 97, 98, 99 or up to 100 monomeric components, e.g., nucleic acids. As such, the "universal handles" described herein can be generic sequences suitable as an annealing site for extension by a polymerase as described elsewhere herein, e.g., a reverse transcriptase, a DNA polymerase, or the like, or contain extension primer binding sites, sequencing primer binding sites, or the like.

The term "unique molecular indices" (UMIs) means the sequences of nucleotides applied to or identified in DNA molecules that can be used to distinguish individual DNA molecules from one another. Since UMIs are used to identify DNA molecules, they are also referred to as unique molecular identifiers. UMIs may be sequenced along with the DNA molecules with which they are associated to determine whether the read sequences are those of one source DNA molecule or another.

As used herein, the term "splint oligonucleotide" refers to an oligonucleotide that is used as a template to facilitate the extension or ligation of nucleic acid sequences to an existing nucleic acid product in a template dependent manner to form an extended nucleic acid product, but that is not extended or incorporated into a nucleic acid product. By way of example only, in some embodiments described herein, a splint oligonucleotide can include the following components: (i) a sequence that enables hybridization to a cognate handle sequence present in a nucleic acid product to be extended; (ii) a barcode sequence; and (iii) a sequence that is a template for the incorporation of a handle sequence different from the handle in (i) into an extended nucleic acid product, as shown in FIG. 38. Splint oligonucleotides optionally include a means to facilitate removal from reaction mixtures, e.g., a biotin moiety or the like. In some aspects, splint oligonucleotides also include a modification that prevents extension of the splint oligonucleotide from the 3' end (e.g., a 3' amino, a 3' phosphate, a 3' dideoxy, or the like).

As used herein, the term "nucleic acid synthesis" refers to any in vitro method for making new strand of polynucleotide or elongating existing polynucleotide (i.e., DNA or RNA). Synthesis, according to the disclosure, includes amplification, which increases the number of copies of a polynucleotide template sequence with the use of a polymerase. Polynucleotide synthesis results in the incorporation of nucleotides into a polynucleotide (i.e., a primer), thereby forming a new polynucleotide molecule complementary to the polynucleotide template. The formed polynucleotide molecule and its template can be used as templates to synthesize additional polynucleotide molecules.

As used herein, the term "template DNA molecule" refers to a strand of a nucleic acid from which a complementary nucleic acid strand is synthesized by a DNA polymerase, for example, in a primer extension reaction.

As used herein, the term "template dependent manner" refers to a process that involves the template dependent extension of a primer molecule (e.g., DNA synthesis by DNA polymerase, cDNA synthesis by reverse transcriptase, or the like). The term "template dependent manner" typically refers to polynucleotide synthesis of RNA or DNA wherein the sequence of the newly synthesized strand of polynucleotide is dictated by the well-known rules of complementary base pairing.

As used herein, the term "complementary" refers to the broad concept of sequence complementarity between regions of two polynucleotide strands or between two nucleotides through base-pairing. It is known that an adenine nucleotide is capable of forming specific hydrogen bonds ("base pairing") with a nucleotide which is thymine or uracil. Similarly, it is known that a cytosine nucleotide is capable of base pairing with a guanine nucleotide.

By "tag" or "oligonucleotide tag" is meant an oligonucleotide portion of the library at least part of which encodes information. "Taq" can be any nucleotide sequence added to the nucleic acid with oligonucleotide-tethered nucleotide. Non-limiting examples of such information include the addition (e.g., by a binding reaction) of a component (i.e., a scaffold or a building block, as in a scaffold tag or a building block tag, respectively), the headpiece m the library, the identity of the library (i.e., as in an identity tag), the use of the library (i.e., as in a use tag), and/or the origin of a library member (i.e., as in an origin tag).

As used herein, the term "library", when used in reference to nucleic acids, is intended to mean a collection of nucleic acids having different chemical compositions (e.g., different sequence, different length, etc.). Typically, the nucleic acids in a library will be different species having a common feature or characteristic of a genus or class, but otherwise differing M some way. For example, a library can include nucleic acid species that differ in nucleotide sequence, but that are similar with respect to having a sugar-phosphate backbone. A library can be created using techniques known in the art. Nucleic acids exemplified herein can include nucleic acids obtained from any source, including for example, digestion of a genome (e.g., a human genome) or a mixture of genomes. In another example, nucleic acids can be those obtained from metagenomic studies of a particular environment or ecosystem. The term also includes artificially created nucleic acid libraries such as DNA libraries.

The terms "click chemistry" and "click reaction" are used interchangeably herein and are intended to be consistent with their use in the art. Generally, click chemistry reactions are fast (e.g. quick to completion of reaction), simple, easily purified, and regiospecific. Click chemistry includes reactions such as, but not limited to, copper catalyzed azide-alkyne cycloaddition (CuAAC); strain-promoted azide-alkyne cycloaddition (SPAAC) also known as copper-free click chemistry; strain-promoted alkyne-nitrone cycloaddition (SPANC); alkyne hydrothiolation; and alkene hydrothiolation. Click chemistry using copper as a catalyst often includes a Cu(I) stabilizing ligand that is labile. Without being bound by any particular theory, the ligand can stabilize or protect the Cu(I) ion from oxidizing from the reactive Cu(I) to Cu(II) and can also act as a proton acceptor reducing or eliminating requirement of a base in the reaction. Click chemistry between polynucleotides can in some embodiments, be assisted by using a moiety that brings the two reacting partners in close enough proximity to react.

As used herein, and unless otherwise specified, the term "azide" or "azido" refers to $N_3$, or —N=N$^+$=N$^-$, or —N—N$^+$≡N.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 10%, 9%, 8%, 7%, 6%, 5%, 4%, 3%, 2%, 1%, 0.5%, or 0.05% of a given value or range.

As used herein, "labels" are chemical or biochemical moieties useful for labeling a nucleic acid. "Labels" include, for example, fluorescent agents, chemiluminescent agents, affinity agents, blocking groups, chromogenic agents, quenching agents, radionucleotides, enzymes, substrates, cofactors, inhibitors, nanoparticles, magnetic particles, and other moieties known in the art. Labels are capable of generating a measurable signal and may be covalently or non-covalently joined to an oligonucleotide or nucleotide. In some examples, an oligonucleotide or a portion of an oligonucleotide of oligonucleotide-tethered nucleotide as disclosed herein may serve as a label.

As used herein, the term "linker," as used herein, refers to a single covalent bond or a series of stable covalent bonds incorporating nonhydrogen atoms chosen from of C, N, O, S and P. Exemplary linking members include at least one moiety chosen from —C(O)NH—, —C(O)C—, —NH—, —S—, —O—, alkyl, alkenyl, and alkynyl chain. A linker may also comprise a combination of 2 or more linking members.

As used herein, the term "alkyl" or "alkylene" refers to a radical derived from a saturated, linear or branched hydrocarbon chain, for example, from 1 to 12 carbon atoms or 1 to 6 carbon atoms, 1 to 4 carbon atoms or 2 to 3 carbon atoms. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and any isomers, methylene, ethylene, propylene, isopropylene, n-butylene, pentylene, and the like.

As used herein, the term "alkenyl" and "alkenylene" refers to a radical group derived from a straight or branched hydrocarbon chain of 2 to 10 carbon atoms containing at least one carbon-carbon double bond. Examples include ethenyl (vinyl), 1-propenyl, 2-propenyl isopropenyl, butenyl, buta-1,4-dienyl, pentenyl, hexenyl, ethenylene), propenylene, butenylene, hexenylene, and the like.

As used herein, the term "alkynyl" or "alkynylene" refers to a divalent group derived from a straight or branched hydrocarbon chain of 2 to 10 carbon atoms containing at least one carbon-carbon triple bond.

The term "amino" refers to the $NR^1R^2$ type, where $R^1$ and $R^2$ in dependently are selected from hydrogen and C1-C8 alkyl groups.

As used herein, the term "polyalkylene glycol" refers to straight or branched polyalkylene glycol polymers such as polyethylene glycol, polypropylene glycol, and polybutylene glycol. Exemplary polyalkylene glycols have from 2 to 10 alkylene glycol units. The term "alkylene glycol subunit" refers to a single alkylene glycol unit. For example, an ethylene glycol subunit would be —O—CH$_2$—CH$_2$—. Exemplary polyalkylene glycols include polyethylene glycol having 2 to 10 ethylene glycol units, and in particular embodiments, having 2, 4, or 6 ethylene glycol units also referred to as PEG2, PEG4 and PEG6 respectively.

The term "alkoxy" or the group —OR$^3$ refers to wherein R$^3$ is a C1-8 alkyl group. Examples include OC1-8alkyl, such as —OMe (methoxy), —OEt (ethoxy), —O(nPr) (n-propoxy), —O(iPr) (isopropoxy), —O(nBu) (n-butoxy), —O(iBu) (isobutoxy), —O(tBu) (tert-butoxy), and the like.

It will be understood that the chemical structures disclosed herein are representations of one of the possible resonance structures by which each given structure can be represented. Further, it will be understood that, by definition, resonance structures are merely a graphical representation used by those of skill in the art to represent electron delocalization, and that the present disclosure is not limited in any way by showing one particular resonance structure for any given structure The term "isolated", when used herein in reference to a nucleic acid polymer, means a nucleic acid polymer, which by virtue of its origin or manipulation is separated from at least some of the components with which it is naturally associated or with which it is associated when initially obtained. By "isolated," it is alternatively or additionally meant that the nucleic acid polymer of interest is produced or synthesized by the hand of man.

The present disclosure will now be described in further detail, by way of example only, with reference to the following Examples and related Figures.

EXAMPLES

The following are examples of methods, uses, and compositions disclosed herein. It is understood that various other embodiments may be practiced, given the general and detailed descriptions provided above. The following examples are given for the purpose of illustrating the present teachings and shall not be construed as being a limitation on the scope of the disclosure or claims.

Example 1. Preparation of Oligonucleotide-Tethered Nucleotides

A. Preparation of Azide-Modified Nucleotides

Amino-modified nucleotides, such as 5-propargylamino-dCTP (compound 6) or 7-deaza-7-propargylamino-dATP (compound 7) are commercially available from Jena Bioscience (SKU NU-1611-1 and NU-809). Utilizing different linkers bearing azido-NHS-esters corresponding azido-substituted-dCTPs were synthesized by reaction with the desired 2,5-dioxopyrrolidin-1-yl 2-azido-compound in a pH 9 solution of Na$_2$CO$_3$/NaHCO$_3$ (FIG. 7) giving the yields in interval of 50-90%.

According to the same reaction conditions the azido-C2-dATP was synthesized (FIG. 8).

B. Preparation of Alkyne-Modified Oligonucleotide

Oligomer: (AldU)TTATATATTATTGGAGACTGAC-TACCAGATGTAACA (SEQ ID NO: 33) is commercially available with the alkyne modification from a variety of commercial suppliers. The sequence of this oligonucleotide was originally disclosed in Stasevskij et al, 2017, however in this example the alkyne modification is added first to the 5'-end base of the oligonucleotide. Oligonucleotides that are alkyne modified at their 5'-terminal nucleobase or 5'-terminal phosphate are commercially available from various commercial suppliers.

C. Click Reaction—Synthesis of Oligonucleotide-Tethered-dCTPs

For all Click azide-alkyne cycloaddition reactions, the "CuAAC Biomolecule Reaction Buffer Kit (THPTA based)" (cat. No. CLK-072, Jena Bioscience) was used according to the manufacturer instructions. The reaction conditions were as follows: 42 µM oligomer (SEQ ID NO: 33 or SEQ ID NO: 23), 2 mM CuSO$_4$, 10 mM THPTA, 0.1 M sodium ascorbate, 78 mM sodium phosphate buffer (pH 7), 84 µM Azide precursor.

Using the Click-reaction five different oligonucleotide-tethered deoxynucleotides were synthesized (FIG. 9). Reaction mixtures were analyzed and purified with liquid chromatography. The results of these reactions are summarized in Table 1.

| Oligonucleotide SEQ ID | Nucleotide with azide modification | Reaction Time | Conversion |
|---|---|---|---|
| 33 | Azido-C2-dCTP | 50 min | 81% |
| 33 | Azido-C4-dCTP | 1 h 30 min | 76% |
| 33 | Azido-C6-dCTP | 1 h | 70% |
| 33 | Azido-PEG2-dCTP | 1 h | 72% |
| 33 | Azido-PEG4-dCTP | 1 h 30 min | 80% |
| 23 | Azido-C2-dCTP | 50 min | 82% |
| 23 | Azido-C4-dCTP | 3 h | 51% |
| 23 | Azido-C6-dCTP | 1 h | 74% |
| 23 | Azido-PEG2-dCTP | 2 h | 66% |
| 23 | Azido-PEG4-dCTP | 1 h 30 min | 68% |

Click reactions, resulting in oligonucleotide-tethered nucleotides can also be made using azido-modified nucleotides and oligonucleotides with alkene group attached to the phosphate of the 5' terminus of the oligonucleotide (as shown in compound of formula C1) via hexynyl linker, for example, when an oligonucleotide is modified with Alxyl (Metabion) modification. Compound of formula E2 is provided as an example.

D. Click Reaction—Synthesis of Oligonucleotide-Tethered-ddUTP

Compound 9 was subsequently utilized m a cycloaddition (click) reaction with an oligonucleotide (SEQ ID NO: 33 or SEQ ID NO: 23) (FIG. 10). "CuAAC Biomolecule Reaction Buffer Kit (THPTA based)" from Jena Bioscience was used for the Click reaction. The product, compound 10, was purified by reverse phase chromatography and confirmed by mass spectrometry. Alternatively, oligonucleotide with alkyne group attached to the phosphate of the 5' terminus of the oligonucleotide via hexynyl linker was used in a click reaction with Compound 9.

Example 2. Incorporation of Oligonucleotide-Tethered-dNTP by Different Polymerases A selection of different polymerases has been tested for capability of incorporating oligonucleotide-tethered-dNTPs into synthesized strand. According to the literature, it is expected for enzymes from family A, family B, the reverse transcriptase (RT) family, and terminal deoxynucleotidyl transferase (TdT) to be capable of incorporating bulky nucleotide analogs. Nevertheless, this may depend on the nucleotide analog itself (Anderson et. al, 2005; Tauraite et al, 2017).

A. Incorporation of Oligonucleotide-Tethered Deoxynucleotides

TABLE 2

| Substrate name | SEQ ID | Substrate composition | |
|---|---|---|---|
| Cy5-29\|\|49 | 24 | Cy5-TGCAGACATGGGTAGGCATCCTTGGCGTA | 29 nt |
| | 27 | ACGTCTGTACCCATCCGTAGGAACCGCATGACATCGACTCAACTCGCTG | 49 nt |
| Cy5-B29\|\|30 | 24 | Cy5-TGCAGACATGGGTAGGCATCCTTGGCGTA | 29 nt |
| | 28 | ACGTCTGTACCCATCCGTAGGAACCGCATG | 30 nt |
| Cy5-29 | 24 | Cy5-TGCAGACATGGGTAGGCATCCTTGGCGTA | 29 nt |

T in bold represents biotin-modification.

The experimental system was based on the extension of the protruding 5' end in the duplex of a primer and an oligonucleotide (e.g. duplex of SEQ ID NOS: 24 and 27, FIG. 31). Reaction with native dNTPs resulted in the complete filling of the protruding end and primer elongation whereas incorporation of a single oligonucleotide-tethered deoxy/dideoxynucleotide resulted in primer labeling with oligonucleotide. Primer extension reactions were conducted at optimal buffers and temperatures of each tested polymerase. Reaction products were then resolved on a 15% TBE-Urea PAGE. Primer extension products were detected as the elongation primer SEQ ID NO: 24 had 5'-Cy5 fluorescent label.

A type polymerase (Taq DNA Polymerase, rec.): 2 pmol Cy5-29\|\|49 substrate (SEQ ID NOS: 24 and 27, FIG. 31), 20 pmol OTDN, 1× Taq buffer, 2.5 U Taq DNA polymerase (Thermo Scientific, #EP0405), 25 mM $MgCl_2$, incubated 95° C. for 10 s, and then at 60° C. for 10 min.

B type polymerase (Phusion exo-, Thermo Scientific): 2 pmol Cy5-29\|\|49 substrate, 20 pmol OTDN, incubated at 95° C. for 10 s, and then at 60° C. for 10 min.

Figure 11A:
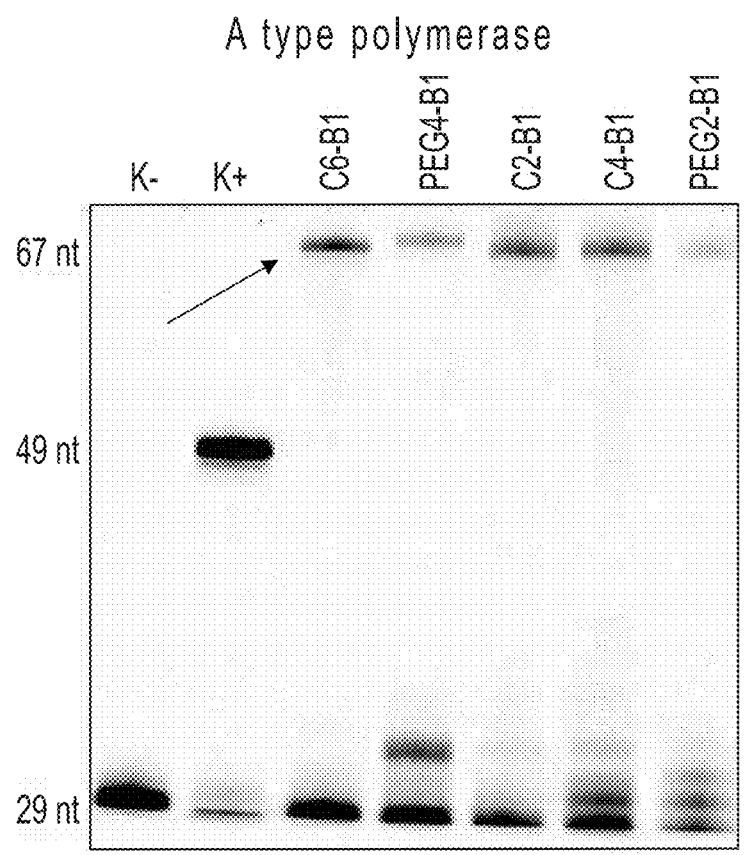
FIGS. 11A-11C depict the results of an experiment that tests the ability of different types of polymerases to incorporate an oligonucleotide-tethered nucleotide. Arrows indicate the click-reaction product; K– lane shows Cy5-labeled strand before the reaction, K+ lane shows reaction product using the 4 native dNTPs (A and B) or using dCTP (C); C6-B1, PEG4-B1, C2-B1, C4-B1 and PEG2-B1 correspond to the click reaction products as provided in Table 1, B1 corresponds to SEQ ID NO: 33.
Figure 11B:
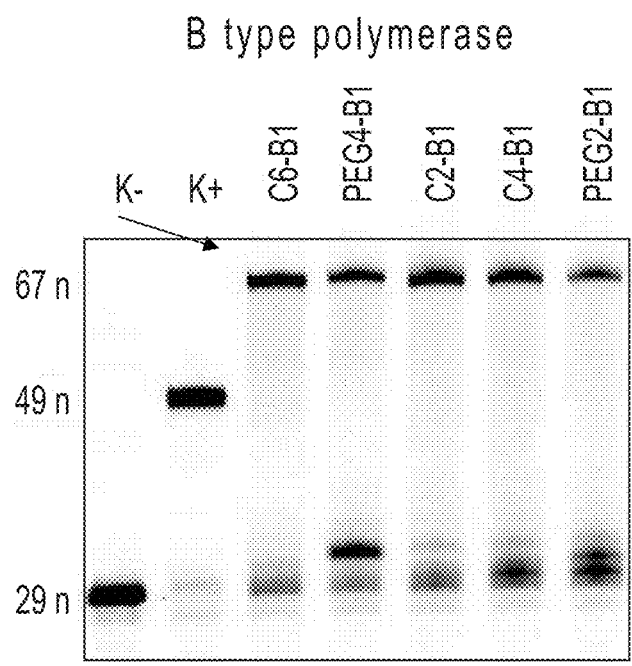
Figure 11C:
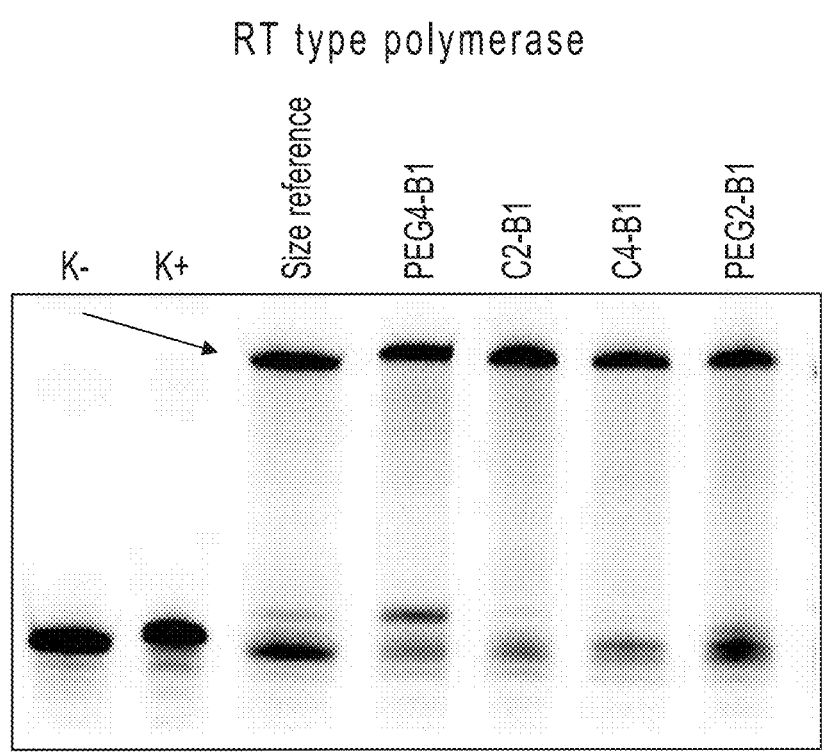

RT type polymerase (Maxima H-): 5 pmol Cy5-B29\|\|30 substrate (SEQ ID NOS: 24 and 28, FIG. 32), 50 pmol OTDN, 200 U Maxima H- RT (Thermo Scientific, #EP0752), 1×RT buffer, incubated at 50° C. for 20 min (FIGS. 11A-11C).

As can be seen from FIGS. 11A-11C, under reaction conditions (such as buffer and reaction temperature) typical and recommended for the corresponding enzymes, all tested polymerases were able to incorporate the oligonucleotide-tethered nucleotides. Also, oligonucleotide-tethered nucleotides that comprised various linkers were incorporated by each of the tested polymerases.

Figure 12B:
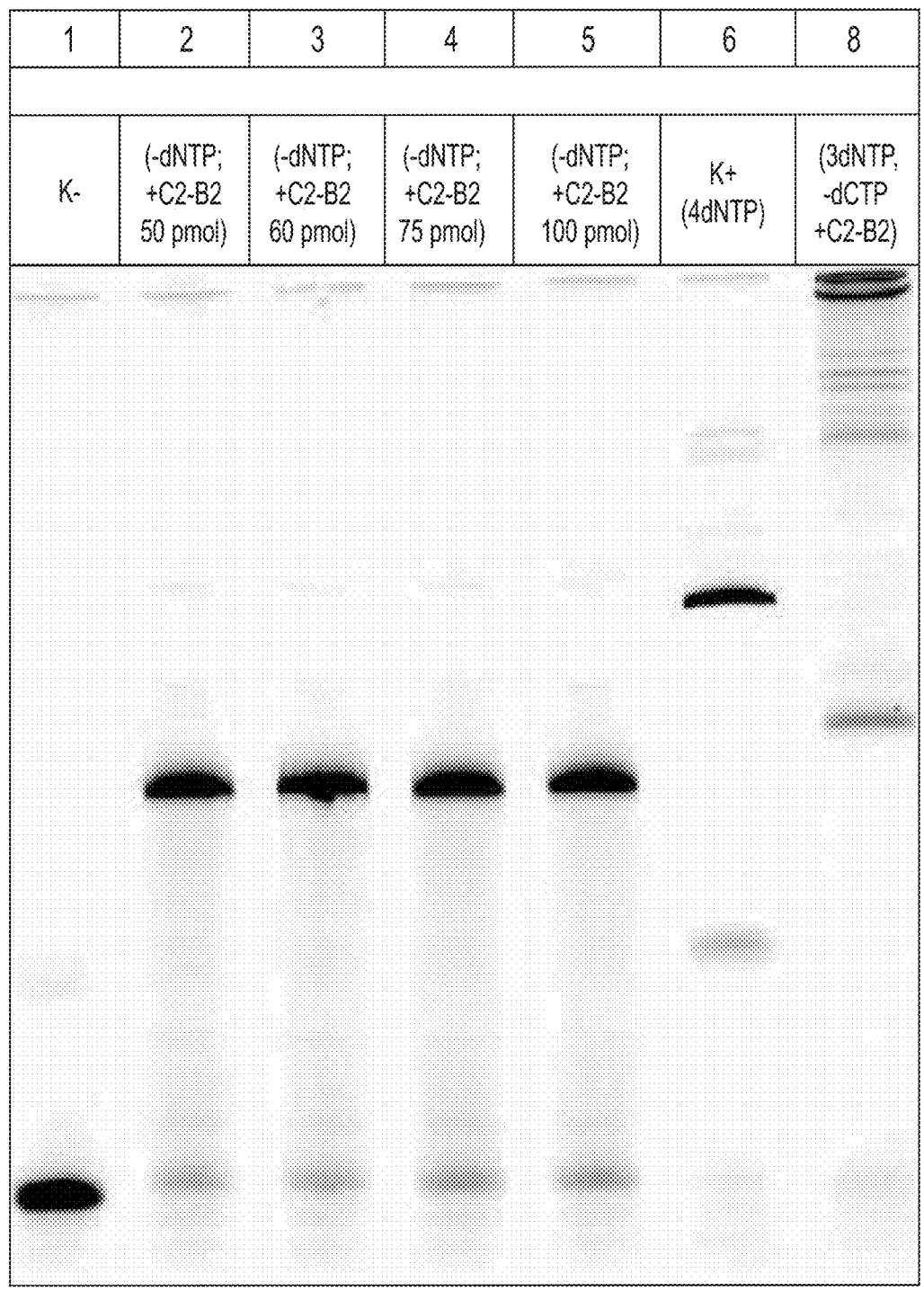

It was also confirmed that RT polymerase is capable of performing multiple incorporation of oligonucleotide-tethered deoxynucleotides. A 112 nt RNA fragment (SEQ ID NO: 30) was annealed to a Cy5-labeled complementary DNA primer (SEQ ID NO: 29) and subjected to primer extension reaction conditions with RT polymerase (FIG. 12A, arrows show oligonucleotide-tethered dCTP incorporation sites). The reaction mixture contained oligonucleotide-tethered deoxycytidine and unmodified (native) dATP, dTTP and dGTP. Reaction products were then resolved on a 20% TBE-Urea PAGE (FIG. 12B). Multiple bands in lane 8 confirms multiple oligonucleotide-tethered nucleotide incorporation events. Thus, under typical reaction conditions (such as buffer and reaction temperature) Maxima H- RT was able to incorporate the oligonucleotide-tethered nucleotides in multiple positions of a synthesized DNA strand. Also, reverse transcriptase was capable of incorporation of the oligonucleotide-tethered nucleotides and further extending the nucleic acid strand when either a DNA/DNA or DNA/RNA primer/template system was used.

B. Incorporation of Oligonucleotide-Tethered Dideoxynucleotide

Similar experimental system as with oligonucleotide-tethered deoxynucleotides was used. Filling of protruding 5' end in the duplex of two annealed oligonucleotides was performed. Reaction with dTTPs resulted in the complete filling of the protruding end and primer elongation by 10 nucleotides whereas incorporation of a single oligonucleotide-tethered dideoxynucleotide resulted in primer labeling with oligonucleotide of 23 nt (SEQ ID NO:2 for terminal deoxynucleotidyl transferase (TdT) and poly(U) polymerase, and SEQ ID NO: 1 for other polymerases reactions).

Figure 13:
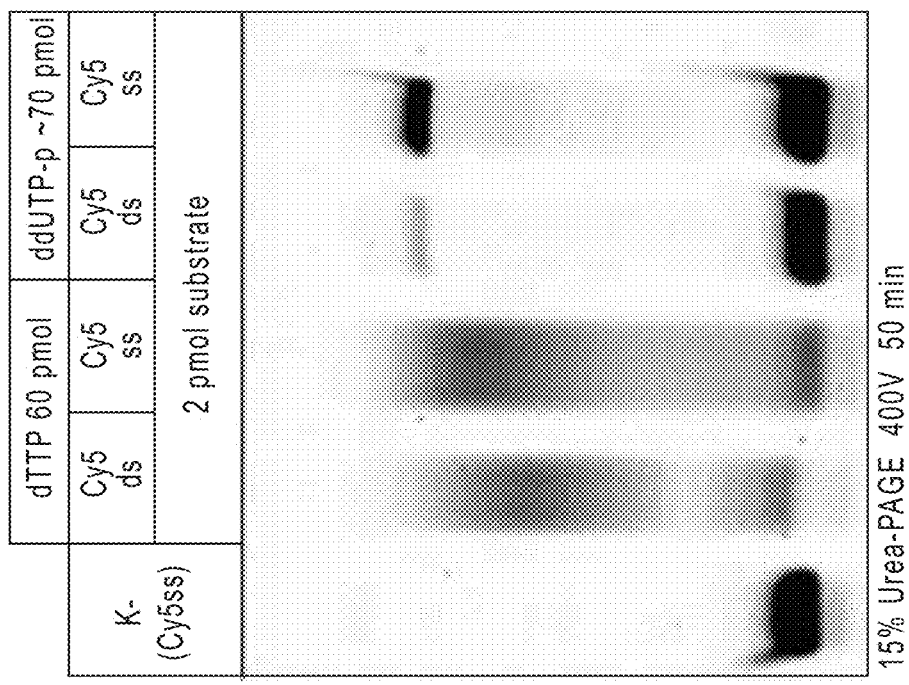
FIG. 13 shows incorporation of ddUTP and a PAGE gel. Namely, a scheme depicting ddUTP incorporation by TdT on double-stranded and single stranded nucleic acid is provided. The results were analyzed using PAGE gel. K– lane shows Cy5-labeled strand before the reaction; ddUTP-p lane shows successful oligonucleotide-tethered ddUTP (SEQ ID NO: 2) incorporation.
Figure 13:
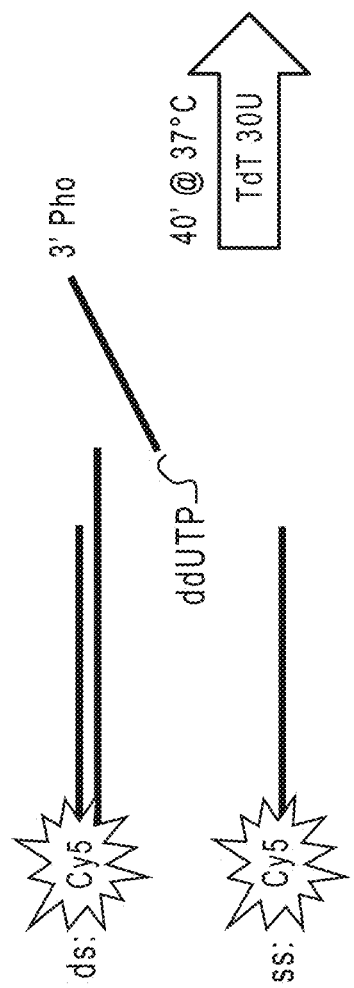
Figure 14:
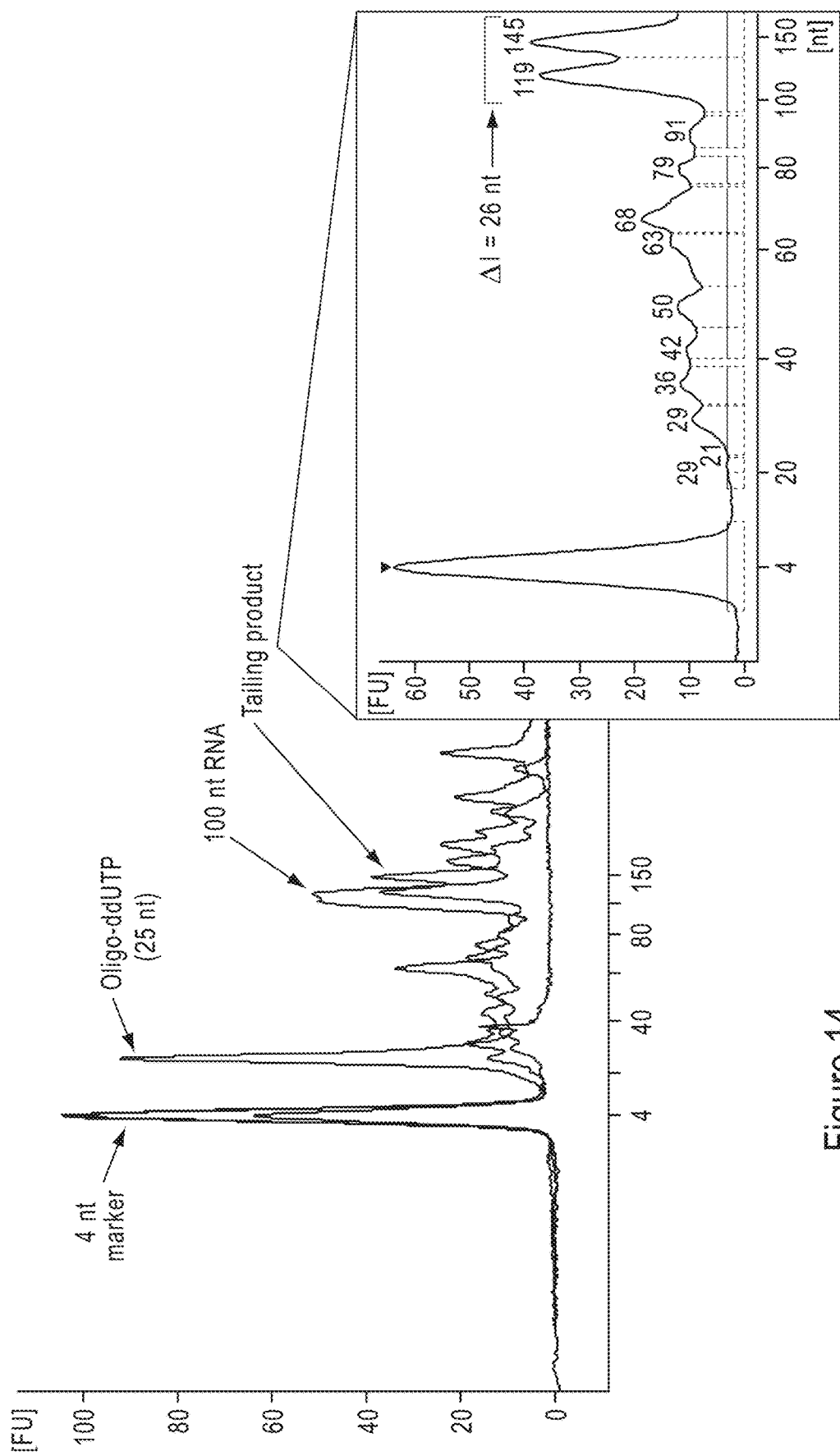
FIG. 14 shows the experimental results of poly(U) polymerase labeling of the 3' ends of RNA. This experiment confirmed that poly(U) polymerase incorporates oligonucleotide-tethered ddUTP.

Primer extension reactions were conducted at optimal buffers and temperatures for each tested polymerase. 2 pmol of substrate oligonucleotide duplex (SEQ ID NOS: 31 and 32, FIG. 33) and 20 pmol of either dTTP or oligonucleotide-tethered ddUTP (corresponding to compound 10 structure) were used per reaction. Reaction products were then resolved on a 15% TBE-Urea PAGE (TdT (Thermo Scientific) results are provided in FIG. 13, results of other polymerases are in FIGS. 15A-15E). Primer extension products were detected as the elongation primer had 5'-Cy5 fluorescent label. The ability of poly(U) polymerase (New England Biolabs, MA, USA) to label 3' ends of RNA by incorporation of oligonucleotide-tethered dideoxynucleotide was tested on synthetic 100 nt transcript. 1 pmol of RNA and 10 pmol of oligonucleotide-tethered ddUTP (SEQ ID NO: 2) were used in a tailing reaction which was conducted according to the manufacturers' recommendations. Reaction products were purified using Collibri™ Library Cleanup Kit (Thermo Scientific) and analyzed on Agilent 2100 Bioanalyzer using Small RNA Kit (FIG. 14). Results of this experiment confirm that poly(U) polymerase incorporates oligonucleotide-tethered ddUTP.

Figures 15A, 15B, 15C:
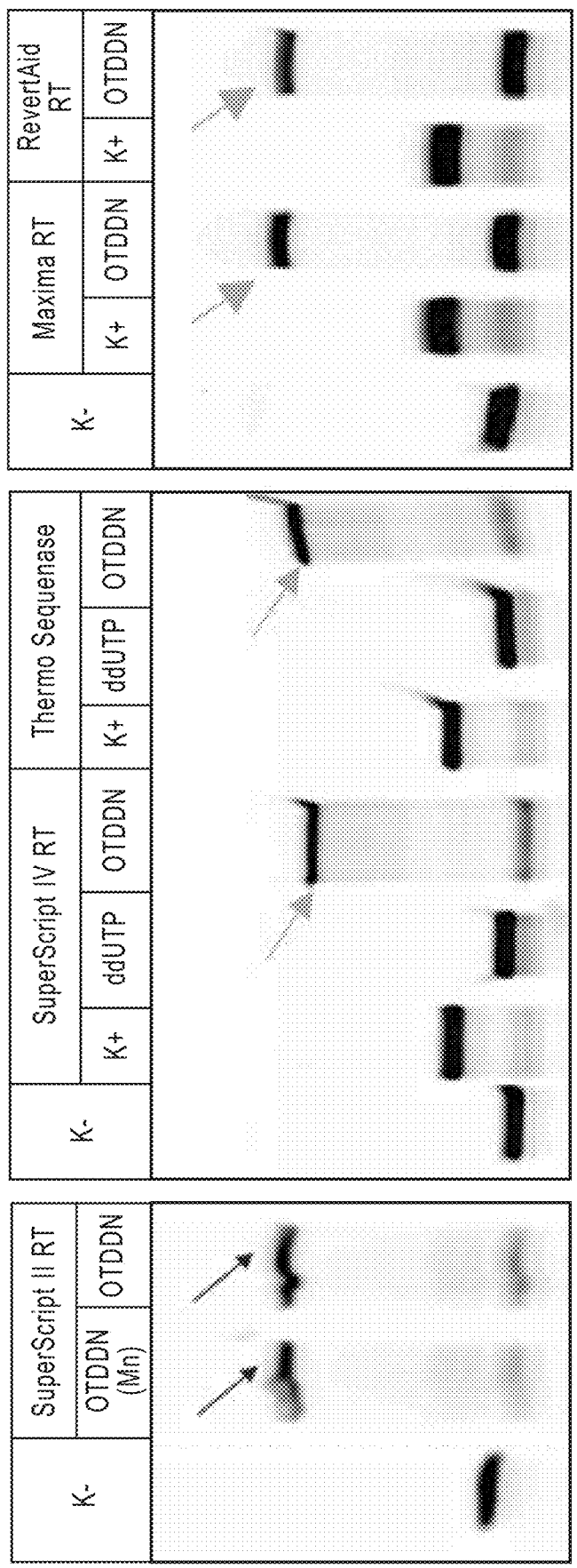
FIGS. 15A-15E show the results of oligonucleotide-tethered nucleotide incorporation experiments with several different polymerases. The arrows indicate successful incorporation events. K– lane shows Cy5-labeled strand before the reaction, K+ lane shows reaction products when native d LIP and dCTP were used. "ddUTP" lanes show incorporation of ddUTP, "OTDDN" lanes show incorporation of oligonucleotide-tethered ddUTP (SEQ ID NO: 1).
Figures 15D, 15E:
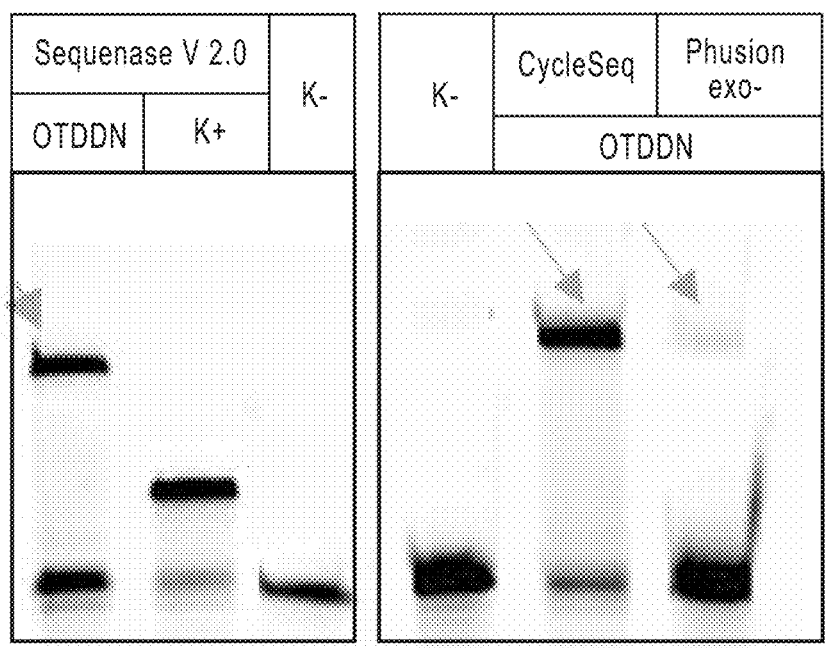

Identified polymerases capable of oligonucleotide-tethered ddUTP incorporation include SuperScript™ IV, SuperScript™ II, Maxima™, RevertAid™ reverse transcriptases, Thermo Sequenase™, Sequenase™ V2.0, CycleSeg™, and Phusion exo- (FIG. 15A-15E), terminal deoxynucleotidyl transferase (TdT) (FIG. 13), and poly(U) polymerase (FIG. 14). The results as provided in this example and FIGS. 13 to 15 show that, advantageously, various types of polymerases, including Type A, B, X polymerases and reverse transcriptases can be used for incorporation of oligonucleotide-tethered dideoxynucleotides of the current disclosure. Additionally, a template-independent RNA polymerase such as PolyU polymerase, is capable of incorporation of an oligonucleotide-tethered dideoxy nucleotide. Also, the incorporation can take place under reaction conditions, such as buffer and temperature, that are typical to a corresponding polymerase.

Example 3. Read-Through Evaluation Experiments

Figure 16:
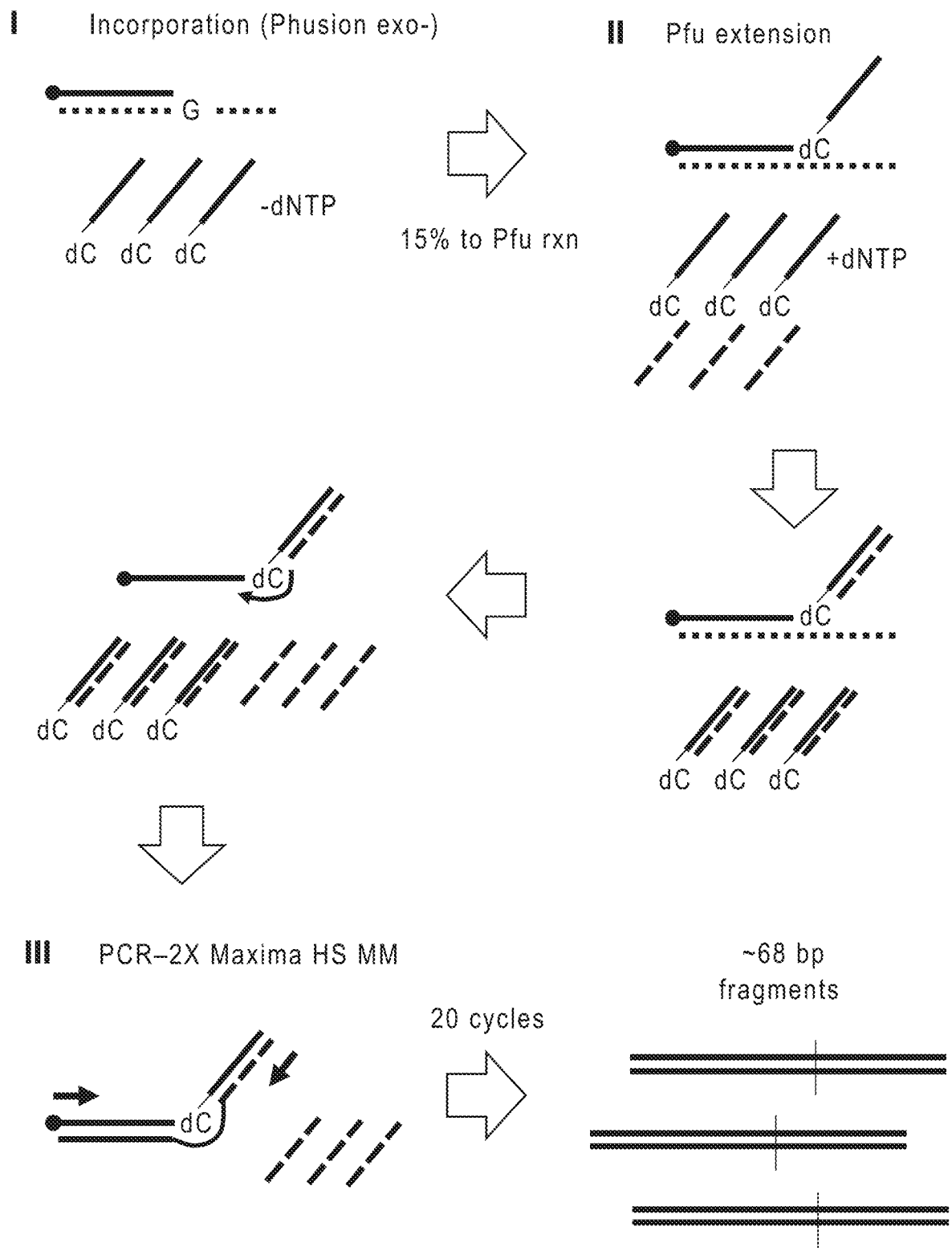
FIG. 16 depicts a scheme of a proof-of-principal experimental model to confirm a polymerase oligonucleotide-tethered primer extension read-through event with the use of specific primers in PCR. First, the first primer is annealed to the template such that the first nucleotide to be incorporated is oligonucleotide-tethered deoxynucleotide (oligonucleotide-tethered dC)(step I). Then a second primer (dashed line in step II) is annealed and Pfu DNA polymerase is added for primer extension. The curved arrow shows read-through position. The extended DNA fragment is then PCR-amplified (step III). To confirm the correct read-through event, the resulting PCR fragment was cloned and Sanger-sequenced (data not shown).

The polymerase read-through of unnatural junction as demonstrated by Stasevskij et al. was confirmed in our experimental model (process scheme in FIG. 16). Briefly, specific primers were designed to yield PCR products only in the event of successful polymerase read through of the incorporated oligonucleotide-tethered nucleotide. First, the first primer is annealed to the template such that the first nucleotide to be incorporated is oligonucleotide-tethered deoxynucleotide, in this particular example, by a Phusion exo- DNA polymerase. Then 15% of the reaction mixture is transferred to another reaction mixture where a second primer is annealed and Pfu DNA polymerase is added for primer extension. The extended fragment is then PCR-amplified with 2× Maxima HS MasterMix (Thermo Scientific; comprises hot start Taq DNA polymerase). To confirm the correct read-through event, the resulting PCR fragment was cloned and Sanger-sequenced (data not shown). The results showed the expected oligonucleotide-tethered nucleotide incorporation position, as well as that a polymerase read-through the linker between the 5'-nucleotide of tethered oligonucleotide and the nucleotide to which the oligonucleotide was tethered.

Figure 17A:
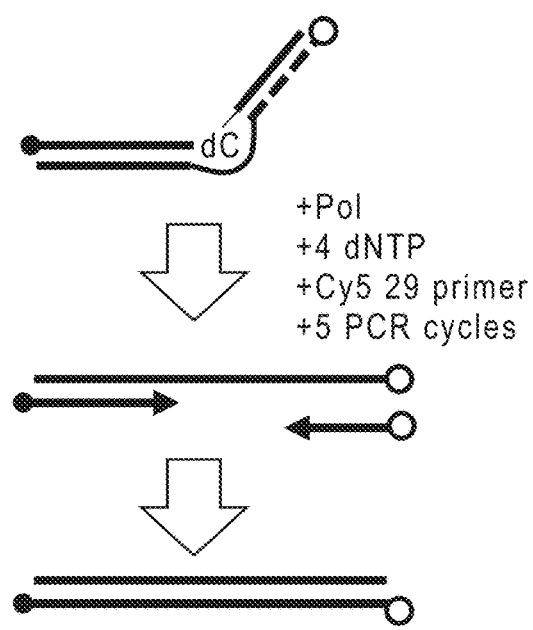
FIGS. 17A-17B show a scheme of another experiment for confirmation of correct read-through product formation.
Figure 17B:
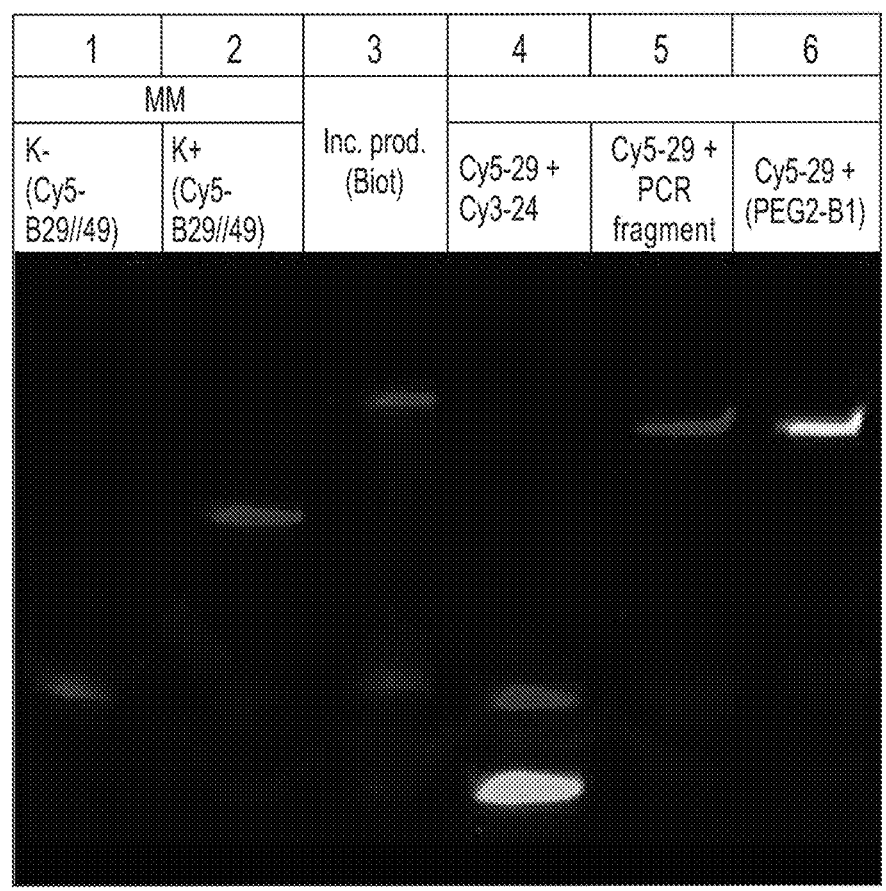

Polymerase primer extension/read through product of incorporated oligonucleotide-tethered nucleotide from the step III of the scheme described above (FIG. 16) was used in another short PCR (FIG. 17A), which contained a single stranded Cy5 29 nt primer complementary to 3' end of the read-through product. As observed in lane 6 (FIG. 17B) the Cy5 extended primer size is matching the Cy3 primer (both dyes were observed), which leads to a conclusion that the polymerase can correctly read through unnatural linker formed by tethered nucleotide when extending the primer that is annealed to tethered oligonucleotide. In one embodiment, the polymerase is Phusion exo-.

Example 4. NGS Library Preparation

Figure 18A:
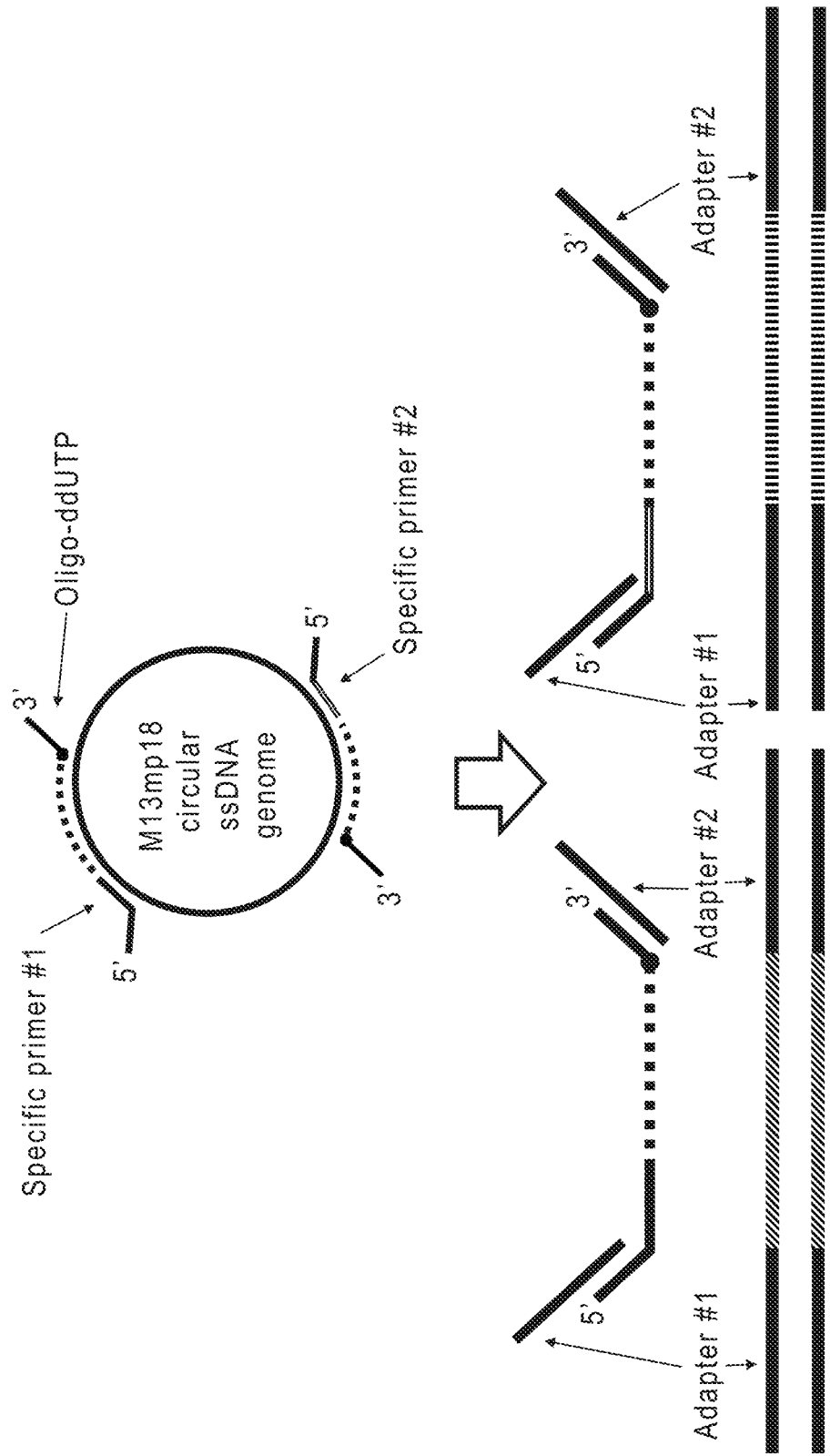
FIGS. 18A-18B show alignment results.

A. Sequencing-Ready Library Preparation by Primer Extension and Random Termination Proof-of-concept (FIG. 3) experiments were conducted using M13mp18 single stranded genomic DNA and *Escherichia coli* genomic DNA, and ATCC™ MSA-1002™ 20 Strain Even Mix Genomic Material (ATCC, VA, USA) as sample inputs. Two specific primers targeting M13mp18 loci were designed such as to contain universal priming sites (1-21 nt of SEQ ID NOs: 8 and 9) at their 5' ends (FIG. 18A):

SEQ ID NO 8:
5'-TACACGACGCTCTTCCGATCTAACGGTACGCCAGAATCTTG-3'

SEQ ID NO: 9:
5'-TACACGACGCTCTTCCGATCTAGAGCCACCACCGGAAC-3'

Figure 18B:
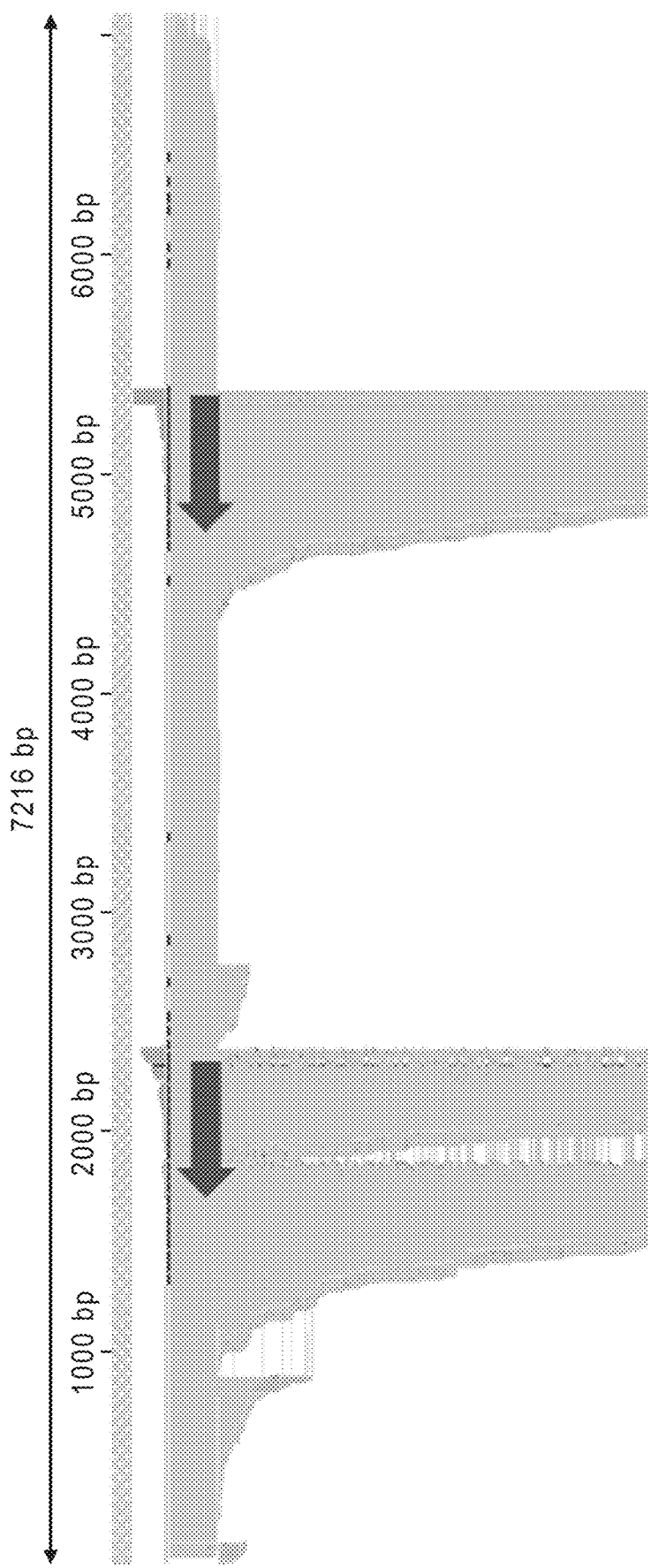

Both primers were mixed with M13mp18 DNA in the following reaction mixture: 125 fmol of each SEQ ID NO: 8 and SEQ ID NO: 9 primer, 100 fmol of M13mp18 DNA, 1.8 pmol of oligonucleotide-tethered ddUTP (SEQ ID NO: 1), 18 pmol of dTTP, 20 pmol of dATP, 20 pmol of dCTP, 20 pmol of dGTP, 40 U Thermo Sequenase™ (Thermo Scientific, MA, USA), 2 µL of Reaction Buffer and water, nuclease-free to 20 µL final reaction volume. The primer extension reaction was performed for 15 cycles of denaturation at 95° C. for 30 s and annealing/extension at 60° C. for 2 min, followed by a final extension at 60° C. for 30 min Reaction products were enriched for oligonucleotide-tethered ddUTP-containing molecules by purification with Dynabeads™ M-270 Streptavidin magnetic beads (Thermo Scientific, MA, USA) according to the manufacturer's instructions for immobilization of nucleic acids. Purified primer extension products were subjected to indexing PCR according to the standard Collibri™ Library Amplification Master Mix (Thermo Scientific, M A, USA) reaction conditions, except for the number of PCR cycles which in this experiment was 30, using 10× Index Primer Mix from the Collibri™ Stranded RNA Library Prep Kit for Illumina™ Systems (Thermo Scientific, MA, USA) to introduce full-length sequencing adapters compatible with Illumina™ instruments. Alternatively, half of the primer extension reaction volume was transferred directly to indexing PCR without the intermediate purification step. After indexing PCR, libraries were purified using the Collibri™ Library Cleanup Kit (Thermo Scientific, MA, USA). The presence of sequencing-ready molecules in the resulting samples was confirmed by qPCR according to the standard Collibri™ Library Quantification Kit (Thermo Scientific, MA, USA) protocol. The resulting libraries were sequenced on the Illumina MiSeq™ using the MiSeq Reagent Nano Kit v2, 300-cycles (Illumina, CA, USA); 2×75 bp paired-end reads were performed. The alignment of sequencing reads to the M13mp18 reference showed the expected coverage of two genomic loci with the 5' ends starting at fixed positions, while the 3' ends—corresponding to the oligonucleotide-tethered ddUTP incorporation loci—occurring at random sites (FIG. 18B). There were no significant differences in sequencing results between samples amplified with or without purification after primer extension reaction.

A Random decamer was designed for testing of oligonucleotide-tethered dideoxynucleotides in a whole genome sequencing application:

SEQ ID NO: 10:
5'-TACACGACGCTCTTCCGATCTNNNNNNNNNN-3'

Figure 19:
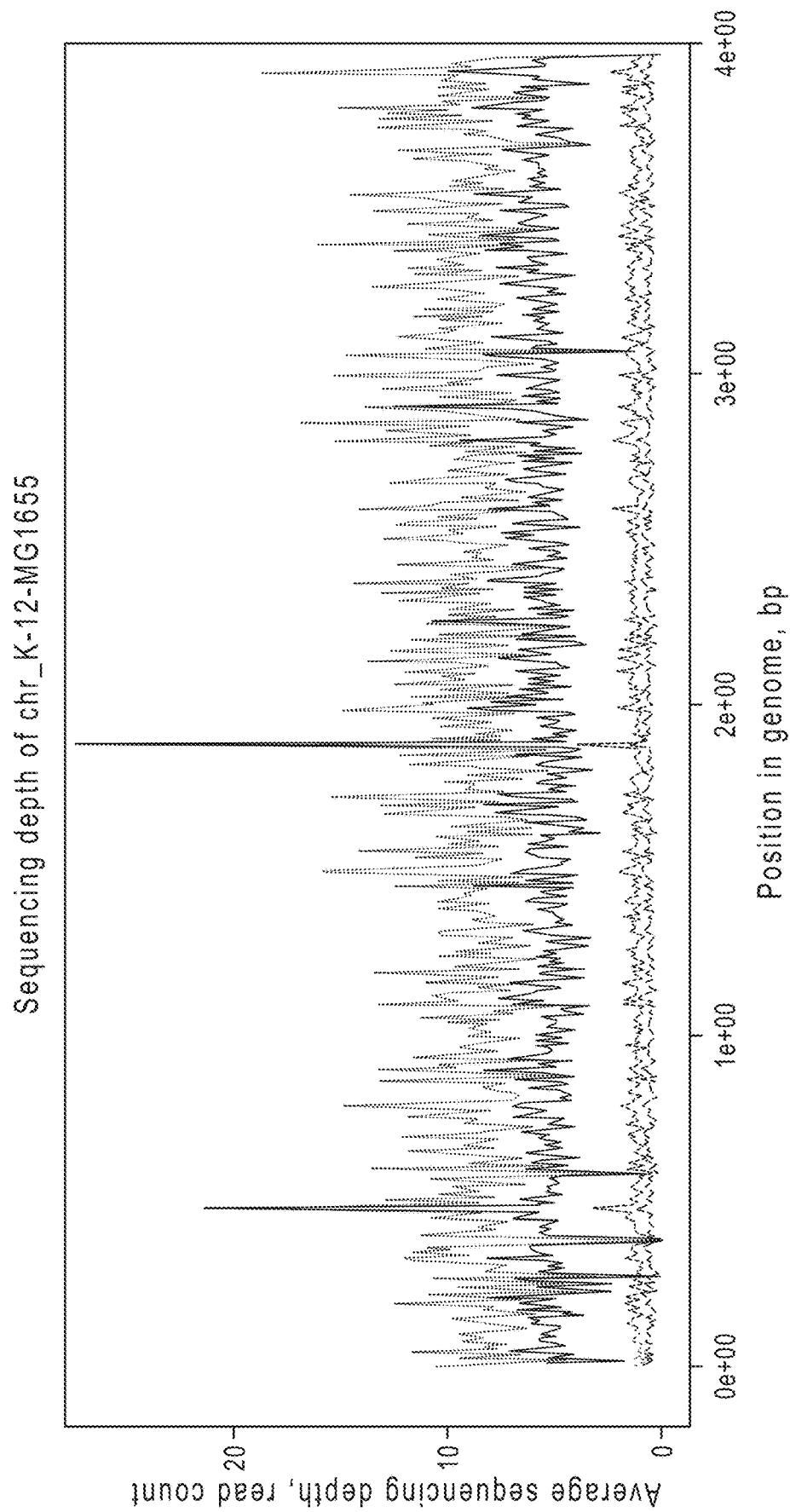
FIG. 19 shows the alignment of reads obtained upon sequencing of an amplicon library generated by the extension of random primers and termination by the incorporation of oligonucleotide-tethered ddNTPs. The alignment indicates coverage of the whole E. coli K-12 chromosome.

The SEQ ID NO: 10 primer was mixed with *E. coli* gDNA in the following reaction mixture: 350 pg-100 ng of *E. coli* gDNA, 10-100 pmol of random decamer, 1.8 pmol of oligonucleotide-tethered ddUTP (SEQ ID NO: 1), 18 pmol of dTTP, 20 pmol of dATP, 20 pmol of dCTP, 20 pmol of dGTP, 40 U Thermo Sequenase™ (Thermo Scientific, MA, USA), 2 µL of Reaction Buffer and water, nuclease-free to 20 µL final reaction volume. The primer extension reaction was performed as follows: denaturation at 92° C. for 3 min followed by cooling to 16° C. and incubation at 16° C. for 5 min, then raising the temperature to 68° C. at 0.1° C./s ramp rate and incubation at 68° C. for 15 min, then 25 cycles of denaturation at 92° C. for 30 s and annealing/extension at 68° C. for 5 min, followed by a final extension at 68° C. for 30 min. Primer extension products were subjected to indexing PCR according to the standard Collibri™ Library Amplification Master Mix (Thermo Scientific, MA, USA) reaction conditions, except for the number of PCR cycles, which in this experiment was 35, using 10× Index Primer Mix from the Collibri™ Stranded RNA Library Prep Kit for Illumina™ Systems (Thermo Scientific, MA, USA) to introduce full-length sequencing adapters compatible with Illumina™ instruments. After indexing PCR, libraries were purified using the Collibri™ Library Cleanup Kit (Thermo Scientific, MA, USA). The presence of sequencing-ready molecules in the resulting samples was confirmed by qPCR according to the standard Collibri™ Library Quantification Kit (Thermo Scientific, MA, USA) protocol. The resulting libraries were sequenced on the Illumina MiSeq™ using the MiSeq Reagent Nano Kit v2, 300-cycles (Illumina, CA, USA); 2×100 bp paired-end reads were performed. The alignment of sequencing reads to the *E. coli* K-12 reference showed the alignment rate of >75% with reads distributed along the whole *E. coli* chromosome (FIG. 19).

Figure 20A:
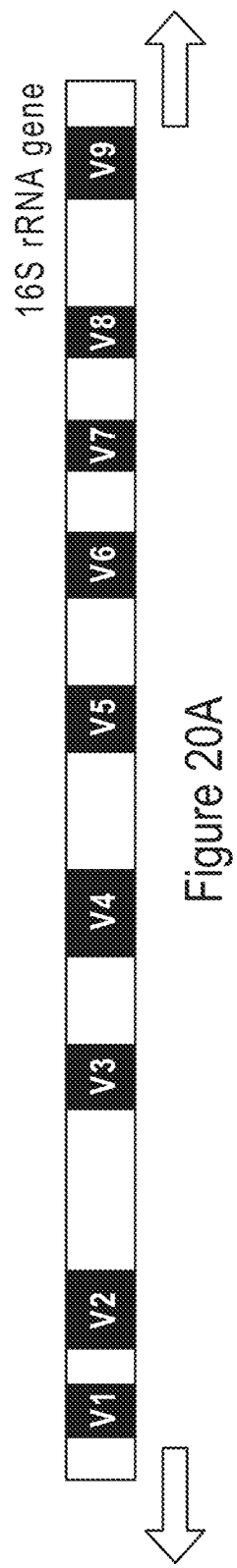
FIGS. 20A-20C show a principle of the analysis of 16S rRNA gene genomic context.
Figure 20B:
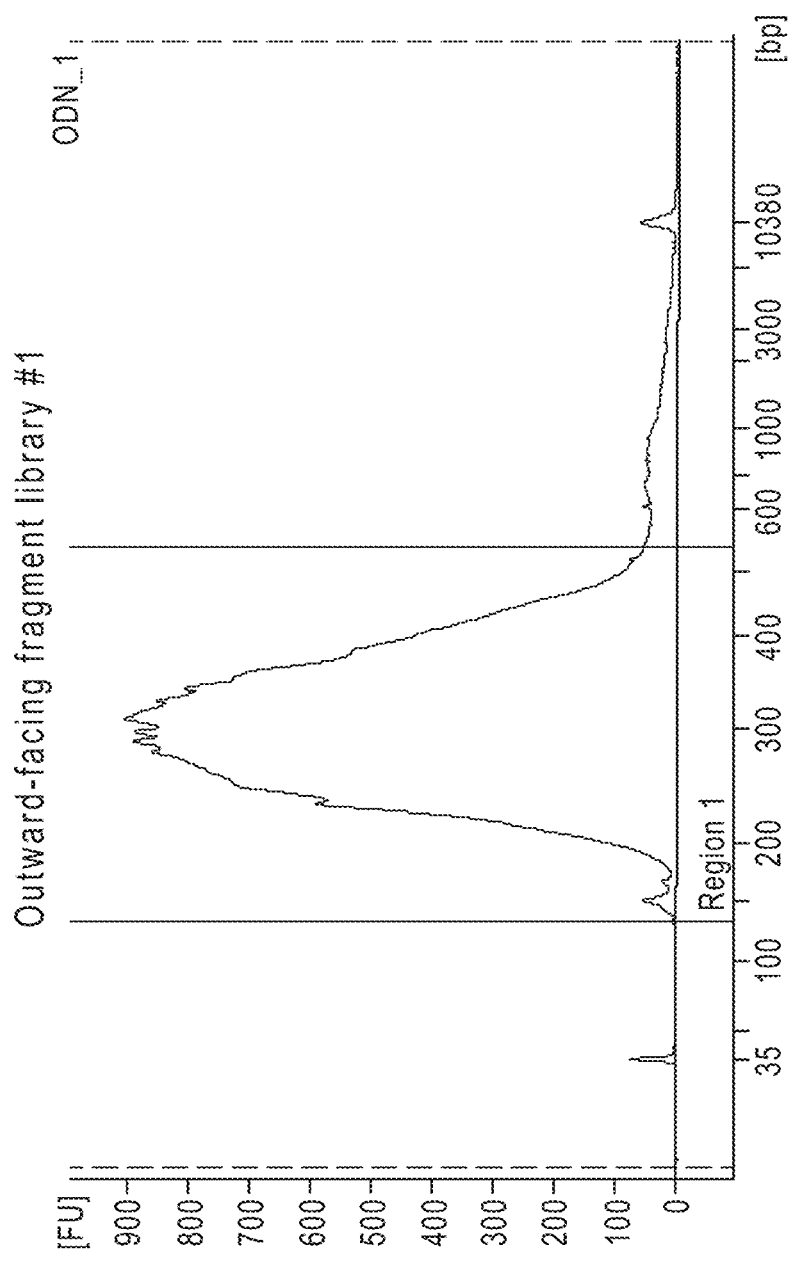
Figure 20C:
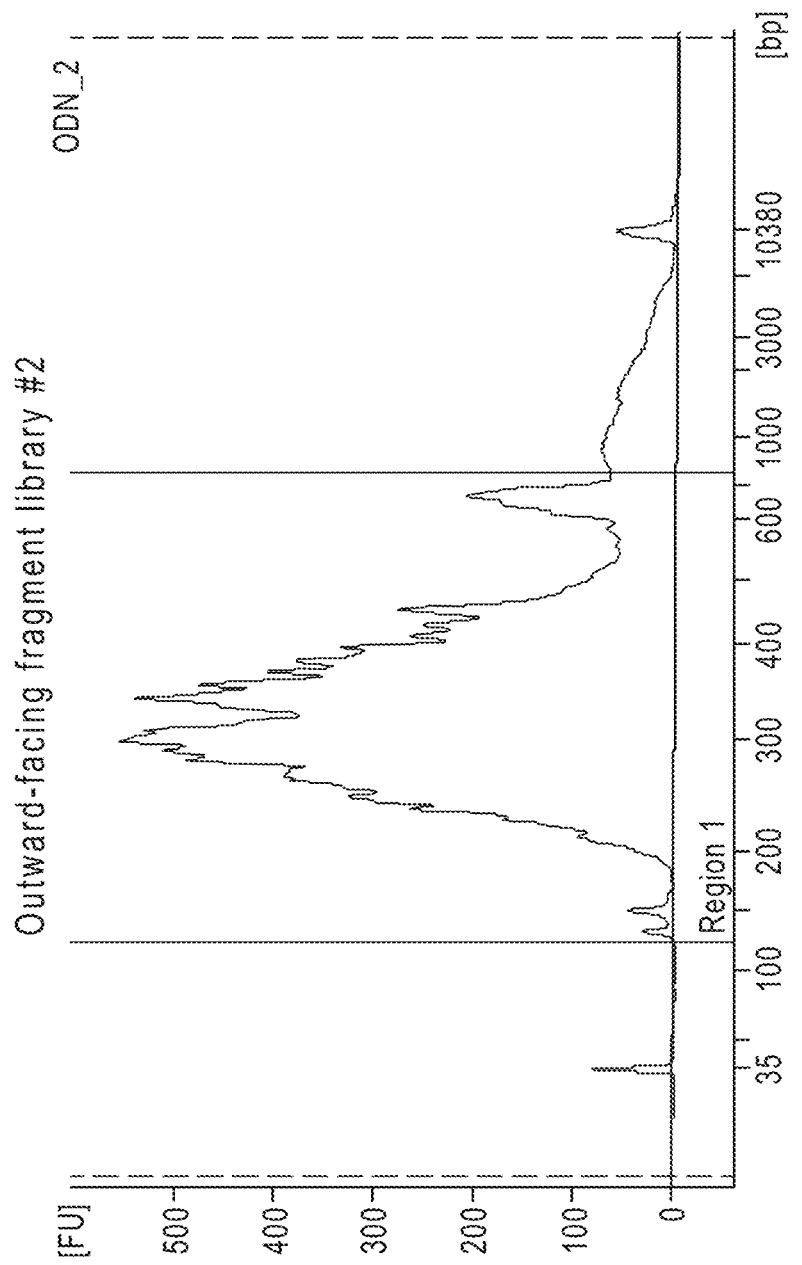

Specific primers targeting bacterial 16S rRNA gene ends and facing outwards were designed to demonstrate the applicability of oligonucleotide-tethered nucleotide technology for the analysis of 16S rRNA gene genomic context (FIGS. 20A-C). The principle is applicable for any experimental system which aims to investigate unknown sequence regions nearby known specific loci.

```
SEQ ID NO: 11:
CTCTTTCCCTACACGACGCTCTTCCGATCTAAGTCGTAACAAGGTAACCG

SEQ ID NO: 12:
CTCTTTCCCTACACGACGCTCTTCCGATCTCTGAGCCAKRATCAAACTCT

SEQ ID NO: 13:
CTCTTTCCCTACACGACGCTCTTCCGATCTCTGAACCAAGATCAAATTCT

SEQ ID NO: 14:
CTCTTTCCCTACACGACGCTCTTCCGATCTCTAAGCCAGGATCAAACTCT

SEQ ID NO: 15:
CTCTTTCCCTACACGACGCTCTTCCGATCTCTGAGCCAGAATCGAACCCT
```

Primers SEQ ID NO: 12, SEQ ID NO: 13, SEQ ID NO: 14 and SEQ ID NO: 15 were mixed at 4:1:1:1 molar ratio respectively. Multiplex primer extension reaction was assembled: 1 μL of ATCC™ MSA-1002™ 20 Strain Even Mix Genomic Material (ATCC, VA, USA), 12.5 pmol of SEQ ID NO: 11 primer, 12.5 pmol of SEQ ID NO: 12, SEQ ID NO: 13, SEQ ID NO: 14 and SEQ ID NO: 15 primer mix, 1.8 pmol of oligonucleotide-tethered ddU (SEQ1), 0.18 pmol of oligonucleotide-tethered ddCTP (SEQ ID NO: 3), 18 pmol of dTTP, 18 pmol of dCTP, 20 pmol of dGTP, 20 pmol of dATP, 40 U Thermo Sequenase™ (Thermo Scientific, MA, USA), 2 μL of Reaction Buffer and water, nuclease-free to 20 μL final reaction volume. Reaction conditions were as follows: initial denaturation for 4 min at 95° C., 15 cycles of linear extension/termination ration (1 min at 95° C., 30 sat 45° C., 1 min at 72° C.), final extension for 5 min at 60° C. Reaction products were purified using the Collibri™ Library Cleanup Kit (Thermo Scientific, MA, USA). Final amplification and introduction of full-length Illumina™-compatible adapters was performed according to the standard Collibri™ Library Amplification Master Mix (Thermo Scientific, MA, USA) reaction conditions, except for the number of PCR cycles, which in this experiment was 20, using 10× Index Primer Mix from the Collibri™ Stranded RNA Library Prep Kit for Illumina™ Systems (Thermo Scientific, MA, USA). After indexing PCR, libraries were purified using the Collibri™ Library Cleanup Kit (Thermo Scientific, MA, USA).

The presence of sequencing-ready molecules in all produced libraries was confirmed by qPCR according to the standard Collibri™ Library Quantification Kit (Thermo Scientific, MA, USA) protocol. The resulting libraries were sequenced on the Illumina MiSeq™ using the MiSeq Reagent Kit v2, 300-cycles (Illumina, CA, USA); 2×150 bp paired-end reads were performed.

Figure 21:
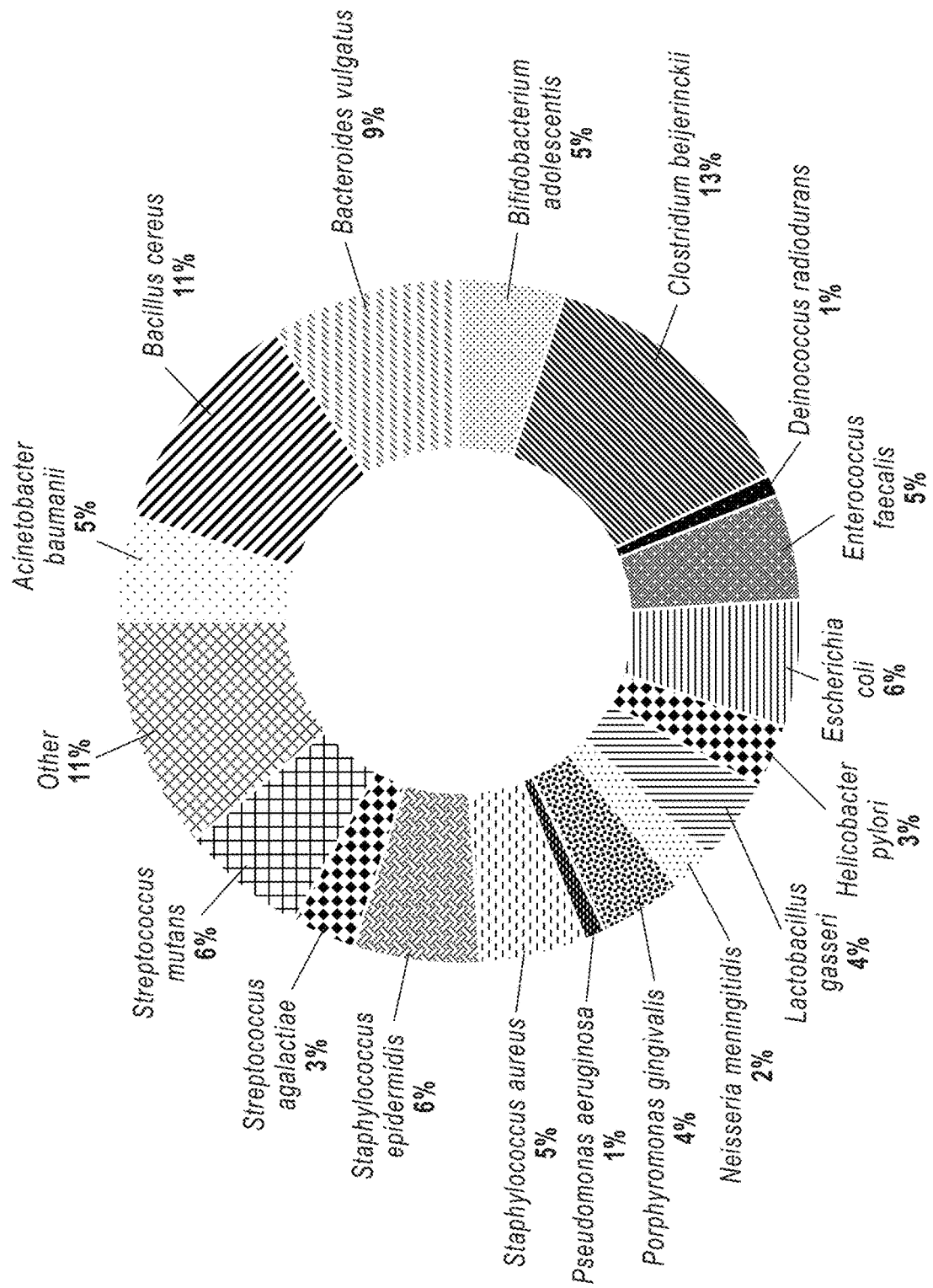
FIG. 21 depicts the results of ATCC™ MSA-1002™ microbiome standard sequencing according to the principles depicted in FIG. 20.

The results indicated that outward-facing libraries are able to characterize complex bacterial populations: 17 out of 20 expected species were identified in outward-facing fragment library sample (FIG. 21).

B. Sequencing-Ready Library Preparation Covering Whole Transcript Length

Figure 22:
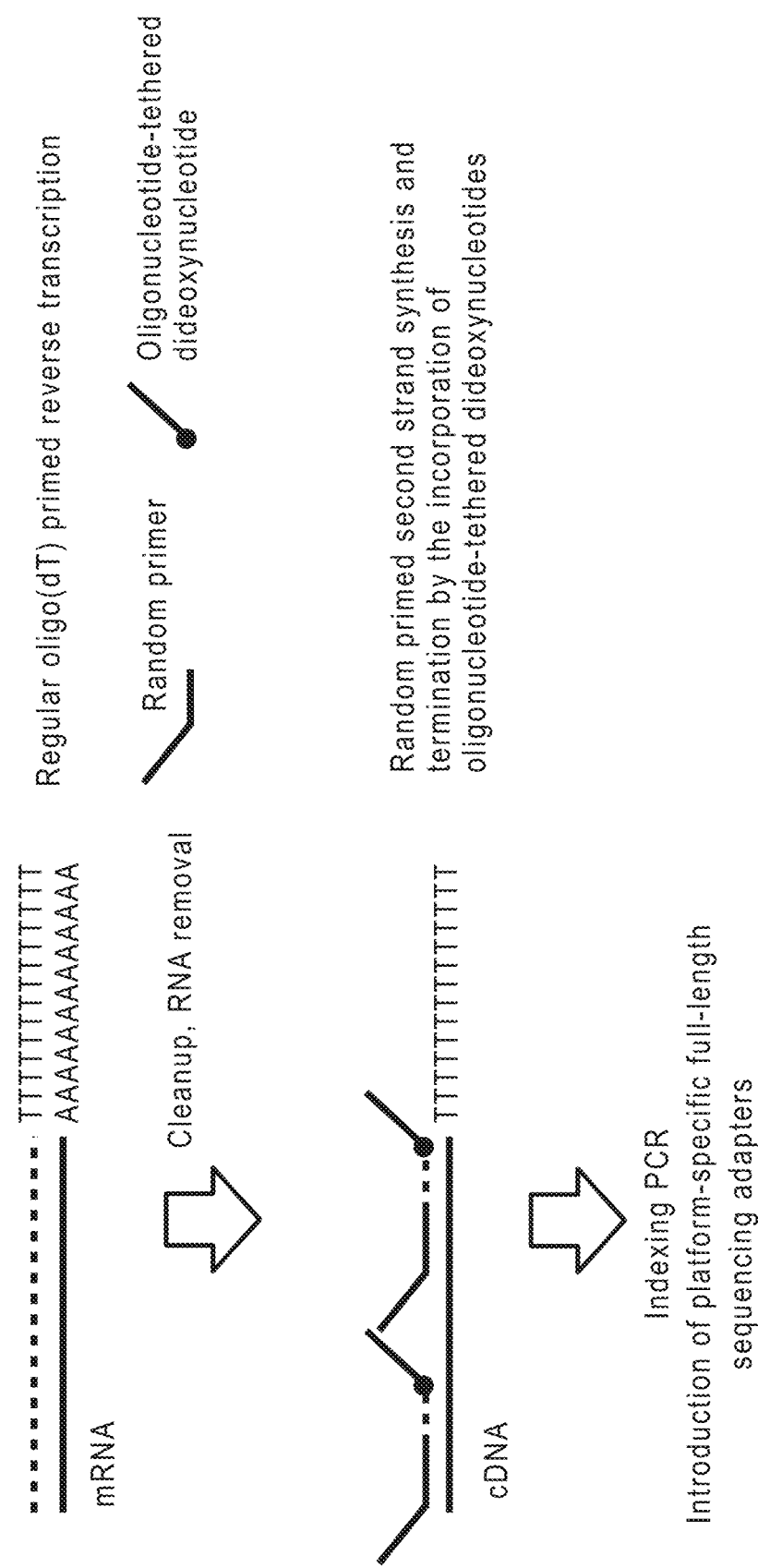
FIG. 22 shows the basic principle of strand-specific mRNA sequencing library preparation, which includes generation of fragment library covering the whole transcript length by the extension of random primers and DNA synthesis termination by the incorporation of oligonucleotide-tethered dideoxynucleotides. Generation of a tagged fragment library is performed during the second strand synthesis. The library of tagged DNA fragments may then be amplified using PCR primers, which in turn introduce platform-specific adapter sequences. The length of tagged DNA fragments may be controlled through the adjustment of oligonucleotide-tethered dideoxynucleotide concentration and/or ratio relative to the corresponding native deoxynucleotide.
Figure 23:
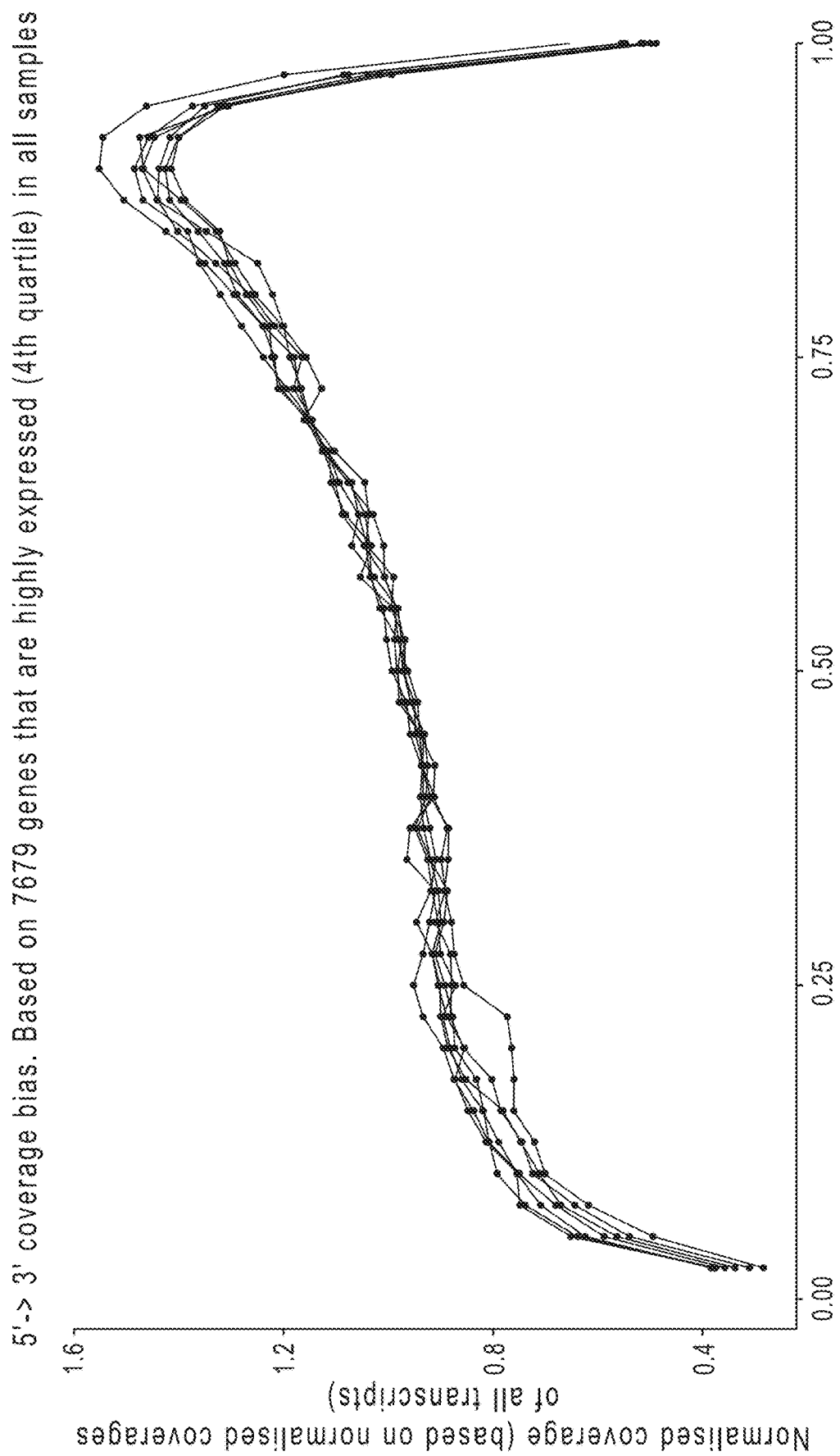
FIG. 23 shows gene body coverage calculated for mRNA sequencing libraries prepared according to the principle depicted in FIG. 22.

Proof-of-concept (FIG. 22) experiments were performed using human total RNA as a sample input. First, 1 μl of total a Universal Human Reference RNA (Thermo Scientific, MA, USA) sample was reverse transcribed using oligo(dT)$_{30}$ primer according to the standard protocol for SuperScript™ IV Reverse Transcriptase (Thermo Scientific, MA, USA). The resulting cDNA was purified using the Collibri™ Library Cleanup Kit according to the protocol for the cleanup of fragmented RNA (described in the Collibri™ Stranded RNA Library Prep Kit (Thermo Scientific, MA, USA) manual). For the second strand synthesis the following reaction mixture was assembled: purified cDNA, 1 pmol of random primer (SEQ ID NO. 10), 18 pmol of oligonucleotide-tethered ddUTP (SEQ ID NO: 1), 180 pmol of dTTP, 200 pmol of dATP, 200 pmol of dCTP, 200 pmol of dGTP, 40 U Thermo Sequenase™ (Thermo Scientific, MA, USA), 2 μL of Reaction Buffer and water, nuclease-free to 20 μL final reaction volume. Reaction conditions: denaturation at 95° C. for 3 min, cooling to 16° C. and incubation at 16° C. for 5 min, primer extension at 50° C. for 30 min. After the single cycle of random primer extension, reaction products were enriched for oligonucleotide-tethered ddUTP-containing molecules by purification with Dynabeads™ M-270 Streptavidin magnetic beads (Thermo Scientific, MA, USA) according to the manufacturers' instructions for immobilization of nucleic acids. Purified primer extension products were subjected to indexing PCR according to the standard Collibri™ Library Amplification Master Mix (Thermo Scientific, MA, USA) reaction conditions (the number of PCR cycles was 20), using 10× Index Primer Mix from the Collibri™ Stranded RNA Library Prep Kit for Illumina™ Systems (Thermo Scientific, MA, USA) to introduce full-length sequencing adapters compatible with Illumina™ instruments. The presence of sequencing-ready molecules in the resulting samples was confirmed by qPCR according to the standard Collibri™ Library Quantification Kit (Thermo Scientific, MA, USA) protocol. The resulting libraries were sequenced on the Illumina MiSeq™ using the MiSeq Reagent Nano Kit v2, 300-cycles (Illumina, CA, USA); 2×75 bp paired-end reads were performed. Data analysis revealed the alignment rate to human genome of 94.4-97.2%, strand specificity of 97.8-98.7% and gene body coverage across the entire transcript with a slight bias towards 3' end typical for mRNA sequencing libraries (FIG. 23).

C. Sequencing-Ready Library Preparation Covering 3' Ends of Transcripts

Figure 24:
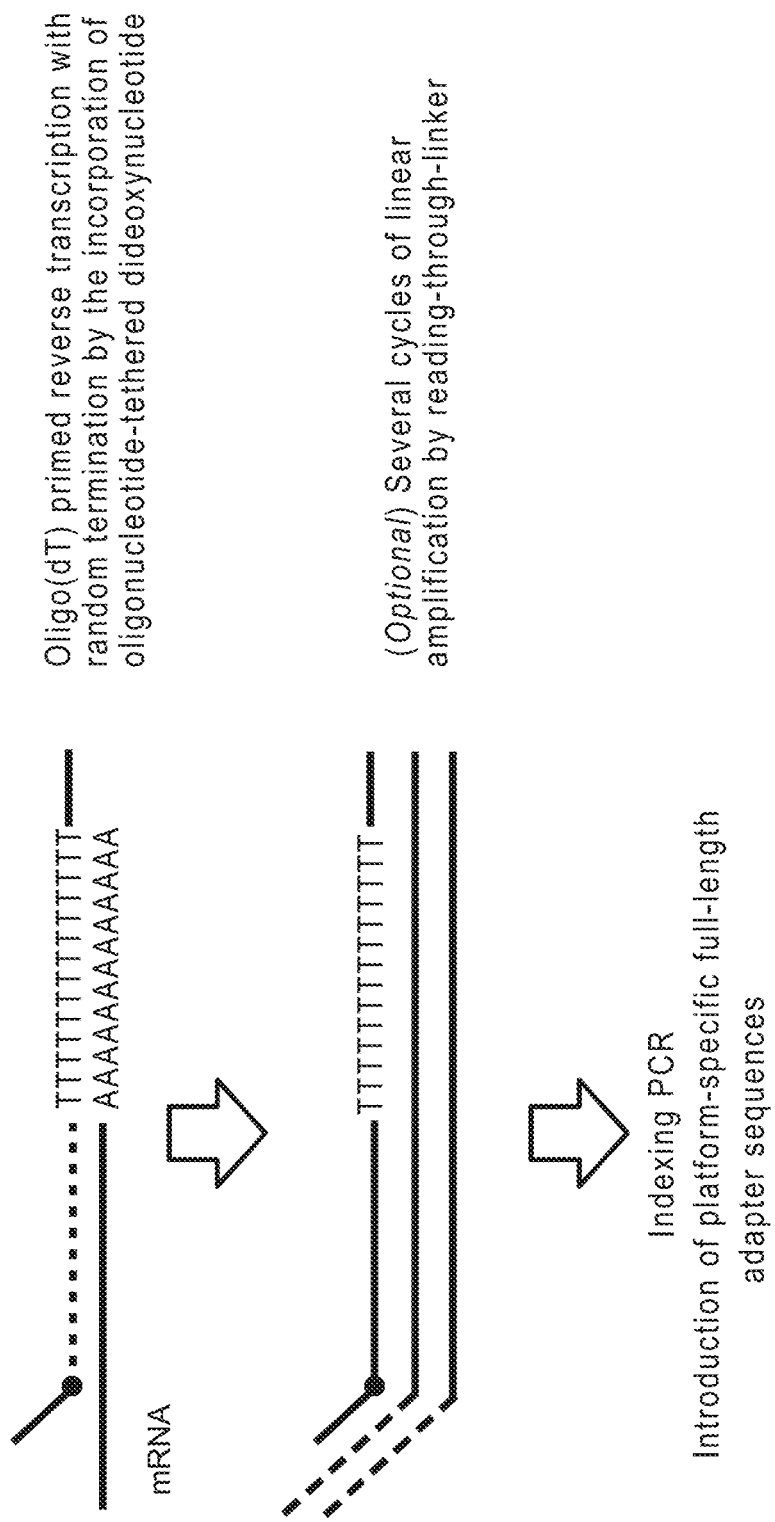
FIG. 24 shows the basic principle of strand-specific mRNA sequencing library preparation, which includes generation of fragment library covering the 3' ends of transcripts by the extension of oligo(dT) reverse transcription primers and cDNA synthesis termination by the incorporation of oligonucleotide-tethered dideoxynucleotides. The library of tagged cDNA fragments may then be preamplified by linear extension of primer complimentary to oligonucleotide conjugated to dideoxynucleotide. This procedure, conducted employing a polymerase with high read-through-linker activity, may improve transcript detection sensitivity. Final amplification is then performed by PCR using primers that introduce platform-specific adapter sequences. The length of tagged cDNA fragments may be controlled through the adjustment of oligonucleotide-tethered dideoxynucleotide concentration and ratio relative to the corresponding native deoxynucleotide at the reverse transcription step. The oligonucleotide-tethered dideoxynucleotide concentration and ratio relative to the corresponding native deoxynucleotide may generate inserts of similar size across broad range of RNA input amounts.

Proof-of-concept (FIG. 24) experiments were performed using human total RNA as a sample input. Total Universal Human Reference RNA (Thermo Scientific, MA, USA) sample was reverse transcribed using oligo(dT) primer

```
SEQ ID NO: 16:
5'-AAGCAGTGGTATCAACGCAGAGTACTTTTTTTTT

TTTTTTTTTTTTTTTTTTTT-3'
```

Reverse transcription reaction mixture: 20 pg-1 μg of total RNA, ERCC ExFold RNA Spike-In (optional, the amount is chosen according to the manufacturers' instructions; Thermo Scientific, MA, USA), 50 pmol of reverse transcription primer (SEQ ID NO: 16), 10 pmol of oligonucleotide-tethered ddUTP (SEQ ID NO: 1), 10 pmol of dTTP, 20 pmol of dATP, 20 pmol of dCTP, 20 pmol of dGTP, 1 μL 100 mM DTT, 4 μL of 5× RT Buffer for SuperScript™ IV (Thermo Scientific, MA, USA), 200 U of SuperScript™ IV (Thermo Scientific, MA, USA) and water, nuclease-free to 20 μL final reaction volume. The reaction was conducted at 50° C. for 30 min. Reaction products were enriched for oligonucleotide-tethered ddUTP-containing molecules by purification with Dynabeads™ M-270 Streptavidin magnetic beads (Thermo Scientific, MA, USA) according to the manufacturers' instructions for immobilization of nucleic acids. Tagged cDNAs may then be subjected directly to indexing PCR according to the standard Collibri™ Library Amplification Master Mix (Thermo Scientific, MA, USA) reaction conditions. The number of PCR cycles in this experiment was 20-25, depending on the starting input amount, and indexing primers were as follows:

```
SEQ ID NO: 17:
5'-AATGATACGGCGACCACCGAGATCTACACGCCT

GTCCGCGGAAGCAGTGGTATCAACGCAGAGTAC-3'

SEQ ID NO: 18:
5'-CAAGCAGAAGACGGCATACGAGATGTGACTGGAG

TTCAGACGTGTGCTCTTCCGATCT-3'
```

Figure 25:
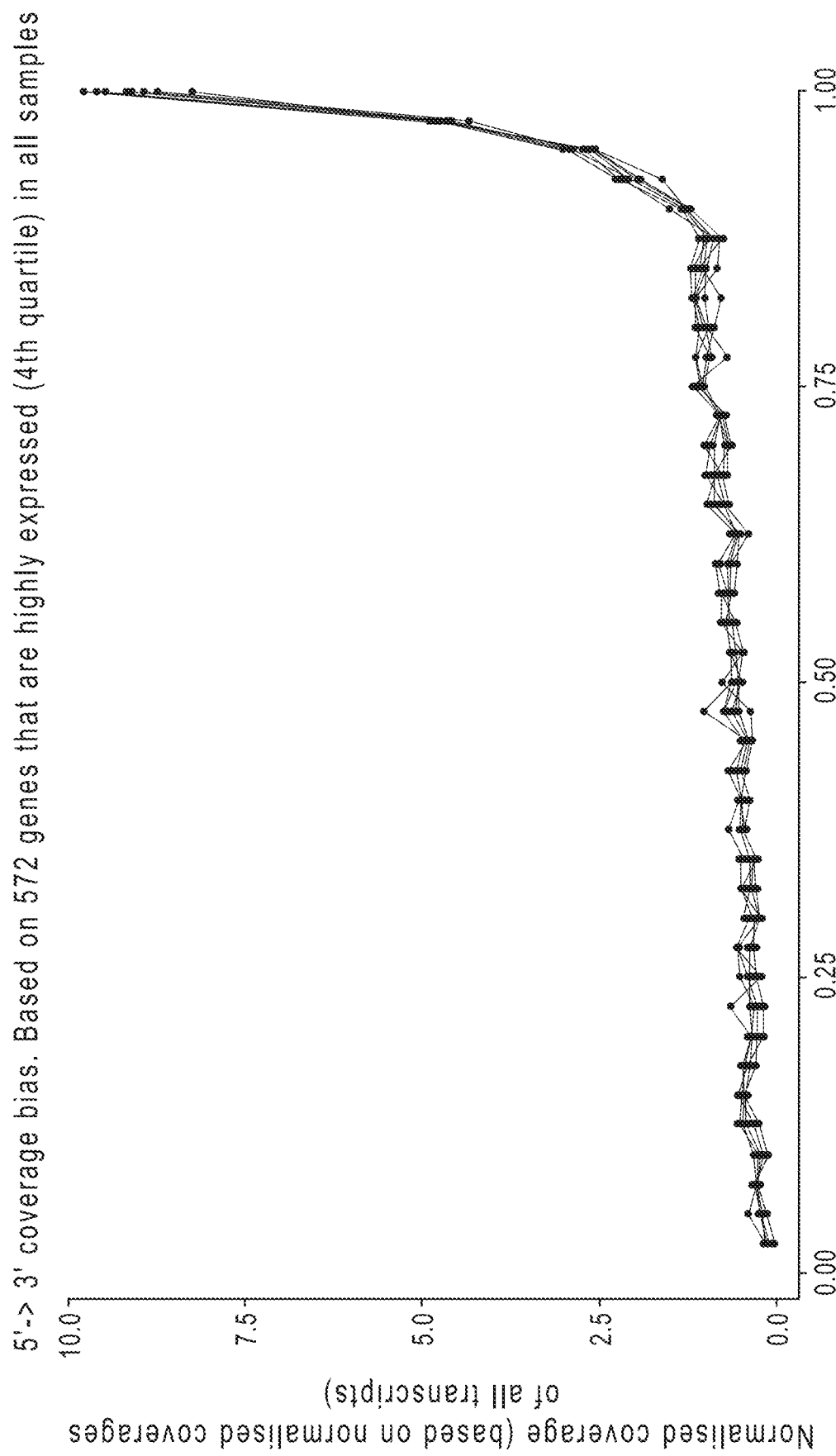
FIG. 25 shows gene body coverage calculated for mRNA sequencing libraries prepared according to the principle depicted in FIG. 24.

Alternatively, samples may be linearly preamplified employing polymerase exhibiting higher efficiency of reading through atypical linker than polymerase used for amplification. In this case, purified tagged cDNAs were subjected to the following reaction: cDNA, 4 μL of 5× Phusion™ HF buffer (Thermo Scientific, MA, USA), 1 μL of dNTP mix (2 mM each), 1.2 pmol of primer complimentary to oligonucleotide conjugated to ddUTP (SEQ ID NO: 18), 2.5 U Phusion exo- (Thermo Scientific, MA, USA) and water, nuclease-free to 20 μL final reaction volume. Primer extension was performed for 10 cycles of denaturation at 95° C. for 1 min, annealing at 60° C. for 1 mire and extension at 72° C. for 1 min Reaction products were then purified using the Collibri™ Library Cleanup Kit according to the protocol for the cleanup of fragmented RNA (described in the Collibri™ Stranded RNA Library Prep Kit (Thermo Scientific, MA, USA) manual). After linear preamplification samples were PCR amplified in an asymmetric fashion to complete the introduction of full-length sequencing adapters: 20 μL of purified linear amplification products, 25 μL of Collibri™ Library Amplification Master Mix, 46 pmol of SEQ ID NO: 17 primer, 4.6 pmol of SEQ ID NO: 19: 5'-CAAGCAGAAGACGGCATACGA-3' primer and water, nuclease-free to 50 μL final reaction volume. PCR conditions were as recommended in the standard Collibri™ Library Amplification Master Mix (Thermo Scientific, MA, USA) protocol, except that the number of PCR cycles in this experiment was 20-25, depending on the starting input amount. After PCR, libraries were purified using the Collibri™ Library Cleanup Kit (Thermo Scientific, MA, USA). The presence of sequencing-ready molecules in the resulting samples was confirmed by qPCR according to the standard Collibri™ Library Quantification Kit (Thermo Scientific, MA, USA) protocol. The resulting libraries were sequenced on the Illumina MiSeq™ using the MiSeq Reagent Kit v2, 300-cycles (Illumina, CA, USA); paired-end reads (R1 of 10 bp and R2 of 75 bp) were performed. Data analysis showed the alignment rate to human genome of >90%, strand specificity of >99% and gene body coverage with strong bias towards the 3' end (FIG. 25).

Figure 26A:
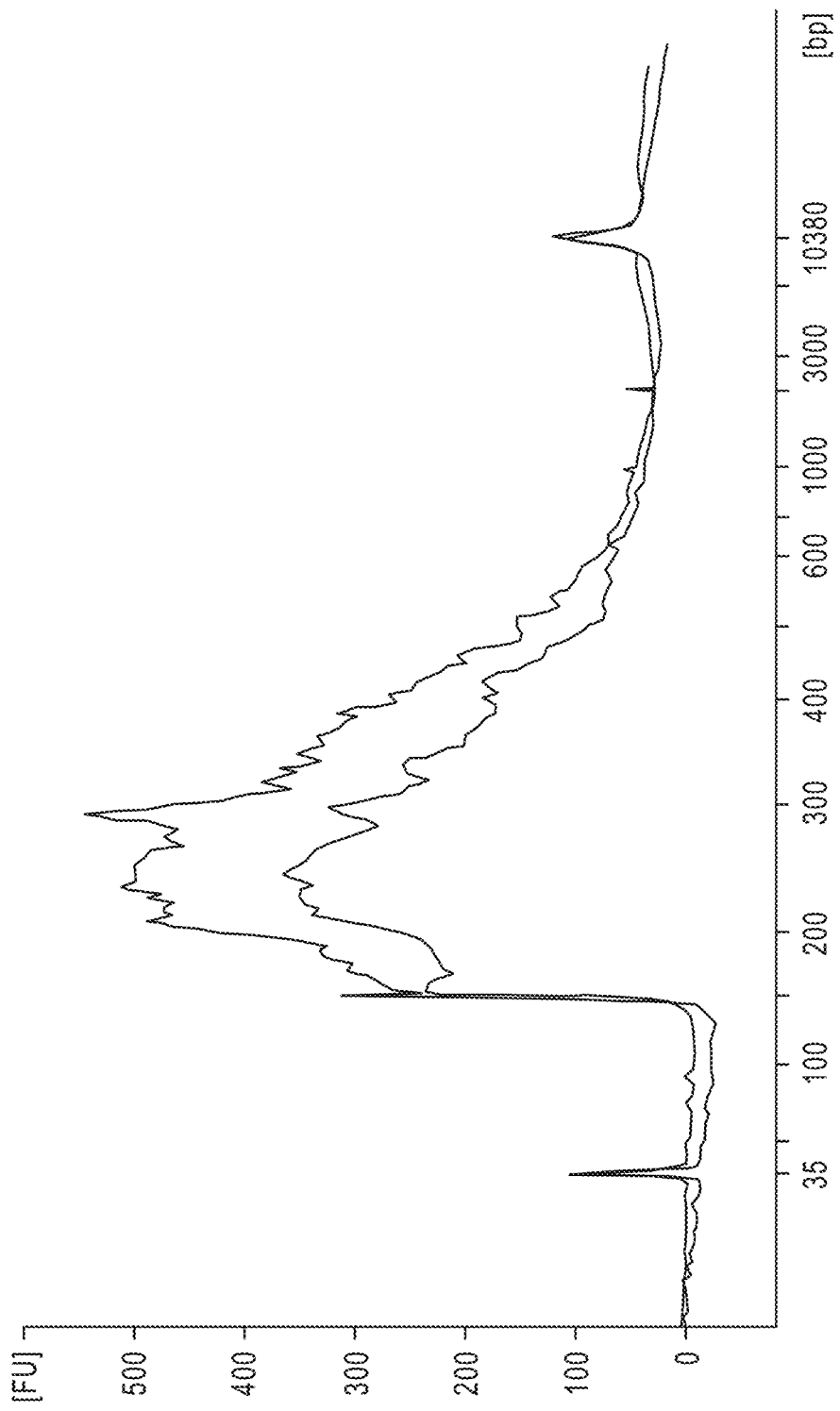
FIGS. 26A-26B show the results of 3' mRNA-seq library preparation using an oligonucleotide-tethered nucleotide.
Figure 26B:
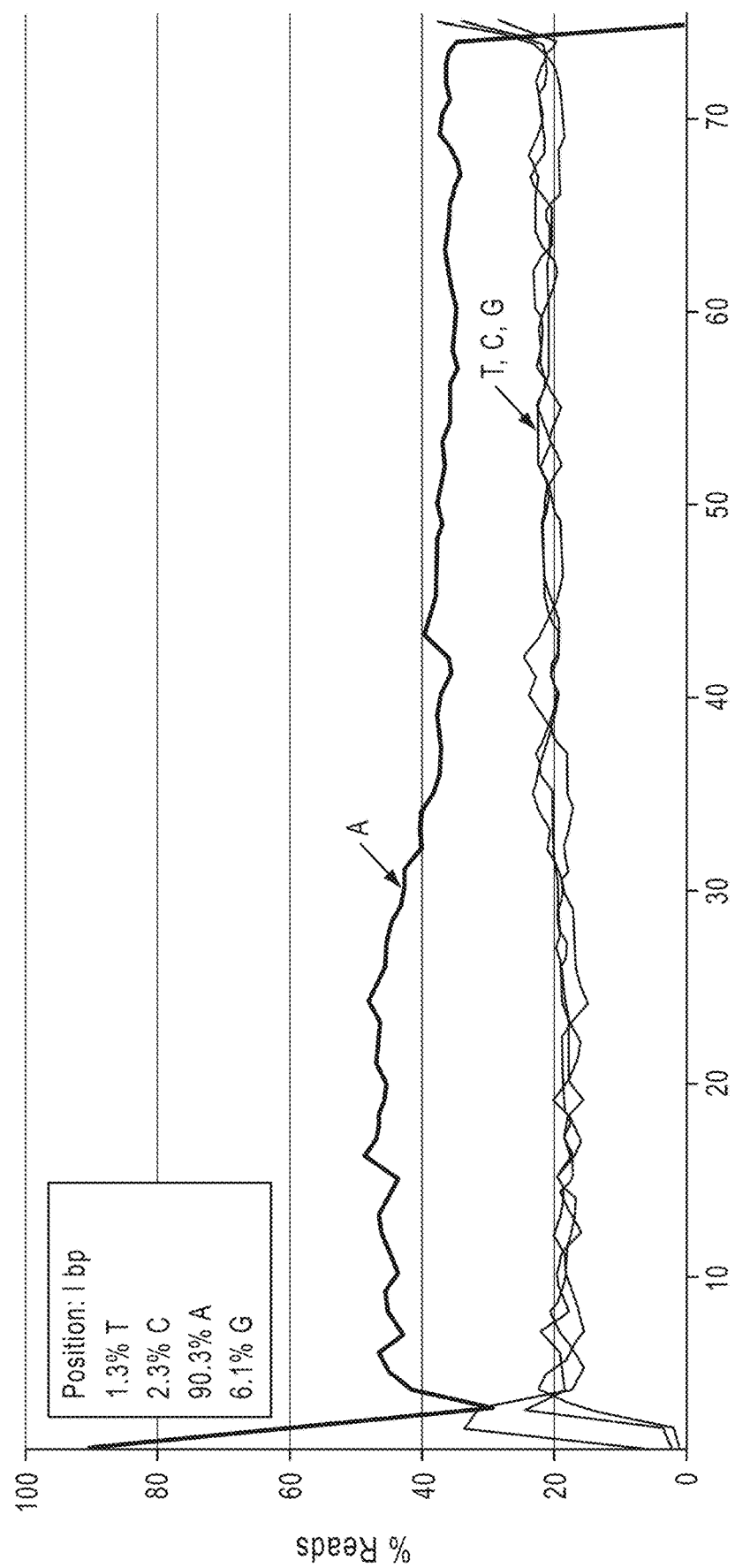
Figure 27A:
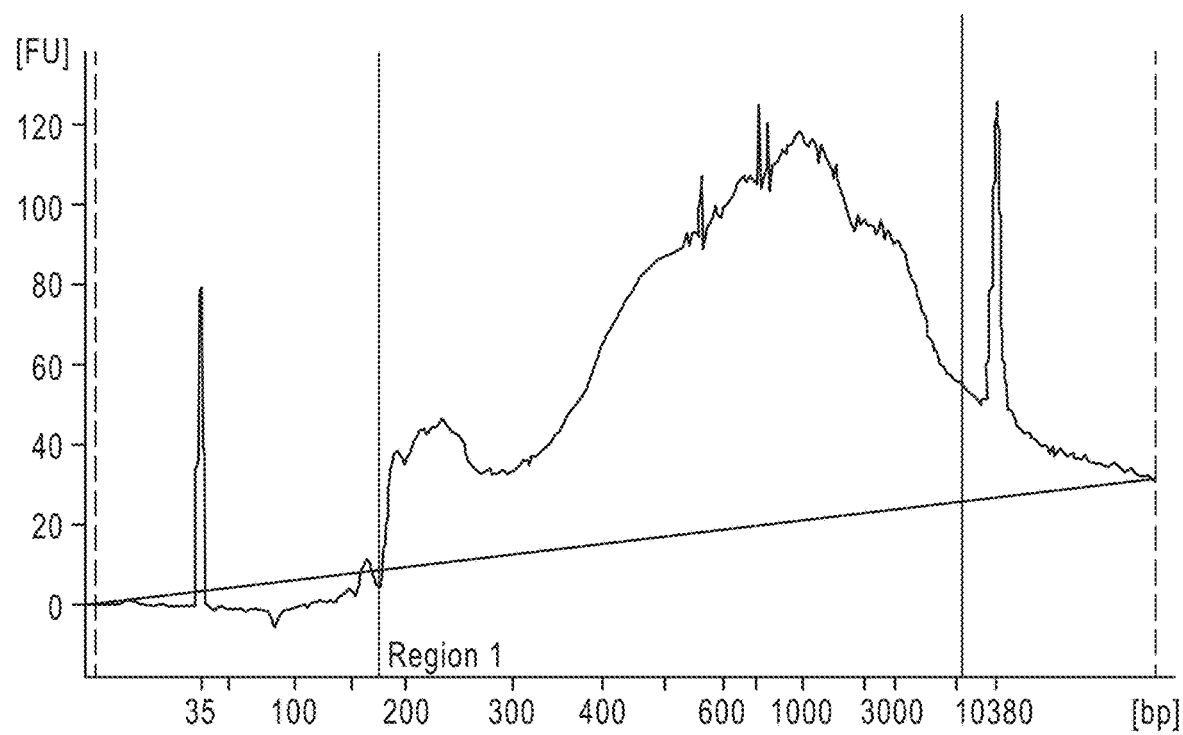
FIGS. 27A-27D show the results of a proof-of-concept experiment that incorporated oligonucleotide-tethered nucleotide technology into a single cell RNA-sequencing library preparation workflow.
Figure 27B:
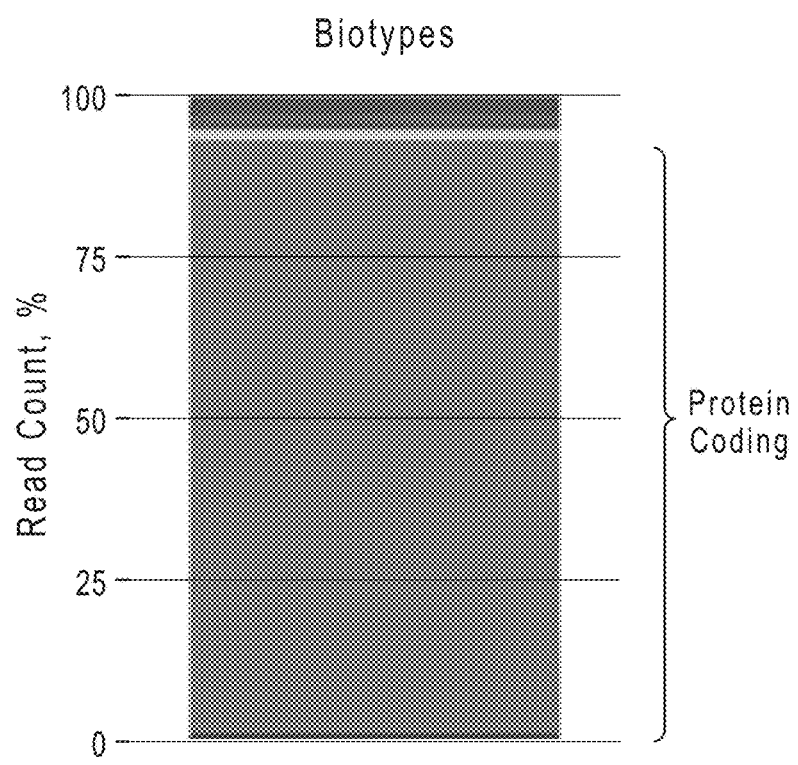
Figure 27C:
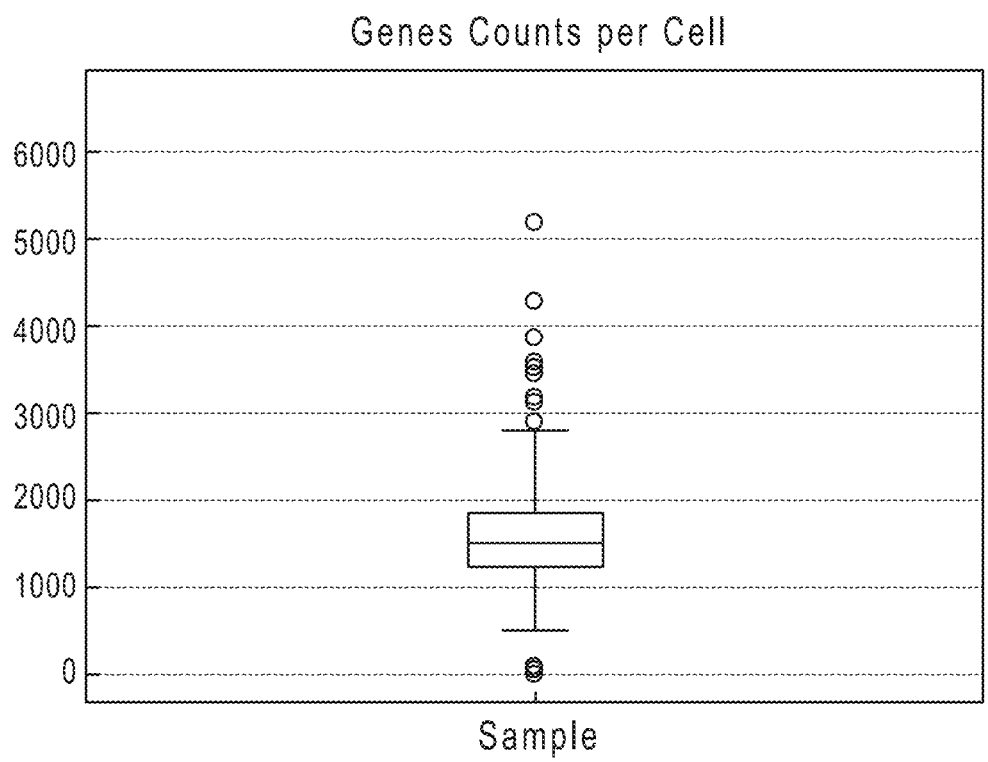
Figure 27D:
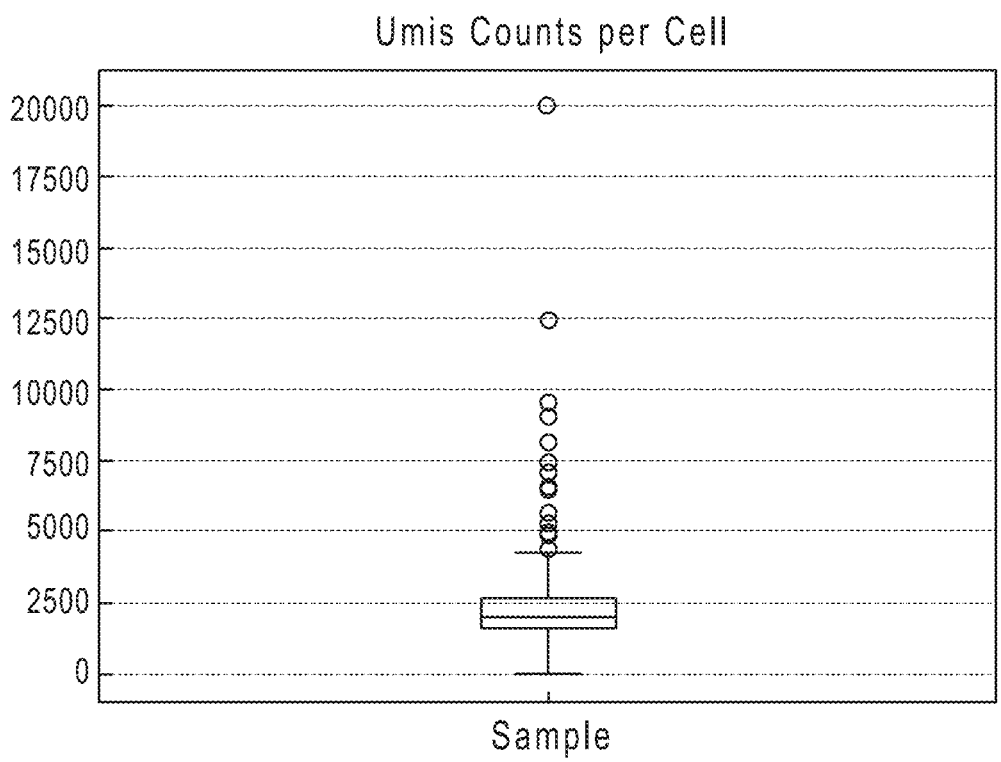

Alternatively, sequencing data of the equivalent quality was obtained using the oligonucleotide-tethered nucleotide of SEQ ID NO: 4 which was synthesized using oligonucleotide with 5' hexynyl modification. Reverse transcription reaction conditions and downstream processing of 3' mRNA-seq libraries were as described above. The resulting libraries exhibited the expected base composition in sequencing reads starting from the oligonucleotide-tethered nucleotide incorporation site (FIG. 26A-26B).

Sequencing-ready libraries covering 3' ends of mRNA may also be prepared from the plurality of single cells. The mixture of HEK293 and BALB/3T3 cells was prepared according to the recommendations for the Nadia™ instrument (Dolomite Bio, Blacktrace Holdings Ltd, Royston, UK) which was used for co-encapsulation of cells and barcoded beads. Barcoded beads (ChemGenes, MA, USA) bearing an oligo(dT)$_{30}$ primer (SEQ ID NO: 40), bead-specific barcodes and randomized regions which served as unique molecular identifiers (UMI) were prepared as recommended by Dolomite Bio and used to prime cDNA synthesis and introduce compartment-specific and molecule-specific tags.

Following encapsulation, the emulsion was broken and beads were washed as recommended in the standard Drop-seq for Nadia™ protocol. Beads were then subjected to the reverse transcription reaction which was conducted as follows: 44 μL of 5× SuperScript IV Buffer (Thermo Scientific, MA, USA), 344 pmol of oligonucleotide-tethered ddCTP (SEQ ID NO: 3), 50 nmol of dATP, 50 nmol of dCTP, 50 nmol of dGTP, 50 nmol of dTTP, 11 μL of 100 mM DTT, 44 μL of 20% Ficoll™ PM400 (Sigma-Aldrich, MO, USA), 220 U of RNaseOUT™ Recombinant Ribonuclease Inhibitor (Thermo Scientific, MA, USA), 2200 U of SuperScript IV (Thermo Scientific, MA, USA), and nuclease-free water to 220 μL final volume. Beads were suspended in 200 μL of reverse transcription reaction mixture and incubated at room temperature for 30 min following by the second incubation at 50° C. for 1 h. Beads were then washed according to the standard Drop-seq for Nadia™ protocol instructions and subjected to linear amplification: ~2000 beads, 10 μL of 5× Phusion HF Buffer (Thermo Scientific, MA, USA), 5 nmol of dATP, 5 nmol of dCTP, 5 nmol of dGTP, 5 nmol of dTTP, 300 pmol of oligonucleotide of SEQ18, 6.25U of Phusion exo- (Thermo Scientific, MA, USA), and nuclease-free water to 50 μL of final reaction volume. Linear amplification was executed for 10 cycles of denaturation at 95° C. for 1 min, annealing at 60° C. for 1 min, extension at 72° C. for 1 min. Reaction products were then purified using the Collibri™ Library Cleanup Kit (Thermo Scientific, MA, USA), beads were discarded at this step. Purified linear amplification products were then amplified using the Collibri™ Library Amplification Master Mix (Thermo Scientific, MA, USA), 46 pmol of SEQ17 primer and 4.6 pmol of SEQ19 primer. The number of PCR cycles was 25.

The presence of sequencing-ready molecules in the resulting library was confirmed by qPCR according to the standard Collibri™ Library Quantification Kit (Thermo Scientific, MA, USA) protocol. The library was then sequenced on the Illumina MiSeq™ using the MiSeq Reagent Kit v2, 300-cycles (Illumina, CA, USA); paired-end reads (R1 of 21 bp and R2 of 75 bp) were performed. Data analysis showed the expected capture of protein-coding portion of the cell transcriptome (FIGS. 27A-27D).

Alternatively, cells may be encapsulated with barcoding beads and RT/lysis mix in droplets, and the emulsion may be broken after reverse transcription reaction.

D. Sequencing-Ready Library Preparation Covering 5' Ends of Transcripts

Figure 28:
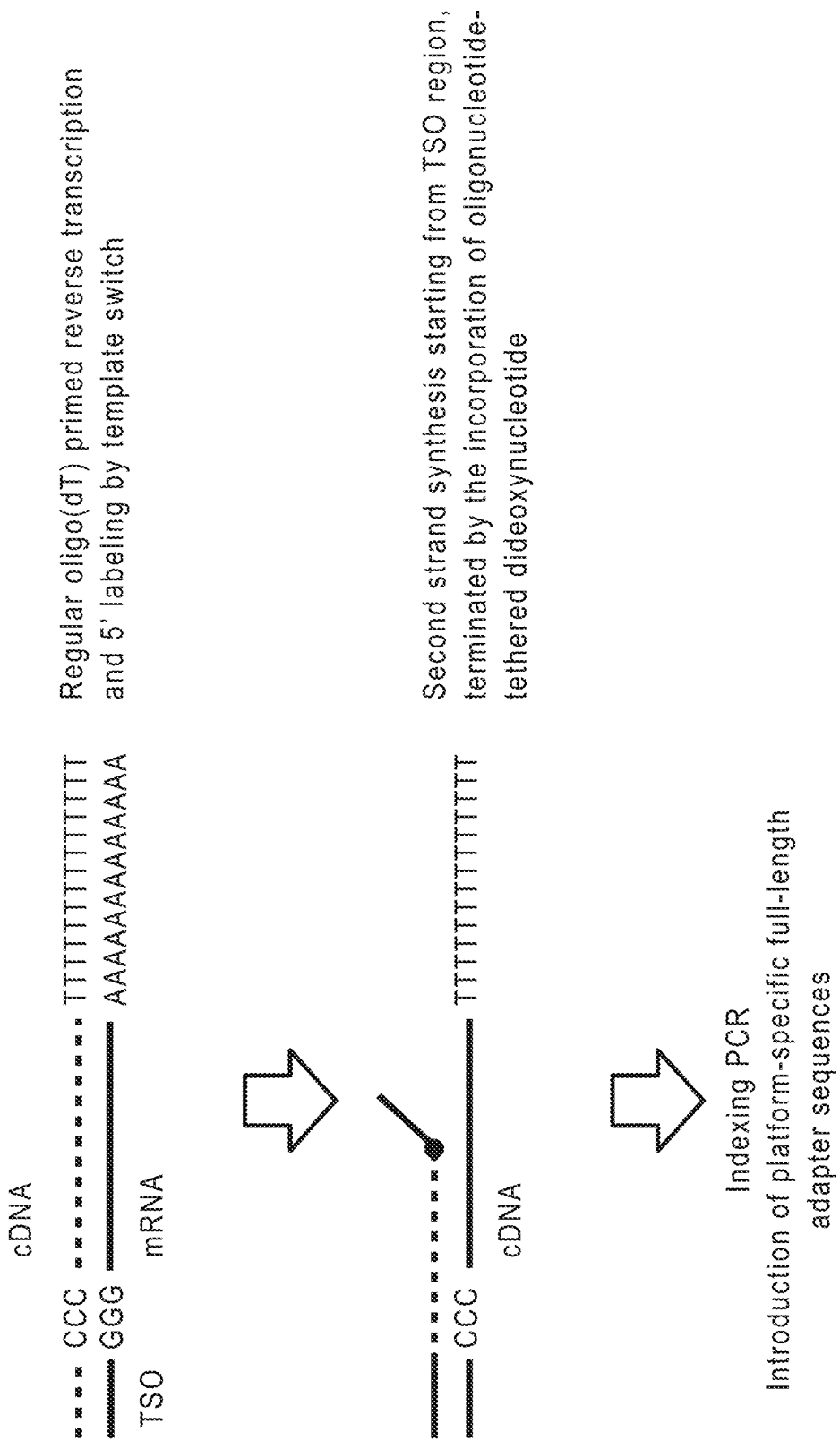
FIG. 28 shows the basic principle of strand-specific mRNA sequencing library preparation, which includes generation of a fragment library covering the 5' ends of transcripts by the extension of second strand synthesis primer and DNA synthesis termination by the incorporation of oligonucleotide-tethered dideoxynucleotides. The library of tagged DNA fragments may then be amplified using PCR primers, which in turn introduce platform-specific adapter sequences. The length of tagged DNA fragments may be controlled through the adjustment of oligonucleotide-tethered dideoxynucleotide concentration and/or ratio relative to the corresponding native deoxynucleotide.

Proof-of-concept (FIG. 28) experiments were performed using human total RNA as a sample input. First, total Universal Human Reference RNA (Thermo Scientific, MA, USA) sample was reverse transcribed using oligo(dT) primer (SEQ ID NO: 9) and a template switch oligonucleotide of the following sequence, where the "r" preceding the "G" indicates a ribonucleotide base:

SEQ ID NO: 20:
5'-CCAGGACCAGCGATTCNNNNNNNNNrGrGrG-3'

Reaction mixture: 1 µg of total RNA, 50 pmol of reverse transcription primer (SEQ ID NO: 16), 4 µL of 5× RT Buffer for SuperScript™ IV (Thermo Scientific, MA, USA), 1 µL of dNTP mix (10 mM each), 1 µL of 100 mM DTT, 3 µL of 50% (w/v) PEG-8000, 200 U of SuperScript™ IV (Thermo Scientific, MA, USA) and water, nuclease-free to 19 µL final volume. Reverse transcription reaction was conducted at 50° C. for 10 min. Then reaction mixture was supplemented with 20 pmol of template switch oligonucleotide (SEQ ID NO: 20) and incubated at 50° C. for additional 15 min. cDNA was then purified using the Collibri™ Library Cleanup Kit according to the protocol for the cleanup of fragmented RNA (described in the Collibri™ Stranded RNA Library Prep Kit (Thermo Scientific, MA, USA) manual). Second strand synthesis was performed using primer SEQ ID NO: 21 complementary (underlined) to the cDNA region corresponding to the SEQ ID NO: 20 oligonucleotide, which tagged 5' ends of transcripts:

SEQ ID NO: 21:
5'-CAGTGGTATCAACGCAGAGTA*CCAGGA*

*CCAGCGATTC*-3'

Figure 29:
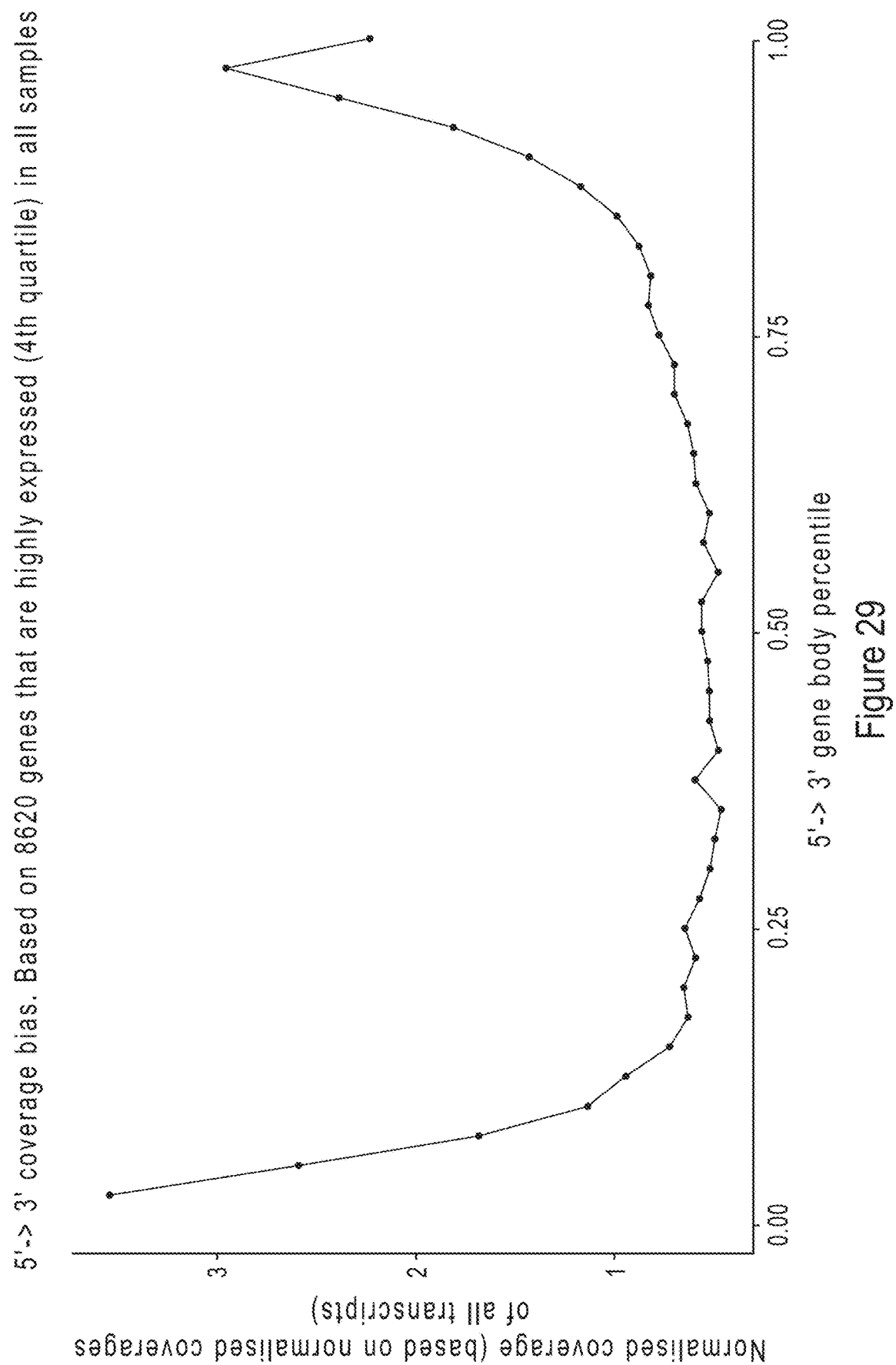
FIG. 29 shows gene body coverage calculated for mRNA sequencing libraries prepared according to the principle depicted in FIG. 28.

Second strand synthesis reaction mixture: purified cDNA, 1 pmol of SEQ ID NO: 21 primer, 1.8 pmol of oligonucleotide-tethered ddUTP (SEQ ID NO: 1), 18 pmol of dTTP, 20 pmol of dATP, 20 pmol of dCTP, 20 pmol of dGTP, 40 U Thermo Sequenase™ (Thermo Scientific, MA, USA), 2 µL of Reaction Buffer and water, nuclease-free to 20 µL final reaction volume. The primer extension reaction was performed for 1 cycle of denaturation at 95° C. for 3 min, then 10 cycles of denaturation at 95° C. for 30 s and annealing/extension at 60° C. for 2 min, following with a final extension at 60° C. for 5 min Reaction products were enriched for oligonucleotide-tethered ddUTP-containing molecules by purification with Dynabeads™ M-270 Streptavidin magnetic beads (Thermo Scientific, MA, USA) according to the manufacturers' instructions for immobilization of nucleic acids. Purified primer extension products were subjected to indexing PCR according to the standard Collibri™ Library Amplification Master Mix (Thermo Scientific, MA, USA) reaction conditions, except for the number of PCR cycles which in this experiment was 25, using primers SEQ ID NO: 17 or SEQ ID NO: 18 to introduce full-length sequencing adapters compatible with Illumina™ instruments. After indexing, PCR libraries were purified using the Collibri™ Library Cleanup Kit (Thermo Scientific, MA, USA). The presence of sequencing-ready molecules in the resulting samples was confirmed by qPCR according to the standard Collibri™ Library Quantification Kit (Thermo Scientific, MA, USA) protocol. The resulting libraries were sequenced on the Illumina MiSeq™ using the MiSeq Reagent Nano Kit v2, 300-cycles (Illumina, CA, USA); paired-end reads (R1 of 100 bp and R2 of 75 bp) were performed. Data analysis revealed the alignment rate to human genome of 83%, strand specificity of 91.1% and gene body coverage with bias towards the 5' end (FIG. 29).

E. PCR-Free Sequencing-Ready Library Preparation

As long as polymerases integrated into sequencing platforms are able to read through conjugation linker, PCR-free sequencing-ready library preparation is possible both from DNA and RNA samples. One-step primer extension, using primer with a 5' anchor corresponding to the full-length adapter, and termination by incorporation of oligonucleotide-tethered dideoxynucleotides bearing the second full-length platform-specific adapter sequence, enable generation of fully sequencing-ready single-stranded libraries which may be subjected to sequencing without amplification step. This provides advantage that less library preparation steps are needed. When RNA samples are used, such strategy provides further advantage in that only synthesis of first strand cDNA is needed to achieve a sequencing-ready single stranded DNA comprising adapters at 5' and 3' ends.

Figure 35A:
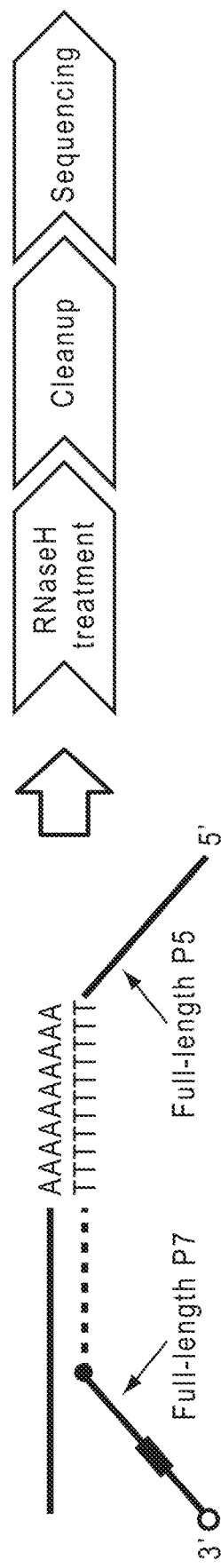
FIG. 35A-35C show the basic principle of PCR-free RNA library preparation using oligonucleotide-tethered dideoxynucleotides containing full-length sequencing adapter modification. Upon sequencing of the resulting libraries, reads of expected structure correspond to cDNA fragments and cover the expected portion of transcripts.

The below experiments (a corresponding scheme is provided in FIG. 35A) were performed using Universal Human Reference RNA (Thermo Fisher) as an input. 500 ng of RNA were reverse transcribed using reverse transcription primer (SEQ ID NO: 34) comprising full-length Illumina P5 adapter (1-57 nucleotides of SEQ ID NO: 34).

SEQ ID NO: 34:
5'-AATGATACGGCGACCACCGAGATCTACACTCTTTCCCTACACGACG

CTCTTCCGATCTTTTTTTTTTTTTTTTTTTTTTTTTTTTTT-3'

RNA was mixed with 50 pmol of reverse transcription primer, 20 pmol of dNTP mix, 2 pmol of oligonucleotide-tethered ddCTP (SEQ ID NO: 35), 200 U of SuperScript IV reverse transcriptase in 1× SuperScript IV RT buffer (Thermo Scientific, MA, USA) supplemented with 5 mM DTT; reaction volume was 20 µL. Reaction was performed at 50° C. for 30 min, followed by inactivation at 80° C. for 10 min.

SEQ ID NO: 35:
ddCTP-AldU-AGATCGGAAGAGCACACGTCTGAACTCCAGTCACATGC

CTAAATCTCGTATGCCGTCTTCTGCTTG-3'-BIOTIN

Figure 35B:
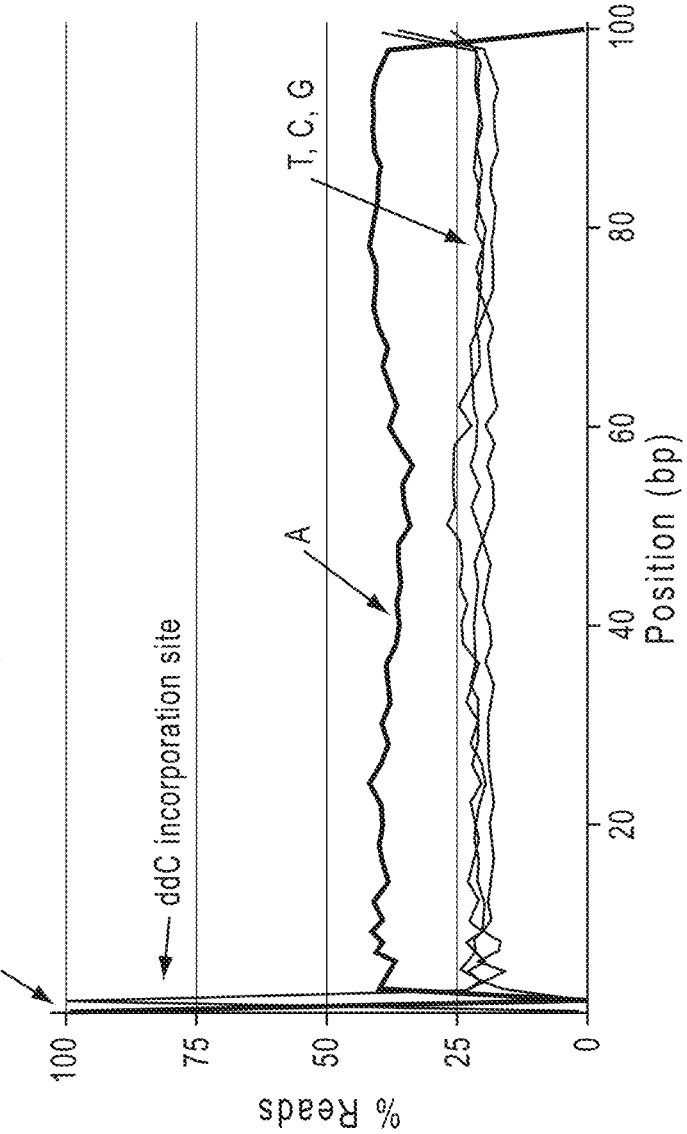
Figure 35C:
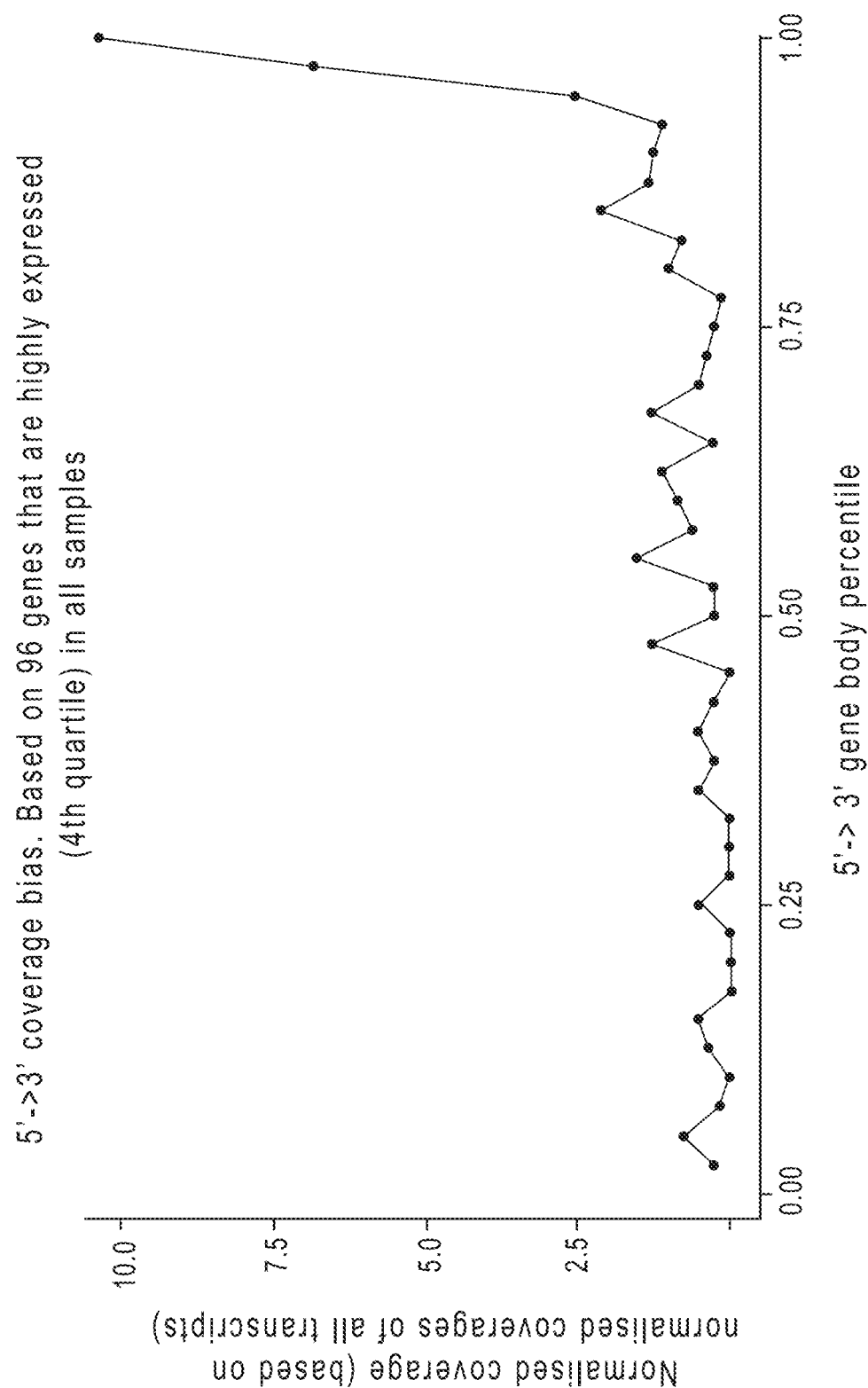

After inactivation, RNase H (Thermo Scientific, MA, USA) was added to the reaction mixture to degrade RNA strand from RNA:cDNA duplexes. Reaction with RNase H was incubated at 37° C. for 20 min. cDNA labeled with oligonucleotide-tethered dideoxynucleotide was purified with Dynabeads M-270 Streptavidin magnetic beads (Thermo Scientific, MA, USA) according to the manufacturers' instructions for immobilization of nucleic acids. Purified cDNA fragments were directly subjected (advantageously, NaOH denaturation step was not needed, as fragment library is already in ssDNA form) to sequencing on an Illumina. MiSeq instrument using the MiSeq Nano Reagent Kit v2, 300-cycles (Illumina, CA, USA); 25 bp R1 and 100 bp R2 paired-end reads were performed. Data analysis revealed the presence of reads of correct structure (i.e. R2 starting from AG nucleotides which correspond to AldU modification within the oligonucleotide-tethered dideoxynucleotide, and ddCTP incorporation site, FIG. 35B). 93% of such reads corresponded to protein coding genes and covered 3' termini of transcripts as is expected from experimental design (FIG. 35C).

Similar principle can be employed for PCR-free library preparation from DNA samples. Full-length adapter handle can be added to 5' region of any random or sequence-specific primer which can be extended by DNA polymerase capable of oligonucleotide-tethered dideoxynucleotide incorporation. As an example, Thermo Sequenase or Phusion exo- DNA polymerase may be used.

F. Linear Amplification of DNA and Sequencing-Ready Library Preparation

Linear DNA amplification is performed via in vitro transcription using T7 RNA polymerase, which initiates RNA synthesis specifically from the T7 promoter SEQ ID NO: 5. DNA tagging with T7 promoter sequence is achieved via incorporation of oligonucleotide-tethered nucleotide, which includes such sequence.

In vitro transcription initiation from the oligonucleotide-tethered nucleotide (SEQ ID NO: 22) was performed to test the ability of such complexes to serve as initiation sites for RNA synthesis. SEQ ID NO: 22 oligonucleotide-tethered deoxynucleotide was incorporated into oligonucleotide duplex SEQ ID NOS: 24+SEQ ID NO: 25 by the extension of SEQ ID NO: 24 oligonucleotide.

```
SEQ ID NO: 24:
5'-TGCAGACATGGGTAGGCATCCTTGGCGTA-3'

SEQ ID NO: 25:
5'-GTACGCCAAGGATGCCTACCCATGTCTGCA-3'
```

Complementary strand (SEQ ID NO: 26) was then added to ensure that T7 RNA polymerase promoter is double-stranded.

```
SEQ ID NO: 26:
5'-CTAATACGACTCACTATAGGTGTTACATCTGGTAGTCAGTCTCCAA
TAAATATATAAA-3'
```

Figure 30:
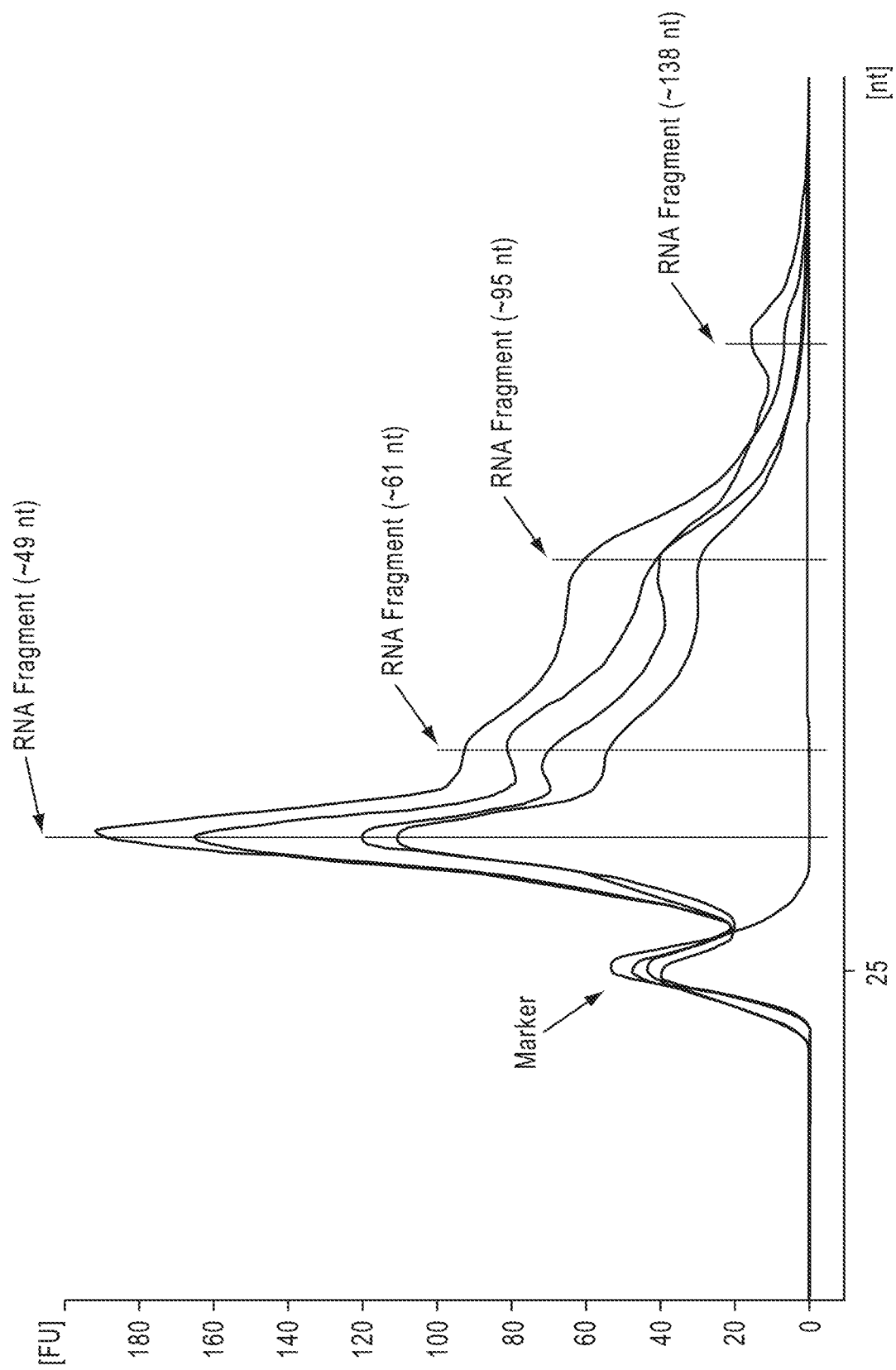
FIG. 30 shows in vitro transcription products generated from the T7 RNA polymerase promoter included in the oligonucleotide-tethered nucleotide sequence. RNA fragment peak of ~49 nt denotes transcription product which synthesis was terminated at the linker site, and RNA fragment peak of ~95 nt denotes the migration of the same transcript affected by secondary structures. RNA fragment peak of ~61 nt length denotes transcription product which was synthesized with linker hopping. ~138 nt RNA fragment peak denotes the migration of the same transcript affected by secondary structures. The results indicate that T7 promoter sequence included in the oligonucleotide-tethered nucleotide is functional and may serve as in vitro transcription initiation site.
Figure 34A:
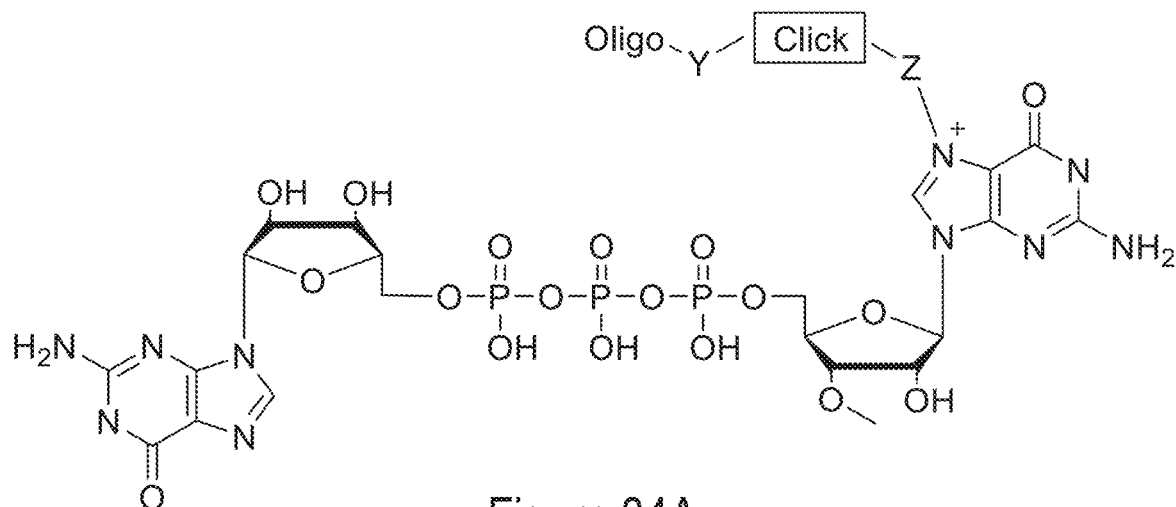
FIGS. 34A-34G depict the structures of several exemplary anti-reverse cap analogs.
Figure 34B:
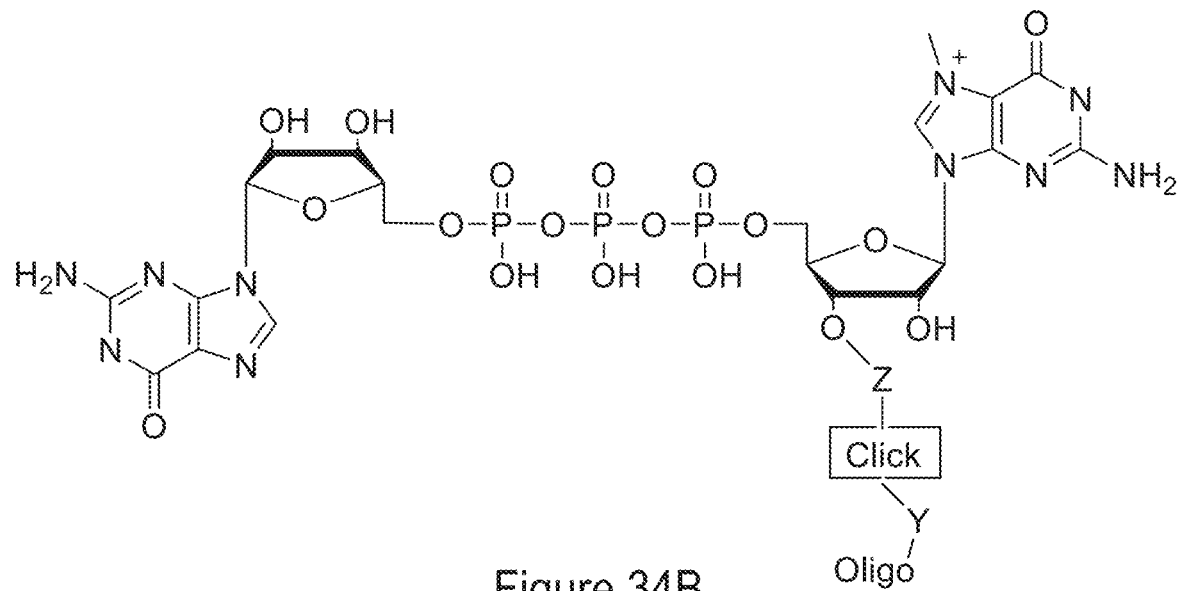
Figure 34C:
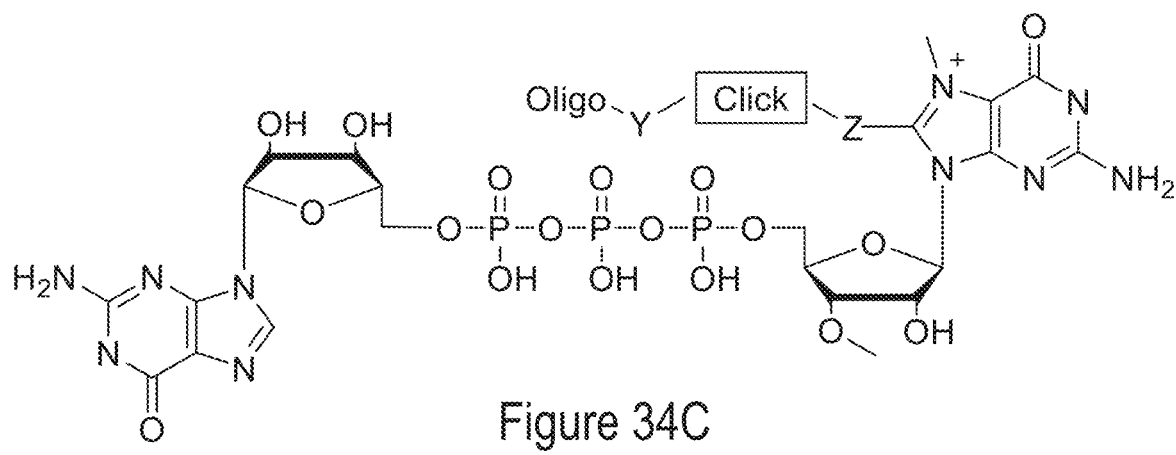
Figure 34D:
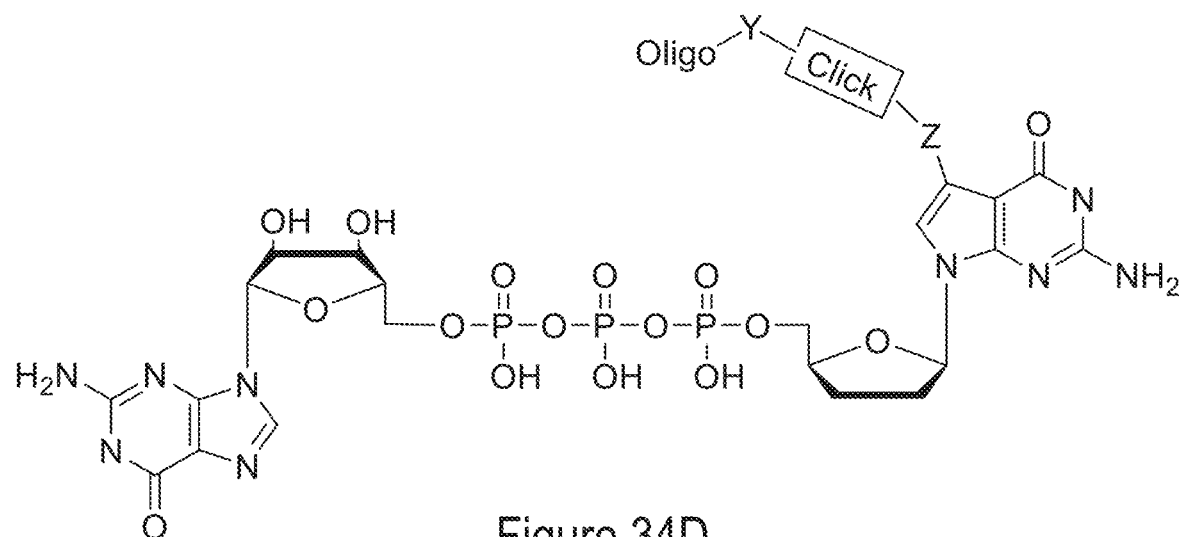
Figure 34E:
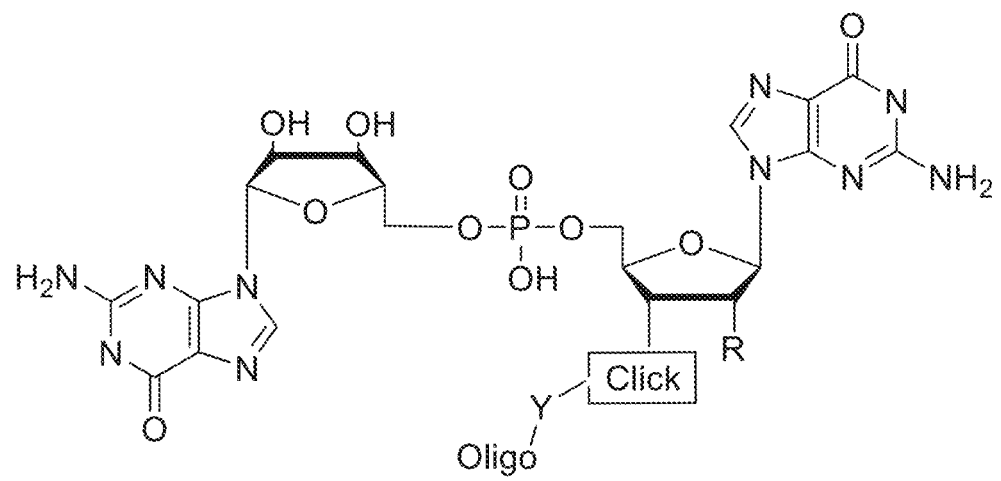
Figure 34F:
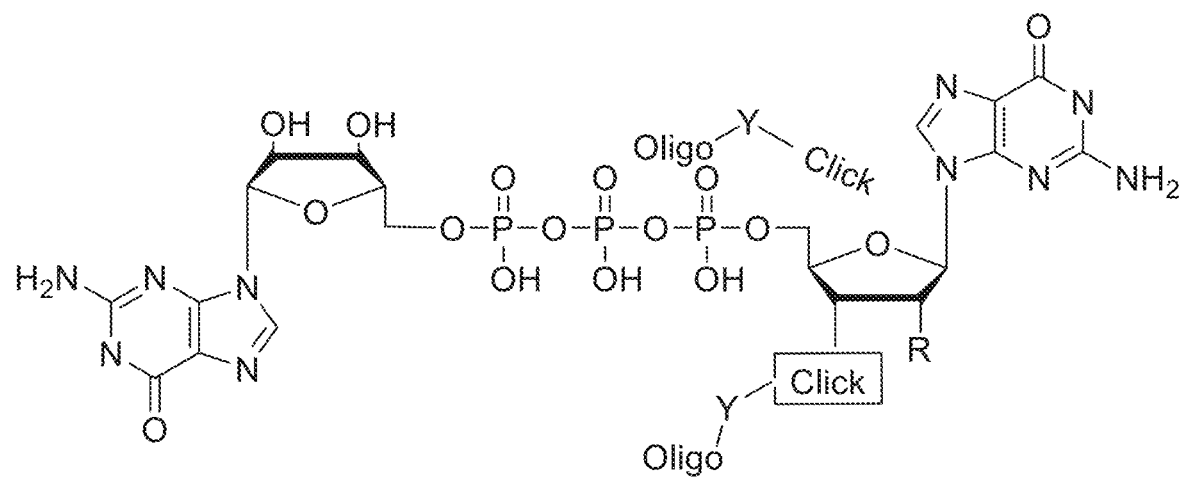
Figure 34G:
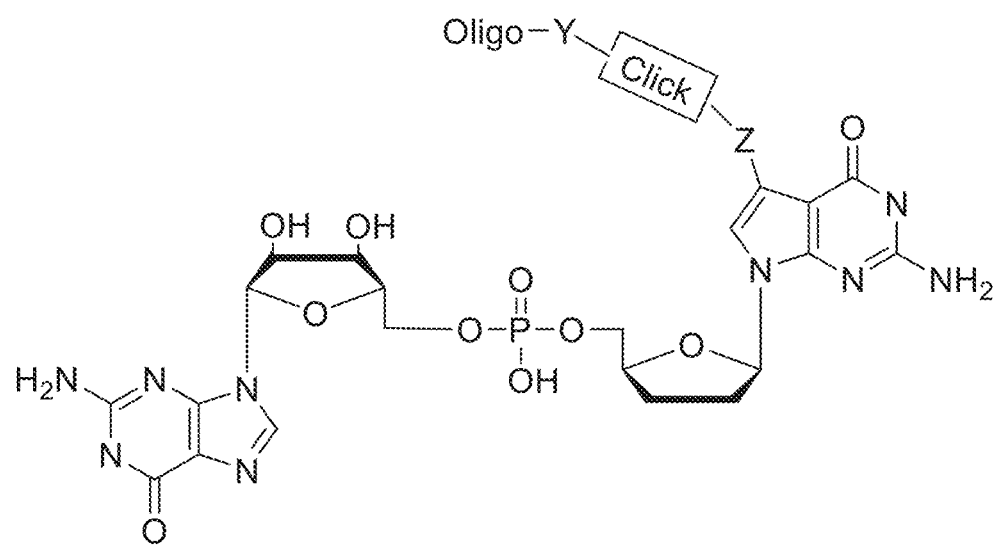

In vitro transcription was performed according to the recommended TranscriptAid™ T7 High Yield Transcription Kit (Thermo Scientific, MA, USA) reaction conditions, the incubation at 37° C. was performed overnight. Transcription products were then treated with DNase I to remove the template, and RNA was purified using the Agencourt AMPureXP™ magnetic beads (Beckman Coulter, CA, USA). The resulting transcripts were analyzed on Agilent 2100 Bioanalyzer using RNA Pico 6000 Kit. The results indicated the presence of RNA transcripts (FIG. 30). The results indicate that T7 promoter sequence included in the oligonucleotide-tethered nucleotide is functional and may serve as in vitro transcription initiation site, and T7 RNA polymerase was able to read through the unnatural linker of oligonucleotide-tethered nucleotide.

Example 5. DNA End Labeling

A. Tagging of 5' Termini of Nucleic Acids

In some embodiments, the oligonucleotide may be attached to anti-reverse cap analog (ARCA) or similar structures (FIG. 34A-34G). In this case, the oligonucleotide is conjugated to the nucleotide through its 3' terminus. Such oligonucleotide-tethered capping nucleotides are useful for tagging of 5' termini of nucleic acids during their de novo synthesis by in vitro transcription. Oligonucleotide-tethered capping nucleotide may be incorporated into RNA, DNA or chimeric transcripts by RNA polymerases, such as T7 RNA polymerase, T3 RNA polymerase, or engineered mutant variants of such polymerases.

In some situations, the oligonucleotide provides a pre-designed priming site at the 5' terminus for subsequent amplification. An additional priming site at the 3' terminus may be added via tagging with the oligonucleotide-tethered nucleotide, addition of a homopolymeric tail using TdT, PAP or PUP, or ligation of single stranded adapter.

B. Template-Independent DNA End Labeling

Template-independent DNA 3' end labeling with any pre-designed sequence may be achieved through the incorporation of oligonucleotide-tethered dideoxynucleotides (OTDDNs) by terminal deoxynucleotidyl transferase (TdT). After a first round of labeling, a complementary strand may be synthesized upon primer extension from an oligonucleotide conjugated to the dideoxynucleotide by any polymerase capable of reading through the conjugation linker. The second round of DNA end labeling may then be performed as the newly synthesized strand will have an accessible 3' end.

The experiments were performed using template oligonucleotide (SEQ ID NO: 36) of the following sequence:

```
SEQ ID NO: 36:
Phosphate-
5'-GCGGCGACCAAATCGTTGTAAAGATCGGAAGAGCGTCGTGTA-3'
```

The first 3' end labeling was performed using 2 pmol of template oligonucleotide (SEQ ID NO: 36), 100 pmol of oligonucleotide-tethered nucleotide of SEQ ID NO: 4, 40 U of TdT enzyme (Thermo Scientific, MA, USA) in 1× TdT buffer; and the reaction volume was 30 μL. The reaction mixture was incubated at 37° C. for 1.5 hour, followed by reaction termination at 70° C. for 10 min. Tagged template oligonucleotide was purified by ethanol precipitation and used for second strand synthesis. Purified DNA was mixed with 30 U of Phusion exo- DNA polymerase (Thermo Scientific, MA, USA), 4 pmol of labeled primer (SEQ ID NO: 37) and 16 pmol of unlabeled primer (SEQ ID NO: 38) complementary to the oligonucleotide-tethered dideoxy-nucleotide, and 0.2 mM of dNTP mix in 1× Phusion GC Buffer (Thermo Scientific, MA, USA).

```
SEQ ID NO: 37:
Cy5-5'-CAGACGTGTGCTCTTCCGATCT-3'

SEQ ID NO: 38:
5'-CAGACGTGTGCTCTTCCGATCT-3'
```

The reaction mixture was incubated in a thermal cycler using the following cycling conditions: 20 cycles of denaturation at 98° C. for 1 minute, annealing at 60° C. for 1 min and extension at 72° C. for 1 min. Reaction products were either purified by ethanol precipitation or treated with Exo I (Thermo Scientific, MA, USA) at 37° C. for 30 min Part of the samples were treated (FIG. 36B) with Lambda exonuclease (Thermo Scientific, MA, USA) for either 2, 10 or 30 min. Lambda exonuclease was inactivated by heating at 80° C. for 10 min Free nucleotides were removed using Zeba Spin Desalting Columns, 7K MWCO (Thermo Scientific, MA, USA), and samples were purified by ethanol precipitation.

Figure 36A:
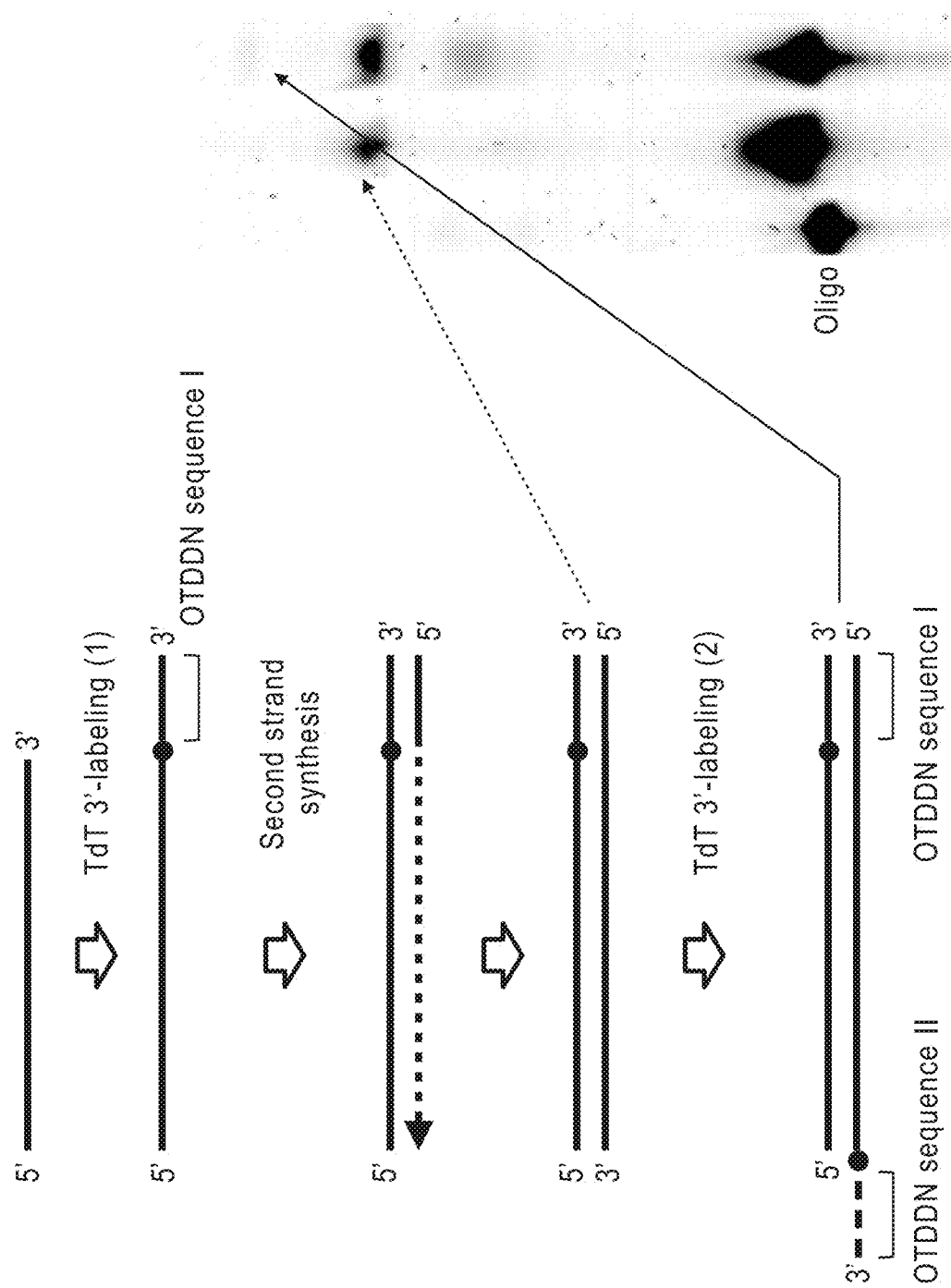
As shown in FIG. 36A, the ends of double-stranded, single-stranded and partially double-stranded DNA may be labeled.

Lambda exonuclease treatment removed the template strand leaving only the second strand for subsequent labeling. In cases where lambda exonuclease treatment was not performed, double stranded duplex was subjected to second round of labeling (FIG. 36A). Products of the first labeling reaction were mixed with 100 pmol of oligonucleotide-tethered dideoxynucleotide SEQ ID NO: 4, and 30 U of TdT enzyme in 1× TdT buffer (Thermo Scientific, MA, USA); the reaction volume was 16 μL. Reaction mixtures were incubated at 37° C. for 1.5 hour, followed by inactivation at 70° C. for 10 minutes. Reaction products were then resolved on a 15% TBE-Urea PAGE.

Figure 36B:
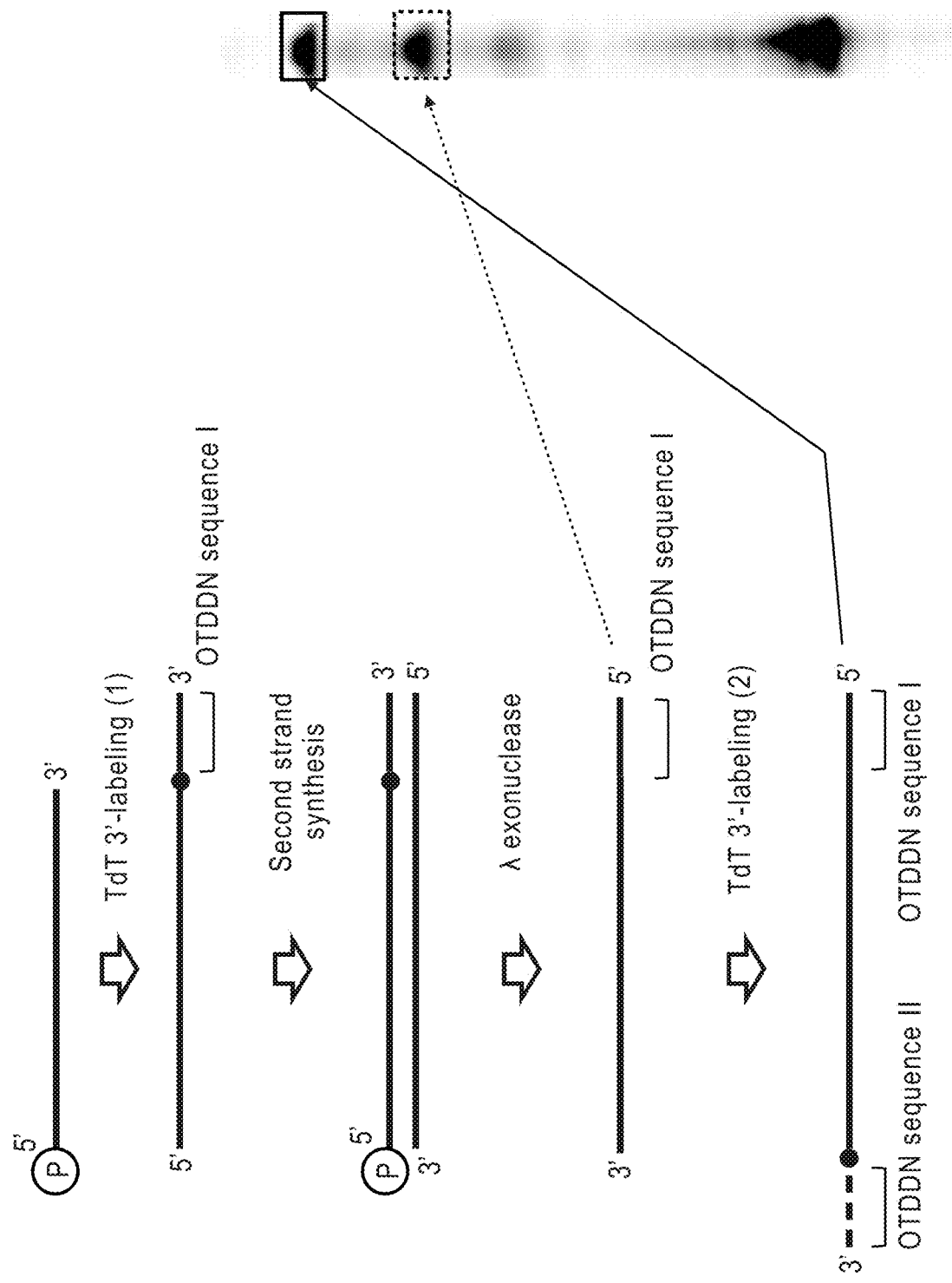

Dual labeling products were visible in all cases. As ssDNA is a better substrate for TdT, labeling was more efficient when single-stranded second strand was used as a template in the second labeling reaction (FIG. 36B).

C. Template-Dependent DNA End Labeling

Creating a plurality of DNA fragments labeled by oligonucleotide-tethered dideoxynucleotides at both termini can be template dependent and resulting fragments could be used to prepare a sequencing-ready library.

Figure 37A:
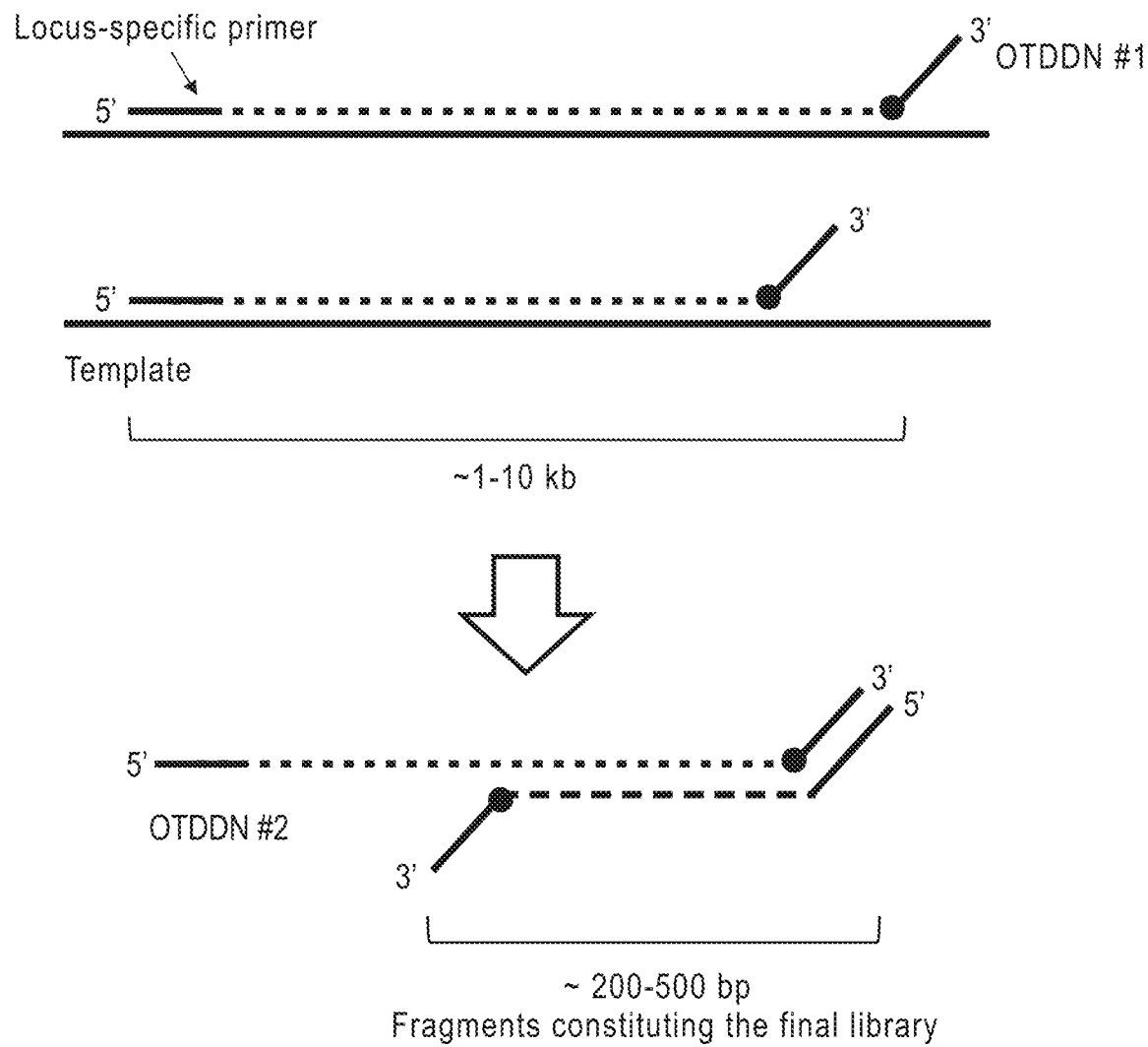
FIG. 37A-37C show the principle of template-dependent DNA end labeling with oligonucleotide-tethered dideoxynucleotides (OTDDN) that generate a plurality of DNA fragments having known sequences at both termini (FIG. 37A). The results indicate that such dual tagging principle can be employed for sequencing library preparation (FIG. 37B-37C).

The experiments were performed according the principle depicted in FIG. 37A. *E. coli* genomic DNA was used as a template. 5 ng of DNA were mixed with 20 U of Phusion exo- enzyme (Thermo Scientific, MA, USA), 12.5 pmol of specific primer (SEQ ID NO: 39), 0.4 pmol of oligonucleotide-tethered dideoxynucleotide SEQ ID NO: 4, 4 nmol of dNTP mix in 20 μL of 1× Phusion HF Buffer (Thermo Scientific, MA, USA).

SEQ ID NO: 39:
5'-AAGTCGTAACAAGGTAACCG-3'

Figure 37B:
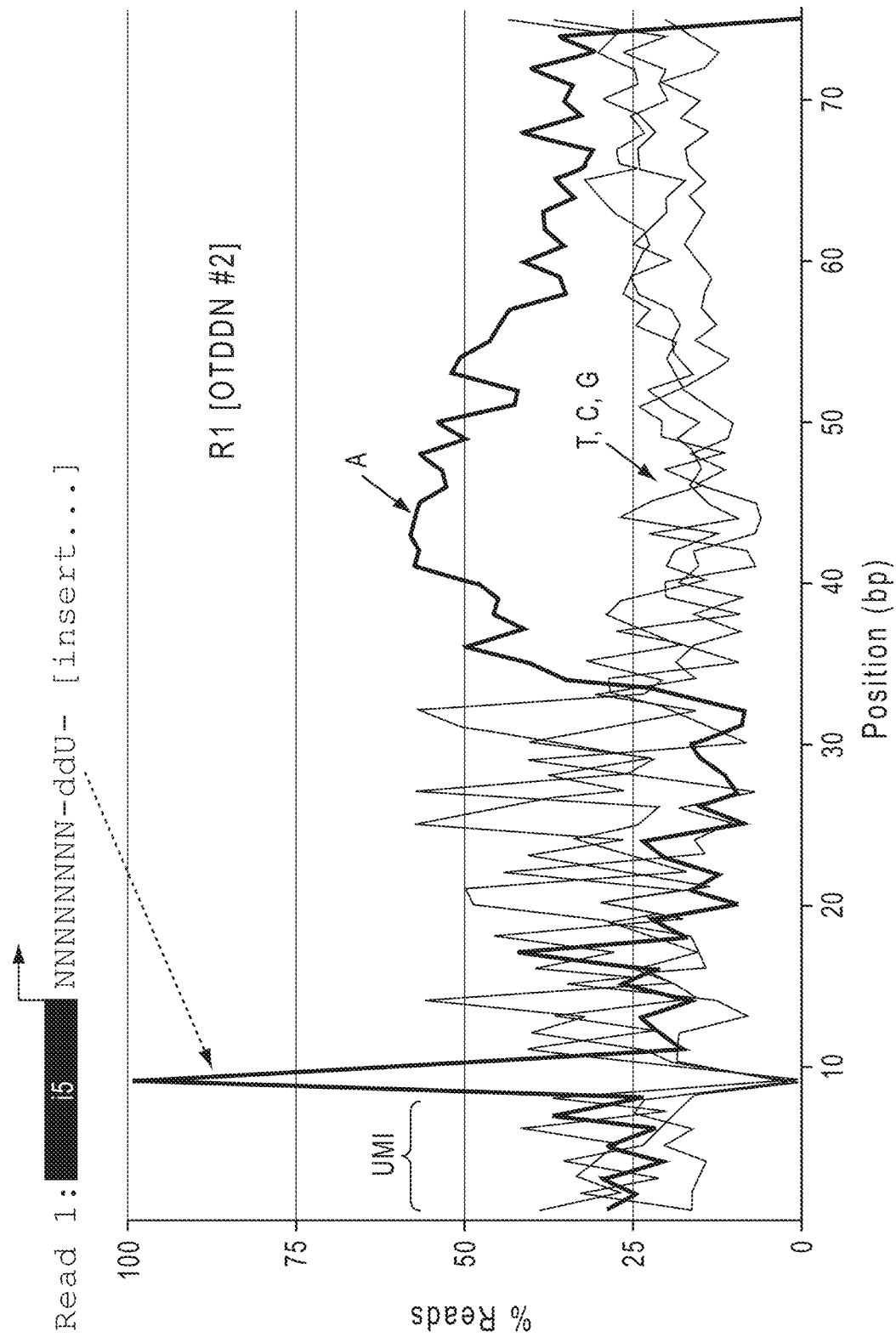
Figure 37C:
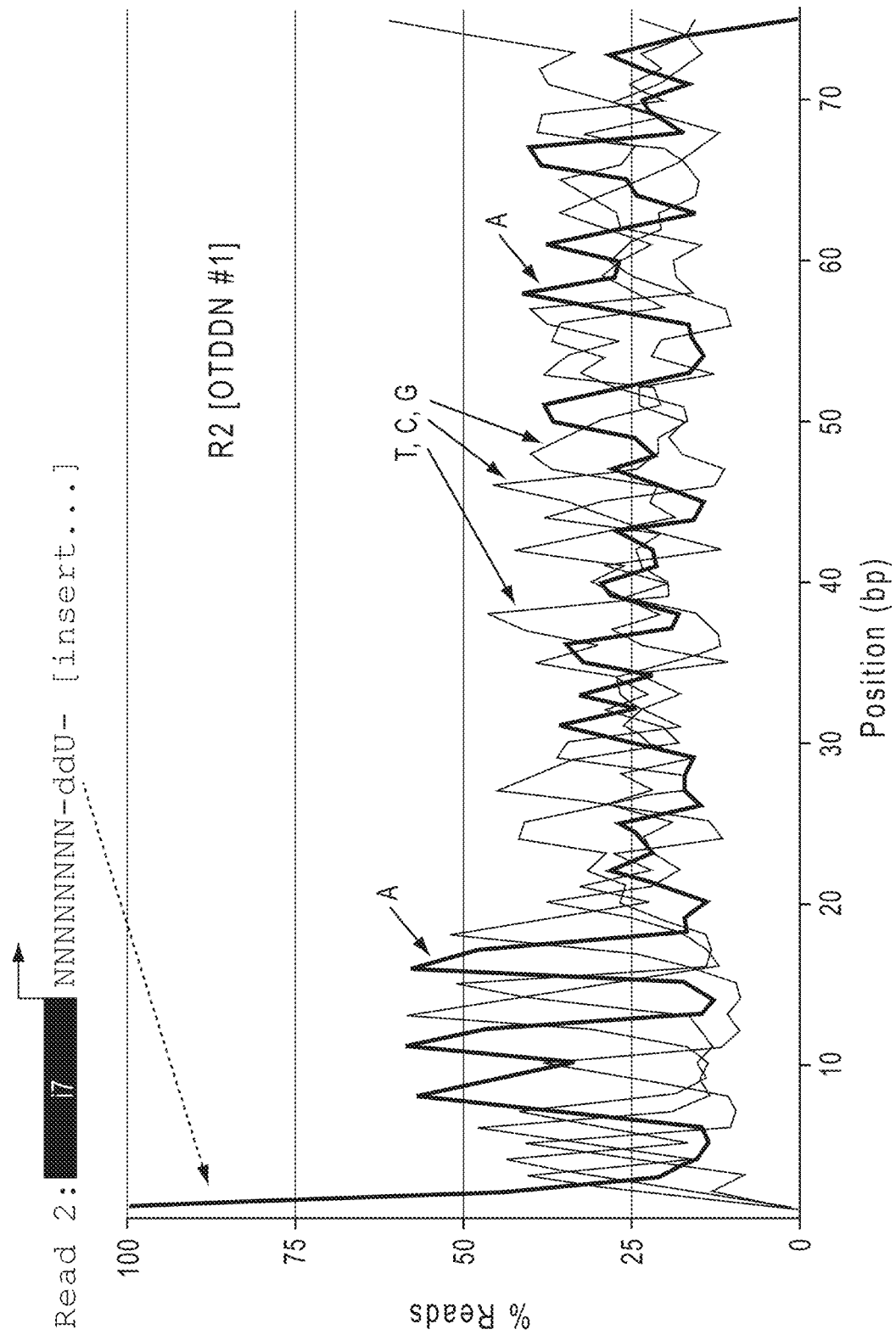

Primer extension and termination reaction was performed as follows: initial denaturation at 98° C. for 30 s, followed by 15 cycles of denaturation at 98° C. for 1 min, annealing at 45° C. for 30 s, extension at 72° C. for 3 min; final extension was performed at 72° C. for 10 min Reaction products were purified using Dynabeads Cleanup Beads (Thermo Scientific, MA, USA). Purified DNA was subjected to the second round of labeling by primer extension and termination from the first oligonucleotide-tethered dideoxynucleotide region. Purification products were mixed with 20 U of Phusion exo- (Thermo Scientific, MA, USA), 10 pmol of primer SEQ ID NO: 18, 10 pmol of oligonucleotide-tethered dideoxynucleotide SEQ ID NO: 6, 10 nmol of dNTP mix in 50 μL of 1× Phusion HF Buffer (Thermo Scientific, MA, USA). The reaction conditions were identical to the previous reaction except that primer annealing step was performed at 60° C. Reaction products were purified using Dynabeads Cleanup Beads (Thermo Scientific, MA, USA). Dually tagged DNA fragments were enriched by amplification in 1× Collibri Library Amplification Master Mix (Thermo Scientific, MA, USA) with 50 pmol of primer SEQ ID NO: 17 and 50 pmol of primer SEQ ID NO: 19. The cycling conditions were as follows: initial denaturation at 98° C. for 30 s, followed by 25 cycles of denaturation at 98° C. for 10 s, annealing at 60° C. for 30 s, extension at 72° C. for 30 s, the final extension was performed at 72° C. for 1 min. Reaction products were purified using Dynabeads Cleanup Beads (Thermo Scientific, MA, USA). The resulting library was sequenced on an Illumina MiSeq instrument using MiSeq Reagent Kit v2, 300-cycle (Illumina, CA, USA); 2×150 bp paired-end reads were performed. Data analysis revealed the presence of reads of a correct structure, i.e. those having A nucleotide at $9^{th}$ position in R1, and A nucleotide at the first position in R2 (FIGS. 37A-37C). Those reads aligned to *E. coli* genome.

The principle described above can be fulfilled with any combination of DNA polymerases able to incorporate oligonucleotide-tethered dideoxynucleotides and read through the conjugation linker, including but not limited to combinations with Thermo Sequenase. The amount of OTDDNs used at each labeling step can be modified leading to the regulation of obtainable DNA fragment sizes.

Example 6. Improved Workflow for Generating a Nucleic Acid Library for Single Cell Analysis In some embodiments, one more oligonucleotide-tethered dideoxy nucleotides (OTddNTPs) can be used in a combinatorial barcoding reaction, e.g. to facilitate improved single cell analysis workflows with cells or nuclei. For example, in some embodiments, the OTddNTPs can be incorporated into single cell workflows such as whole transcriptome analysis, whole genome analysis, directed mRNA analysis, short RNA (e.g., miRNAs) analysis, single cell protein analysis, and the like. By way of example only, provided herein is a workflow to analyze the transcriptomes of single cells within a population of cells (See, FIG. 38). In some embodiments, the method can include steps to fix and permeabilize cells within a cell population, such that nucleic acids and proteins within the cell remain intact and fixed within their cell of origin. At the same time, the permeabilization step functions to enable reagents (e.g., polymerases, nucleotides, primers, and the like) to enter the cells wherein they can function in, e.g. reverse transcription, primer extension, ligation amplification reactions and the like. Many methods of fixing and permeabilizing cells are known in the art. By way of example, methods for fixing and permeabilizing cells useful in the embodiments disclosed herein include, but are not limited to, those described in Rosenberg, et al. (2018) *Science* (360) 176-182, Supplementary Materials, U.S. Patent Application Publication No. U.S. 2016/0138086, and International Patent Application Publication No. WO 2014/060843.

In some embodiments, improved combinatorial barcoding can include the steps of splitting the fixed/permeabilized cells into more than one first portion (e.g., 96, 384, or any other number of portions). Each first portion can be contacted with a first extension primer. The first extension primers can include a first universal handle sequence. As used herein, the term "universal sequence" refers to a sequence that is present in all primers. As such, the term "first universal handle sequence" present in a first extension primer refers to a handle sequence that is present in all first extension primers.

The first (e.g., forward) extension primer can include a first barcode sequence. Primers may also include a 3' sequence that enables random priming to polynucleotides of interest (e.g., a random primer, a poly(T) sequence (e.g., a 30-mer of T's), or a target-specific sequence, in addition to the first barcode. In some embodiments, the first primers are reverse transcription primers include a combination of primers comprising a first barcode and a 3' poly(T), and primers comprising a first barcode and a random primer sequence. In some embodiments, the reverse transcription primer can include a universal handle at the 5' end. In some embodiments the reverse transcription primer can include a unique molecular tag.

In some embodiments, the reverse transcription primers include an oligonucleotide-tethered nucleotide as described herein.

In addition to the reverse transcription primers, the fixed/permeabilized cells can be contacted with a reverse transcriptase, dNTPs, and one or more oligonucleotide-tethered ddNTPs under conditions that allow reverse transcription to occur. The oligonucleotide-tethered ddNTPs may be incorporated in the first strand cDNA synthesis step randomly along the cDNA, such that termination point of the cDNA is random for each mRNA message. As such, if cDNAs are subsequently amplified, the random termination point can be used to determine which amplification products originate from a single mRNA/cDNA.

In some embodiments, the oligonucleotide that is tethered to the ddNTP includes a universal handle at the 3' end. In some embodiments, the cells can subsequently be contacted with one or more blocking oligonucleotides that are capable of binding (e.g., via a complementary nucleotide sequence) and inhibiting binding and/or extension from unbound reverse transcription primers. In some embodiments, the cells are not subsequently contacted with one or more blocking oligonucleotides.

Following the reverse transcription reaction, the portions of fixed/permeabilized cells can be pooled and split unto more than one portion again (e.g., 96, 384, or any other number of portions) for a second round of barcode addition.

Example 7. Comparison of OTDDN Workflow Versus SPLiT-Seq Workflow

Figure 40:
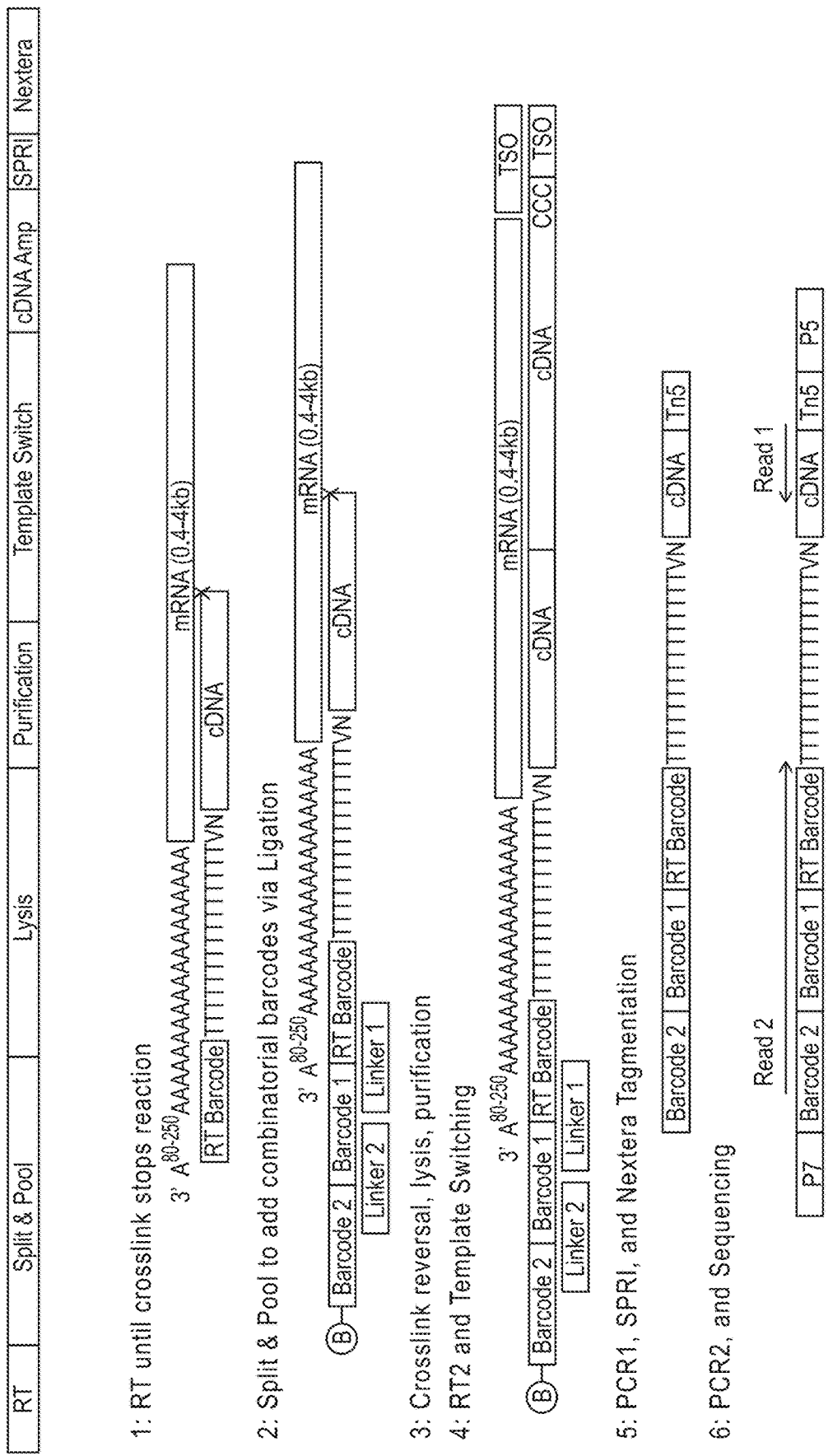
FIG. 40 summarizes the SPLiT-seq protocol from Rosenberg et al., *Science* 360, 176-182 (2018). P5 and P7 represent sequences related to sequencing on Illumina platforms. RT=reverse transcription; SPRT=solid phase reversible immobilization; Tn5=transposase Tn5; TSO=template switch oligonucleotide.
Figure 41:
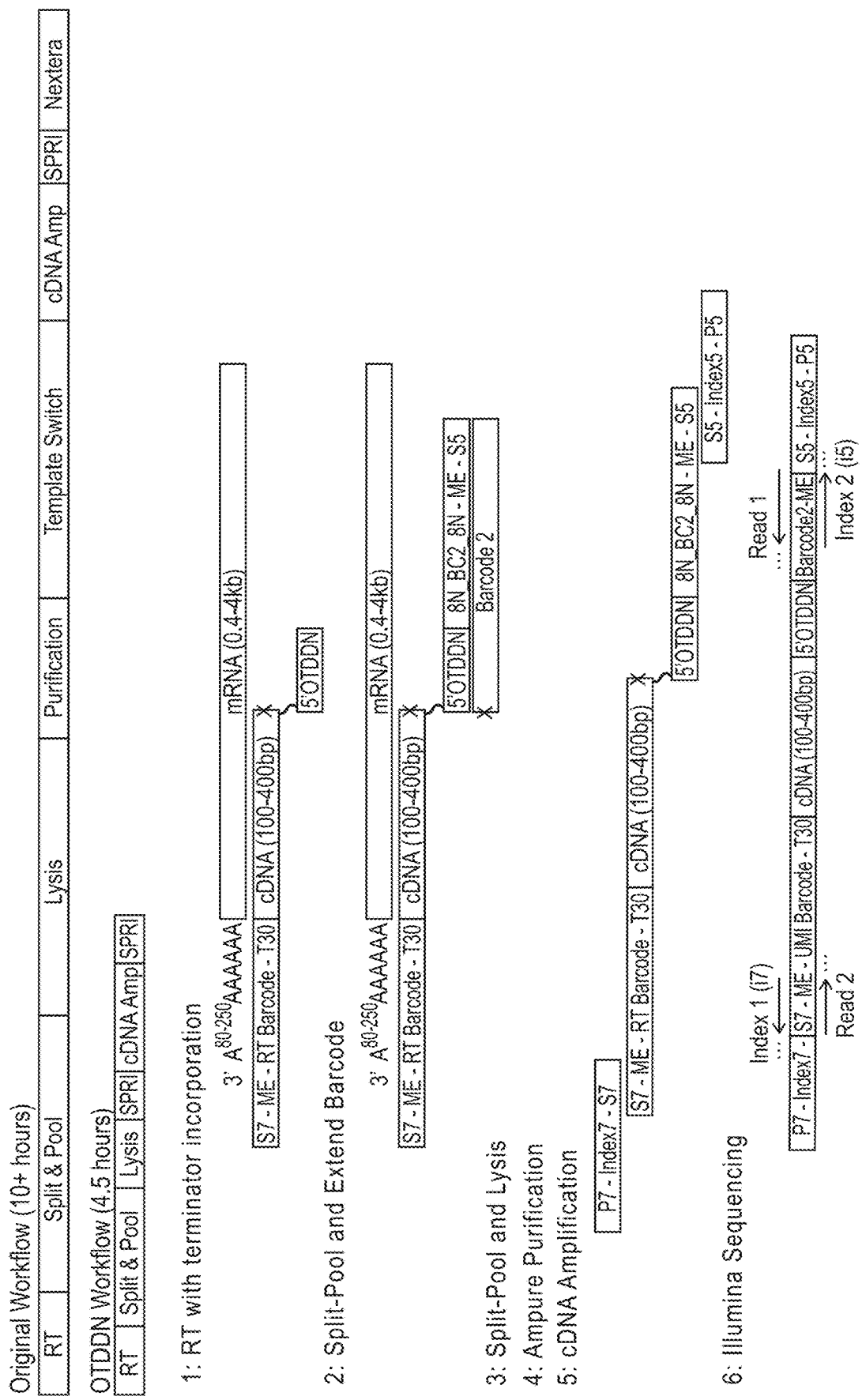
FIG. 41 summarizes the present combinatorial barcoding protocol which uses oligonucleotide-tethered dideoxynucleotides ("OTDDN Workflow") compared to the traditional SPLiT-seq protocol ("Original Workflow"). S5 and S7 sequences represent handle sequences for adapter addition during amplification. P5, P7, Index 5, and Index 7 represent sequences related to sequencing on Illumina platforms. ME=mosaic end.
Figure 42A:
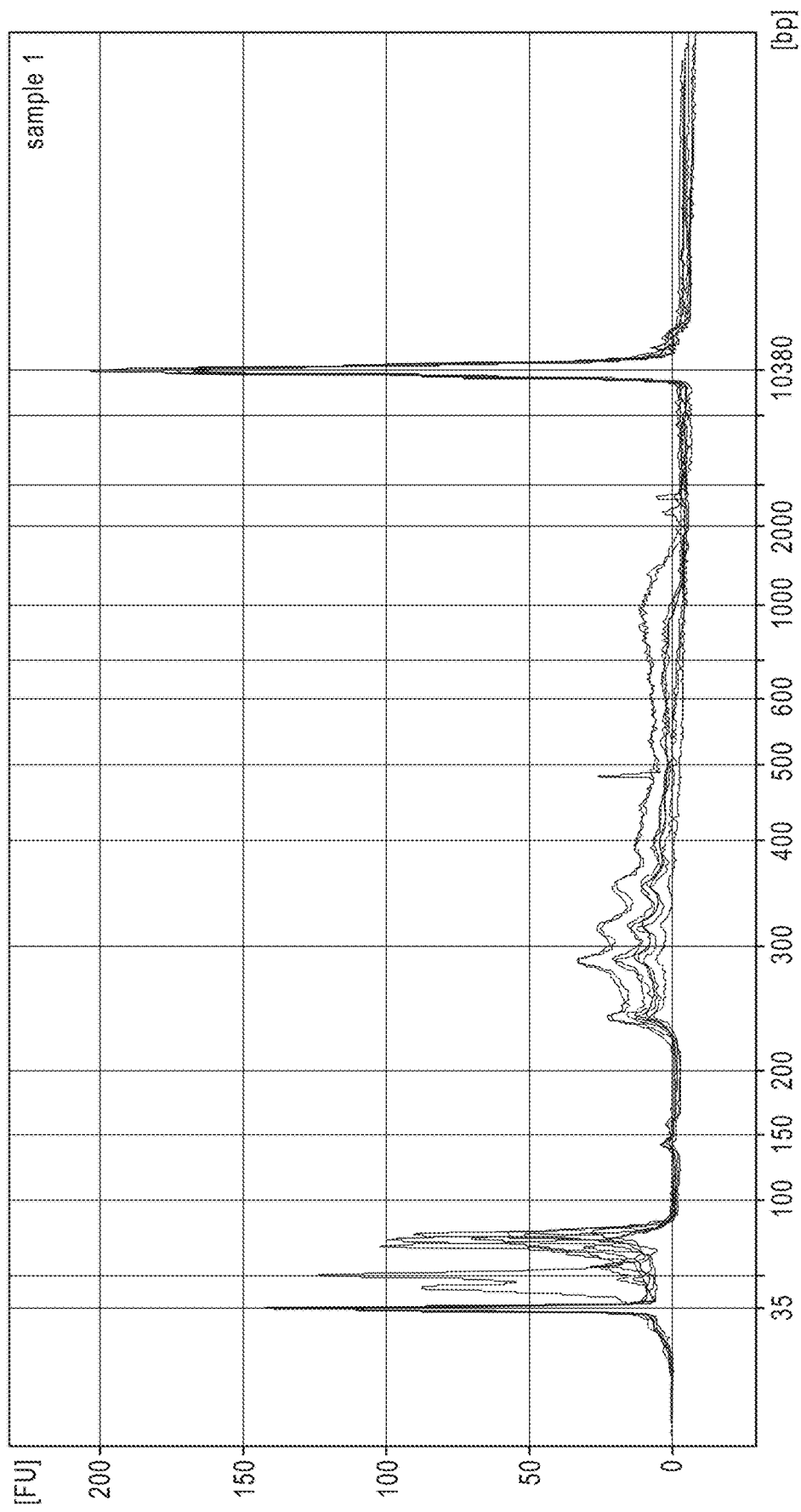
FIGS. 42A and 42B are Agilent 2100 Bioanalyzer electropherograms of an NGS library preparation of RNA prepared from induced pluripotent stem cells (iPSCs) using the oligonucleotide-tethered dideoxynucleotide (OTDDN) combinatorial barcoding workflow described herein according to Example 9, following a first (A) and second (B) amplification reactions.
Figure 42B:
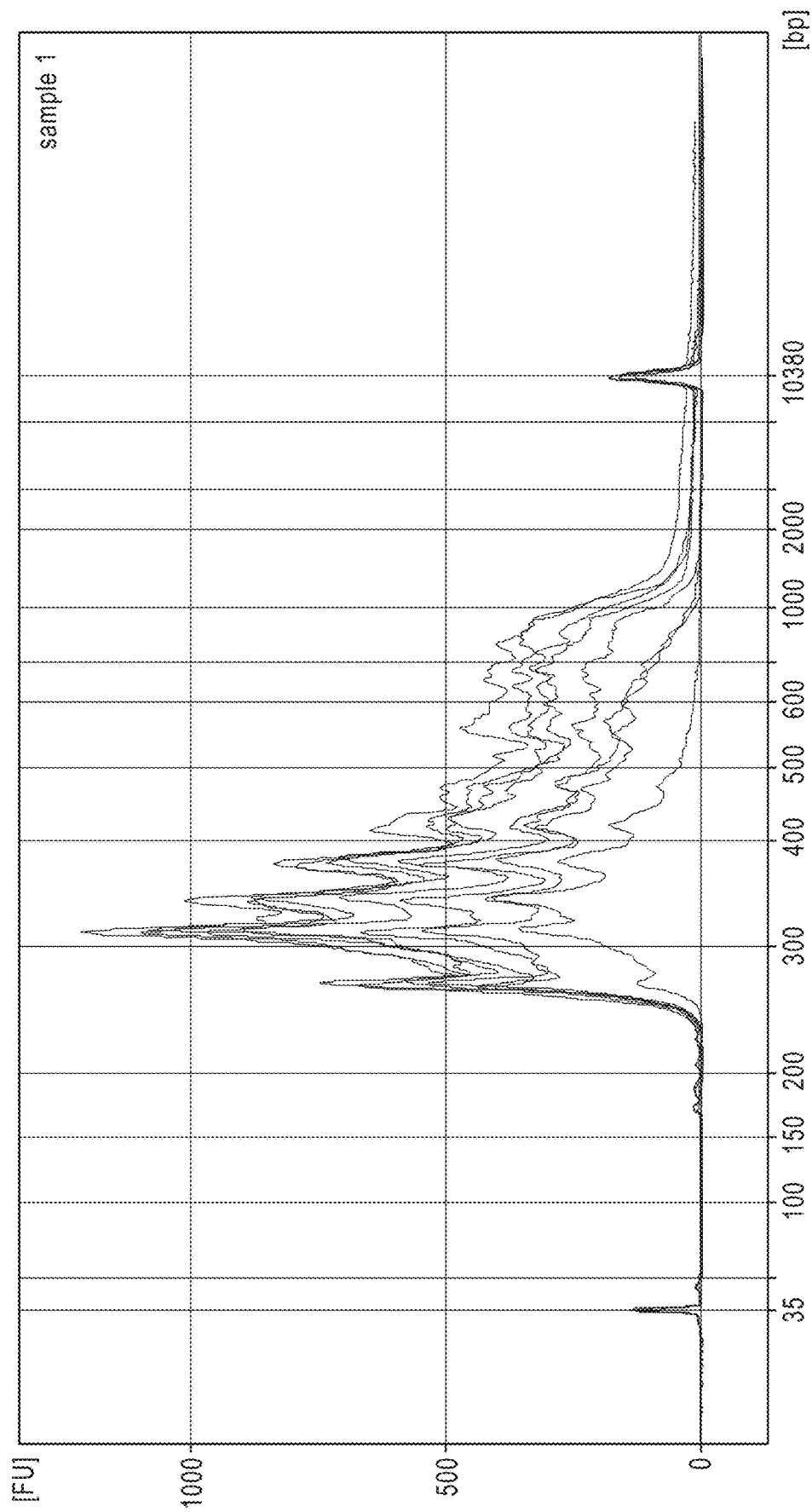

The SPLiT-seq workflow is a well-known method for single cell or nuclei transcriptome analysis that uses cross-linking, template switching, incorporation of barcodes via ligation, and Nextera fragmentation as summarized in FIG. 39 (See Rosenberg et al., *Science* 360, 176-182 (2018)). The protocol disclosed in Rosenberg et al. may take up to 10+ hours to prepare a library of nucleotides for nucleic acid sequencing and transcriptome analysis. Furthermore, addition of barcodes via polymerization (extension of the 3' oligo present on the OTDDN) is significantly more efficient than the use T4 DNA ligase to add barcodes onto cDNA and DNA sequences, as in the protocol described in Rosenberg et al. As such, the workflows described herein reduce the amount of time and the manipulator's required, and provide the potential to significantly improve sensitivity as compared to the Rosenberg protocol. An oligonucleotide-tethered dideoxynucleotide workflow (OTDDN workflow, such as that described in Example 6 and FIG. 40) can avoid multiple workflow steps (such as, for example, template switch and Nextera fragmentation steps) to significantly reduce the workflow time to approximately 4.5 hours. As such, the OTDDN combinatorial barcoding can significantly reduce the workflow time compared to the 10+ hours needed for the traditional SPLiT-seq protocol.

In this OTDDN workflow, a first S7-ME-RT barcode-T30 primer can bind to polyA tails of mRNA and allow reverse transcription (RT). The S7 sequence serves as a handle for adding adapters during amplification and the mosaic end (ME) sequence is used for sequencing on Illumina platforms. Further, in the representative method of FIG. 40, adapters specific for Illumina sequencing methods (P7, P5, Index7, and Index5) are added to allow Illumina sequencing. However, the present method does not require that specific Illumina adapters be added, and the methodology is flexible for any sequencing platform.

Example 8. Splitting and Pooling Methods with Unique Barcodes

Single cell resolution can be achieved in library preparations with a variety of methods, such as separation by flow cytometry or droplet methodologies. The compositions and methods disclosed herein provide for improved methods of combinatorial barcoding to generate single cell resolution, wherein the cells or nuclei from a sample are split, barcoded, and pooled multiple times. In this way, samples from a given single cell can receive multiple barcodes based on the introduction of different barcodes via multiple rounds of splitting, barcoding, and pooling. This process results in samples from a single cell having a unique set of multiple barcodes (i.e., a combination of barcodes) compared to other single cells that were in the same original sample.

The power of the present split-pool method is that the barcoding scales directly with the number of available barcodes. Split pooling also allows processing of cells in bulk, and is amenable to multiplexing as described herein.

Example 9. Representative OTDDN-Based Combinatorial Barcoding Workflow for Single Cell or Nuclei Resolution This Example describes experiments in which OTDDN-based combinatorial barcoding was used to prepare an NGS-ready library of nucleic acids for single cell analysis from HEK293 cells, NTH-3T3 cells, induced pluripotent stem cells (iPSCs), and peripheral blood mononuclear cells (PBMC's).

Step 1: Cell Preparation. HEK-293, NIH-3T3, iPSCs, or PBMCs were fixed by incubating cells with either 1% or 2.5% paraformaldehyde/1% TrixtonX 100 for 30 minutes in the presence of an RNase inhibitor. Cells were diluted to approximately $5\text{-}10 \times 10^5$ cells/mL and filtered with Flowmi™ 40 μm cell strainer into a cell dilution buffer containing 1% Triton X100 and 200U or SUPERASE® RNAse inhibitor. Cells were counted using a Countess® II cell counter in duplicate (15 μl cell+15 μl Trypan blue stain 0.4%). If cell density was greater than $1 \times 10^6$ cells/mL, cells were diluted to $\sim 5 \times 10^5$ and then filtered.

Step 2: Reverse Transcription (RT). An RT master mix was prepared on ice/cold block as described in Table 3.

TABLE 3

RT Master Mix

| Component | Vol/rxn | 96 well Master Mix |
|---|---|---|
| 4× SSIV Buffer | 5 | 600 |
| 10× dNTP Mix: (1 μM dTTP, dGTP, dATP, 0.5 μM dCTP, 0.5 μM ddCTP-oligo (OTDDN)) | 2 | 240 |
| 20% PEG6000 | 4 | 480 |
| Enzyme mix (1 U Superase RNase Inhibitor; 30 U SuperScript IV) | 3 | 360 |
| Single Cell Mixture (100 cells/μL) | 1 | 120 |
| H₂O | 5 | 600 |
| Total | 20 | 2400 |

RT Master Mix was aliquoted at 20 μL per well into a 96 well RED MicroAmp EnduraPlate. Each well of the EnduraPlate was pre-loaded with 50 pmoles of a first extension primer. First extension primers included a unique barcode (i.e., a well-specific barcode), and a universal $1^{st}$ handle sequence. The plate was sealed, vortexed briefly, and centrifuged to collect liquid. The oligo portion of the OTDDN present in the RT Master Mix contained a $2^{nd}$ universal handle sequence.

Reverse transcription was performed at 50° C. for 30 minutes followed by a hold at 4° C.

Step 3: Tethered Oligo Extension. The RT reactions from Step 2 were combined/pooled into a clean pre-cooled 25-mL reservoir, mixed well, and were transferred into 2×1.5 ml Eppendorf tubes. Tubes were centrifuged at 800×g for 3 min, after which the supernatant was removed.

The contents of each tube were resuspended with 1 mL wash buffer containing 1× SSIV buffer and 1% Triton X100, and mixed by pipetting. Samples were centrifuged at 800×g for 3 minutes, then the supernatant was removed. The wash was repeated for two total washes.

The contents of each tube were resuspended with 1 mL RT wash buffer and mixed by pipetting. Cells were filtered with a Flowmi™ 40 μm cell strainer into a single pre-cooled 25 mL reservoir. The Oligo Extension Master Mix set forth in Table 5 was added to the filtered cell mixture and mixed well by pipetting.

TABLE 5

Oligo Extension Master Mix:

| Component | Volume |
|---|---|
| 5× RT buffer | 120 μL |
| 100 mM DTT | 120 μL |
| 10 mM dNTP mix | 120 μL |
| SSIV RT | 120 μL |

20 μL of the pooled cells in the Primer Extension Master mix was added to each well of a 96-well BLUE Micro Amp EnduraPlate, pre-loaded with 50 pmoles splint oligonucleotides containing a region complimentary to the second universal handle sequence, a unique barcode (i.e., a well-specific barcode), and a universal 3rd handle sequence. Oligo extension across the splints was performed at for 50° C. for 20 minutes followed by a hold at 4° C.

Step 4: Cell Lysis. 2× Lysis buffer was pre-warmed to 37° C. for at least 10 minutes. Extension reactions were stopped by adding 2 μL 0.5M EDTA to each well and mixing well. Cells were pooled in a pre-cooled reservoir, mixed well and then transferred to two 1.5 mL Eppendorf tubes. The cells were pelleted by centrifugation at 800×g for 3 min, then the supernatant was removed). The cell pellets were resuspended in 1 mL Cell Wash buffer containing 1% Triton X100 and mixed by pipetting. The cell wash was repeated and the pellets were combined in 700 μL cell wash buffer. Samples were mixed and filtered through a Flowmi™ 40 μm cell strainer into a new 1.5-mL tube. 25 μL of the filtered cells were aliquoted into each well of a 96 well plate containing 100 μg Proteinase K and 25 μL 2× Lysis Buffer.

The digestion was incubated at 55-56° C., 300 rpm for 30 minutes an Eppendorf Thermomixer®.

Step 5: Purification of extended primers with Ampure™ beads (a type of SPRI beads). Ampure Beads were brought to room temperature and mixed thoroughly. For each reaction, 45 μL of beads was pipetted into each well, and purified according to manufacturer's protocol. Beads were resuspended with 25 μl low TE buffer and incubated at room temperature for 2 minutes, put back into the magnetic rack. The supernatant was taken for library amplification.

Step 6: Amplification of the Library. 25 μL Collibri™ Library Amplification Master Mix (ThermoFisher Scientific, Waltham, Mass.) supplemented with 20U Pfusion™ exo-polymerase was aliquoted to each well of a 96 well plate. 24 μl LTE eluted cDNA was added to each well containing the PCR Master Mix. 1 μL 50 μM barcoded PCR primers was added to each well. The barcoded PCR primers included a forward primer that had a sequencing adapter at the 5' end and a sequence matching the 1st handle sequence, and a reverse PCR primer that included in the 5' to 3' direction, a sequencing adapter, a unique (well-specific) barcode, and a sequence matching the 3rd handle sequence. PCR was performed as described in Table 8.

TABLE 8

PCR amplification protocol

| Stage | Temp | Time |
|---|---|---|
| Hold | 98° C. | 30 sec |
| 5 Cycles | 98° C. | 10 sec |
|  | 60° C. | 30 sec |
|  | 72° C. | 2 min |
| 18 cycles | 98° C. | 10 sec |
|  | 64° C. | 30 sec |
|  | 72° C. | 30 sec |
|  | 72° C. | 1 min |
| Hold | 4° C. | Hold |

Step 7: Library Purification. 40 μL of Ampure™ beads was pipetted into each well, and the reaction mixtures were purified according to the manufacturer's protocol, and eluted into a final volume of. 28 μl LTE Step 8: Library Amplification and Quantitation. Library amplification was skipped, and the method moved directly to sequencing if library yield was generated than 2 nM as measured by Bioanalyzer (250-550 base pairs).

A library amplification master mix was prepared as described in Table 9.

TABLE 9

Components of library amplification master mix

| Component | 1 RXN | 24 Rxn |
|---|---|---|
| 5× HiFi Amp mix | 8 μL | 208 |
| 10× Library Amp Primers | 4 μL | 104 |

12 μL of the master mix was aliquoted into each well library well from above (the eluted libraries did not need to be transferred to a new well for cycling). Amplification was performed using the program described in Table 10.

TABLE 10

Amplification protocol

| Stage | Temp | Time |
|---|---|---|
| Hold | 98° C. | 15 sec |
| 9 Cycles | 98° C. | 15 sec |
|  | 64° C. | 1 min |
| Hold | 4° C. | Hold |

Step 9: Library Purification. Ampure beads were brought to room temperature and mixed thoroughly. For each reaction, 32 μL of beads was pipetted into each well, and purified according to the manufacturer's instructions and eluted into 25 μL low TE buffer. The yield and library profile was assessed on a Bioanalyzer.

At this point, the library is ready for sequencing, which may be performed by a variety of sequencing methods. Adapters added during cDNA amplification may be specific to a sequencing platform.

Figure 43:
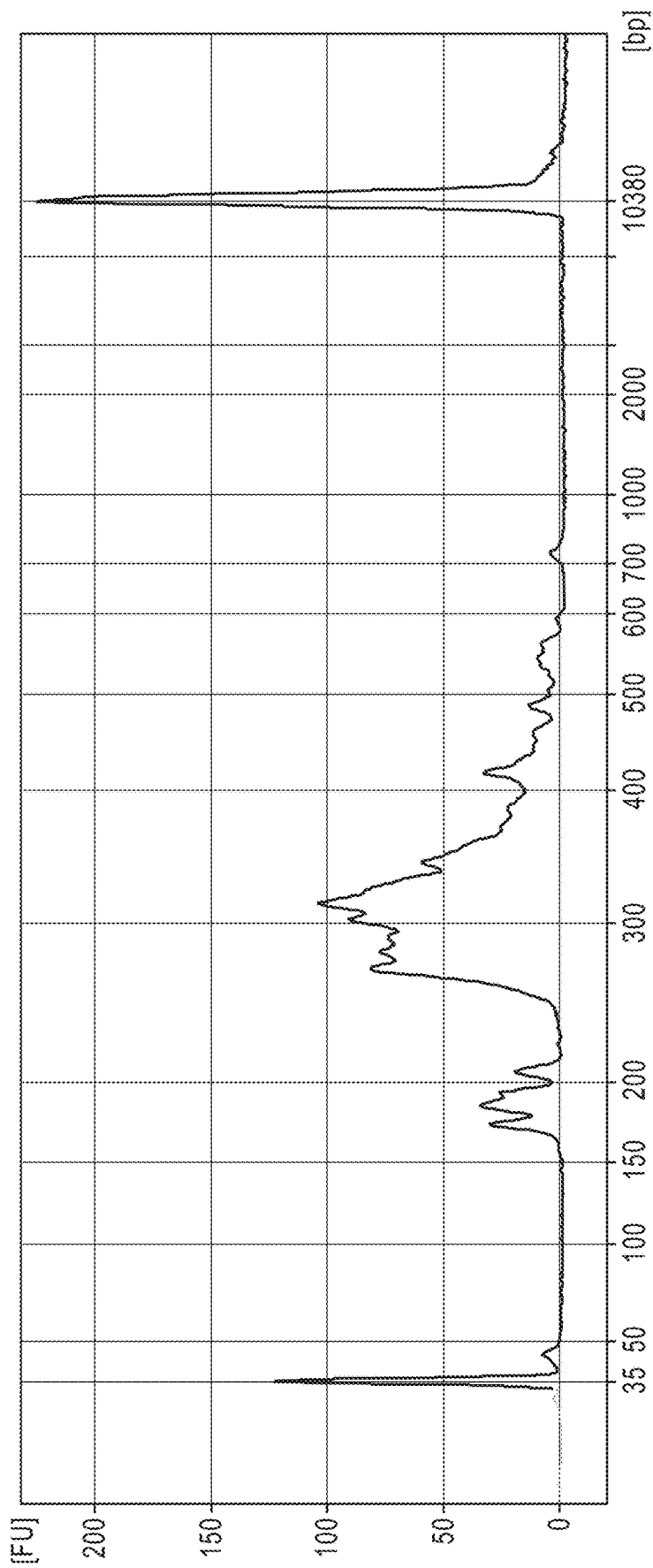
FIG. 43 is an Agilent 2100 Bioanalyzer electropherogram of a library preparation of RNA prepared from peripheral blood mononuclear cells (PBMCs) using the oligonucleotide-tethered dideoxynucleotide (OTDDN) combinatorial barcoding workflows described herein according to Example 9.

FIGS. 43A and 43B show the average yield and average size of a nucleic acid library prepared from iPSCs following the protocol described above after a first amplification (1.2 nM and 350 base pairs, respectively) and second amplification (45 nM and 350-400 base pairs) as determined via Bioanalyzer.

FIG. 44 shows the average yield and average size of a nuclei acid library prepared from PBMCs following the protocol described above.

Figure 45:
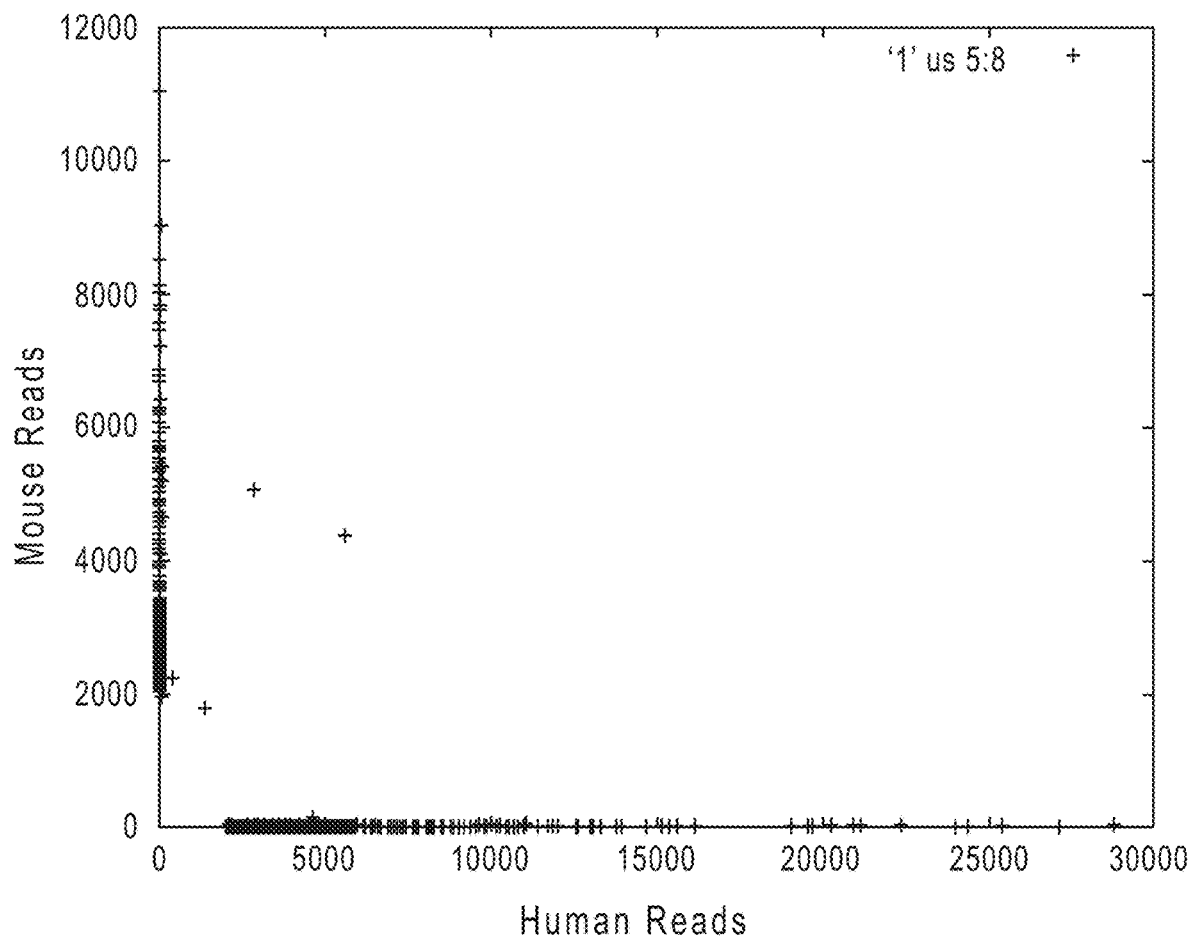
FIG. 45 shows single cell resolution when the combinatorial barcoding workflows described herein were used to prepare nucleic acid libraries from HEK-293 and NIH-3T3 cells. HEK-293 and NIH-3T3 libraries were mixed and processed together. Mapped reads were sorted by barcode and plotted by species. Barcodes on the X-axis are reads of human sequences (Human Reads), while barcodes on the Y-axis are reads of mouse sequences (Mouse Reads). Barcodes off the axes are due to 2 or more cells that share the same barcodes (i.e., a lack of single cell resolution).

FIG. 45 shows PBMCs was also tested with master mixes and dried plates. After a second PCR amplification, wherein all the reaction was amplified, the product size and shape appeared correct. To test single cell resolution of the OTDDN combinatorial barcoding methods described herein, the nucleic acid libraries prepared from NIH-3T3 mouse cells and HEK-293 human cells were mixed and analyzed on an Illumina MiSeq™ according to the manufacturer's instructions. Mapped reads were sorted by barcode and plotted by species. As shown in FIG. 45, barcodes on the X-axis are reads of human sequences (Human Reads), while barcodes on the Y-axis are reads of mouse sequences (Mouse Reads). Barcodes on the axes thus can be single cells, while any barcodes off the axes are due to 2 or more cells that share the same barcodes.

Data from FIG. 45 indicate that the non-single cell rate was approximately 0.5% at 1,000 cells. These values are favorable with the non-single cell rates claimed by other methods, such as 10× claims of 0.9% at 1,000 cells and BD claims of 0.6% at 1,000 cells.

Single cell resolution was also shown using combined PBMC and iPSC samples. The results shown in Table 14 show little overlap between transcripts between the two cell types, and data from each cell type showed the presence of transcripts known to be expressed in those cells.

TABLE 14

Results from combined PBMC and iPSC samples

| Transcript | PBMC | iPSC |
| --- | --- | --- |
| POU5F1 (OCT4) | 0 | 318 |
| NANOG | 2 | 34 |
| SOX2 | 0 | 66 |
| LIN28A | 2 | 1502 |
| CD4 | 3591 | 241 |
| CD44 | 4320 | 0 |

Example 14. Embodiments

The following is list of representative items of different embodiments described herein.

Item 1. An oligonucleotide-tethered nucleotide of formula (I):

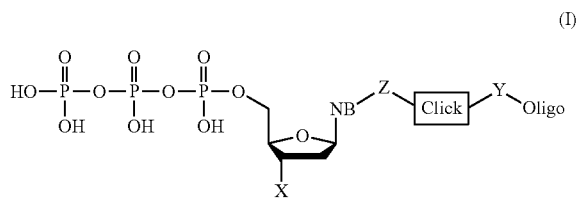

or a salt thereof,
wherein X is H, $N_3$, or OH;
NB represents a nucleobase chosen from adenine, 7-deaza-adenine, cytosine, guanine, 7-deazaguanine, thymine, uracil and inosine;
Z and Y are linkers, wherein Z and Y each independently comprise at least one linking moiety chosen from amino, amido, alkyl, alkenyl, alkynyl, thioether, sulfonyl, sulfonamido, ether, ketone, carbonyl, anhydride, ester, imide, urea, urethane, or any combination thereof;
Click is the product of a click reaction; and
Oligo is an oligonucleotide of 3 to 100 nucleotides in length.

Item 2. The oligonucleotide-tethered nucleotide of item 1, wherein Click is a product of a click reaction between one of the following pairs of functional groups:
 i) alkynyl and azido;
 ii) azido and alkynyl,
 iii) thiol and alkynyl;
 iv) alkynyl and thiol;
 v) thiol and alkenyl;
 vi) alkenyl and thiol;
 vii) azido and cyclooctanyl;
 viii) cyclooctanyl and azido;
 xi) nitrone and cyclooctanyl; and
 xii) cyclooctanyl and nitrone;

Item 3. An oligonucleotide-tethered nucleotide of formula (II):

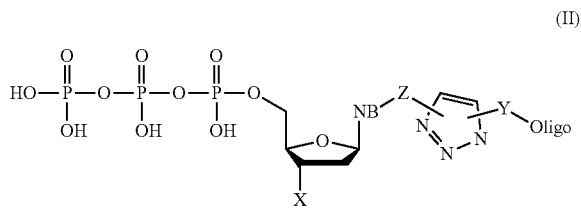

or a salt thereof,
wherein X is H, OH, $N_3$;
NB represents a nucleobase chosen from adenine, 7-deaza-adenine, cytosine, guanine, 7-deazaguanine, thymine, uracil and inosine;
Z and Y are linkers, wherein Z and Y each independently comprise at least one linking moiety chosen from amino, amido, alkyl, alkenyl, alkynyl, thioether, sulfonyl, sulfonamido, ether, ketone, carbonyl, anhydride, ester, imide, urea, urethane, or any combination thereof; and
Oligo is an oligonucleotide of 3 to 100 nucleotides in length.

Item 4. The oligonucleotide-tethered nucleotide of any one of items 1 to 3, wherein X is OH.

Item 5. The oligonucleotide-tethered nucleotide of any one of items 1 to 3, wherein X is H.

Item 6. The oligonucleotide-tethered nucleotide of any one of items 1 to 5, wherein the alkylene is a $C_1$-$C_6$ alkylene.

Item 7. The oligonucleotide-tethered nucleotide of any one of items 1 to 6, wherein the alkenylene is a $C_2$-$C_6$ alkenylene.

Item 8. The oligonucleotide-tethered nucleotide of any one of items 1 to 7, wherein the alkynylene is a $C_2$-$C_6$ alkynylene.

Item 9. The oligonucleotide-tethered nucleotide of any one of items 1 to 8, wherein the polyalkylene glycol has 2 to 8 glycol units.

Item 10. The oligonucleotide-tethered nucleotide of any one of items 1 to 9, wherein the oligonucleotide is tethered to the nucleotide at its 5' end.

Item 11. The oligonucleotide-tethered nucleotide of any one of items 1 to 10, wherein one of Z and Y is covalently bound to the 1 position of the triazole ring, and the other of Z and Y is covalently bound to the 4 position of the triazole ring.

Item 12. The oligonucleotide-tethered nucleotide of item 11, wherein Z is covalently bound to the 1 position of the triazole ring, and Y is covalently bound to the 1 position of the triazole ring.

Item 13. The oligonucleotide-tethered nucleotide of item 11, wherein Z is covalently bound to the 4 position of the triazole ring and Y is covalently bound to the 1 position of the triazole ring.

Item 14. The oligonucleotide-tethered nucleotide of item 11, having formula (III)

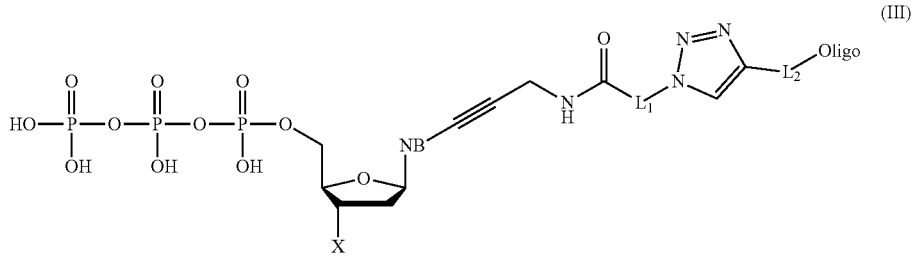

or a salt thereof,
wherein
$L_1$ is a linker comprising an alkylene, a polyalkylene glycol, or a combination thereof, and
$L_2$ is a linker comprising an alkynylene.

Item 15. The oligonucleotide-tethered nucleotide of item 14, wherein $L_1$ comprises a polyalkenylene glycol having 2, 4, or 6 alkenylene glycol groups.

Item 16. The oligonucleotide-tethered nucleotide of item 14 or 15, wherein the polyalkenylene glycol is polyethylene glycol.

Item 17. The oligonucleotide-tethered nucleotide of item 14, wherein $L_1$ comprises an alkylene having 1 to 12 carbon atoms.

Item 18. The oligonucleotide-tethered nucleotide of item 17, wherein the alkylene is methylene, ethylene, n-propylene, isopropylene, 1-butylene, cis-2-butylene, trans-2-butylene, isobutylene, 1-pentylene, cis-2-pentylene, trans-2-pentylene, isopentylene, or hexylene.

Item 19. The oligonucleotide of item 14, wherein $L_2$ is hexynyl.

Item 20. The oligonucleotide-tethered nucleotide of any one of items 1 to 19, wherein the nucleobase is a pyrimidine and wherein pyrimidine is tethered to the oligonucleotide at the 5 position of the nucleobase.

Item 21. The oligonucleotide-tethered nucleotide of any one of items 1 to 19, wherein the nucleobase is a purine, and wherein the purine is tethered to the oligonucleotide at the 7 position of the nucleobase.

Item 22. The oligonucleotide-tethered nucleotide of any one of items 1 to 21, wherein the salt is a quaternary ammonium salt.

Item 23. The oligonucleotide-tethered nucleotide of any one of items 1 to 22, wherein the oligonucleotide comprises a barcode sequence, an adapter sequence, a unique molecular identifier, or any combination thereof.

Item 24. A method for tagging a nucleic acid with an oligonucleotide comprising:
providing the nucleic acid to be tagged,
contacting the nucleic acid with at least one oligonucleotide-tethered nucleotide of any one of items 1 to 23, at least one nucleotide, and a polymerase, thereby producing the tagged nucleic acid.

Item 25. The method of item 24, further comprising annealing a primer to the nucleic acid.

Item 26. The method of item 24 or 25, wherein the nucleic acid is tagged at the 5' end, the 3' end, or both.

Item 27. The method of item 26, wherein the nucleic acid is tagged at multiple positions.

Item 28. The method of any one of items 24 to 27, wherein the nucleic acid is tagged with the oligonucleotide-tethered oligonucleotide during a nick translation or a gap-filling reaction.

Item 29. The method of any one of items 24 to 28, further comprising ligating adapter sequences to the 3' end of the nucleic acid.

Item 30. The method of any one of items 24 to 29, further comprising subjecting the tagged nucleic acid to PCR.

Item 31. The method of any one of items 24 to 31, wherein the nucleic acid is DNA or RNA.

Item 32. The method of any one of items 24 to 31, wherein the polymerase is a Type-A DNA polymerase, Type B DNA polymerase, Type X DNA polymerase, or a reverse transcriptase.

Item 33. The method of any one of items 24 to 32, wherein the polymerase is Taq DNA polymerase, Vent® DNA polymerase, Deep Vent™ DNA polymerase, Pfx DNA polymerase, Pwo polymerase, SuperScript™ IV, SuperScript™ TT, SuperScript™ ITT, Maxima™, RevertAid™ reverse transcriptases, Thermo Sequenase™, Sequenase™ V2.0, CycleSeg™, Phusion exo-, Terminal deoxynucleotidyl Transferase (TdT), Maxima H, Therminator™ polymerase, Q5 DNA polymerase, AccuTaq DNA polymerase, T7 DNA polymerase, T3 DNA polymerase, T4 DNA polymerase, T7 RNA polymerase, T3 RNA polymerase, SP6 RNA polymerase, DNA polymerase 1, Klenow fragment, Tth DNA polymerase, Phusion® DNA polymerase, SuperFi DNA polymerase, Platinum Taq DNA polymerase, Herculase II Fusion DNA polymerase, PfuUltra Fusion II HS DNA polymerase, Bst DNA polymerase large fragment, Stoeffel fragment, 9° N™ DNA polymerase, Pfu DNA polymerase, Tfl DNA polymerase, Phi29 polymerase, Tli DNA polymerase, eukaryotic DNA polymerase beta, telomerase, KOD HiFi DNA polymerase, KOD DNA polymerase, Q-beta replicase, AMV reverse transcriptase, M-MLV reverse transcriptase, Phi6 reverse transcriptase, HIV-1 reverse transcriptase, polyA polymerase (PAP), polyU polymerase (PUP), and variants and derivatives thereof.

Item 34. The method of any one of items 24 to 32, wherein the polymerase is TdT.

Item 35. The method of any one of items 24 to 34, wherein the nucleotide is chosen from dideoxyadenosine triphosphate, dideoxyguanosine triphosphate, dideoxythymidine triphosphate, dideoxyuridine triphosphate, dideoxycytidine triphosphate, and any combination thereof.

Item 36. The method of any one of items 24 to 35, wherein the concentration of oligonucleotide-tethered nucleotide in step c ranges from 1 fmol to 10 μmol.

Item 37. The method of any one of items 24 to 36, wherein the molar ratio of oligonucleotide-tethered nucleotide to a corresponding native nucleotide ranges from 1:1 to 1:1000.

Item 38. The method of any one of items 24 to 37, further comprising performing at least one clean up step.

Item 39. A method for generating a library of nucleic acids from a polynucleotide sample comprising
- optionally fragmenting the polynucleotide sample to generate a plurality of polynucleotide fragments;
- annealing a first primer to the polynucleotide fragments;
- contacting the plurality of polynucleotide fragments with a nucleic acid polymerase, at least one nucleotide, and an oligonucleotide-tethered oligonucleotide to form a nucleic acid strand comprising the oligonucleotide-tethered nucleotide;
- annealing a second primer to the tethered oligonucleotide to form a second annealed complex; and
- contacting the second annealed complex with the nucleic acid polymerase to produce a nucleic acid molecule from the tethered oligonucleotide.

Item 40. The method of item 39, wherein the oligonucleotide-tethered nucleotide is an oligonucleotide tethered nucleotide of anyone of items 1 to 23.

Item 41. The method of item 39 or 40, wherein the second primer comprises an adapter sequence, a barcode sequence, or both.

Item 42. The method of any one of items 39 to 41, wherein the oligonucleotide-tethered nucleotide further comprises an affinity tag.

Item 43. The method of any one of items 39 to 42, wherein the second primer is at least partially complimentary to the tethered oligonucleotide.

Item 44. The method of any one of items 39 to 43, wherein the first primer, the second primer, or both comprise a universal sequence.

Item 45. The method of any one of items 39 to 44, where the tethered oligonucleotide comprises an adapter sequence, a T7 promotor sequence, a barcode, a universal molecular identifier, or any combination thereof.

Item 46. The method of any one of items 39 to 45, wherein the polymerase is a Type-A DNA polymerase, Type B DNA polymerase, Type X DNA polymerase, or a reverse transcriptase.

Item 47. The method of any one of items 39 to 46, wherein the polymerase is chosen from Taq DNA polymerase, Vent® DNA polymerase, Deep Vent™ DNA polymerase, Pfx DNA polymerase, Pwo polymerase, SuperScript™ IV, SuperScript™ II, SuperScript™ III, Maxima™, RevertAid™ reverse transcriptases, Thermo Sequenase™, Sequenase™ V2.0, CycleSeq™, Phusion exo-, Terminal deoxynucleotidyl Transferase (TdT), Maxima H, Therminator™ polymerase, Q5 DNA polymerase, AccuTaq DNA polymerase, T7 DNA polymerase, T3 DNA polymerase, T4 DNA polymerase, T7 RNA polymerase, T3 RNA polymerase, SP6 RNA polymerase, DNA polymerase 1, Klenow fragment, Tth DNA polymerase, Phusion® DNA polymerase, SuperFi DNA polymerase, Platinum Taq DNA polymerase, Herculase II Fusion DNA polymerase, PfuUltra Fusion II HS DNA polymerase, Bst DNA polymerase large fragment, Stoeffel fragment, 9° N™ DNA polymerase, Pfu DNA polymerase, Tfl DNA polymerase, Phi29 polymerase, Tli DNA polymerase, eukaryotic DNA polymerase beta, telomerase, KOD HiFi DNA polymerase, KOD DNA polymerase, Q-beta replicase, AMV reverse transcriptase, M-MLV reverse transcriptase, Phi6 reverse transcriptase, HIV-1 reverse transcriptase, polyA polymerase (PAP), polyU polymerase (PUP), and variants and derivatives thereof.

Item 48. The method of any one of items 39 to 47, wherein the nucleotide is chosen from dideoxyadenosine triphosphate, dideoxyguanosine triphosphate, dideoxythymidine triphosphate, dideoxycytidine triphosphate, and any combination thereof.

Item 49. The method of anyone of items 39 to 48, further comprising amplifying the library.

Item 50. The method of any one of items 39 to 41, wherein the concentration of oligonucleotide-tethered nucleotide in step (a) ranges from 1 fmol to 10 µmol.

Item 51. The method of any one of items 39 to 50, wherein the molar ratio of oligonucleotide-tethered nucleotide to a corresponding native nucleotide ranges from 1:1 to 1:1000.

Item 52. The method of any one of items 39 to 51, further comprising performing at least one clean up step after step (c).

Item 53. The method of any one of items 39 to 52, wherein the nucleic acid is DNA.

Item 54. The method of any one of item 39 to 53, wherein the nucleic acid is RNA.

Item 55. The method of item 54, further comprising reverse transcribing the RNA to producing a corresponding cDNA.

Item 56. A method for preparing an oligonucleotide-tethered nucleotide according to any one of items 1 to 23, comprising:
- providing a nucleotide covalently bound to a first functional group capable of undergoing a click reaction with a second functional group;
- providing an oligonucleotide covalently bound to the second functional group capable of undergoing a click reaction to form the triazole ring;
- contacting the nucleotide with the oligonucleotide to form the click reaction product,
- wherein, the first and second functional groups are, respectively, chosen from:
  i) alkynyl and azido;
  ii) azido and alkynyl,
  iii) thiol and alkynyl;
  iv) alkynyl and thiol;
  v) thiol and alkenyl;
  vi) alkenyl and thiol;
  vii) azido and cyclooctanyl;
  viii) cyclooctanyl and azido;
  xi) nitrone and cyclooctanyl; and
  xii) cyclooctanyl and nitrone.

Item 57. The method of item 56, where in the first and second functional groups are, respectively, chosen from i) alkynyl and azido; and ii) azido and alkynyl.

Item 58. The method of item 57, wherein step (c) comprises contacting the nucleotide with the oligonucleotide in the presence of a copper catalyst and copper (I) ligand to form a 1,2,3-triazole.

Item 59. The method of any one of items 56 to 58, wherein the nucleotide is a deoxynucleotide or dideoxynucleotide.

Item 60. The method of any one of items 58 or 59, wherein the copper catalyst comprises copper (1), or copper (11), wherein when the catalyst is copper (11), a reducing agent is present.

Item 61. The method of any one of items 58 to 60, wherein the copper catalyst is $Cu(NO_3)_2$ $Cu(OAc)$, $CuSO_4$ or any combination thereof.

Item 62. The method of any one of item 60 or 61, wherein the reducing agent comprises ascorbate, Tris(2-Carboxyethyl) Phosphine (TCEP), 2.4.6-trichlorophenol (TCP), NADH, NADPH, thiosulfate, metallic copper, quinone, hydroquinone, Vitamin K, glutathione, cysteine, 2-mercaptoethanol, dithiothreitol, Fe(II), Co(II), an applied electric potential, Al, Be, Co, Cr, Fe, Mg, Mn, Ni, Zn, Au, Ag, Hg, Cd, Zr, Ru, Fe, Co, Pt, Pd, Ni, Rh, W, or any combination thereof.

Item 63. The method of item 62, wherein the reducing agent comprises sodium ascorbate.

Item 64. The method of any one of items 58 to 63, wherein the ligand comprises tris(benzyltriazolylmethyl)amine.

Item 65. A kit for producing a sequencing library comprising:
an oligonucleotide-tethered nucleotide according to any one of items 1 to 21, and at least one of
(i) A, C, G, U and T nucleotides,
(ii) a polymerase,
(iii) a primer and/or an adapter sequence,
(iv) a buffer, or
(v) a salt.

Item 66. The kit of item 65, wherein the kit comprises A, C, G, U and T nucleotides.

Item 67. The kit of item 65 or 66, wherein the kit comprises the polymerase.

Item 68. The kit of item 67, wherein the polymerase is a wild type polymerase, a modified polymerase, mutant polymerase, an engineered polymerase, or a combination thereof.

Item 69. The kit of any one of items 65 to 68, wherein the polymerase is Taq DNA polymerase, Vent® DNA polymerase, Deep Vent™ DNA polymerase, Pfx DNA polymerase, Pwo polymerase, SuperScript™ IV, SuperScript™ II, SuperScript™ III, Maxima™, RevertAid™ reverse transcriptases, Thermo Sequenase™, Sequenase™ V2.0, CycleSeq™, Phusion exo-, Terminal deoxynucleotidyl Transferase (TdT), Maxima H, Therminator™ polymerase, Q5 DNA polymerase, AccuTaq DNA polymerase, T7 DNA polymerase, T3 DNA polymerase, T4 DNA polymerase, T7 RNA polymerase, T3 RNA polymerase, SP6 RNA polymerase, DNA polymerase 1, Klenow fragment, Tth DNA polymerase, Phusion® DNA polymerase, SuperFi DNA polymerase, Platinum Taq DNA polymerase, Herculase II Fusion DNA polymerase, PfuUltra Fusion II HS DNA polymerase, Bst DNA polymerase large fragment, Stoeffel fragment, 9° N™ DNA polymerase, Pfu DNA polymerase, Tfl DNA polymerase, Phi29 polymerase, Tli DNA polymerase, eukaryotic DNA polymerase beta, telomerase, KOD HiFi DNA polymerase, KOD DNA polymerase, Q-beta replicase, AMV reverse transcriptase, M-MLV reverse transcriptase, Phi6 reverse transcriptase, and HIV-1 reverse transcriptase, polyA polymerase (PAP), polyU polymerase (PUP), and variants and derivatives thereof.

Item 70. The kit of any one of items 65 to 69, wherein the kit comprises one or more primer, adapter, barcode, or unique molecular identifier sequences.

Item 71. The kit of any one of items 65 to 70, wherein the kit comprises the at least one buffer.

Item 72. The kit of any one of items 65 to 71, wherein the kit comprises the at least one salt.

Item 73. A method of preparing nucleic acid library comprising:
annealing a first primer comprising a universal sequence to the nucleic acid sample, contacting the nucleic acid sample with a nucleic acid polymerase, at least one nucleotide, and at least one oligonucleotide-tethered dideoxynucleotide to form a plurality of nucleic acid strands comprising the oligonucleotide-tethered dideoxynucleotide terminating the strand;
annealing a second primer which is at least partially complementary to the tethered oligonucleotide, and
allowing the polymerase to extend the second annealed primer,
thereby producing a library of nucleotides comprising the universal sequence and tethered oligonucleotide sequence at its ends.

Example 15. Further Embodiments

The following is list of additional representative embodiments of different embodiments described herein. Embodiments may be in accordance with any one of the following numbered clauses.

Clause 1. A method for tagging a nucleic acid with an oligonucleotide comprising:
a. providing the nucleic acid to be tagged,
b. contacting the nucleic acid with a polymerase and at least one oligonucleotide-tethered nucleotide of Formula (A):

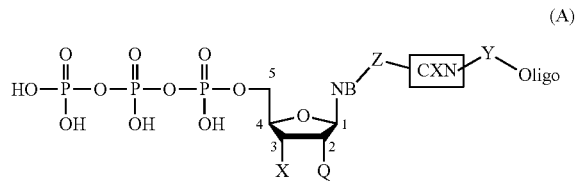

or a salt thereof
wherein NB is a nucleobase;
Oligo is an oligonucleotide of 3 to 100 nucleotides;
each of X and Q are independently chosen from, H, OH, $N_3$, halo, alkyl, alkoxy, alkyl, alkenyl, alkynyl, acyl, cyano, amino, ester, and amido;
each of Z and Y are independently chosen from a bond, amino, amido, alkyl, alkenyl, alkynyl, thioether, sulfonyl, sulfonamido, ether, ketone, carbonyl, anhydride, ester, imido, urea, urethane, and combinations thereof; and
CXN is chosen from alkylene, alkenylene, alkynylene, ketone, carbonate, ester, ether, anhydride, amido, amino, aminoalkylene, imino, amido, diazo, carbamate ester, phosphodiester, sulfide, disulfide, sulfonyl, sulfonamido, and a heterocyclic group containing from one to four N, O, S atom(s) or a combination thereof where heterocyclic group is optionally substituted at carbon, nitrogen or sulfur atom(s), thereby producing the first tagged nucleic acid.

Clause 2. The method of clause 1, wherein the contacting comprises contacting the nucleic acid with at least one oligonucleotide-tethered nucleotide, at least one nucleotide not tethered to an oligonucleotide, and a polymerase.

Clause 3. The method of clause 1 or 2 further comprising annealing a primer to the nucleic acid.

Clause 4. The method of any one of clauses 1 to 3, wherein the nucleic acid is tagged at the 5' end, the 3' end, or both.

Clause 5. The method of any one of clauses 2 to 4, wherein the nucleic acid is tagged at multiple positions.

Clause 6. The method of any one of clauses 1 to 5, wherein the nucleic acid is tagged with the oligonucleotide-tethered nucleotide during a nick translation or a gap-filling reaction.

Clause 7. The method of any one of clauses 1 to 6, further comprising adding adapter sequences to the 3' end of the nucleic acid.

Clause 8. The method of any one of clauses 1 to 7, wherein the nucleic acid is a double stranded nucleic acid and the method further comprises subjecting the tagged nucleic acid to PCR.

Clause 9. The method of any one of clauses 1 to 8, wherein the polymerase is terminal deoxynucleotidyl transferase.

Clause 10. The method of any one of clauses 1 to 9, wherein the oligonucleotide-tethered nucleotide is a dideoxynucleotide, optionally wherein the dideoxynucleotide is chosen from dideoxyadenosine triphosphate, dideoxyguanosine triphosphate, dideoxythymidine triphosphate, dideoxyuridine triphosphate, dideoxycytidine triphosphate, and any combination thereof.

Clause 11. The method of any one of clauses 1 to 10, further comprising performing at least one clean up step.

Clause 12. The method of any one of clauses 1 to 11, further comprising:
  a. annealing a primer which is at least partially complementary to the tethered oligonucleotide after producing a first tagged nucleic acid strand, and
  b. contacting the first tagged nucleic acid strand and annealed primer with a nucleic acid polymerase and at least one nucleotide not tethered to an oligonucleotide; and
  c. allowing a polymerase to extend from a 3' hydroxyl on the primer annealed to the tethered oligonucleotide to form a second nucleic acid strand.

Clause 13. The method of clause 12 further comprising contacting the tagged nucleic acid strands with an exonuclease after forming the second nucleic acid strand, wherein the first nucleic acid strand is degraded by the exonuclease.

Clause 14. The method of clause 12 further comprising contacting the tagged nucleic acid strands with an exonuclease after forming the second nucleic acid strand, wherein the first nucleic acid strand is strand has a 5'-phosphate, and the exonuclease is a lambda exonuclease.

Clause 15. The method of any one of clauses 12 to 14, further comprising:
  a. providing at least one second nucleic acid strand;
  b. contacting the second nucleic acid strand with a terminal deoxynucleotidyl transferase and at least one second oligonucleotide-tethered nucleotide of Formula (A):

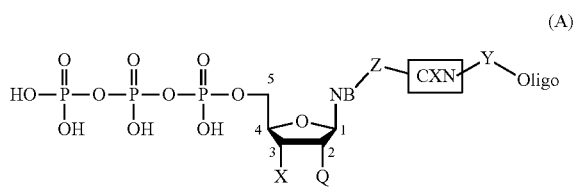

(A)

or a salt thereof
wherein NB is a nucleobase;
Oligo is an oligonucleotide of 3 to 100 nucleotides;
each of X and Q are independently chosen from, H, OH, $N_3$, halo, alkyl, alkoxy, alkyl, alkenyl, alkynyl, acyl, cyano, amino, ester, and amido;
each of Z and Y are independently chosen from a bond, amino, amido, alkyl, alkenyl, alkynyl, thioether, sulfonyl, sulfonamido, ether, ketone, carbonyl, anhydride, ester, imido, urea, urethane, and combinations thereof; and
CXN is chosen from alkylene, alkenylene, alkynylene, ketone, carbonate, ester, ether, anhydride, amido, amino, aminoalkylene, imino, imido, diazo, carbamate ester, phosphodiester, sulfide, disulfide, sulfonyl, sulfonamido, and a heterocyclic group containing from one to four N, O, S atom(s) or a combination thereof where heterocyclic group is optionally substituted at carbon, nitrogen or sulfur atom(s), thereby producing a tagged nucleic acid with different tags at the 5' and 3' ends.

Clause 16. A method for generating a library of nucleic acids from a sample comprising one or more polynucleotides comprising
  a. annealing a first primer to the one or more polynucleotides;
  b. contacting the one or more polynucleotides with a nucleic acid polymerase, at least one nucleotide not tethered to an oligonucleotide, and a first oligonucleotide-tethered nucleotide to form one or more first nucleic acid strands comprising a first oligonucleotide-tethered nucleotide;
  c. annealing a second primer to the tethered oligonucleotide to form a second annealed complex; and
  d. contacting the second annealed complex with the nucleic acid polymerase and, optionally, at least one nucleotide not tethered to an oligonucleotide to produce a second nucleic acid strand.

Clause 17. A method for generating a library of nucleic acids from a sample comprising one or more polynucleotides comprising
  a. annealing a first primer to the one or more polynucleotides;
  b. contacting the one or more polynucleotides with a nucleic acid polymerase, at least one nucleotide not tethered to an oligonucleotide, and a first oligonucleotide-tethered nucleotide to form one or more first nucleic acid strands comprising a first oligonucleotide-tethered nucleotide;
  c. annealing a splint oligonucleotide to the tethered oligonucleotide to form a second annealed complex; and
  d. contacting the second annealed complex with the nucleic acid polymerase and, optionally, at least one nucleotide not tethered to an oligonucleotide to produce a second nucleic acid strand.

Clause 18. The method of clause 16 or 17, wherein the one or more polynucleotides comprise a plurality of polynucleotide fragments generated before annealing of the first primer.

Clause 19. The method of any one of clauses 16 or 18, wherein the one or more polynucleotides comprise mRNA.

Clause 20. The method of any one of clauses 16 to 19, wherein the one or more polynucleotides comprises an oligonucleotide-tethered binding agent (OTBA).

Clause 21. The method of any one of clauses 16 to 20, wherein the one or more polynucleotides comprises a combination of mRNA and one or more OTBA's.

Clause 22. The method of any of clauses 16 to 21, wherein after contacting the second annealed complex with the nucleic acid polymerase, the polymerase extends from the 3' hydroxyl of the tethered oligonucleotide across the splint oligonucleotide.

Clause 23. The method of any one of clauses 12 to 22, wherein the primer comprises a universal sequence, a random sequence and/or a target-specific sequence.

Clause 24. The method any one of clauses 16 to 23, wherein the first oligonucleotide-tethered nucleotide is an oligonucleotide-tethered dideoxynucleotide, and the first nucleic acid strand comprises the oligonucleotide-tethered dideoxynucleotide at its 3' end.

Clause 25. The method of any one of clauses 16 and 18 to 23, wherein the contacting the second annealed complex with the nucleic acid polymerase is done in the presence of at least one nucleotide not tethered to an oligonucleotide and a second oligonucleotide-tethered dideoxynucleotide, and the second nucleic acid strand comprises the oligonucleotide-tethered dideoxynucleotide at its 3' end.

Clause 26. The method of any one of clauses 16 and 18 to 24, wherein the tethered oligonucleotide in the first oligonucleotide-tethered dideoxynucleotide and the tethered oligonucleotide in the second oligonucleotide-tethered dideoxynucleotide are different.

Clause 27. A method for generating a library of nucleic acids from a sample comprising one or more nucleic acids, optionally wherein the sample comprises a plurality of cells, comprising:
 a. annealing a first primer to the one or more nucleic acids,
 b. contacting the one or more nucleic acids with a nucleic acid polymerase, at least one nucleotide not tethered to an oligonucleotide, and at least one oligonucleotide-tethered dideoxynucleotide to form a plurality of nucleic acid strands comprising the oligonucleotide-tethered dideoxynucleotide at their 3' end;
 c. annealing a second primer which is at least partially complementary to the tethered oligonucleotide, and
 d. allowing the polymerase to extend from a 3' hydroxyl of the second primer annealed to the tethered oligonucleotide, thereby producing a library of double-stranded nucleic acids.

Clause 28. A method for generating a library of nucleic acids from a sample comprising one or more nucleic acids, optionally wherein the sample comprises a plurality of cells, comprising:
 a. annealing a first primer to the one or more nucleic acids,
 b. contacting the one or more nucleic acids with a nucleic acid polymerase, at least one nucleotide not tethered to an oligonucleotide, and at least one oligonucleotide-tethered dideoxynucleotide to form a plurality of nucleic acid strands comprising the oligonucleotide-tethered dideoxynucleotide at their 3' end;
 c. annealing a splint oligonucleotide which is at least partially complementary to the tethered oligonucleotide, and
 d. allowing the polymerase to extend from a 3' hydroxyl of the tethered oligonucleotide, thereby producing a library of nucleic acids.

Clause 29. The method of clause 27 or 28, wherein the first primer comprises a universal sequence, a random sequence and/or a target-specific sequence.

Clause 30. The method of any one of clauses 27 to 29, wherein the one or more nucleic acids in the sample comprise poly(A) mRNA.

Clause 31. The method of any one of clause 27 to 29, wherein the one or more nucleic acids in the sample comprises a tethered oligonucleotide of an OTBA.

Clause 32. The method of clause 31, wherein the tethered oligonucleotide of the OTBA comprises a cell marker binding agent index.

Clause 33. The method of clause 27 to 29 or 32, wherein the one or more nucleic acids in the sample comprise mRNA and an MBA.

Clause 34. The method of any one of clauses 27 to 32, wherein the cell marker is expressed by a portion of the cells in the sample.

Clause 35. The method of clause 34, wherein the cell marker is a cell surface marker.

Clause 36. The method of any of clauses 20, 21, or 31 to 35, wherein the binding agent of the OTBA comprises an aptamer or an antibody or a functional fragment thereof.

Clause 37. The method of any one of clauses 28 to 36 wherein a sample comprising one or more nucleic acids comprises more than one cell or cell nuclei, wherein the cells or cell nuclei, or subpopulations thereof may comprise one or more cell markers, wherein the sample is split into two or more first portions before step annealing the first primer, and wherein each first portion comprises a subpopulation of cells or cell nuclei of the original sample.

Clause 38. The method of 37, wherein the first primer is a first extension primer comprising a first universal handle sequence on the 5' end and a first barcode, said first barcode being common among the first extension primers in each first portion, but different from the first barcodes present in extension primers in other first portions; and
 wherein the oligonucleotide of the oligonucleotide-tethered dideoxynucleotide comprises a universal handle sequence; and
 wherein said first portions are contacted under conditions that enable extension of the first extension primers to form first nucleic acid extension products that comprise the oligonucleotide-tethered dideoxynucleotide(s), and
 wherein extension of the first nucleic acid extension products is terminated by incorporation of the oligonucleotide-tethered dideoxynucleotide.

Clause 39. The method of clause 38, further comprising:
 a. combining the first portions after formation of the first nucleic extension products;
 b. splitting the combined first portions into two or more second portions; and
 c. contacting each second portion with a polymerase, at least one nucleotide that is not an oligonucleotide-tethered nucleotide, and a splint oligonucleotide,
 wherein the splint oligonucleotide comprises:
  i. an oligonucleotide sequence capable of annealing to the first universal handle under extension conditions,
  ii. a sequence that is a template for a second barcode, wherein the second barcodes of each second portion are common, but are different from the second barcodes of other second portions, and
  iii. a sequence that is a template for a third universal handle,
 wherein the 3'OH of the tethered oligonucleotide of the first extension products is extended across the splint oligonucleotide to generate second nucleic acid extension products that comprise the second barcode sequence and third universal handle sequence.

Clause 40. The method of clause 39 further comprising:
 a. combining the second portions;
 b. splitting the combined second portions into two or more third portions;
 c. contacting each third portion with amplification primers, wherein the amplification primers anneal to and extend across the second extension products or their complements from the first universal handle and the third universal handle, and wherein the amplification primers optionally comprise third and/or fourth barcodes respectively, and first and/or second adapter sequences, respectively, to generate said nucleic acid library, wherein the combination of the first, second, and third barcode sequences (or complements thereof) are unique to amplification products originating from a single cell.

Clause 41. The method of any one of clauses 16 to 40, wherein the first primer, second primer, amplification primers, or splint oligonucleotide comprises an adapter sequence, a barcode sequence, a unique molecular identifier, an index sequence, a promoter sequence, a universal handle, a universal sequence, a random sequence, a target-specific sequence, or any combination thereof.

Clause 42. The method of any one of clauses 1 to 41, wherein the oligonucleotide-tethered nucleotide further comprises an affinity tag.

Clause 43. The method of any one of clauses 16, 18 to 27 or 29 to 39, wherein the second primer is at least partially complementary to the tethered oligonucleotide.

Clause 44. The method of any one of clauses 16 to 43, wherein the first primer, the second primer, or both comprise a universal sequence.

Clause 45. The method of any one of clauses 1 to 44, where the tethered oligonucleotide comprises an adapter sequence, a T7 promotor sequence, a barcode, a universal molecular identifier, a universal handle, a universal sequence, an adapter sequence, a random sequence, a target-specific sequence, a promoter sequence, an index sequence or any combination thereof.

Clause 46. The method of any one of clauses 1 to 45, wherein the polymerase is a Type-A DNA polymerase, Type B DNA polymerase, Type X DNA polymerase, or a reverse transcriptase.

Clause 47. The method of any one of clauses 1 to 46, wherein the polymerase is chosen from Taq DNA polymerase, Vent® DNA polymerase, Deep Vent™ DNA polymerase, Pfx DNA polymerase, Pwo polymerase, SuperScript™ IV, SuperScript™ 11, SuperScript™ 111, Maxima™, RevertAid™ reverse transcriptases, Thermo Sequenase™, Sequenase™ V2.0, CycleSeg™, Phusion exo-, Terminal deoxynucleotidyl Transferase (TdT), Maxima H, Therminator™ polymerase, Q5 DNA polymerase, AccuTaq DNA polymerase, T7 DNA polymerase, T3 DNA polymerase, T4 DNA polymerase, T7 RNA polymerase, T3 RNA polymerase, SP6 RNA polymerase, DNA polymerase 1, Klenow fragment, Tth DNA polymerase, Phusion® DNA polymerase, SuperFi DNA polymerase, Platinum Taq DNA polymerase, Herculase II Fusion DNA polymerase, PfuUltra Fusion II HS DNA polymerase, Bst DNA polymerase large fragment, Stoeffel fragment, 9° N™ DNA polymerase, Pfu DNA polymerase, Tfl DNA polymerase, Phi29 polymerase, Tli DNA polymerase, eukaryotic DNA polymerase beta, telomerase, KOD HiFi DNA polymerase, KOD DNA polymerase, Q-beta replicase, AMV reverse transcriptase, M-MLV reverse transcriptase, Phi6 reverse transcriptase, HIV-1 reverse transcriptase, polyA polymerase (PAP), polyU polymerase (PUP), and variants and derivatives thereof.

Clause 48. The method of any one of clauses 1 to 47, wherein the oligonucleotide-tethered nucleotide is chosen from dideoxyadenosine triphosphate, dideoxyguanosine triphosphate, dideoxythymidine triphosphate, dideoxyuridine triphosphate, dideoxycytidine triphosphate, or any combination thereof.

Clause 49. The method of any one of clauses 26 to 48, further comprising amplifying the library.

Clause 50. The method of any one of clauses 26 to 49, wherein the concentration of oligonucleotide-tethered nucleotide ranges from 1 fmol to 10 µmol.

Clause 51. The method of any one of clauses 26 to 50, wherein the molar ratio of oligonucleotide-tethered nucleotide to a corresponding nucleotide not tethered to an oligonucleotide ranges from 1:1 to 1:1000.

Clause 52. The method of any one of clauses 26 to 51, further comprising performing at least one clean up step after forming one or more nucleic acid extension or nucleic acid amplification products.

Clause 53. The method of any one of clauses 1 to 52, wherein the nucleic acid is DNA.

Clause 54. The method of any one of clause 1 to 53, wherein the nucleic acid is RNA.

Clause 55. The method of clause 54, further comprising reverse transcribing the RNA to producing a corresponding cDNA before annealing a first primer or before generating a plurality of polynucleotide fragments.

Clause 56. The method of any one of clauses 26 to 55, further comprising fixing and permeabilizing the cells prior to annealing the first primer and/or splitting the sample.

Clause 57. The method of any one of clauses 26 to 56, further comprising lysing the cells after generating one or more extension and/or amplification products.

Clause 58. The method of any one of clauses 37 to 57, whereinafter generating first nucleic acid extension products, the first portions or combined first portions are contacted with a blocking oligonucleotide, wherein the blocking oligonucleotide prevents hybridization of first extension primers to cellular nucleic acids.

Clause 59. The method of any one of clauses 37-58, further comprising the step of removing the splint oligonucleotides after generating the second nucleic acid extension products and prior to contacting the third portion with a second extension primer.

Clause 60. The method of any one of clauses 37-59, wherein the splint oligonucleotides comprise a binding moiety, the method comprising the step of contacting the second portions or combined second portions with a compound comprising a cognate capture moiety.

Clause 61. The method of clause 60 wherein the binding moiety and the cognate capture moiety are a binding pair chosen from the binding pairs of streptavidin and biotin, maltose and maltose binding protein, glutathione and glutathione S-transferase, chitin and chitin binding protein, or an aptamer and its antigen.

Clause 62. The method of clause 60 or 61, wherein the cognate capture moiety is immobilized on a solid support.

Clause 63. The method of clause 62, wherein the solid support comprises a bead.

Clause 64. The method of clause 63, wherein the bead is a magnetic or paramagnetic bead.

Clause 65. The method of any one of clauses 37 to 64, wherein the first primer comprises a sequence capable of hybridizing to an mRNA under extension conditions.

Clause 66. The method of clause 65, wherein the first primer comprises a poly(T) at the 3' end.

Clause 67. The method of clause 65, wherein the first primer comprises a random sequence at the 3' end.

Clause 68. The method of clause 65, wherein the first portion is contacted with a mixture of first primers, wherein at least one first primer comprises a poly(T) sequence at the 3' end and at least one first primer comprises a random sequence.

Clause 69. An oligonucleotide-tethered nucleotide of Formula (A):

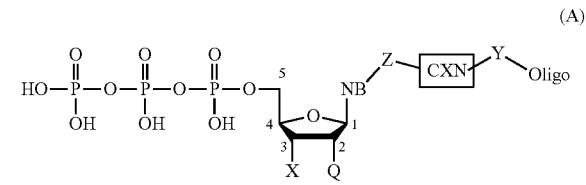

(A)

or a salt thereof
wherein NB is a nucleobase;
Oligo is an oligonucleotide of 3 to 100 nucleotides;

each of X and Q are independently chosen from, H, OH, N₃, halo, alkyl, alkoxy, alkyl, alkenyl, alkynyl, acyl, cyano, amino, ester, and amido;

each of Z and Y are independently chosen from a bond, amino, amido, alkyl, alkenyl, alkynyl, thioether, sulfonyl, sulfonamido, ether, ketone, carbonyl, anhydride, ester, imido, urea, urethane, and combinations thereof; and CXN is chosen from alkylene, alkenylene, alkynylene, ketone, carbonate, ester, ether, anhydride, amido, amino, aminoalkylene, imino, amido, diazo, carbamate ester, phosphodiester, sulfide, disulfide, sulfonyl, sulfonamido, and a heterocyclic group containing from one to four N, O, S atom(s) or a combination thereof where heterocyclic group is optionally substituted at carbon, nitrogen or sulfur atom(s).

Clause 70. The oligonucleotide-tethered nucleotide of clause 68, wherein Oligo is chosen from

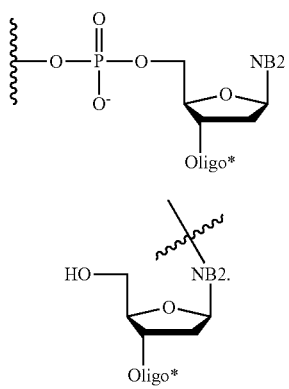

where Oligo* is the remaining 2 to 99 nucleotides from the Oligo group and NB2 is a nucleobase.

Clause 71. The oligonucleotide-tethered nucleotide of clause 69 or clause 70, wherein CXN is chosen from 5-membered heterocycles and 6-membered heterocycles each having from 1 to 3 heteroatoms.

Clause 72. The oligonucleotide-tethered nucleotide of any one of clauses 69 to 71, wherein CXN is chosen from pyrrolo, thiophenyl, furanyl, pyrrolidinyl, thiolanyl, tetrahydrofuranyl, isoxazolyl, oxazolo, pyrazolo, imidazolyl, isothiazolo, thiazolyl, triazolo, oxadiazolo, thiadiazolo, pyranyl, thiopyranyl, pyridinyl, tetrahydropyranyl, tetrahydrothiopyranyl, piperidinyl, pyridazinyl, pyrimidinyl, pyrazinyl, hexahydropyridazinyl, hexahydropyrimidinyl, piperazinyl, dioxanyl, morpholino, thiazinyl, oxazino, dithianyl, triazinyl, dithiazino, thiadiazino, triazinanyl, or oxathiazino.

Clause 73. The oligonucleotide-tethered nucleotide of any one of clauses 69 to 72, wherein CXN is Click wherein Click is a product of a click reaction.

Clause 74. The oligonucleotide-tethered nucleotide of any one of clauses 69 to 73, wherein CXN is Click and wherein Click is a product of a click reaction between one of the following pairs of functional groups:
  i) alkynyl and azido;
  ii) thiol and alkynyl;
  iii) thiol and alkenyl;
  iv) azido and cyclooctanyl; and
  v) cyclooctanyl and nitron.

Clause 75. The oligonucleotide-tethered nucleotide of any one of clauses 69 to 74, wherein CXN is

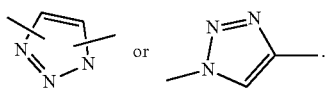

Clause 76. The oligonucleotide-tethered nucleotide of any one of clauses 69 to 75, wherein Z and Y are each independently chosen from bond, amino, amido, alkylene, alkenylene, alkynylene, ether, ketone, carbonyl, anhydride, ester, imide, or any combination thereof.

Clause 77. The oligonucleotide-tethered nucleotide of any one of clauses 69 to 76, wherein Y is alkylene or alkynylene.

Clause 78. The oligonucleotide-tethered nucleotide of any one of clauses 69 to 77, wherein Z is a combination of one or more of alkynylene, alkylene, ether and amido.

Clause 79. The oligonucleotide-tethered nucleotide of any one of clauses 69 to 78, wherein —NB—Z— is NB—HN-L₁-, NB—(CH—CH)C(O)(CH₂CH₂)NHC(O) (CH₂)₅-L₁,

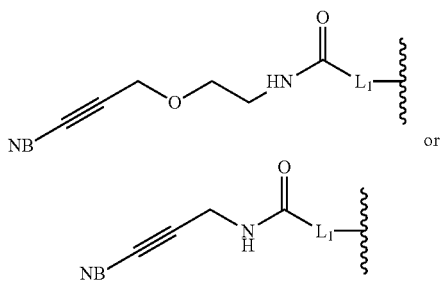

where L₁ is chosen from alkylene, alkenylene, alkynylene, and polyalkylene glycol.

Clause 80. The oligonucleotide-tethered nucleotide of clause 69 wherein the compound of Formula (A): is chosen from the compounds of Formula (B1)-(B4)

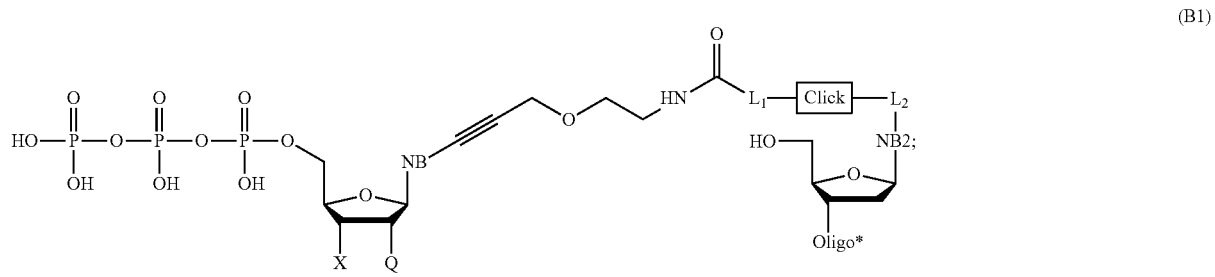

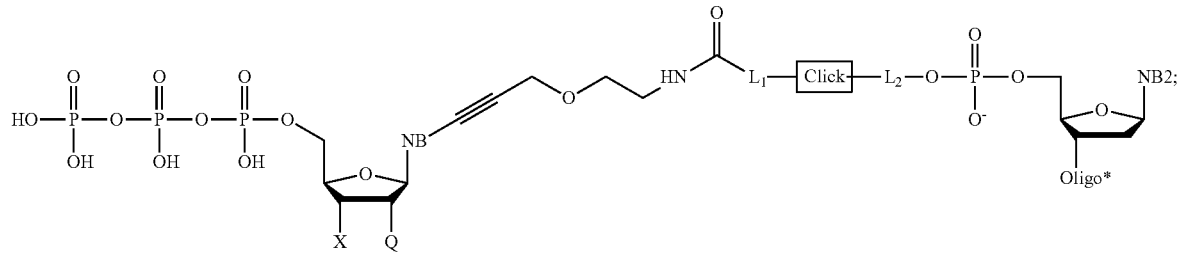

(B2)

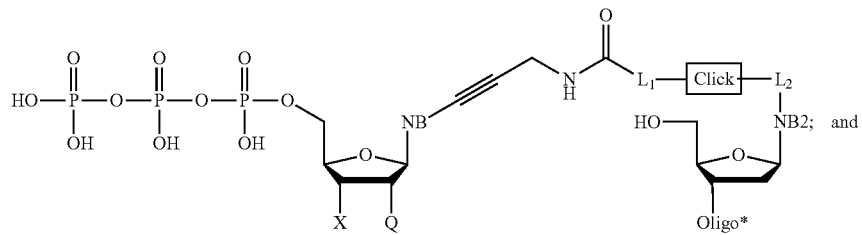

(B3)

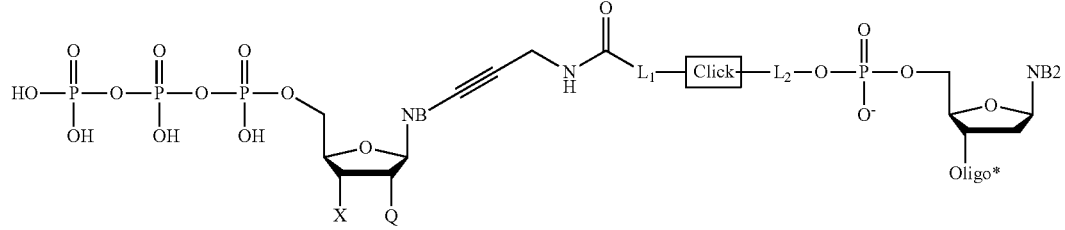

(B4)

and salts thereof wherein oligo* is the remaining 2 to 99 nucleotides from the Oligo group and NB2 is a nucleobase; Click is a product of a click reaction; $L_1$ is chosen from alkylene, alkenylene, alkynylene, and polyalkylene glycol; $L_2$ is alkylene or alkynylene.

Clause 81. The oligonucleotide-tethered nucleotide of clause 79 or 80, wherein $L_1$ is chosen from C1-C12 alkylene, C2-C12 alkenylene, C2-C12 alkynylene, and polyalkylene glycol having from 2 to 8 glycol units Clause 82. The oligonucleotide-tethered nucleotide any of clauses 79 to 81, wherein $L_1$ is chosen from polyethylene glycol with 2 glycol units (PEG2), polyethylene glycol with 4 glycol units (PEG4), or polyethylene glycol with 6 glycol units (PEG6), methylene, ethylene, n-propylene, isopropylene, 1-butylene, cis-2-butylene, trans-2-butylene, isobutylene, 1-pentylene, cis-2-pentylene, trans-2-pentylene, isopentylene, and hexylene.

Clause 83. The oligonucleotide-tethered nucleotide of any one of clauses 79 to 82, wherein $L_1$ is chosen from —$CH_2$—, —$(CH_2)_3$—, —$(CH_2)_5$—, PEG2, and PEG4. Clause 84. The oligonucleotide-tethered nucleotide of any one of clauses 80 to 83, wherein $L_2$ is C1-C12 alkylene or C1-C12 alkynylene.

Clause 85. The oligonucleotide-tethered nucleotide of any one of clauses 80 to 84, wherein $L_2$-Oligo is —$(CH_2)_4$-Oligo or —$(CH_2)_4$C≡C-Oligo.

Clause 86. The oligonucleotide-tethered nucleotide of any one of clauses 69 to 85, wherein X is chosen from H, OH, F, $N_3$, and amino.

Clause 87. The oligonucleotide-tethered nucleotide any one of clauses 69 to 86, wherein X is chosen from H, $N_3$, and OH Clause 88. The oligonucleotide-tethered nucleotide of any one of clauses 69 to 87, wherein X is OH.

Clause 89. The oligonucleotide-tethered nucleotide of any one of clauses 69 to 87, wherein X is H.

Clause 90. The oligonucleotide-tethered nucleotide of any one of clauses 69 to 89, wherein Q is II, OII, F, Cl, Br, I, an $N_3$.

Clause 91. The oligonucleotide-tethered nucleotide of any one of clauses 69 to 90, wherein Q is H.

Clause 92. The oligonucleotide-tethered nucleotide of any one of clauses 69 to 91, wherein Oligo or Oligo* is bonded to Y at its 5' end.

Clause 93. The oligonucleotide-tethered nucleotide of any one of clauses 69 to 92, wherein NB and NB2 are independently a nucleobase chosen from adenine, 7-deaza-adenine, cytosine, guanine, 7-deazaguanine, thymine, uracil and inosine.

Clause 94. The oligonucleotide-tethered nucleotide of any one of clauses 69 to 93, wherein NB is a pyrimidine and wherein pyrimidine is tethered to the oligonucleotide at the 5 position of the nucleobase.

Clause 95. The oligonucleotide-tethered nucleotide of any one of clauses 69 to 93, wherein NB is a purine, and wherein the purine is tethered to the oligonucleotide at the 7 position of the nucleobase.

Clause 96. The oligonucleotide-tethered nucleotide of any one of clauses 69 to 95, wherein the salt of the compound of Formula (A) is a quaternary ammonium salt.

Clause 97. The oligonucleotide-tethered nucleotide of any one of clauses 69 to 96, wherein Oligo is an oligonucleotide comprising a barcode sequence, an adapter sequence, a unique molecular identifier, a random sequence, a target-specific sequence, a universal handle, a universal sequence, a promoter sequence, an index sequence or any combination thereof.

Clause 98. The method of any one of clauses 1-68, wherein the oligonucleotide-tethered nucleotide is chosen from oligonucleotide-tethered nucleotides according to any one of clauses 69 to 97.

Clause 99. A kit for producing a sequencing library comprising:
a. an oligonucleotide-tethered nucleotide according to any one of clauses 69-97, and
b. at least one of
(i) A, C, G, L and/or T nucleotides,
(ii) a polymerase,
(iii) a primer and/or an adapter sequence,
(iv) a buffer, or
(v) a salt Clause 100. The kit of clause 99, wherein the kit comprises A, C, G, U and/or T nucleotides.

Clause 101. The kit of clause 99 or 100, wherein the kit comprises the polymerase.

Clause 102. The kit of clause 101, wherein the polymerase is a wild type polymerase, a modified polymerase, mutant polymerase, an engineered polymerase, or a combination thereof.

Clause 103. The kit of any one of clauses 99 to 102, wherein the polymerase is Taq DNA polymerase, Vent® DNA polymerase, Deep Vent™ DNA polymerase, Pfx DNA polymerase, Pwo polymerase, SuperScript™ IV, SuperScript™ II, SuperScript™ III, Maxima™, RevertAid™ reverse transcriptases, Thermo Sequenase™, Sequenase™ V2.0, CycleSeq™, Phusion exo-, Terminal deoxynucleotidyl Transferase (TdT), Maxima H, Therminator™ polymerase, Q5 DNA polymerase, AccuTaq DNA polymerase, T7 DNA polymerase, T3 DNA polymerase, T4 DNA polymerase, T7 RNA polymerase, T3 RNA polymerase, SP6 RNA polymerase, DNA polymerase 1, Klenow fragment, Tth DNA polymerase, Phusion® DNA polymerase, SuperFi DNA polymerase, Platinum Taq DNA polymerase, Herculase II Fusion DNA polymerase, PfuUltra. Fusion II HS DNA polymerase, Bst DNA polymerase large fragment, Stoeffel fragment, 9° N™ DNA polymerase, Pfu DNA polymerase, Tfl DNA polymerase, Phi29 polymerase, Tli DNA polymerase, eukaryotic DNA polymerase beta, telomerase, KOD HiFi DNA polymerase, KOD DNA polymerase, Q-beta replicase, AMV reverse transcriptase, M-MLV reverse transcriptase, Phi6 reverse transcriptase, and HIV-1 reverse transcriptase, polyA polymerase (PAP), polyU polymerase (PUP), and variants and derivatives thereof.

Clause 104. The kit of any one of clauses 99 to 103, wherein the kit comprises one or more primer, adapter, barcode, or unique molecular identifier sequences.

Clause 105. The kit of any one of clauses 99 to 104, wherein the kit comprises the at least one buffer.

Clause 106. The kit of any one of clauses 96 to 105, wherein the kit comprises the at least one salt.

Clause 107. A kit for combinatorial barcoding of nucleic acids, comprising:
a. an oligonucleotide-tethered nucleotide according to any one of clauses 71-99, and
b. at least one of
(i) A, C, G, U and/or T nucleotides,
(ii) a polymerase,
(iii) a primer and/or an adapter sequence,
(iv) a buffer;
(v) a plurality of nucleic acid barcodes. and
(vi) one or more cell marker binding agents.

Clause 108. The kit of clause 107, wherein the nucleotide of the oligonucleotide-tethered nucleotide is a dideoxynucleotide.

Clause 109. The kit of any one of clauses 107 to 108, wherein the oligonucleotide of the oligonucleotide-tethered nucleotide comprises a universal handle sequence.

Clause 110. The kit of any one of clauses 107 to 109, wherein the polymerase is a reverse transcriptase, a DNA polymerase, or both.

Clause 111. The kit of any one of clauses 107 to 110, wherein the plurality of nucleic acid barcodes comprise a first plurality of nucleic acid barcodes provided in individual compartments.

Clause 112. The kit of clause 111, further comprising a second and optionally a third, fourth, fifth, or sixth plurality of nucleic acid barcodes provided in individual compartments.

Clause 113. The kit of any one of clauses 111 to 112, wherein the individual compartments are provided in a multi-well plate.

Clause 114. The kit of any one of clauses 111 to 113, wherein the plurality of nucleic acid barcodes are in lyophilized form.

Clause 115. The kit of any one of clauses 111 to 114, wherein the plurality of nucleic acid barcodes are in solution form.

Clause 116. The kit of any one of clauses 111 to 115, wherein the nucleic acid barcodes of the first plurality of barcodes comprise an extension primer, wherein each extension primer comprises, in 5' to 3' direction, a first universal handle and a first nucleic acid barcode.

Clause 117 The kit of any one of clauses 112 to 115, wherein the nucleic acid barcodes on the second plurality of barcodes comprise a splint oligonucleotide, wherein the splint oligonucleotide comprises, in 5' to 3' direction, a sequence that anneals to a second universal handle, a sequence that is a template for a second nucleic acid barcode, and a sequence that is a template for a third universal handle.

Clause 118. The kit of any one of clauses 112 to 116, wherein the nucleic acid barcodes on the third plurality of barcodes comprise an extension primer, and wherein the extension primer optionally comprises a sequencing adapter sequence.

Clause 119. The kit of any one of clauses 107 to 118, further comprising one or more cell marker binding agents.

Clause 120. The kit of clause 119, wherein each cell marker binding agent is an oligonucleotide tethered OTBA, comprising an oligonucleotide tethered to a cell marker binding agent.

Clause 121. A method for preparing an oligonucleotide-tethered nucleotide according to any one of clauses 69 to 97, comprising:
a. providing a nucleotide covalently bound to a first functional group capable of undergoing a click reaction with a second functional group;
b. providing an oligonucleotide covalently bound to the second functional group capable of undergoing a click reaction to form the triazole ring;
c. contacting the nucleotide with the oligonucleotide to form the click reaction product,
wherein, the first and second functional groups are, respectively, chosen from:
i) alkynyl and azido;
ii) azido and alkynyl,
iii) thiol and alkynyl;
iv) alkynyl and thiol;
v) thiol and alkenyl;
vi) alkenyl and thiol;
vii) azido and cyclooctanyl;
viii) cyclooctanyl and azido;
xi) nitrone and cyclooctanyl; and
xii) cyclooctanyl and nitrone.

Clause 122. The method of clause 121, where in the first and second functional groups are, respectively, chosen from i) alkynyl and azido; and ii) azido and alkynyl.

Clause 123. The method of clause 121, wherein step (c) comprises contacting the nucleotide with the oligonucleotide in the presence of a copper catalyst and copper (I) ligand to form a 1,2,3-triazole.

Clause 124. The method of any one of clauses 121 to 123, wherein the nucleotide is a deoxynucleotide or dideoxynucleotide.

Clause 125. The method of any one of clauses 123 or 124, wherein the copper catalyst comprises copper (I), or copper (II), wherein when the catalyst is copper (II), a reducing agent is present.

Clause 126. The method of any one of clauses 123 to 125, wherein the copper catalyst is $Cu(NO_3)_2$ Cu(OAc), $CuSO_4$ or any combination thereof.

Clause 127. The method of clause 125 or 126, wherein the reducing agent comprises ascorbate, Tris(2-Carboxyethyl) Phosphine (TCEP), 2.4.6-trichlorophenol (TCP), NADH, NADPH, thiosulfate, metallic copper, quinone, hydroquinone, Vitamin K, glutathione, cysteine, 2-mercaptoethanol, dithiothreitol, Fe(II), Co(II), an applied electric potential, Al, Be, Co, Cr, Fe, Mg, Mn, Ni, Zn, Au, Ag, Hg, Cd, Zr, Ru, Fe, Co, Pt, Pd, Ni, Rh, W, or any combination thereof.

Clause 128. The method of clause 127, wherein the reducing agent comprises sodium ascorbate.

Clause 129. The method of any one of clauses 123 to 128, wherein the ligand of the copper (I) ligand comprises tris(benzyltriazolylmethyl)amine or tris(3-hydroxypropyltriazolylmethyl)amine.

Clause 130. Use of an oligonucleotide-tethered nucleotide according to any of clauses 69 to 97 in the preparation of a nucleic acid library.

Clause 131. Use of an oligonucleotide-tethered nucleotide according to any of clauses 69 to 97 in tagging a nucleic acid.

Clause 132. Use of an oligonucleotide-tethered nucleotide according to any of clauses 69 to 97 in tagging a nucleic acid with a combination of barcodes.

From the examples described herein, one skilled in the art can easily ascertain the essential principles of this disclosure and without departing from the spirit and scope thereof, can make various modifications and changes of the disclosure in adapting to specific uses and conditions.

What is claimed is:

1. A method for generating a library of nucleic acids from a sample comprising one or more nucleic acids, optionally wherein the sample comprises a plurality of cells or cell nuclei, comprising:
   a. annealing a first primer which is at least partially complementary to the one or more nucleic acids,
   b. contacting the one or more nucleic acids with a first nucleic acid polymerase, at least one nucleotide not tethered to an oligonucleotide, and at least one oligonucleotide-tethered dideoxynucleotide to form a plurality of first extension products comprising the oligonucleotide-tethered dideoxynucleotide at the 3' end;
   c. annealing a splint oligonucleotide which is at least partially complementary to the tethered oligonucleotide of the first extension products, and
   d. contacting the first extension products with a nucleic acid polymerase and one or more nucleotides to allow the polymerase to extend across the annealed splint from the 3' hydroxyl of the tethered oligonucleotide to produce a second extension product, thereby producing a library of nucleic acids,
   wherein if the sample comprises a plurality of cells or cell nuclei, the cells or cell nuclei are fixed and permeabilized prior to annealing the first primer.

2. The method of claim 1, wherein the sample is treated with an oligonucleotide-tethered binding agent (OTBA) prior to fixation.

3. The method of claim 2, wherein the tethered oligonucleotide of the OTBA comprises a cell marker binding agent index, and wherein binding agent of the OTBA comprises an aptamer or an antibody or a functional fragment thereof.

4. The method of claim 1, wherein a sample comprising one or more nucleic acids comprises more than one cell or cell nuclei, wherein the cells or cell nuclei may comprise one or more cell markers, wherein the sample is split into two or more first portions before step a, and wherein each first portion comprises a subpopulation of cells or cell nuclei of the original sample.

5. The method of claim 4, wherein the first primer comprises a first universal handle sequence and a first barcode, said first barcode being common among the first primers in each first portion, but different from the first barcodes present in first primers in other first portions; and wherein the oligonucleotide of the oligonucleotide-tethered dideoxynucleotide comprises a second universal handle sequence.

6. The method of claim 5, further comprising, before step c:
   a. combining the first portions after formation of the first nucleic extension products and
   b. splitting the combined first portions into two or more second portions, wherein the second portions comprise the splint oligonucleotide; wherein the splint oligonucleotide comprises:
      i. an oligonucleotide sequence that anneals to the second universal handle on the tethered oligonucleotide;
      ii. a template sequence for a second barcode, wherein the second barcodes of each second portion are common, but are different from the second barcodes of other second portions, and
      iii. a template sequence for a third universal handle;
   wherein the second extension products comprise the second barcode and third universal handle.

7. The method of claim 6 further comprising:
   a. combining the second portions;
   b. splitting the combined second portions into two or more third portions;
   c. contacting each third portion with amplification primers, wherein the amplification primers are capable of hybridizing to and extending from the first universal handle and the third universal handle, and wherein the amplification primers optionally comprise third and/or fourth barcodes respectively, and first and/or second adapter sequences, respectively, to generate amplification products, wherein the combination of the first, second, and third barcode sequences (or complements thereof) of the amplification products are unique to the amplification products originating from a single cell or nucleus.

8. The method of claim 1, wherein the primer, the tethered oligonucleotide, or both comprises a random sequence, a target-specific sequence or both.

9. The method of claim 1, wherein one or more of the primer, the tethered oligonucleotide, or the splint oligonucleotide comprises a universal handle, a universal sequence, a unique molecular identifier, an adapter sequence, a promoter sequence, a barcode sequence, an index sequence, or any combination thereof.

10. The method of claim 1, wherein the polymerase is a DNA polymerase or an RNA polymerase.

11. The method of claim 1, wherein the nucleic acid is DNA or RNA.

* * * * *

SEQUENCE LISTING

```
<160> NUMBER OF SEQ ID NOS: 48

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: alkyne modified dU

<400> SEQUENCE: 1
uagatcggaa gagcacacgt ctg                                               23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: alkyne modified dU

<400> SEQUENCE: 2
uagatcggaa gagcacacgt ctg                                               23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: alkyne modified dU
```

```
<400> SEQUENCE: 3
uagatcggaa gagcacacgt ctg                                            23

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
agatcggaag agcacacgtc tg                                             22

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
taatacgact cactatag                                                  18

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: alkyne modified dU
<220> FEATURE:
<221> NAME/KEY: modified_base
<222> LOCATION: (2)..(9)
<223> OTHER INFORMATION: a, c, t, g, unknown or other

<400> SEQUENCE: 6
unnnnnnnna gatcggaaga gcgtcgtgta                                     30

<210> SEQ ID NO 7
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: alkyne modified dU

<400> SEQUENCE: 7
uagatcggaa gagcacacgt ctgaactcca gtcacatgcc taaatctcgt atgccgtctt    60
ctgcttg                                                              67

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 8
tacacgacgc tcttccgatc taacggtacg ccagaatctt g        41

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tacacgacgc tcttccgatc tagagccacc accggaac        38

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(31)
<223> OTHER INFORMATION: a, c, t, g, unknown or other

<400> SEQUENCE: 10
tacacgacgc tcttccgatc tnnnnnnnnn n        31

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctctttccct acacgacgct cttccgatct aagtcgtaac aaggtaaccg        50

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctctttccct acacgacgct cttccgatct ctgagccakr atcaaactct        50

<210> SEQ ID NO 13
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctctttccct acacgacgct cttccgatct ctgaaccaag atcaaattct        50

<210> SEQ ID NO 14
<211> LENGTH: 50
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 14
ctctttccct acacgacgct cttccgatct ctaagccagg atcaaactct                 50

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctctttccct acacgacgct cttccgatct ctgagccaga atcgaaccct                 50

<210> SEQ ID NO 16
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aagcagtggt atcaacgcag agtactttttt tttttttttt tttttttttt ttttt          55

<210> SEQ ID NO 17
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aatgatacgg cgaccaccga gatctacacg cctgtccgcg gaagcagtgg tatcaacgca      60
gagtac                                                                 66

<210> SEQ ID NO 18
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
caagcagaag acggcatacg agatgtgact ggagttcaga cgtgtgctct tccgatct        58

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
caagcagaag acggcatacg a                                                21

<210> SEQ ID NO 20
<211> LENGTH: 27
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(24)
<223> OTHER INFORMATION: a, c, t, g, unknown or other

<400> SEQUENCE: 20
ccaggaccag cgattcnnnn nnnnggg                                           27

<210> SEQ ID NO 21
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cagtggtatc aacgcagagt acccaggacc agcgattc                              38

<210> SEQ ID NO 22
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: alkyne modified dU

<400> SEQUENCE: 22
utttatatat ttattggaga ctgactacca gatgtaacac ctatagtgag tcgtattag       59

<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: alkyne modified dU

<400> SEQUENCE: 23
tuatatattt attggagact gactaccaga tgtaaca                               37

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgcagacatg ggtaggcatc cttggcgta                                        29

<210> SEQ ID NO 25
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 25
gtacgccaag gatgcctacc catgtctgca                                        30

<210> SEQ ID NO 26
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ctaatacgac tcactatagg tgttacatct ggtagtcagt ctccaataaa tatataaa         58

<210> SEQ ID NO 27
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gtcgctcaac tcagctacag tacgccaagg atgcctaccc atgtctgca                   49

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gtacgccaag gatgcctacc catgtctgca                                        30

<210> SEQ ID NO 29
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ccggggatcc catgtg                                                       16

<210> SEQ ID NO 30
<211> LENGTH: 112
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 30
gggaaagcuu uuacauuuuc gcgauaccgu ccagcgacau ucuuccucgg uacauaaucu       60
ccuuuggcgu uucccgaugu ccgucacgca caugggaucc ccgdguaccg ag              112

<210> SEQ ID NO 31
<211> LENGTH: 39
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aaaaaaaaaa tacgccaagg atgcctaccc atgtctgca                                 39

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tgcagacatg ggtaggcatc cttggcgta                                            29

<210> SEQ ID NO 33
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: alkyne modified dU

<400> SEQUENCE: 33
uttatatatt tattggagac tgactaccag atgtaaca                                  38

<210> SEQ ID NO 34
<211> LENGTH: 88
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aatgatacgg cgaccaccga gatctacact ctttccctac acgacgctct tccgatcttt         60
tttttttttt tttttttttt tttttttt                                            88

<210> SEQ ID NO 35
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: alkyne modified dU

<400> SEQUENCE: 35
uagatcggaa gagcacacgt ctgaactcca gtcacatgcc taaatctcgt atgccgtctt         60
ctgcttg                                                                   67

<210> SEQ ID NO 36
<211> LENGTH: 42
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 36
gcggcgacca aatcgttgta aagatcggaa gagcgtcgtg ta                        42

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cagacgtgtg ctcttccgat ct                                             22

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cagacgtgtg ctcttccgat ct                                             22

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
aagtcgtaac aaggtaaccg                                                20

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tttttttttt tttttttttt tttttttttt                                     30

<210> SEQ ID NO 41
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tttttttttt tttt                                                      14

<210> SEQ ID NO 42
<211> LENGTH: 10
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 42
aaaaaaaaaa                                                            10

<210> SEQ ID NO 43
<211> LENGTH: 269
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (20)..(269)
<223> OTHER INFORMATION: This region may encompass 80-250 nucleotides

<400> SEQUENCE: 43
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaa                                      269

<210> SEQ ID NO 44
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: a, c, t, g, unknown or other

<400> SEQUENCE: 44
tttttttttt tttttvn                                                    17

<210> SEQ ID NO 45
<211> LENGTH: 256
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (7)..(256)
<223> OTHER INFORMATION: This region may encompass 80-250 nucleotides

<400> SEQUENCE: 45
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaa                                                    256

<210> SEQ ID NO 46
<211> LENGTH: 30
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 46
aaaaaaaaaa aaaaaaaaaa aaaaaaaaaa                                      30

<210> SEQ ID NO 47
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
aaaaaaaaaa aaa                                                        13

<210> SEQ ID NO 48
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tttttttttt t                                                          11
```